US007999093B2

(12) United States Patent
Allen et al.

(10) Patent No.: US 7,999,093 B2
(45) Date of Patent: Aug. 16, 2011

(54) NITRATE TRANSPORT COMPONENTS

(75) Inventors: Stephen M. Allen, Wilmington, DE (US); Kanwarpal Singh Dhugga, Johnston, IA (US); Kevin Fengler, Wilmington, DE (US); Howard P. Hershey, Cumming, IA (US); Victor Llaca, Newark, DE (US); Dale Loussaert, Clive, IA (US); Lu Liu, Redwood City, CA (US); Xiaomu Niu, Johnston, IA (US); Haiyin Wang, Johnston, IA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 970 days.

(21) Appl. No.: 11/504,116

(22) Filed: Aug. 15, 2006

(65) Prior Publication Data

US 2007/0044176 A1 Feb. 22, 2007

Related U.S. Application Data

(60) Provisional application No. 60/708,318, filed on Aug. 15, 2005.

(51) Int. Cl.
*C07H 21/04* (2006.01)
*A01H 1/00* (2006.01)
*C07K 14/415* (2006.01)
*C12N 15/00* (2006.01)

(52) U.S. Cl. ........... 536/23.6; 435/6; 435/468; 435/419; 435/320.1; 530/370; 536/23.1; 800/278; 800/295

(58) Field of Classification Search ............. 435/6, 69.1, 435/468, 183, 419, 320.1; 536/23.2, 23.6; 800/278, 295
See application file for complete search history.

(56) References Cited

U.S. PATENT DOCUMENTS

2004/0214272 A1* 10/2004 La Rosa et al. .............. 435/69.1

OTHER PUBLICATIONS

E. J. Hewitt et al., Nitrate Metabolism, Chapter 20, pp. 633-681, 1976.

Mathilde Orsel et al., Analysis of the NRT2 Nitrate Transporter Family in *Arabidopsis*. Structure and Gene Expression, Plant Physiology, vol. 129:886-896, 2002.

Yiping Tong et al., A Two-Component, High-Affinity Nitrate Uptake System in Barley, The Plant Journal, vol. 41:442-450, 2005.

National Center for Biotechnology Information General Identifier No. 29412128, Mar. 31, 2003, Accession No. AY129953, S. Quaggiotti et al., Expression of a Putative High-Affinity NO3-Transporter and of a H+-ATPase in Relation to Whole Plant Nitrate Transport Physiology in Two Maize Genotypes Differently Responsive to Low Nitrogen Availability.

National Center for Biotechnology Information General Identifier No. 33941728, Aug. 19, 2003, Accession No. CG069548, C. A. Whitelaw et al., Maize Genomics Consortium.

National Center for Biotechnology Information General Identifier No. 34245424, Aug. 26, 2003, Accession No. CG328158, C.A. Whitelaw et al., Consortium for Maize Genomics.

National Center for Biotechnology Information General Identifier No. 32105143, Jun. 19, 2003, Accession No. CC700367, C. A. Whitelaw et al., Consortium for Maize Genomics.

National Center for Biotechnology Information General Identifier No. 34245411, Aug. 26, 2003, Accession No. CG328145, C. A. Whitelaw et al., Consortium for Maize Genomics.

National Center for Biotechnology Information General Identifier No. 34082540, Aug. 21, 2003, Accession No. CG191479, C. A. Whitelaw et al., Maize Genomics Consortium.

National Center for Biotechnology Information General Identifier No. 33992813, Aug. 20, 2003, Accession No. CG109376, C. A. Whitelaw et al., Maize Genomics Consortium.

National Center for Biotechnology Information General Identifier No. 34913806, Nov. 9, 2004, Accession No. NP_918250, The NCBI Genome Assembly Consortium.

National Center for Biotechnology Information General Identifier No. 50904699, Nov. 9, 2004, Accession No. XP_463838, The NCBI Genome Assembly Consortium.

National Center for Biotechnology Information General Identifier No. 13624657, Apr. 12, 2001, Accession No. CAC36942, J. J. Zhou et al., Functional Expression and Kinetic Characterisation of NAR2 Gene of *Arabidopsis* in Xenopus Oocyte.

Henk Doddema et al., Uptake of Nitrate by Mutants of *Arabidopsis thaliana*, Disturbed in Uptake or Reduction of Nitrate, Physiol. Plant, vol. 45:332-338, 1979.

WPC Stemmer, PNAS, DNA Shuffling by Random Fragmentation and Reassembly: In Vitro Recombination for Molecular Evolution, vol. 91:10747-10751, 1994.

Andreas Crameri et al., DNA Shuffling of a Family of Genes From Diverse Species Accelerates Directed Evolution, Nature, vol. 391:288-291, 1998.

Jon E. Ness et al., DNA Shuffling of Subgenomic Sequences of Subtilisin, Nature Biotechnology, vol. 17:893-896, 1999.

A. A. Meharg et al., NO-3 Transport Across the Plasma Membrane of *Arabidopsis thaliana* Root Hairs: Kinetic Control by pH and Membrane Voltage, J. Membrane Biol., vol. 145:49-66, 1995.

Bruno Touraine et al., NO3- and CIO3-Fluxes in the CHL1-5 Mutant of *Arabidopsis thaliana*, Plant Physiol., vol. 114:137-144, 1997.

Kun-Hsiang Liu et al., CHL1 is a Dual-Affinity Nitrate Transporter of *Arabidopsis* Involved in Multiple Phases of Nitrate Uptake, The Plant Cell, vol. 11:865-874, 1999.

Quaggiotti, S. et al., Expression of a Putative High-Affinity NO3 Transporter and of a H+-ATPase in Relation to Whole Plant Nitrate Transport Physiology in Two Maize Genotypes Differently Responsive to Low Nitrogen Availability, J. of Exp. Botany, vol. 54:1023-1031, 2003.

(Continued)

*Primary Examiner* — Phuong T Bui

(57) ABSTRACT

This invention relates to isolated nucleic acid fragments encoding high affinity nitrate transport components. The invention also relates to the construction of recombinant DNA constructs encoding all or a portion of nitrate transport components, in sense or antisense orientation, wherein expression of the recombinant DNA construct may alter levels of the nitrate transport components in a transformed host cell.

4 Claims, 7 Drawing Sheets

OTHER PUBLICATIONS

Vidmar, J. J. et al., Isolation and Characterization of HVNRT 2.3 and HVNRT 2.4, cDNAs Encoding High Affinity Transporters From Roots of Barley, Plant Physiology, vol. 122:783-792, 2000.

Santi, S. et al., Induction of Nitrate Uptake in Maize Roots: Expression of a Putative High-Affinity Nitrate Transporter and Plasma Membrane H+-ATPase Isoforms, J. of Exp. Botany, vol. 54:1851-1864, 2003.

Quaggiotti, S. et al., Effect of Low Molecular Size Humic Substances on Nitrate Uptake and Expression Gens Involves in Nitrate Transport in Maize (*Zea mays* L.), J. of Exp. Botany, vol. 55(398):803-813, 2004.

Barton, G. J., Protein Sequence Alignment and Database Scanning,, Protein Structure Prediction, A Practical Approach, pp. 31-63, 1996.

George, D. G. et al., Current Methods in Sequence Comparison and Analysis, Macromolecular Sequencing and Synthesis Selected Methods and Applications, pp. 127-149,, 1988.

Shiela E. Unkles et al., Two perfectly conserved arginine residues are required for substrate binding in a high-affinity nitrate transporter, PNAS, Dec. 14, 2004, pp. 17549-17554, vol. 101, No. 50.

Laurence J. Trueman et al., Molecular cloning of higher plant homologues of the high-affinity nitrate transporters of *Chlamydomonas reinhardtii* and *Aspergillus nidulans*, Gene, 1996, pp. 223-231, vol. 175.

* cited by examiner

NITRATE TRANSPORT COMPONENTS

CROSS REFERENCE TO RELATED APPLICATIONS

This application claims the benefit of U.S. Provisional Application No. 60/708,318, filed Aug. 15, 2005 the entire content of which is herein incorporated by reference.

FIELD OF THE INVENTION

This invention is in the field of plant molecular biology. More specifically, this invention pertains to nucleic acid fragments encoding high affinity nitrate transporters in plants and seeds.

BACKGROUND OF THE INVENTION

Higher plants are autotrophic organisms that can synthesize all of their molecular components from inorganic nutrients obtained from the local environment. Nitrogen is a key element in many compounds present in plant cells. It is found in the nucleoside phosphates and amino acids that form the building blocks of nucleic acids and proteins, respectively. Availability of nitrogen for crop plants is an important limiting factor in agricultural production, and the importance of nitrogen is demonstrated by the fact that only oxygen, carbon, and hydrogen are more abundant in higher plant cells. Nitrogen present in the form of ammonia or nitrate is readily absorbed and assimilated by higher plants.

Nitrate is the principal source of nitrogen that is available to higher plants under normal field conditions. Thus, the nitrate assimilation pathway is the major point of entry of inorganic nitrogen into organic compounds (Hewitt et al. (1976) Plant Biochemistry, pp 633-6812, Bonner, and Varner, eds. Academic Press, NY). Although some plants directly utilize ammonia, under certain conditions, nitrate is generally the major form of nitrogen available to plants.

Nitrate uptake by root cells is the first step of the nitrate assimilation pathway in higher plants (Orsel et al. (2002) Plant Physiology 129: 886-896). Plants have developed two different uptake systems to cope with the varying availability of nitrate in cultivated soils. The low-affinity nitrate transport system is used preferentially when external nitrate concentration is high, whereas the high-affinity transport system (HATS) takes place at very low external concentrations.

In higher plants, two gene families have been identified: the NRT1 and NRT2 families involved in the low-affinity transport system and HATs, respectively. The complexity of nitrate/nitrite transport is enhanced by the fine regulation that occurs at the transcriptional level: both low and high-affinity systems have constitutive and inducible components that are clearly distinct. Furthermore, some members of the nitrate transporters require a second gene product, a NAR2-type polypeptide for function (Tong et al. (2005) The Plant Journal 41: 442-450).

The nucleotide sequences of the instant application and the methods of their use can increase the efficiency by which nitrogen can be used.

SUMMARY OF THE INVENTION

The present invention includes isolated polynucleotides encoding a polypeptide required for high affinity nitrate transport, wherein the amino acid sequence of the polypeptide and the amino acid sequence of SEQ ID NO: 36 or 49, have at least 80%, 85%, 90%, 95%, 99% or 100% identity (b) the complement of the nucleotide sequence, wherein the complement and the nucleotide sequence contain the same number of nucleotides and are 100% complementary. The polypeptide preferably comprises the amino acid sequence of SEQ ID NO: 36 or 49. The nucleotide sequence preferably comprises the nucleotide sequence of SEQ ID NO: 35 or 48.

In a first embodiment, the present invention includes an isolated polynucleotide comprising: (a) a nucleotide sequence encoding a polypeptide required for high affinity nitrate transport, wherein the polypeptide has an amino acid sequence of at least 80%, 85%, 90%, 95%, 99% or 100% sequence identity based on the Clustal V method of alignment when compared to a polypeptide SEQ ID NO: 36 or 49.

(b) a complement of the nucleotide sequence, wherein the complement and the nucleotide sequence contain the same number of nucleotides and are 100% complementary.

In a second embodiment, this invention concerns such isolated nucleotide sequence or its complement which comprises at least two motifs corresponding substantially to any of the amino acid sequences set forth in SEQ ID NO: 50, 51 or 52, wherein said motif is substantially a conserved subsequence. Examples of such motifs, among others that can be identified, are shown in SEQ ID NO: 50, 51 or 52. Also of interest is the use of such fragment or a part thereof in antisense inhibition or co-suppression in a transformed plant.

In a third embodiment this invention concerns such isolated nucleotide fragment complement thereof wherein the fragment or a part thereof is useful in antisense inhibition or co-suppression of a protein altering nitrate transport in a transformed plant.

In a fourth embodiment, this invention concerns an isolated nucleic acid fragment comprising a promoter wherein said promoter consists essentially of the nucleotide sequence set forth in SEQ ID NO: 37, 38, 46, 47, 56, 65, 67, 68, 69, 70, 71, 72, 73, 74, 89 or 90, or said promoter consists essentially of a fragment or subfragment that is substantially similar and functionally equivalent to the nucleotide sequence set forth in SEQ ID NO: 37, 38, 46, 47, 56, 65, 67, 68, 69, 70, 71, 72, 73, 74, 89 or 90.

In a fifth embodiment, this invention concerns recombinant DNA constructs comprising any of the foregoing nucleic acid fragment or complement thereof or part of either operably linked to at least one regulatory sequence. Also, of interest are plants comprising such recombinant DNA constructs in their genome, plant tissue or cells obtained from such plants and seeds obtained from these plants.

In a sixth embodiment, this invention concerns a method of altering nitrate transport in plants which comprises:

(a) transforming a plant with a recombinant DNA construct comprising:

i) a first recombinant DNA construct comprising an isolated polynucleotide encoding a HAT polypeptide, operably linked to at least one regulatory sequence; and ii) at least one additional recombinant DNA construct comprising an isolated polynucleotide encoding a NAR polypeptide, operably linked to at least one regulatory sequence, (b) growing the transformed plant of (a) under conditions suitable for the expression of the recombinant DNA constructs; and selecting those transformed plants having altered nitrate transport. Corn plants comprising these recombinant constructs are also part of this invention.

In a seventh embodiment, this invention concerns a method to isolate nucleic acid fragments encoding polypeptides associated with altering nitrate transport which comprises:

(a) comparing SEQ ID NO: 36, 49, 55, or 58 with other polypeptide sequences associated with altering plant nitrate transport;

(b) identifying the conserved sequences(s) or 4 or more amino acids obtained in step (a);

(c) making region-specific nucleotide probe(s) or oligomer (s) based on the conserved sequences identified in step (b); and (d) using the nucleotide probe(s) or oligomer(s) of step (c) to isolate sequences associated with altering nitrate transport by sequence dependent protocols.

In an eighth embodiment, this invention also concerns a method of mapping genetic variations related to altering plant nitrate transport:

(a) crossing two plant varieties; and (b) evaluating genetic variations with respect to:

(i) a nucleic acid sequence selected from the group consisting of SEQ ID NOs: 35, 48, 54, and 57; or (ii) a nucleic acid sequence encoding a polypeptide selected from the group consisting of SEQ ID NOs: 36, 49, 55, and 58;

in progeny plants resulting from the cross of step (a) wherein the evaluation is made using a method selected from the group consisting of: RFLP analysis, SNP analysis, and PCR-based analysis.

In a ninth embodiment, this invention concerns a method of molecular breeding to obtain altered plant nitrate transport, comprising:

(a) crossing two plant varieties; and (b) evaluating genetic variations with respect to:

(i) a nucleic acid sequence selected from the group consisting of SEQ ID NOs:35, 48, 54, and 57; or (ii) a nucleic acid sequence encoding a polypeptide selected from the group consisting of SEQ ID NOs: 36, 49, 55, and 58;

in progeny plants resulting from the cross of step (a) wherein the evaluation is made using a method selected from the group consisting of: RFLP analysis, SNP analysis, and PCR-based analysis.

In a tenth embodiment, this invention concerns a method of altering the level of expression of a high affinity nitrate transporter polypeptide in a host cell comprising: (a) transforming a host cell with a recombinant DNA construct comprising:

(b) a nucleotide sequence encoding a high affinity nitrate transporter polypeptide, wherein the polypeptide has an amino acid sequence of at least 80% sequence identity, based on the Clustal V method of alignment, when compared to one of SEQ ID NO: 36 or 49 and the polypeptide alters nitrate transport, the complement thereof or at least two motifs corresponding substantially to any of the amino acid sequences set forth in SEQ ID NOs: 50, 51 and 52, wherein said motif is a substantially conserved subsequence operably linked to at least one regulatory sequence; and (c) growing the transformed host cell under conditions that are suitable for expression of the recombinant DNA construct wherein expression of the recombinant DNA construct results in production of altered levels of the polypeptide required for nitrate transport in the transformed host cell.

In an eleventh embodiment, this invention concerns a corn plant, comprising a first DNA construct comprising an isolated HAT polypeptide, operably linked to at least one regulatory sequence; and at least one additional recombinant DNA construct comprising an isolated polynucleotide, operably linked to at least one regulatory sequence, encoding a polypeptide selected from the group consisting of a NAR2.

An additional embodiment of this invention concerns a method for altering plant nitrogen transport, comprising:

(a) transforming a plant with a recombinant DNA construct comprising:

i) a first recombinant DNA construct comprising an isolated polynucleotide encoding a HAT polypeptide, operably linked to at least one regulatory sequence; and ii) at least one additional recombinant DNA construct comprising an isolated polynucleotide, operably linked to at least one regulatory sequence, encoding a polypeptide selected from the group consisting of a NAR;

(b) growing the transformed plant of (a) under conditions suitable for the expression of the recombinant DNA construct; and (c) selecting those transformed plants having altered nitrate transport.

Further embodiments of this invention include shuffled HAT variants with improved kinetic parameters, recombinant DNA constructs comprising the nucleotide sequences encoding these variants and plants and transformed cells comprising in their genome these recombinant DNA construct. Also included in this invention are corn plants comprising a first recombinant DNA construct comprising a nucleotide sequence encoding a shuffled HAT variant, operably linked to at least one regulatory sequence and at least one additional recombinant DNA construct comprising an isolated polynucleotide, operably linked to at least one regulatory sequence, encoding a polypeptide selected from the group consisting of a NAR.

Yet another embodiment of this invention sets forth a method for altering plant nitrogen transport, comprising: a) transforming a plant with a recombinant DNA construct comprising a first recombinant DNA construct comprising a nucleotide sequence encoding a shuffled HAT variant, operably linked to at least one regulatory sequence and at least one additional recombinant DNA construct comprising an isolated polynucleotide, operably linked to at least one regulatory sequence, encoding a polypeptide selected from the group consisting of a NAR; and b) growing the transformed plant of (a) under conditions suitable for the expression of the recombinant DNA construct; and selecting those transformed plants having altered nitrate transport.

Biological Deposits

The following plasmid has been deposited with the American Type Culture Collection (ATCC), 10801 University Boulevard, Manassas, Va. 20110-2209, and bears the following identification, deposit designation, and date of deposit.

| Plasmid | Accession Number | Date of Deposit |
|---|---|---|
| PHP27621 | ATCC | Aug. 11, 2006 |

BRIEF DESCRIPTION OF THE SEQUENCE LISTINGS

The invention can be more fully understood from the following detailed description and the accompanying drawings and Sequence Listing, which form a part of this application.

Figure 1:
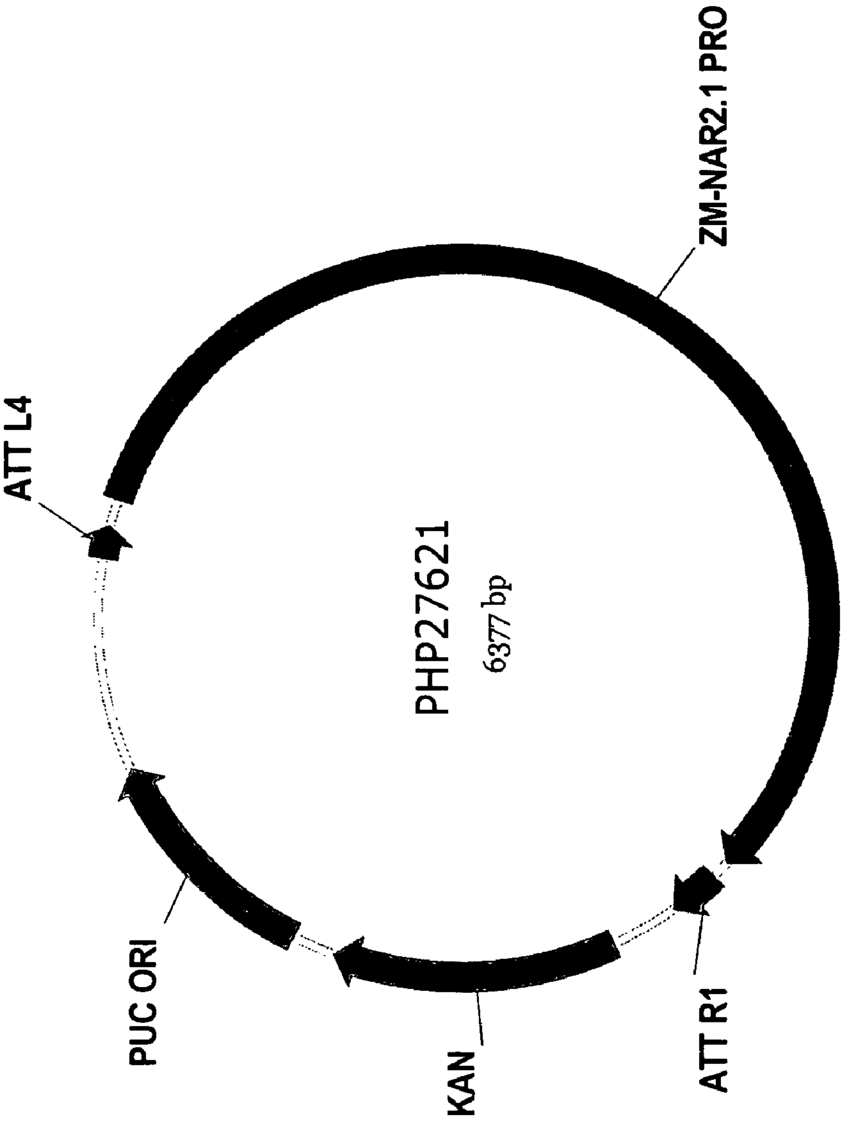
FIG. 1 is a schematic of vector PHP27621.

SEQ ID NO: 1 is the forward primer used in Example 3.

SEQ ID NO: 2 is the reverse primer used in Example 3.

SEQ ID NO: 3 is the T7 primer used in Example 3 for confirmatory BAC ends sequencing.

SEQ ID NO: 4 is the SP6 primer used in Example 3 for confirmatory BAC ends sequencing.

SEQ ID NO: 5 through 33 are the sequencing primers used to cover the region on BAC clone bacc.pk139.d24 containing the HAT4 gene.

SEQ ID NO: 34 represents the 3924 bp of the maize genomic sequence containing the ORF (Nucleotides 2015-3583 (Stop)) of the gene encoding the high affinity nitrate transporter (HAT4) isolated from BAC clone bacc.pk139.d24.

SEQ ID NO: 35 is 1569 bp of the nucleotide sequence of the ORF of SEQ ID NO: 34.

SEQ ID NO: 36 is the amino acid sequence encoded by nucleotides 2015-3580 of SEQ ID NO: 34.

SEQ ID NO: 37 is the 2014 bp, extending from Nucleotides 1-2014 of the putative promoter of the maize high affinity nitrate transporter genomic sequence shown in SEQ ID NO: 34.

SEQ ID NO: 38 is 1014 bp, extending from Nucleotide 1001-2014 of the putative promoter of the maize high affinity nitrate transporter genomic sequence shown in SEQ ID NO: 34.

SEQ ID NO: 39-42 are the forward and reverse primers used in Example 4.

SEQ ID NO: 43 is the T3 primer used in Example 4.

SEQ ID NO: 44 is the T7 primer used in Example 4.

SEQ ID NO: 45 represents the 5812 bp of the maize genomic sequence containing the ORF (Nucleotides 2264-3450 and 5087-5357 (Stop)) of the gene encoding a high affinity nitrate transporter (HAT7).

SEQ ID NO: 46 is the 2263 bp, extending from Nucleotides 1-2263 of the putative promoter of the maize high affinity nitrate transporter genomic sequence shown in SEQ ID NO: 45.

SEQ ID NO: 47 is the 1263 bp, extending from Nucleotides 1001-2263 of the putative promoter of the maize high affinity nitrate transporter genomic sequence shown in SEQ ID NO: 45.

SEQ ID NO: 48 is 1455 bp of the coding sequence, extending from Nucleotides 2264-3450 and 5087-5354 of SEQ ID NO: 45.

SEQ ID NO: 49: is the amino acid sequence encoded by SEQ ID NO: 48.

SEQ ID NO: 50 is a conserved sequence motif useful in identifying genes belonging to the high affinity nitrate transporter of genes.

SEQ ID NO: 51 is a conserved sequence motif useful in identifying genes belonging to the high affinity nitrate transporter of genes.

SEQ ID NO: 52 is a conserved sequence motif useful in identifying genes belonging to the high affinity nitrate transporter of genes.

SEQ ID NO: 53 is the 1561 bp of the sequence containing the ORF (nucleotides 757-1368 (Stop)) encoding a corn NAR2-type polypeptide (NAR2.1).

SEQ ID NO: 54 is the 612 bp of the coding sequence, extending from nucleotides 758-1369 (Stop) of SEQ ID NO: 53.

SEQ ID NO: 55 is the amino acid sequence encoded by nucleotides 758-1366 of SEQ ID NO: 54.

SEQ ID NO: 56 is the 756 bp, extending from Nucleotides 1-756 of the putative promoter of the sequence shown in SEQ ID NO: 53.

SEQ ID NO: 57 is the 594 bp of the ORF (nucleotides 1-594 (Stop)) encoding a NAR2-type polypeptide (NAR2.2).

SEQ ID NO: 58 is the amino acid sequence encoded by nucleotides 1-591 of the ORF of SEQ ID NO: 57.

SEQ ID NO: 59 is the NAR2.1 specific outer primer used in Example 6.

SEQ ID NO: 60 is the NAR2.1 specific inner primer used in Example 6.

SEQ ID NO: 61-64 are the sequencing primers used to sequence the NAR2.1 promoter upstream region.

SEQ ID NO: 65 shows an additional 2917 bp of the putative NAR2.1 promoter.

SEQ ID NO: 66 shows the 4498 bp of the complete NAR2.1 gene, including an intron extending from nucleotides 3655-3841.

SEQ ID NO: 67 is the 3506 bp, extending from Nucleotides 1-3506 of the putative promoter of the NAR2.1 genomic sequence shown in SEQ ID NO: 66.

SEQ ID NO: 68 is 1014 bp, extending from Nucleotide 1001-2014 of the putative promoter of the NAR2.1 genomic sequence shown in SEQ ID NO: 66.

SEQ ID NO: 69 is 1492 bp, extending from Nucleotide 2015-3506 of the putative promoter of the NAR2.1 genomic sequence shown in SEQ ID NO: 66.

SEQ ID NO: 70 is 3621 bp of the genomic fragment isolated in Example 14.

SEQ ID NO: 71 is 3236 bp of the putative Nar promoter from B73, extending from Nucleotides 1-3236 of SEQ ID NO: 70.

SEQ ID NO: 72 is 1000 bp of the putative Nar promoter from B73, extending from Nucleotides 1-1000 of SEQ ID NO: 70.

SEQ ID NO: 73 is 2236 bp of the putative Nar promoter from B73, extending from Nucleotides 1001-3236 of SEQ ID NO: 70.

SEQ ID NO: 74 is 1237 bp of the putative Nar promoter from B73, extending from Nucleotides 2000-3236 of SEQ ID NO: 70.

SEQ ID NO: 75 through 78 are the forward and reverse primers described in Example 14.

SEQ ID NO: 79-84 are the sequencing primers used to sequence the Nar promoter from B73 as described in Example 14.

SEQ ID NO: 85 is the sequence of vector pENTR-5' described in Example 14.

SEQ ID NO: 86 is the sequence of vector PHP27621 described in Example 16.

SEQ ID NO: 87 is the sequence of vector PHP27660 described in Example 17.

SEQ ID NO: 88 is the sequence of vector PHP27860 described in Example 17.

SEQ ID NO: 89 is 3324 bp of the putative Nar promoter from B73, comprising Nucleotides 1-1523 and 1821-3324 of SEQ ID NO: 70.

SEQ ID 90: is 500 bp of the putative Nar promoter from B73, extending from Nucleotides 2825-3324 of SEQ ID NO: 70.

SEQ ID NO:91: represents the 2025 bp of the maize sequence containing the ORF (Nucleotides 250-1812(Stop)) of the gene encoding the high affinity nitrate transporter (HAT5) isolated from clone cfp4n.pk008.p6:fis.

SEQ ID NO:92 is the amino acid sequence encoded by the ORF of SEQ ID NO: 91.

SEQ ID NO: 93 is the sequence of vector PHP27280 described in Example 20.

SEQ ID NO: 94 is the sequence of vector PHP27281 described in Example 20.

SEQ ID NO: 95 is the sequence of vector PHP27282 described in Example 20.

SEQ ID NO: 96 is the sequence of vector PHP27283 described in Example 20.

The Sequence Listing contains the one letter code for nucleotide sequence characters and the three letter codes for amino acids as defined in conformity with the IUPAC-IUBMB standards described in *Nucleic Acids Research* 13:3021-3030 (1985) and in the *Biochemical Journal* 219 (No. 2): 345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

The disclosure of each reference set forth herein is incorporated herein by reference in its entirety.

The term "NAR" refers to nitrate assimilation related genes. These type of genes and the NAR polypeptides encoded by them are a component of the high affinity nitrate uptake system in plants.

The term "HAT" is used interchangeably with high affinity nitrate transporter.

As used herein, an "isolated nucleic acid fragment" is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the portion or subsequence encodes an active enzyme or functional protein (for example, the portion or subsequence may be a portion of coding and/or non-coding regions and need not encode an active enzyme or functional protein. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme or functional protein, in the appropriate orientation relative to a plant promoter sequence.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins and Sharp (1989) *CABIOS.* 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature. A "foreign" gene refers to a gene not normally found in the host organism, but that is introduced into the host organism by gene transfer. Foreign genes can comprise native genes inserted into a non-native organism, or recombinant DNA constructs. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters, which cause an isolated nucleic acid fragment to be expressed in most cell types, at most times are commonly referred to as "constitutive promoters". New promoters of various types useful in plant cells are constantly being discovered; numerous examples may be found in the compilation by Okamuro and Goldberg, (1989) *Biochemistry of Plants* 15:1-82.

It is further recognized that since in most cases the exact boundaries of regulatory sequences have not been completely defined, DNA fragments of some variation may have identical promoter activity. As used herein, "substantially similar and functionally equivalent subfragment of a promoter" refers to a portion or subsequence of a promoter sequence which is capable of controlling the expression of a coding sequence or functional RNA.

Specific examples of promoters that may be useful in expressing the nucleic acid fragments of the invention include, but are not limited to, the promoters disclosed in this application (SEQ ID NOs: 37, 38, 46, 47, 56, 65, 67, 68, 69, 70, 71, 72, 73, 74, 89 or 90).

An "intron" is an intervening sequence in a gene that does not encode a portion of the protein sequence. Thus, such sequences are transcribed into RNA but are then excised and are not translated. The term is also used for the excised RNA sequences.

An "exon" is a portion of the sequence of a gene that is transcribed and is found in the mature messenger RNA derived from the gene, but is not necessarily a part of the sequence that encodes the final gene product.

The term "deduced nucleotide sequence" refers to a DNA sequence after removal of intervening sequences, based on homology to other DNA sequences encoding the same protein.

The term "deduced amino acid sequence" refers to a polypeptide sequence derived from a DNA sequence after removal of intervening sequences, based on homology to other proteins encoded by DNA sequences encoding the same protein.

The term "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107, 065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of an isolated nucleic acid fragment involves transcription of the isolated nucleic acid fragment and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (*London*) 327:70-73; U.S. Pat. No. 4,945,050), or an Agrobacterium-mediated method using an appropriate Ti plasmid containing the transgene (Ishida Y. et al., 1996, Nature Biotech. 14:745-750). The term "transformation and "transformed" as used herein refer to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al, *Cold Spring Harbor Symp. Quant. Biol.* 51:263-273 (1986); Erlich et al, European Patent Application 50,424; European Patent Application 84,796; European Patent Application 258,017, European Patent Application 237,362; Mullis, European Patent Application 201,184, Mullis et al U.S. Pat. No. 4,683,202; Erlich, U.S. Pat. No. 4,582,788; and Saiki et al, U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747-1757).

In one aspect, this invention includes an isolated polynucleotide comprising a nucleotide sequence encoding a polypeptide required for high affinity nitrate transport, wherein the polypeptide has an amino acid sequence of at least 80%, 85%, 90%, 95%, or 99% sequence identity, based on the Clustal V method of alignment, when compared to one of SEQ ID NO: 36 or 49. The polypeptide may also comprise SEQ ID NO: 36 or 49, and the nucleotide sequence may comprise SEQ ID NO: 35 or 48.

Also included in the present invention is a complement of any of the foregoing nucleotide sequences, wherein the complement and the nucleotide sequence consist of the same number of nucleotides and are 100% complementary.

In another aspect, this invention includes isolated polynucleotides as described herein (or complements), wherein the nucleotide sequence comprises at least two, three, four, or five motifs selected from group consisting of SEQ ID NOs: 50, 51 and 52, wherein said motif is a substantially conserved subsequence.

"Motifs" or "subsequences" refer to short regions of conserved sequences of nucleic acids or amino acids that comprise part of a longer sequence. For example, it is expected that such conserved subsequences (for example SEQ ID NOs: 50, 51 and 52) would be important for function, and could be used to identify new homologues of high affinity nitrate transporter-homologues in plants. It is expected that some or all of the elements may be found in a high affinity nitrate transporter-homologue. Also, it is expected that at least one or two of the conserved amino acids in any given motif may differ in a true high affinity nitrate transporter-homologue.

In another aspect, a polynucleotide of this invention or a functionally equivalent subfragment thereof is useful in antisense inhibition or cosuppression of expression of nucleic acid sequences encoding proteins required for high affinity nitrate transport, most preferably in antisense inhibition or cosuppression of an endogenous high affinity nitrate transporter or heterologous high affinity nitrate transporter gene.

Protocols for antisense inhibition or co-suppression are well known to those skilled in the art and are described above.

In still a further aspect, this invention includes an isolated nucleic acid fragment comprising (a) a promoter consisting essentially of SEQ ID NO: 37, 38, 46, 47, 56, 65, 67, 68, 69, 70, 71, 72, 73, 74, 89 or 90 or (b) a substantially similar and functionally equivalent subfragment of said promoter.

Also of interest are recombinant DNA constructs comprising any of the above-identified isolated nucleic acid fragments or isolated polynucleotides or complements thereof or parts of such fragments or complements, operably linked to at least one regulatory sequence.

Plants, plant tissue or plant cells comprising such recombinant DNA constructs in their genome are also within the scope of this invention. Transformation methods are well known to those skilled in the art and are described above. Any plant, dicot or monocot can be transformed with such recombinant DNA constructs.

Examples of monocots include, but are not limited to, corn, wheat, rice, sorghum, millet, barley, palm, lily, *Alstroemeria*, rye, and oat. Examples of dicots include, but are not limited to, soybean, rape, sunflower, canola, grape, guayule, columbine, cotton, tobacco, peas, beans, flax, safflower, alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue. The plant tissue may be in plant or in organ, tissue or cell culture.

In another aspect, this invention includes a method of altering plant nitrate transport, comprising:

(a) transforming a plant with a recombinant DNA construct comprising i) A recombinant DNA construct comprising an isolated polynucleotide encoding a HAT polypeptide, operably linked to at least one regulatory sequence; and ii) at least one additional recombinant DNA construct comprising an isolated polynucleotide encoding a NAR polypeptide, operably linked to at least one regulatory sequence.

(b) growing the transformed plant of (a) under conditions suitable for the expression of the recombinant DNA construct; and selecting those transformed plants having altered nitrate transport.

As used herein, altering plant nitrate transport may result in increased or decreased changes.

The regeneration, development, and cultivation of plants from single plant protoplast transformants or from various transformed explants is well known in the art (Weissbach and Weissbach, In: Methods for Plant Molecular Biology, (Eds.), Academic Press, Inc. San Diego, Calif., (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous isolated nucleic acid fragment that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue.

The particular method of regeneration will depend on the starting plant tissue and the particular plant species to be regenerated.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *BiolTechnology* 6:923 (1988), Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258, (1995)).

Transformation of monocotyledons using electroporation, particle bombardment, and *Agrobacterium* have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603-618 (1990), Fromm et al., *BiolTechnology* 8:833 (1990), Koziel et al., *BiolTechnology* 11: 194, (1993), Armstrong et al., *Crop Science* 35:550-557 (1995)); oat (Somers et al., *BiolTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135-1148, (1996); Abedinia et al., *Aust. J. Plant Physiol.* 24:133-141 (1997); Zhang and Wu, *Theor. Appl. Genet.* 76:835 (1988); Zhang et al. *Plant Cell Rep.* 7:379, (1988); Battraw and Hall, *Plant Sci.* 86:191-202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454-457 (1988); Marcotte et al., *Plant Cell* 1:523-532 (1989); McCarty et al., *Cell* 66:895-905 (1991); Hattori et al., *Genes Dev.* 6:609-618 (1992); Goff et al., *EMBO J.* 9:2517-2522 (1990)).

Transient expression systems may be used to functionally dissect isolated nucleic acid fragment constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

In a still further aspect, this invention includes a method to isolate nucleic acid fragments encoding polypeptides associated with altering plant nitrate transport, which comprises:

(a) comparing SEQ ID NO: 36 or 49 with other polypeptide sequences associated with altering plant nitrate transport;

(b) identifying conserved sequences of 4 or more amino acids obtained in step (a);

(c) making region-specific nucleotide probe(s) or oligomer(s) based on the conserved sequences identified in step (b); and (d) using the nucleotide probe(s) or oligomer(s) of step (c) to isolate sequences associated with altering plant nitrate transport by sequence dependent protocols.

Examples of conserved sequence elements that would be useful in identifying other plant sequences associated with altering plant nitrate transport can be found in the group comprising, but not limited to, the nucleotides encoding the polypeptides of SEQ ID NOs: 50, 51, and 52.

In another aspect, this invention also includes a method of mapping genetic variations related to altering plant nitrate transport comprising:

(a) crossing two plant varieties; and (b) evaluating genetic variations with respect to:

(i) a nucleic acid sequence selected from the group consisting of SEQ ID NO: 35 and 48; or (ii) a nucleic acid sequence encoding a polypeptide selected from the group consisting of SEQ ID NOs: 36 and 49 in progeny plants resulting from the cross of step (a) wherein the evaluation is made using a method selected from the group consisting of: RFLP analysis, SNP analysis, and PCR-based analysis.

In another embodiment, this invention includes a method of molecular breeding to obtain altered plant nitrate transport:

(a) crossing two plant varieties; and (b) evaluating genetic variations with respect to:

(i) a nucleic acid sequence selected from the group consisting of SEQ ID NOs: 35 and 48; or (ii) a nucleic acid sequence encoding a polypeptide selected from the group consisting of SEQ ID NOs: 36 and 49 in progeny plants resulting from the cross of step (a) wherein the evaluation is made using a method selected from the group consisting of: RFLP analysis, SNP analysis, and PCR-based analysis.

The terms "mapping genetic variation" or "mapping genetic variability" are used interchangeably and define the process of identifying changes in DNA sequence, whether from natural or induced causes, within a genetic region that differentiates between different plant lines, cultivars, varieties, families, or species. The genetic variability at a particular locus (gene) due to even minor base changes can alter the pattern of restriction enzyme digestion fragments that can be generated. Pathogenic alterations to the genotype can be due to deletions or insertions within the gene being analyzed or even single nucleotide substitutions that can create or delete a restriction enzyme recognition site. RFLP (restriction fragment length polymorphisms) analysis takes advantage of this and utilizes Southern blotting with a probe corresponding to the isolated nucleic acid fragment of interest.

Thus, if a polymorphism (i.e., a commonly occurring variation in a gene or segment of DNA; also, the existence of several forms of a gene (alleles) in the same species) creates or destroys a restriction endonuclease cleavage site, or if it results in the loss or insertion of DNA (e.g., a variable nucleotide tandem repeat (VNTR) polymorphism), it will alter the size or profile of the DNA fragments that are generated by digestion with that restriction endonuclease. As such, individuals that possess a variant sequence can be distinguished from those having the original sequence by restriction fragment analysis. Polymorphisms that can be identified in this manner are termed RFLPs. RFLPs have been widely used in human and plant genetic analyses (Glassberg, UK Patent Application 2135774; Skolnick et al, Cytogen. *Cell Genet.* 32:58-67 (1982); Botstein et al, *Ann. J. Hum. Genet.* 32:314-331 (1980); Fischer et al (PCT Application WO 90/13668; Uhlen, PCT Application WO 90/11369).

A central attribute of "single nucleotide polymorphisms" or "SNPs" is that the site of the polymorphism is at a single nucleotide. SNPs have certain reported advantages over RFLPs or VNTRs. First, SNPs are more stable than other classes of polymorphisms. Their spontaneous mutation rate is approximately $10^{-9}$ (Kornberg, DNA Replication, W.H. Freeman & Co., San Francisco, 1980), approximately, 1,000 times less frequent than VNTRs (U.S. Pat. No. 5,679,524). Second, SNPs occur at greater frequency, and with greater uniformity than RFLPs and VNTRs. As SNPs result from sequence variation, sequencing random genomic or cDNA molecules can identify new polymorphisms. SNPs can also result from deletions, point mutations and insertions. Any single base alteration, whatever the cause, can be a SNP. The greater frequency of SNPs means that they can be more readily identified than the other classes of polymorphisms.

SNPs can be characterized using any of a variety of methods. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism or by other biochemical interpretation. SNPs can be sequenced by a number of methods. Two basic methods may be used for DNA sequencing, the chain termination method of Sanger et al, *Proc. Natl. Acad. Sci.* (U.S.A.) 74:5463-5467 (1977), and the chemical degradation method of Maxam and Gilbert, *Proc. Natl. Acad. Sci.* (U.S.A.) 74: 560-564 (1977).

Furthermore, single point mutations can be detected by modified PCR techniques such as the ligase chain reaction ("LCR") and PCR-single strand conformational polymorphisms ("PCR-SSCP") analysis. The PCR technique can also be used to identify the level of expression of genes in extremely small samples of material, e.g., tissues or cells from a body. The technique is termed reverse transcription-PCR ("RT-PCR").

The term "molecular breeding" defines the process of tracking molecular markers during the breeding process. It is common for the molecular markers to be linked to phenotypic traits that are desirable. By following the segregation of the molecular marker or genetic trait, instead of scoring for a phenotype, the breeding process can be accelerated by growing fewer plants and eliminating assaying or visual inspection for phenotypic variation. The molecular markers useful in this process include, but are not limited to, any marker useful in identifying mapable genetic variations previously mentioned, as well as any closely linked genes that display synteny across plant species. The term "synteny" refers to the conservation of gene placement/order on chromosomes between different organisms. This means that two or more genetic loci, that may or may not be closely linked, are found on the same chromosome among different species. Another term for synteny is "genome colinearity".

The nucleic acid fragments of the instant invention may be used to create transgenic plants in which the disclosed polypeptides are present at higher or lower levels than normal or in cell types or developmental stages in which they are not normally found. This would have the effect of altering the level of nitrogen transport and accumulation in those cells. Nitrogen deficiency in plants results in stunted growth, and many times in slender and often woody stems. In many plants the first signal of nitrogen deficiency is chlorosis (yellowing of the leaves).

Overexpression of the proteins of the instant invention may be accomplished by first making a recombinant DNA construct in which the coding region is operably linked to a promoter capable of directing expression of a gene in the desired tissues at the desired stage of development. For reasons of convenience, the recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant recombinant DNA construct can then be made. The choice of plasmid vector is dependent upon the method that will be used to transform host plants. The skilled artisan is well aware of the genetic elements that must be present on the plasmid vector in order to successfully transform, select and propagate host cells containing the recombinant DNA construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct described above may be further supplemented by altering the coding sequence to encode the instant polypeptides with appropriate intracellular targeting sequences such as transit sequences (Keegstra (1989) *Cell* 56:247-253), signal sequences or sequences encoding endoplasmic reticulum localization (Chrispeels (1991) *Ann. Rev. Plant Phys. Plant Mol. Biol.* 42:21-53), or nuclear localization signals (Raikhel (1992) *Plant Phys.* 100:1627-1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded ammonium transporter. An example of a vector for high level expression of the instant polypeptides in a bacterial host is provided (Example 7).

Additionally, the instant polypeptides can be used as targets to facilitate design and/or identification of inhibitors of those enzymes that may be useful as herbicides. This is desirable because the polypeptides described herein catalyze various steps in nitrogen uptake. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174-181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314-331).

The production and use of plant gene-derived probes for use in genetic mapping is described in Bernatzky and Tanksley (1986) *Plant Mol. Biol. Reporter* 4(1):37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319-346, and references cited therein).

In another embodiment, nucleic acid probes derived from the instant nucleic acid sequences may be used in direct fluorescence in situ hybridization (FISH) mapping (Trask (1991) *Trends Genet.* 7:149-154). Although current methods of FISH mapping favor use of large clones (several to several hundred KB; see Laan et al. (1995) *Genome Research* 5:13-20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95-96), polymorphism of PCR-amplified fragments (CAPS; Sheffield et al. (1993) *Genomics* 16:325-332), allele-specific ligation (Landegren et al. (1988) *Science* 241:1077-1080), nucleotide extension reactions (Sokolov (1990) *Nucleic Acid Res.* 18:3671), Radiation Hybrid Mapping (Walter et al. (1997) *Nature Genetics* 7:22-28) and Happy Mapping (Dear and Cook (1989) *Nucleic Acid Res.* 17:6795-6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402-9406; Koes et al. (1995) *Proc. Natl. Acad. Sci USA* 92:8149-8153; Bensen et al. (1995) *Plant Cell* 7:75-84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

The function of the high affinity nitrate transporters and polypeptides required for high affinity nitrate transport can be confirmed using the TUSC Mutant population. The Trait Utility System for Corn (TUSC) is a method that employs genetic and molecular techniques to facilitate the study of gene function in maize. Studying gene function implies that the gene's sequence is already known, thus the method works in reverse: from sequence to phenotype. This kind of application is referred to as "reverse genetics", which contrasts with "forward" methods (such as transposon tagging) that are designed to identify and isolate the gene(s) responsible for a particular trait (phenotype).

Pioneer Hi-Bred International, Inc., has its proprietary collection of maize genomic DNA from approximately 42,000 individual $F_1$ plants (Reverse genetics for maize; Meeley, R and Briggs, S, 1995, Maize Genet. Coop. Newslett. 69:67, 82).

The genome of each of these individuals contains multiple copies of the transposable element family, Mutator (Mu). The Mu family is highly mutagenic; in the presence of the active element Mu-DR, these elements transpose throughout the genome, inserting into genic regions, and often disrupting gene function. By collecting genomic DNA from a large number of individuals (42,000), Pioneer has assembled a library of the mutagenized maize genome. Mu insertion events are predominately heterozygous so; given the recessive nature of most insertional mutations, the $F_1$ plants appear wild-type. Each of the plants was selfed to produce $F_2$ seed, which was collected. In generating the $F_2$ progeny, insertional mutations segregate in a Mendelian fashion and therefore are useful for investigating a mutant allele's effect on the phenotype. The TUSC system has been successfully used by a number of laboratories to identify the function of a variety of genes (Cloning and characterization of the maize An1 gene, Bensen, R J et al., 1995, Plant Cell 7:75-84; Diversification of C-function activity in maize flower development, Mena, M et al., 1996, Science 274:1537-1540; Analysis of a chemical plant defense mechanism in grasses, Frey, M et al., 1997, Science 277:696-699; The control of maize spikelet meristem fate by the APETALA2-like gene Indeterminate spikelet 1, Chuck, G, Meeley, R B, and Hake, S, 1998, Genes & Development 12:1145-1154; A SecY homologue is required for the elaboration of the chloroplast thylakoid membrane and for normal chloroplast gene expression, Roy, L M and Barkan, A., 1998, J. Cell Biol. 141:1-11).

Polynucleotide sequences produced by diversity generation methods or recursive sequence recombination ("RSR") methods (e.g., DNA shuffling) are a feature of the invention. Mutation and recombination methods using the nucleic acids described herein are a feature of the invention. For example, one method of the invention includes recursively recombining one or more nucleotide sequences of the invention as described above and below with one or more additional nucleotides. The recombining steps are optionally performed in vivo, ex vivo, in silico or in vitro. This diversity generation or recursive sequence recombination produces at least one library of recombinant modified HAT polynucleotides. Polypeptides encoded by members of this library are included in the invention.

Descriptions of a variety of diversity generating procedures, including multigene shuffling and methods for generating modified nucleic acid sequences encoding multiple enzymatic domains, are found the following publications and the references cited therein: Soong, N. et al. (2000) "Molecular breeding of viruses" Nat Genet 25(4):436-39; Stemmer, et al. (1999) "Molecular breeding of viruses for targeting and other clinical properties" Tumor Targeting 4:1-4; Ness et al. (1999) "DNA Shuffling of subgenomic sequences of subtilisin" Nature Biotechnology 17:893-896; Chang et al. (1999) "Evolution of a cytokine using DNA family shuffling" Nature Biotechnology 17:793-797; Minshull and Stemmer (1999) "Protein evolution by molecular breeding" Current Opinion in Chemical Biology 3:284-290; Christians et al. (1999) "Directed evolution of thymidine kinase for AZT phosphorylation using DNA family shuffling" Nature Biotechnology 17:259-264; Crameri et al. (1998) "DNA shuffling of a family of genes from diverse species accelerates directed evolution" Nature 391:288-291; Crameri et al. (1997) "Molecular evolution of an arsenate detoxification pathway by DNA shuffling," Nature Biotechnology 15:436-438; Zhang et al. (1997) "Directed evolution of an effective fucosidase from a galactosidase by DNA shuffling and screening" Proc. Natl. Acad. Sci. USA 94:4504-4509; Patten et al. (1997) "Applications of DNA Shuffling to Pharmaceuticals and Vaccines" Current Opinion in Biotechnology 8:724-733; Crameri et al. (1996) "Construction and evolution of antibody-phage libraries by DNA shuffling" Nature Medicine 2:100-103; Crameri et al. (1996) "Improved green fluorescent protein by molecular evolution using DNA shuffling" Nature Biotechnology 14:315-319; Gates et al. (1996) "Affinity selective isolation of ligands from peptide libraries through display on a lac repressor 'headpiece dimer'" Journal of Molecular Biology 255: 373-386; Stemmer (1996) "Sexual PCR and Assembly PCR" In: The Encyclopedia of Molecular Biology. VCH Publishers, New York. pp. 447-457; Crameri and Stemmer (1995) "Combinatorial multiple cassette mutagenesis creates all the permutations of mutant and wildtype cassettes" BioTechniques 18:194-195; Stemmer et al., (1995) "Single-step assembly of a gene and entire plasmid from large numbers of oligodeoxyribonucleotides" Gene, 164:49-53; Stemmer (1995) "The Evolution of Molecular Computation" Science 270: 1510; Stemmer (1995) "Searching Sequence Space" Bio/Technology 13:549-553; Stemmer (1994) "Rapid evolution of a protein in vitro by DNA shuffling" Nature 370:389-391; and Stemmer (1994) "DNA shuffling by random fragmentation and reassembly: In vitro recombination for molecular evolution." Proc. Natl. Acad. Sci. USA 91:10747-10751. Additional details regarding various diversity generating methods can be found in the following U.S. patents, PCT publications, and EPO publications: U.S. Pat. No. 5,605,793 to Stemmer (Feb. 25, 1997), "Methods for In Vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in Vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in Vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

Certain U.S. applications provide additional details regarding various diversity generating methods, including "SHUFFLING OF CODON ALTERED GENES" by Patten et al. filed Sep. 28, 1999, (U.S. Ser. No. 09/407,800); "EVOLUTION OF WHOLE CELLS AND ORGANISMS BY RECURSIVE SEQUENCE RECOMBINATION", by del Cardayre et al. filed Jul. 15, 1998 (U.S. Ser. No. 09/166,188), and Jul. 15, 1999 (U.S. Pat. No. 6,379,964); "OLIGONUCLEOTIDE MEDIATED NUCLEIC ACID RECOMBINATION" by Crameri et al., filed Sep. 28, 1999 (U.S. Pat. No. 6,376,246); "OLIGONUCLEOTIDE MEDIATED NUCLEIC ACID RECOMBINATION" by Crameri et al., filed Jan. 18, 2000 (WO 00/42561); "USE OF CODON-BASED OLIGONUCLEOTIDE SYNTHESIS FOR SYNTHETIC SHUFFLING" by Welch et al., filed Sep. 28, 1999 (U.S. Pat. No. 6,436,675); "METHODS FOR MAKING CHARACTER STRINGS, POLYNUCLEOTIDES & POLYPEPTIDES HAVING DESIRED CHARACTERISTICS" by Selifonov et al., filed Jan. 18, 2000, (WO 00/42560); "METHODS FOR MAKING CHARACTER STRINGS, POLYNUCLEOTIDES & POLYPEPTIDES HAVING DESIRED CHARACTERISTICS" by Selifonov et al., filed Jul. 18, 2000 (U.S. Ser. No. 09/618,579); "METHODS OF POPULATING DATA STRUCTURES FOR USE IN EVOLUTIONARY SIMULATIONS" by Selifonov and Stemmer (WO 00/42559), filed Jan. 18, 2000; and "SINGLE-STRANDED NUCLEIC ACID TEMPLATE-MEDIATED RECOMBINATION AND NUCLEIC ACID FRAGMENT ISOLATION" by Affholter (U.S. Ser. No. 60/186,482, filed Mar. 2, 2000). Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561 by Crameri et al., "Oligonucleotide Mediated Nucleic Acid Recombination;" WO 01/23401 by Welch et al., "Use of Codon-Varied Oligonucleotide Synthesis for Synthetic Shuffling;" WO 00/42560 by Selifonov et al., "Methods for Making Character Strings, Polynucleotides and Polypeptides Having Desired Characteristics;" and WO 00/42559 by Selifonov and Stemmer "Methods of Populating Data Structures for Use in Evolutionary Simulations."

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids, which correspond to the recombined sequences, e.g., in concert with oligonucleotide synthesis gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in WO 00/42560 by Selifonov et al., "Methods for Making Character Strings, Polynucleotides and Polypeptides Having Desired Characteristics" and WO 00/42559 by Selifonov and Stemmer "Methods of Populating Data Structures for Use in Evolutionary Simulations." Extensive details regarding in silico recombination methods are found in these applications. This methodology is generally applicable to the present invention in providing for recombination of nucleic acid sequences and/or gene fusion constructs encoding proteins involved in various metabolic pathways (such as, for example, carotenoid biosynthetic pathways, ectoine biosynthetic pathways, polyhydroxyalkanoate biosynthetic pathways, aromatic polyketide biosynthetic pathways, and the like) in silico and/or the generation of corresponding nucleic acids or proteins.

Many of the above-described methodologies for generating modified polynucleotides generate a large number of diverse variants of a parental sequence or sequences. In some preferred embodiments of the invention, the modification technique (e.g., some form of shuffling) is used to generate a library of variants that is then screened for a modified polynucleotide or pool of modified polynucleotides encoding some desired functional attribute, e.g., improved HAT activity. Exemplary enzymatic activities that can be screened for include, but are not limited to, catalytic rates (conventionally characterized in terms of kinetic constants such as $k_{cat}$ and $K_M$), substrate specificity, and susceptibility to activation or inhibition by substrate, product or other molecules (e.g., inhibitors or activators) and the maximum velocity of an enzymatic reaction when the binding site is saturated with substrate (Vmax).

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn tissues were prepared. The characteristics of the libraries are described in Table 1.

cDNA libraries may be prepared by any one of many available methods. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651-1656). The resulting ESTs are analyzed using a Perkin Elmer Model 377 fluorescent sequencer.

TABLE 1 cDNA Libraries and clones containing NAR2-like sequences from Corn

| Library | Tissue | Clone |
|---|---|---|
| Cnr1c | Corn (*Zea mays*). Plants were Nitrogen starved until all seed reserves were depleted of a Nitrogen source. Plants were induced with addition of Nitrogen, then samples were collected at 30 min-1 hr and 2 hr after Nitrogen. | cnr1c.pk003.m9.f:fis |
| Cbn2 | Corn (*Zea mays* L.) developing kernel two days after pollination | cbn2.pk0042.g4:fis |

Example 2

Identification of cDNA Clones cDNA clones encoding components associated with nitrate transport were identified by conducting BLAST (Basic Local Alignment Search Tool; Altschul et al. (1993) *J. Mol. Biol.* 215:403-410;) and are shown in Table 1.

cDNA clones encoding transporters or components associated with nitrate transport can be identified by conducting BLAST (Basic Local Alignment Search Tool; Altschul et al. (1993) *J. Mol. Biol.* 215:403-410;) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained can be analyzed for similarity to all publicly available DNA sequences contained in the "nr" database using the BLASTN algorithm provided by the National Center for Biotechnology Information (NCBI). The DNA sequences can be translated in all reading frames and compared for similarity to all publicly available protein sequences contained in the "nr" database using the BLASTX algorithm (Gish and States (1993) *Nature Genetics* 3:266-272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Identification and Sequencing of Corn High Affinity Nitrate Transporters (HAT4 and HAT5)

In order to identify homologs of HATs, a public HAT gene (Genbank accession number AY129953), was used to screen Iowa State University MAGI version 2.31 maize genome assembly. A partial clone, MAGI 17514 that showed 85% identity at the nucleotide level and appeared to be a previously unidentified HAT was identified using Blast in the ISU MAGI assembly. This sequence was used to screen the Genbank GSS dataset and some additional homologs of the MAGI sequence were identified; these added about 0.5 kb to the sequence. The GSS dataset consists of sequences set forth in general identification numbers: 33941728, 34245424, 32105143, 34245411, 34082540 and 33992813. The translation of the assembly covered about one half of the gene, at the 3' end. It completely lacked the 5' half of the gene.

In order to isolate the full length HAT4 sequence, BAC clones from two BAC libraries derived from the Maize B73 inbred line were screened using PCR. The libraries had previously been constructed by partial digestion of genomic DNA and inserted in the BamHI and EcoRI sites of the PCUGI (Tomkins, J. P., et al. 2002. Construction and characterization of a deep-coverage bacterial artificial chromosome library for maize. Crop Science 42:928-933) and pTARBAC (pTARBAC2.1 library, Osoegawa, K., et al, Construction Of New Maize, Bovine, Equine And Zebrafish Bac Libraries. Plant And Animal Genome Conference Proceedings. 2001). To facilitate a PCR-based screening, a set of 36 four-dimensional superpools was requested from Amplicon Express (Amplicon Express, 1610NE Eastgate Blvd Pullman, Wash. 99163). Each superpool was derived after the independent growth, isolation and pooling of 4608 clones, more than 165,000 arrayed BAC clones in total. Superpools were subject to PCR reactions, followed by fragment plus-minus determination in agarose gel electrophoresis. PCR primers were designed to amplify a 495-bp fragment located 289 bp downstream the stop codon of a HAT homolog located at the Tigr assembly ID AZM4_32787, which is identical to the sequences assembled from the MAGI and GSS databases described above. PCR reactions were performed with 5 ng Template DNA in a 10-μL reaction that included 5 μL of Hotstar Taq Polymerase Mix (Qiagen) and 5 pmol of the forward and reverse primers (SEQ ID NO:1 and SEQ ID NO:2, respectively). Cycle conditions were an initial denaturation step at 95° C. for 15 minutes, followed by 35 cycles of 95° C. for 30 seconds, 60° C. for 30 seconds and 72° C. for 1 minute. A second round of PCR was performed in matrix plates consisting of lower-complexity combinatorial pools derived from clones represented in positive pools. This narrowed down the positives to particular clones. Two clones, bacc.pk139.d24 and bacc.pk142.b21, were identified and confirmed by PCR analysis. Clone bacc.pk139.d24 was used in subsequent work.

BAC DNA from clone bacc.pk139.d24 was isolated from overnight 250-ml 2×YT+cloramphenicol cultures using a modified alkaline lysis method. Cells were harvested by centrifugation and resuspended in 20 ml of 10-mM EDTA, then lysed by gently adding 40 ml of 0.2-N NaOH/1-% SDS and neutralized with 30 ml of cold 3-M potassium acetate (pH 4.8). Cell debris were removed by centrifugation at 4° C. 15 minutes at 15000×g, followed by filtration through Miracloth. DNA in supernatant was precipitated with 0.7 volumes of isopropanol and resuspended in 9 ml of 50-mM Tris/50-mM EDTA, mixed with 4.5 ml of 7.5-M potassium acetate, placed at −70° C., thawed and centrifuged for 20 minutes at 3500×g. The supernatant was decanted, precipitated with ethanol and resuspended in 0.7 ml of 50-mM Tris/50-mM EDTA. DNase-free RNase A was added to a final concentration of 150 μg/ml and incubated 1 hour at 37° C., followed by phenol:chloroform extraction and ethanol precipitation. Final DNA was resuspended in a total of 400 μl sterile nuclease-free water. DNA insert size, quantity and quality was assessed by Pulsed Field Gel Electrophoresis using a CHEF-Mapper III (Bio-Rad). For confirmatory BAC end sequencing, the T7 (SEQ ID NO:3) and SP6 (SEQ ID NO: 4) primers were used using sequencing conditions described below.

The general strategy to obtain double-strand, contiguous sequence information along the HAT4 gene was by walking from the known "start" sequence defined by the PCR identification primers, previously described. BAC bacc.pk139.d24 DNA was used as template. Sequencing was performed in a ABI3730 capillary sequencer according to manufacturer protocols. Sequencing reactions consisted of 2 μL of BigDye V3.1 Terminator mix (Applied Biosystems), 2 μL of dilution buffer (600 mM Tris HCl pH 9.0, 15 mM MgCl2), 20 pmol of primer, and approximately 1 μg of template DNA in a final reaction volume of 20 μL. Cycle conditions were an initial denaturation at 95° C. for 5 minutes, followed by 99 cycles of 95° C. for 30 seconds, 58° C. for 30 seconds and 64° C. for 4 minutes. Some hard-to-read regions had to be re-sequenced using special cycle and reaction conditions. Excess dye terminator was removed by ethanol precipitation. Trace evaluation, base calling and assembly was based on Phred/Phrap software (Ewing et al. (1998) Genome Res. 8:186-194; Ewing et al. (1998) Genome Res. 8:175-185). Consed (Gordon et al. (1998) Genome Res. 8:195-202) was used for assembly analysis. After every sequence walking step, primers were designed at the ends, avoiding regions of high homology to other genes and to DNA repeats. Homology search was performed using the BLAST program (Basic Local Alignment Search Tool; Altschul et al. (1993) J. Mol. Biol. 215:403-410) against gss, TIGR 4.0, nonredundant, EST, and protein databases (Altschul et al. 1990). Vector NTI was used for primer design and primers were synthesized commercially by MWG Biotech. Primers (SEQ ID NO: 5 through SEQ ID NO: 33) were designed, tested and used to cover region including the HAT gene. SEQ ID NO: 34 describes the genomic sequence containing the HAT 4 gene. SEQ ID NOs: 35 and 36 describe the coding nucleotide and amino acid sequence of the corn HAT4, respectively.

SEQ ID NOs: 37 and 38 show the 2014 bp and 1014 bp putative promoter sequences of the HAT4 gene.

The HAT-5 family was identified via blast homology to the public HATs. One 3' clone cco1n.pk072.i13 had homology to MAGI_56254, which appeared to represent the entire sequence. The TIGR assembly AZM4_2103 corresponded well to the MAGI clone. Databases containing nitrogen induced libraries were re-blasted using this clone and clone cfp4n.pk008.p6 was identified. This clone was sequenced and contains the complete HAT5 gene sequence (SEQ ID NO:91 and 92).

Example 4

Identification and Sequencing of an Additional Corn High Affinity Nitrate Transporter (HAT 7)

A public HAT gene (HAT1, Genbank accession number AY129953) was used to search with Blast, Genbank maize genomic survey sequences (GSS) and maize genomic assemblies (Iowa State University MAGI and Tigr), to try to identify paralogs of AY129953. Along with the HAT4 gene (Example 3) there were other more distant homologs, including MAGI_65216 which corresponded to AZM4_79242, which contained slightly more sequence information than MAGI_65216). Neither of these two clones contained a start Methionine. AN additional hit to AZM4_79246 exhibited similar percent identity when compared to AY129953. AZM4_79246 encoded a start Methionine at nucleotide 2264-2266 and approximately 110 amino acids of coding sequence. Further examination showed that these two assemblies shared clone mates, OGUKX93 and OGUCS47 from the Tigr methylation filtrated library. Therefore it was assumed that AZM4_79242 and AZM4_79246 encode the same gene but have no sequence overlap.

In order to retrieve the full length sequence, PCR was performed using two different forward and two different reverse primers (SEQ ID NOs: 39, 40 and 41, 42, receptively) with T3 (SEQ ID NO: 43) and T7 extensions (SEQ ID NO: 44 at the 5' and 3' end, respectively. HotStart PCR, with an annealing temperature of 58° C. was performed using DNA from eight maize inbred lines (B73, Co159, GT119, Mo17, T218, Oh43 and W23) as templates. All 32 PCR reaction products were run on a agarose 1×TBE gel, excised and cleaned up and sequenced on a 3100 ABI Capillary Sequencer using methods known to those of ordinary skill in the art. The sequences were aligned and the missing sequence information was retrieved. The complete nucleotide sequence of the HAT7 gene is shown in SEQ ID NO: 45. SEQ ID NOs: 46 and 47 describe the 2263 bp and 1263 bp putative promoter sequences of the HAT7 gene and SEQ ID NOs: 48 and 49 describe the coding nucleotide and amino acid sequence of the corn HAT7, respectively.

Example 5

Characterization of Polypeptides Encoding High Affinity Nitrate Transporter

The data in Table 2 represent a calculation of the percent identity of the amino acid sequences set forth in SEQ ID NOs: 36 and 49 and the *Oryza sativa* sequences (NCBI General Identifier Nos. 34913806 and 50904699).

TABLE 2

Percent Identity of Amino Acid Sequences Deduced From the Nucleotide Sequences of cDNA Clones Encoding Polypeptides Homologous to High Affinity Nitrate Transporter (HAT)

| | Percent Identity to | |
|---|---|---|
| SEQ ID NO. | 34913806 | 50904699 |
| 36 | 38.0 | 75.3 |
| 49 | 78.2 | 39.4 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode corn high affinity nitrogen transporters.

Example 6

Identification and Sequencing of Corn Nitrogen Transport Related Genes, (NAR2-1 & NAR2-2)

Examination of blast hits from the maize root library cnr1c, described in Example 1 and Table 2, showed a number of Nitrogen transport related genes. Blast hits were searched with keywords such as nitrate, nitrogen, and transporter. A few of these were homologous to NCBI Accession number: CAC36942, a putative component of high affinity nitrate transporter (NAR2 gene). A TblastN search of maize ESTs, using the sequence of CAC36942 as a query, produced a number of significant hits from different maize libraries. The most 5' clone was identified by aligning the full-length query and the blast hits. A clone from the cnr1c library (cnr1c.pk003.m9.f showed a methionine that was in the same region as the start methionine from CAC36942. This clone also showed an in frame stop codon upstream of the methionine. This clone was submitted for standard full insert sequencing (FIS) and contained the 971 bp of the NAR2.1, spanning nucleotides 591 through 1561 of SEQ ID NO: 53. SEQ ID NO: 53 shows the 1561 bp sequence of the NAR2.1 gene, which was assembled from the sequence information obtained from clone cnr1c.pk003.m9.f:fis and from Tigr sequence AZM4_81138. SEQ ID NOs: 54 and 55 show the coding nucleotide and amino acid sequence of the NAR2.1 gene, respectively. SEQ ID NO: 56 shows 756 bp of the putative promoter of the NAR2.1. Using CAC36942 as a query also showed a different NAR2 homolog, cbn2.pk0042.g4. This clone also had a start Methionine, but because of the quality of the EST sequence the homology to CAC36942 was short. A complete version (Tigr clone AZM4_1475) of this family member was identified by searching the Tigr maize genomic assembly using cbn2.pk0042.g4 as a query. SEQ ID NOs: 57 and 58 show the coding nucleotide and amino acid sequence of the NAR2.2 (Tigr clone AZM4_1475), receptively.

NAR2.1 Promoter Isolation

The sequence information on the NAR2.1 promoter was extended further upstream by performing Genome Walker™ DNA walking (BD BioSciences). This method employs PCR to facilitate the cloning of unknown genomic DNA sequences adjacent to a known sequence. First, pools of unknown genomic DNA were digested with different restriction enzymes that leave blunt ends. Each pool was ligated to adaptors to create Genome Walker" libraries. Eight different corn HG11 libraries were obtained. These libraries were digested with the following restriction enzymes: StuI, EcoRV, PmlI, PvuII, ScaI, DraI, SmaI, and PmeI.

Then two rounds of nested PCR amplification per library were performed. For the first round the outer adaptor primer (AP1, provided with kit) and the Nar2.1 specific outer primer (SEQ ID NO: 59) were used.

PCR was performed using the Advantage®-GC Genomic Polymerase Mix (BD Biosciences) in a 50 μL reaction containing 1 μL l library DNA, 0.5 μL each primer (10 μM), 4 μL dNTPs (2.5 mM), 2.2 μL Mg $(OAc)_2$, 10 μL I 5×GC Genomic PCR Reaction Buffer, 10 μL GC-Melt (5M), 20.8 μL $ddH_2O$, and 1 μL Advantage-GC Genomic Polymerase. The cycling conditions were as follows: 7 cycles of denaturation at 94° C. for 25 seconds and annealing/extension at 72° C. for 6 minutes followed by 32 cycles of denaturation at 94° C. for 25 seconds and annealing/extension at 67° C. for 6 minutes capped off by annealing/extension at 67° C. for 7 minutes.

The primary PCR product was then diluted 1:50 and 1 μL served as the template for the second round of PCR which used the same PCR set-up as the first round. The second round primers were the inner adaptor primer (AP2, provided with the kit) and the Nar2.1 specific inner primer (SEQ ID NO: 60). The cycling conditions for the second round were as follows: 5 cycles of denaturation at 94° C. for 25 seconds and annealing/extension at 72° C. for 6 minutes followed by 25 cycles of denaturation at 94 C for 25 seconds and annealing/extension at 67° C. for 6 minutes capped off by annealing/extension at 67° C. for 7 minutes.

A major PCR product (about 3 kb) was observed in the StuI library. This band was cut-out of the gel and purified using the Qiaquick Gel Extraction Kit (Qiagen) and ligated to a pGEM®-T Easy Vector (Promega). The 20 μL ligation reaction was as follows: 10 μL 2× Rapid Ligation Buffer, 1 μL pGEM®-T Easy Vector (50 ng), 1 μL T4 DNA Ligase (3 Weiss units/μL), and 8 μL insert DNA (13 ng/μL). The reaction was incubated at 4° C. overnight.

The ligation product was transformed into Max Efficiency DH10B (Invitrogen) competent cells. One μL of ligate was added to 20 μL of cells and put on ice for 30 minutes. The cells were heat shocked at 42° C. for 45 seconds and then placed again on ice for 2 minutes. The cells were added to 1 mL of SOC and placed on a shaker at 250 rpm for 1 hr at 37° C. Then, 100 μL of cells were plated onto LB media with Ampicillin, IPTG, and X-Gal to allow for blue/white selection. Only one white colony was obtained.

Plasmid DNA was purified using the Plasmid Mini Kit (Qiagen). The plasmid insert representing the NAR2 upstream promoter region was sequenced using standard primers (SP6 and T7) and custom primers (SEQ ID NOs: 61, 62, 63 and 64). SEQ ID NO: 65 shows the sequence of the additional 2917 bp putative NAR 2.1 promoter.

The sequence of the complete NAR2.1 gene is shown in SEQ ID NO: 66.

Example 7

Expression Pattern of Polypeptides of Instant Application

The expression pattern of high affinity nitrate transporters (HAT) and other polypeptides (NAR) required for high affinity nitrate transport was analyzed via Lynx MPSS Brenner et al (2000) *Proc Natl Acad Sci USA* 97:1665-70).

The expression patterns of NAR2.1 and HAT 1 genes are similar across more than 200 libraries as studied via Lynx MPSS (Brenner et al (2000) *Proc Natl Acad Sci USA* 97:1665-70). They are both expressed only in the cortical cylinder of the root tissue and are similarly induced by nitrate, indicating that the polypeptide products of these two genes form a functional complex for nitrate transport in maize roots.

Tissue-specific expression of NAR2.1 and HAT-1 in maize: Of the 210 libraries from different tissues encompassing the whole of maize plant, NAR2.1 and HAT-1 are expressed only in the root libraries. This indicates the root-specific function for each of these genes.

Expression analysis of NAR2.1 and HAT-1 in maize tissues. MPSS tag abundances were averaged over different tissue libraries. The number of libraries for each tissue was: anther, 3; ear, 15; kernel, 44; leaf, 39; pollen, 1; root, 36; silk, 9; stalk, 19; and tassel, 14.

Induction of nitrate uptake and localization within maize roots: Among the root libraries derived from an inbred line A63, the expression of both NAR2.1 and HAT-1 is similarly induced by nitrate.

Corn roots from etiolated seedlings obtained 7-days after growing in paper rolls in water, were harvested and subjected to different treatments in parallel. The freshly harvested roots were kept on ice as controls. The roots were incubated in an aerated solution containing different nutrients for different lengths of time and then either quickly frozen in liquid N and stored at −80° C. until used for expression analyses or saved between two layers of wet paper towels in ice for further manipulation. A batch of roots that had been treated for four hours in nitrate was manually dissected into cortical cylinder and stele.

Response of NAR2.1 and HAT 1 expression to different nutrient treatments. The roots were treated for either half hour or four hours in a medium containing either 1 mM nitrate (0.5 mM $KNO_3$ and 0.25 mM $Ca(NO_3)_2$) or 1 mM chloride (0.5 mM KCl and 0.25 mM $CaCl_2$). A batch of roots treated for 4 hours with nitrate was separated into cortical cylinder and stele and subjected to MPSS.

Both the NAR2.1 and HAT 1 genes from maize exhibit a similar response to nitrate (N) in the incubation medium which is incremental with time when compared to the parallel control roots incubated in a chloride solution. Also, both these genes are nearly exclusively located in the cortical sleeve and not in the stele. Their similar response to nitrate and their localization strongly indicate that the protein products of these genes make a functional nitrate transport complex in maize roots.

Opposite regulation of expression of NAR2.1 in Illinois High Protein (IHP) and Illinois Low Protein (ILP) maize lines: IHP and ILP are two sets of lines that are derived from a maize population after ~100 years of divergent selection for grain protein in the high and low grain protein directions, respectively (Uribelarrea et al., 2004). Whereas IHP grains contain >20% protein, those of ILP contain <5%. The roots of these two lines were subjected to Lynx MPSS after various treatments.

Roots were either kept in a nitrate solution all the time, starved for two hours for nitrate, or placed in nitrate solution after two hour starvation. Whereas NAR2.1 in IHP responded to nitrate treatment like A63, ILP exhibited an opposite response Given the level of expression of this gene in ILP in nitrate starved roots, which is similar to that of IHP roots kept in nitrate, these results suggest that mechanisms to respond to nitrate in both the directions do exist in maize. However, the mechanism for positive response appears to have been selected as indicated by similar response between IHP and A63, an inbred line with normal grain protein content of ~10%.

Only IHP contained the tag for HAT 1 sequence and showed a similar pattern of expression as for NAR2.1, lending further support to the aforementioned suggestion that NAR2.1 and HAT 1 form a functional complex in maize roots.

Expression of other HAT genes in A63: HAT 4 G was expressed at >10 ppm only in four libraries, all derived from the root tissue. Thus, this gene appears to be root-specific. HAT 7 is expressed in chilled seedlings and three leaf libraries, suggesting that this gene may encode a protein for nitrate uptake from the xylem apoplast into the leaf cells. It is expected that the HAT sequences of the instant application form a functional nitrate transport complex with a NAR sequence.

Example 8

Confirmation of Function of the High Affinity Nitrate Transporters and Polypeptides Required for High Affinity Nitrate Transport Using the TUSC Mutant Population The full genomic sequence for the high affinity nitrate transporter locus can be used to design primers to screen for Mu-insertion mutants in the TUSC population (U.S. Pat. No. 5,962,764, issued Oct. 5, 1999). The pooled TUSC population can be screened with gene specific primers. Alleles of the corn high affinity nitrate transporters and polypeptides required for high affinity nitrate transport can be recovered from this screen, and characterized. Furthermore, function of the sequences of the instant application can be confirmed by complementation studies.

Example 9

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described in Maniatis. The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0242236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobactenum tumefaciens.*

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2, 4-D. After two weeks the tissue can be transferred to regeneration medium (Fromm et al. (1990) *Bio/Technology* 8:833-839).

Example 10

Expression of Recombinant DNA Constructs in Dicot Cells

A seed-specific expression cassette composed of the promoter and transcription terminator from the gene encoding the α-subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3-5 mm in length dissected from surface sterilized, immature seeds of the soybean cultivar A2872, can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a recombinant DNA construct composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µL spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 11

Expression of Recombinant DNA Construct in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-beta-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 12

Electroporation of *Agrobacterium Tumefaciens* LBA4404

Electroporation competent cells (40 μL), such as *Agrobacterium tumefaciens* LBA4404 (containing PHP10523), are thawed on ice (20-30 min). PHP10523 contains VIR genes for T-DNA transfer, an Agrobacterium low copy number plasmid origin of replication, a tetracycline resistance gene, and a Cos site for in vivo DNA bimolecular recombination. PHP10523 is further described in Example 17. Meanwhile the electroporation cuvette is chilled on ice. The electroporator settings are adjusted to 2.1 kV. A DNA aliquot (0.5 μL parental DNA at a concentration of 0.2 μg-1.0 μg in low salt buffer or twice distilled $H_2O$) is mixed with the thawed *Agrobacterium tumefaciens* LBA4404 cells while still on ice. The mixture is transferred to the bottom of electroporation cuvette and kept at rest on ice for 1-2 min. The cells are electroporated (Eppendorf electroporator 2510) by pushing the "pulse" button twice (ideally achieving a 4.0 millisecond pulse). Subsequently, 0.5 mL of room temperature 2×YT medium (or SOC medium) are added to the cuvette and transferred to a 15 mL snap-cap tube (e.g., Falcon™ tube). The cells are incubated at 28-30° C., 200-250 rpm for 3 h.

Aliquots of 250 μL are spread onto plates containing YM medium and 50 μg/mL spectinomycin and incubated three days at 28-30° C. To increase the number of transformants one of two optional steps can be performed:

Option 1: Overlay plates with 30 μL of 15 mg/mL rifampicin. LBA4404 has a chromosomal resistance gene for rifampicin. This additional selection eliminates some contaminating colonies observed when using poorer preparations of LBA4404 competent cells.

Option 2: Perform two replicates of the electroporation to compensate for poorer electrocompetent cells.

Identification of Transformants:

Four independent colonies are picked and streaked on plates containing AB minimal medium and 50 μg/mL spectinomycin for isolation of single colonies. The plates are incubated at 28° C. for two to three days. A single colony for each putative co-integrate is picked and inoculated with 4 mL of 10 g/L bactopeptone, 10 g/L yeast extract, 5 g/L sodium chloride and 50 mg/L spectinomycin. The mixture is incubate for 24 h at 28° C. with shaking. Plasmid DNA from 4 mL of culture is isolated using Qiagen Miniprep and an optional Buffer PB wash. The DNA is eluted in 30 μL. Aliquots of 2 μL are used to electroporate 20 μL of DH10b+20 μL of twice distilled $H_2O$ as per above. Optionally a 15 μL aliquot can be used to transform 75-100 μL of Invitrogen Library Efficiency DH5α. The cells are spread on plates containing LB medium and 50 μg/mL spectinomycin and incubated at 37° C. overnight.

Three to four independent colonies are picked for each putative co-integrate and inoculated 4 mL of 2×YT medium (10 g/L bactopeptone, 10 g/L yeast extract, 5 g/L sodium chloride) with 50 μg/mL spectinomycin. The cells are incubated at 37° C. overnight with shaking. Next, isolate the plasmid DNA from 4 mL of culture using QIAprep® Miniprep with optional Buffer PB wash (elute in 50 μL). Use 8 μL for digestion with SalI (using parental DNA and PHP10523 as controls). Three more digestions using restriction enzymes BamHI, EcoRI, and HindIII are performed for 4 plasmids that represent 2 putative co-integrates with correct SalI digestion pattern (using parental DNA and PHP10523 as controls). Electronic gels are recommended for comparison.

Example 13

Transformation of Maize Using *Agrobacterium*

*Agrobacterum*-mediated transformation of maize is performed essentially as described by Zhao et al. in *Meth. Mol. Biol.* 318:315-323 (2006) (see also Zhao et al., *Mol. Breed.* 8:323-333 (2001) and U.S. Pat. No. 5,981,840 issued Nov. 9, 1999, incorporated herein by reference). The transformation process involves bacterium inoculation, co-cultivation, resting, selection and plant regeneration.

1. Immature Embryo Preparation:

Immature maize embryos are dissected from caryopses and placed in a 2 mL microtube containing 2 mL PHI-A medium.

2. *Agrobacterium* Infection and Co-Cultivation of Immature Embryos:

2.1 Infection Step

PHI-A medium of (1) is removed with 1 mL micropipettor, and 1 mL *Agrobacterum* suspension (including, but not limited to, the *Agrobacterium* described in Example 7) is added. The tube is gently inverted to mix. The mixture is incubated for 5 min at room temperature.

2.2 Co-Culture Step

The *Agrobacterium* suspension is removed from the infection step with a 1 mL micropipettor. Using a sterile spatula the embryos are scraped from the tube and transferred to a plate of PHI-B medium in a 100×15 mm Petri dish. The embryos are oriented with the embryonic axis down on the surface of the medium. Plates with the embryos are cultured at 20° C., in darkness, for three days. L-Cysteine can be used in the co-cultivation phase. With the standard binary vector, the co-cultivation medium supplied with 100-400 mg/L L-cysteine is critical for recovering stable transgenic events.

3. Selection of Putative Transgenic Events:

To each plate of PHI-D medium in a 100×15 mm Petri dish, 10 embryos are transferred, maintaining orientation and the dishes are sealed with parafilm. The plates are incubated in darkness at 28° C. Actively growing putative events, as pale yellow embryonic tissue, are expected to be visible in six to eight weeks. Embryos that produce no events may be brown and necrotic, and little friable tissue growth is evident. Putative transgenic embryonic tissue is subcultured to fresh PHI-D plates at two-three week intervals, depending on growth rate. The events are recorded.

4. Regeneration of T0 Plants:

Embryonic tissue propagated on PHI-D medium is subcultured to PHI-E medium (somatic embryo maturation medium), in 100×25 mm Petri dishes and incubated at 28° C., in darkness, until somatic embryos mature, for about ten to eighteen days. Individual, matured somatic embryos with well-defined scutellum and coleoptile are transferred to PHI-F embryo germination medium and incubated at 28° C. in the light (about 80 μE from cool white or equivalent fluorescent lamps). In seven to ten days, regenerated plants, about 10 cm tall, are potted in horticultural mix and hardened-off using standard horticultural methods.

Media for Plant Transformation:

1. PHI-A: 4 g/L CHU basal salts, 1.0 mL/L 1000× Eriksson's vitamin mix, 0.5 mg/L thiamin HCl, 1.5 mg/L 2,4-D, 0.69 g/L L-proline, 68.5 g/L sucrose, 36 g/L glucose, pH 5.2. Add 100 μM acetosyringone (filter-sterilized).
2. PHI-B: PHI-A without glucose, increase 2,4-D to 2 mg/L, reduce sucrose to 30 g/L and supplemente with 0.85 mg/L silver nitrate (filter-sterilized), 3.0 g/L Gelrite®, 100 μM acetosyringone (filter-sterilized), pH 5.8.
3. PHI-C: PHI-B without Gelrite® and acetosyringonee, reduce 2,4-D to 1.5 mg/L and supplemente with 8.0 g/L agar, 0.5 g/L 2-[N-morpholino]ethane-sulfonic acid (MES) buffer, 100 mg/L carbenicillin (filter-sterilized).
4. PHI-D: PHI-C supplemented with 3 mg/L bialaphos (filter-sterilized).
5. PHI-E: 4.3 g/L of Murashige and Skoog (MS) salts, (Gibco, BRL 11117-074), 0.5 mg/L nicotinic acid, 0.1 mg/L thiamine HCl, 0.5 mg/L pyridoxine HCl, 2.0 mg/L glycine, 0.1 g/L myo-inositol, 0.5 mg/L zeatin (Sigma, Cat. No. Z-0164), 1 mg/L indole acetic acid (IAA), 26.4 μg/L abscisic acid (ABA), 60 g/L sucrose, 3 mg/L bialaphos (filter-sterilized), 100 mg/L carbenicillin (filter-sterilized), 8 g/L agar, pH 5.6.
6. PHI-F: PHI-E without zeatin, IAA, ABA; reduce sucrose to 40 g/L; replacing agar with 1.5 g/L Gelrite®; pH 5.6.

Plants can be regenerated from the transgenic callus by first transferring clusters of tissue to N6 medium supplemented with 0.2 mg per liter of 2,4-D. After two weeks the tissue can be transferred to regeneration medium (Fromm et al., *Bio/Technology* 8:833-839 (1990)).

Transgenic T0 plants can be regenerated and their phenotype determined. T1 seed can be collected.

Furthermore, a recombinant DNA construct containing a validated *Arabidopsis* gene can be introduced into an elite maize inbred line either by direct transformation or introgression from a separately transformed line.

Transgenic plants, either inbred or hybrid, can undergo more vigorous field-based experiments to study yield enhancement and/or stability under nitrogen limiting and nitrogen non-limiting conditions.

Subsequent yield analysis can be done to determine whether plants that contain the validated *Arabidopsis* lead gene have an improvement in yield performance (under nitrogen limiting or non-limiting conditions), when compared to the control (or reference) plants that do not contain the validated *Arabidopsis* lead gene. Plants containing the validated *Arabidopsis* lead gene would have less yield loss relative to the control plants, preferably 50% less yield loss, under nitrogen limiting conditions, or would have increased yield relative to the control plants under nitrogen non-limiting conditions.

Example 14

Evaluating Compounds for Their Ability to Inhibit the Activity of Nitrate Transporters The polypeptides described herein may be produced using any number of methods known to those skilled in the art. Such methods include, but are not limited to, expression in bacteria as described in Example 11, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin, which is specific for the fusion protein tag attached to the expressed enzyme or an affinity resin containing ligands, which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions that permit optimal enzymatic activity.

Assays that enable rapid screening for nitrate transport activity have been described in the literature, including, but not limited to an assay that measures $^{15}N$-enriched nitrate uptake into *Xenopus oocytes* expressing the proteins (Tong et al., The Plant J. (2005) 41:442-450).

Example 15

Expansion of the Linear Nitrate Uptake Range of Higher Plant HATS by Gene Shuffling HATs are known to possess a low Km (in 10 to 100 μM range) and low Vmax (Doddema et al., Kinetics. Physiol. Plant. (1979) 45:332-338, Meharg et al., (1995) J. Membr. Biol. 145:49-66, Touraine et al., Plant Physiol. (1997) 114: 137-144, Liu et al., Plant Cell. (1999) 11(5):865-874). Therefore, the uptake rate of HATs remains constant once the nitrate concentration reaches a level of about 2 to 3 fold higher than their Km.

The most relevant field nitrate concentration is around 2 to 5 mM on a typical modern corn farmland. Within this concentration range, the uptake rate of HATs is well saturated. Extending the linear nitrate uptake of HATs from very low to relevant field concentration would allow maize crop to fully utilize available nitrate for better growth and productivity. Such a transporter would also allow the crop plant to maintain the normal uptake efficiency at lower nitrate input by its enhanced ability to uptake fast at relatively lower nitrate concentration.

Various gene-shuffling methods (Stemmet W P, PNAS (1994) 91: 10747-10751, Crameri et al., Nature (1998) 391: 288-291, Ness et al., Nature Biotech. (1999) 17:893-896) can be used to generate different types of shuffled HATs libraries. For example, libraries can be generated by single gene and family gene shuffling. Additional diversities can be introduced by spiked oligos carrying amino acid mutations.

The shuffled HAT libraries can be functionally expressed in one of the heterologous hosts such as yeast, *E. coli*, and green algae. Preferably, the host lacks the nitrate assimilation pathway except for an endogenous or introduced nitrate reductase. Nitrate uptake rate by functionally expressed shufflants can be assayed by either direct measurement of depletion of nitrate in the assay medium via HPLC or other analytical means or by measurement of nitrite generated by nitrate reductase within the same cell. Nitrite concentration can be easily determined by colorimetrical assay (such as use of Greiss Reagent) or other analytical means (HPLC). Further characterization of the putative hits from screening various shuffled libraries can be achieved by measuring the uptake rates against different concentrations of nitrate. Such assay will provide uptake kinetic parameters of Km and Vmax.

Hits confirmed with improved properties can then be reshuffled to generate a second round of shuffled libraries and the aforementioned screening scheme can be used for identifying second round hits. This process can be repeated until several shuffled variants are identified that meet the desired kinetic properties.

Example 16

Isolation, Cloning and Sequencing of the Nar Promoter from the Maize B73 Inbred Line Identification of a BAC Clone Carrying the Nar Gene A BAC library derived from maize B71 inbred line was screened by PCR using the forward and reverse primers depicted in SEQ ID NOs: 75 and 76, respectively. Cycle conditions were an initial activation step at 95° C. for 15 minutes, followed by 35 cycles at 94° C. for 1 minute, 60° C. for 1 minute and 72° C. for 1 minute. Final extension was at 72° C. for 10 minutes.

A 377 bp product was obtained. BAC clone ZMMBBb0521a1 was identified as carrying the Nar gene.

Cloning of the Nar Promoter from Maize B73 Inbred Line

The Nar promoter was cloned by PCR using the forward and reverse primer with restriction enzyme sites for BamHI and HindIII depicted in SEQ ID NOs: 77 and 78, receptively.

To 1 µl diluted (1:100) BAC DNA from BAC clone ZMMBBb0521a1, 1 µl primer mix at a concentration of 10 µM each, 4 µl DNTPs at a concentration of 2.5 mM, 10 µl 5×HF buffer and 33.5 µl $H_2O$ and 0.5 µl Phusion High Fidelity DNA Polymerase (Finnzymes) were added. Cycle conditions were an initial activation step at 98° C. for 30 seconds, followed by 35 cycles of 98° C. for 10 seconds, 63° C. for 30 seconds and 72° C. for 1 minute. Final Extension was at 72° C. for 10 minutes.

A product of 3621 bp was obtained.

The 3621 bp product was gel purified using the Qiaquick™ Gel Extraction Kit (Qiagen) and eluted with 88 µl Elution Buffer.

To the purified band 10 µl of buffer E (Promega) and 1 µl of each of the restriction enzyme, BamHI and Hind III (each at 10 U/µl) were added. The assay mixture was incubated at 37° C. for 3 hrs and cleaned up with Qiaquick™ PCR Purification Kit (Qiagen).

The pENTR-5' vector (SEQ ID NO: 85) was digested with BamHI and HindIII and dephosphorylated. The purified PCR band was inserted into the prepared pENTR-5' vector using the Epicentre Fast Link Kit. The ligation reaction mixture contained 1.5 µL buffer (10×), 1.5 µL ATP (10×), 1 µL ligase, 1 µL pENTR-5'-vector (~10 ng/µL BamHI/HindIII/dephosphorylated vector), 1 µL promoter insert (~30 ng) and 9 µL H20. The ligaton reaction was allowed to proceed for 15 minutes at room temperature and was stopped by incubating the mixture at 70° C. for 15 minutes.

Transformation into Bacteria and PCR Screen for Insert

1 µL of the ligation mix was added to 20 µL of electrocompetent cells (DH10B ElectroMax-Invitrogen) and the mixture was electroporated with a Gibco BRL Cell Porator, then 1 mL SOC media were added and the mixture was incubated in a shaker at 37° C. for 1 hr. 150 µL of cells were plated on LB plates with Kanamycin selection and grown overnight at 37° C.

12 colonies were picked and 30 µL LB media was added. The colonies were screened using PCR. To 1 µL colony DNA (colony/30 µL LB), 5 µL HotTaq 2× master mix (Qiagen), 1 µL (10 mM primer mix, SEQ ID NO: 77 and 78) and 3 µL $dH_20$ were added. Cycle conditions were an initial activation at 95° C. for 15 minutes, followed by 35 cycles of 95° C. for 50 seconds, 55° C. for 50 seconds and of 72° C. for 4 minutes. Final Extension was at 72° C. for 10 minutes.

Insert Sequencing

DNA carrying the insert was sequenced using the sequence primers depicted in SEQ ID NOs: 79-84. The sequence of the insert is shown in SEQ ID NO: 70. The vector construct carrying the 3621 bp insert was named PHP27621 and is shown in SEQ ID NO: 86 and FIG. 1.

Example 17

Testing the NAR Promoter in Transgenic Maize and *Arabidopsis*

Figure 2:
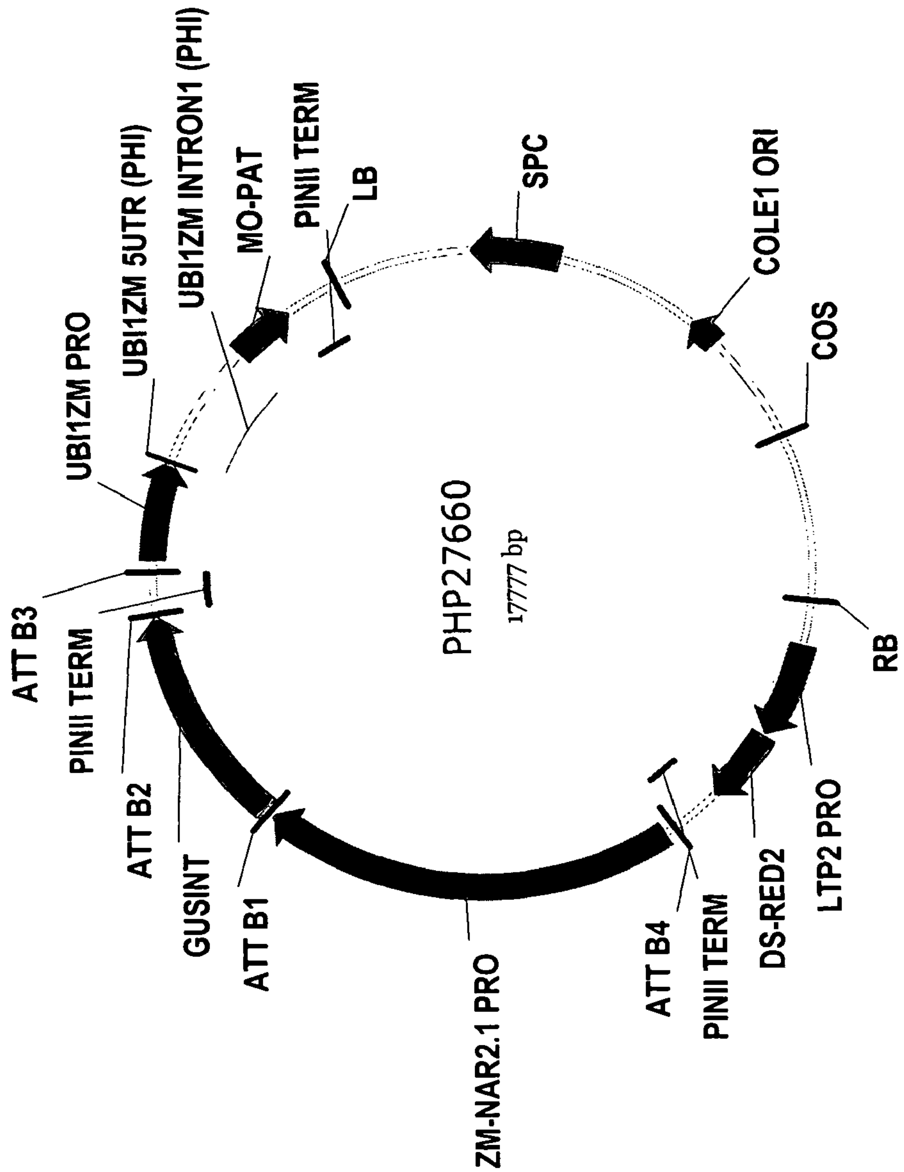
FIG. 2 is a schematic of vector PHP27660.

Using Invitrogen's™ gateway LR Clonase technology a MultiSite Gateway® LR Recombination Reaction was performed to create the corn NAR promoter::GUS::PINII, UBI::MO-PAT::PINII and LTP2::DS-RED PINII JT binary vector (PHP27660, SEQ ID NO: 87 and FIG. 2). The vector PHP27660 contains the following expression cassettes:

1. Ubiquitin promoter::MO-PAT::PINII terminator cassette expressing the PAT herbicide resistance gene used for selection during the transformation process.
2. LTP2 promoter::DS-RED2::PinII terminator cassette expressing the DS-RED color marker gene used for seed sorting.
3. NAR promoter::GUS::PINII terminator cassette expressing the GUS gene under control of the corn NAR promoter.

Figure 3:
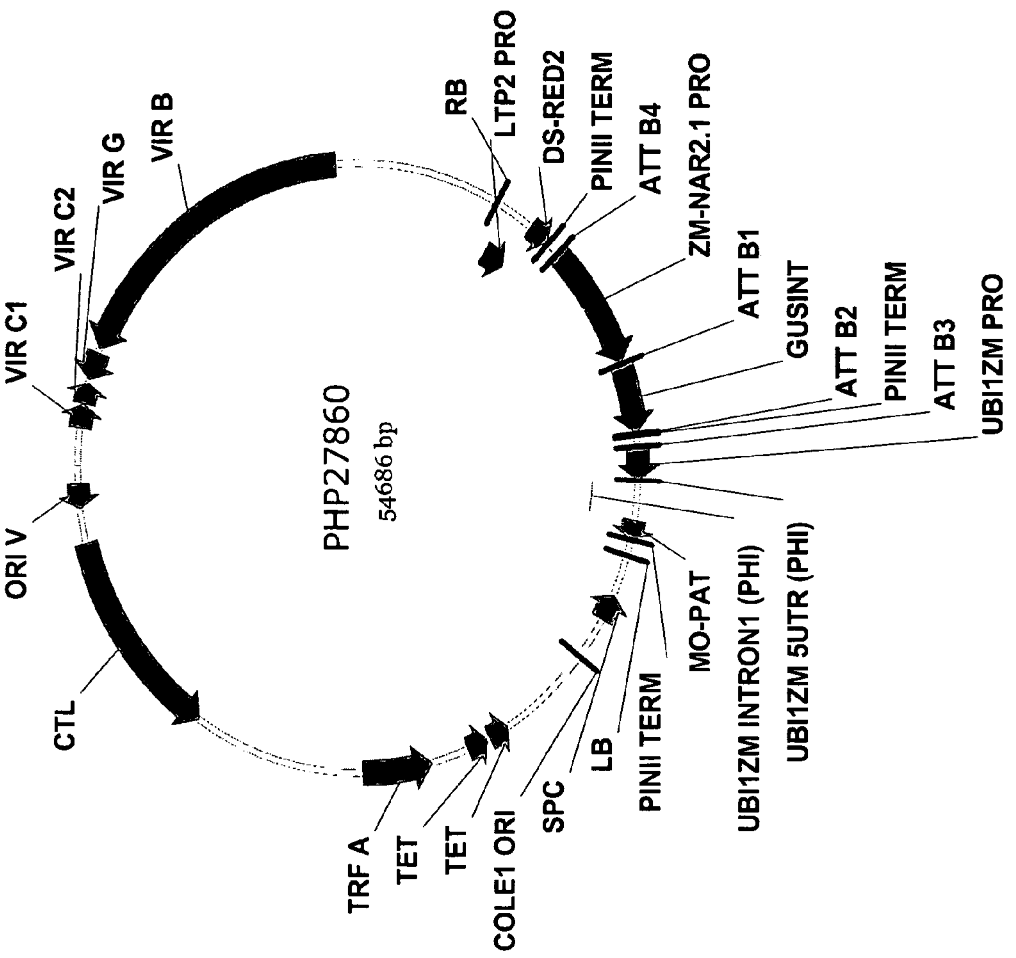
FIG. 3 is a schematic of vector PHP27860.

Vector PHP27660 was electroporated using the protocol outlined in Example 16 into LBA4404 *Agrobacterium* cells containing PHP10523 by electroporation creating the final cointegrate vector PHP27860 (SEQ ID NO: 88 and FIG. 3) was then used for *Agrobacterium*-based maize transformation as described in Example 17. T0 transgenic plants were sampled for GUS expression.

Separately, the same vector (PHP27860) was also used for *Arabidopsis* transformation, following the standard inflorescence-dipping procedures. Transgenic events were selected by herbicide glufosinate spraying on the T1 seedlings. The herbicide-resistant T1 plants were sampled for GUS expression.

Leaf and root tissue samples were collected from transgenic plants at different time points, including seedling stage and at maturity. Freshly collected tissue samples were dissected into small pieces to facilitate penetration of the GUS staining solution. GUS histochemical staining was done following the standard protocol (Jefferson R A, Kavanagh T A, Bevan M W. 1987 GUS fusions: beta-glucuronidase as a sensitive and versatile gene fusion marker in higher plants. EMBO J. 6(13): 3901-3907) incubating at 37° C. overnight.

No significant promoter activity was observed in transgenic maize and *Arabidopsis* tissues.

Example 18

Testing the Effects of Extraneous Junction Sequences on the NAR Promoter in Transgenic Maize and *Arabidopsis*

The Gateway cloning system leaves a short fragment of "foot-print" sequences between components, particularly a 21-bp ATT-B1 fragment between the NAR promoter and the GUS coding region. This has been shown to weaken or even abolish promoter activity in certain cases. This likely is related to the physical distance between basal promoter elements and the start codon. To determine if introducing the ATT-B1 site is negatively affecting the NAR promoter, a construct containing the corn NARpromoter::GUS::PINII cassette is built with a conventional cloning method, i.e., without the use of the Gateway system. Transgenic maize plants are produced via *Agrobacterium*-based transformation, and various tissue samples are collected for GUS expression study as described in Example 17.

Example 19

Testing the Maize NAR Promoter in a Deletion Series

The NAR gene has a nitrate-inducible and root-specific expression pattern. To determine the fragments that determine NAR promoter activity and specificity, a series of constructs containing truncated NAR promoter fragments linked to the sequences for GUS and the PINII end are constructed and tested as described for the full length promoter in Examples 17 and 18.

Using BLASTN (Basic Local Alignment Search Tool; Altschul et al. (1993) *J. Mol. Biol.* 215:403-410;), sequences within the NAR promoter can be identified that might be important for enhancing or suppressing promoter activity. The sequence around 1.5 to 1.9 kb of the NAR promoter shows homology to another gene and a transposon element. Deletion of this fragment as shown in SEQ ID NO: 89 is therefore expected to add information on NAR promoter activity.

In addition truncation that reduce the length of the promoter as shown in SEQ ID NOs: 71, 72, 73, 74 and 90 can also be tested in the same way as described for the full length promoter in Examples 17 and 18. Additional promoter subfragments can be prepared by using primers derived from the 3.6 Kb NAR promoter sequence in PCR.

Example 20

Figure 4:
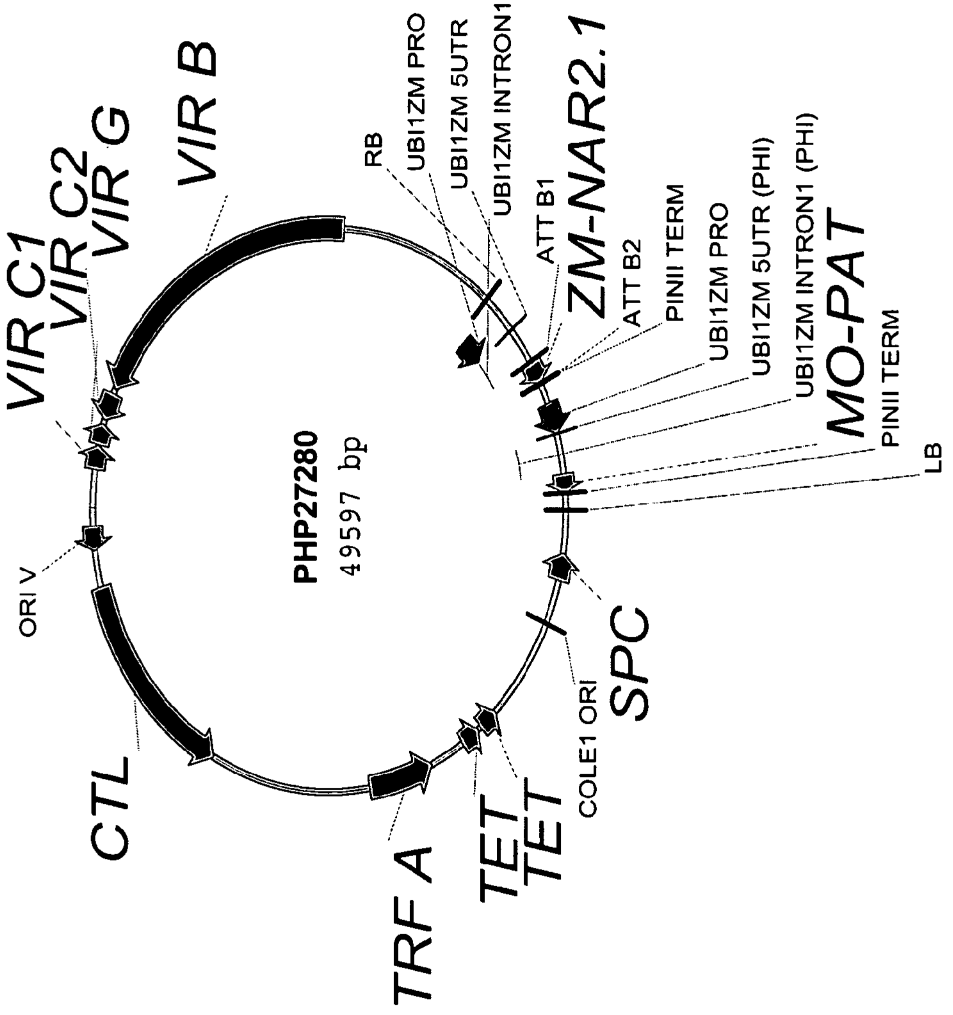
FIG. 4 is a schematic of vector PHP27280.
Figure 5:
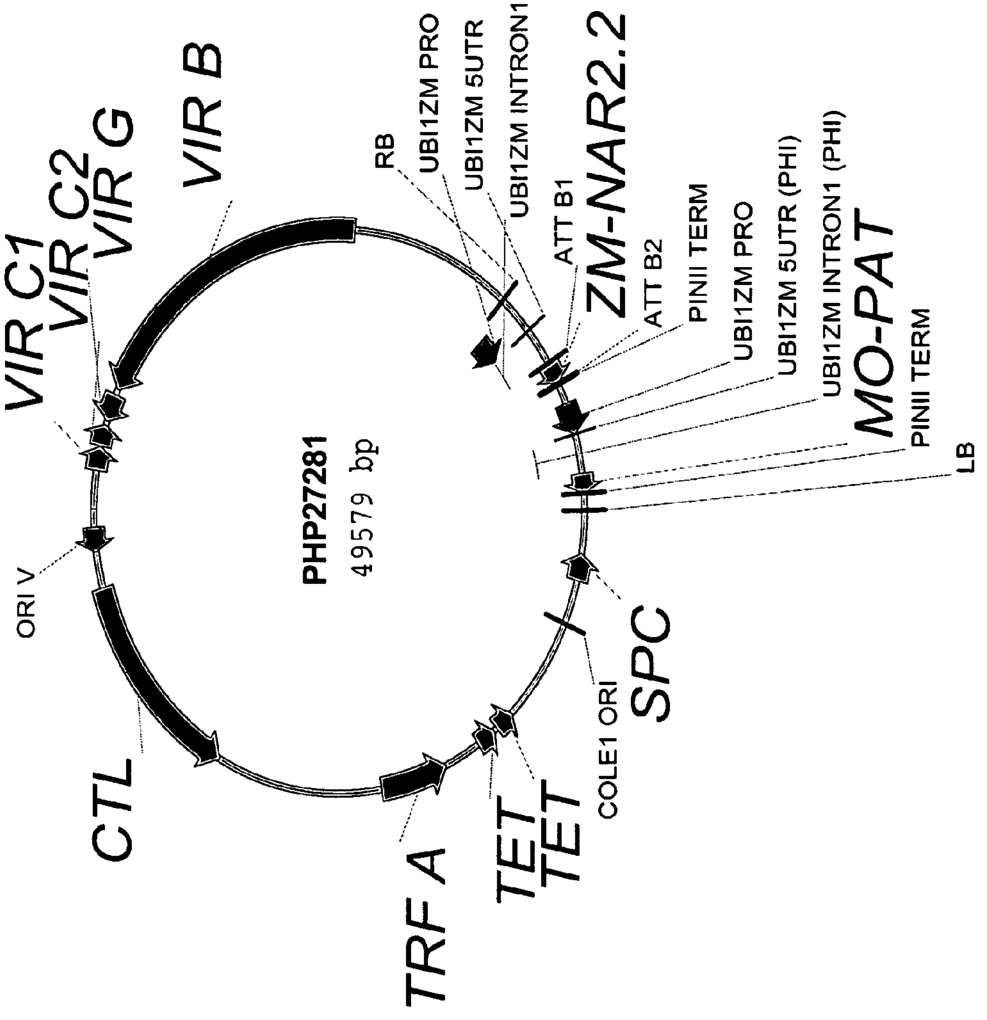
FIG. 5 is a schematic of vector PHP27281.
Figure 6:
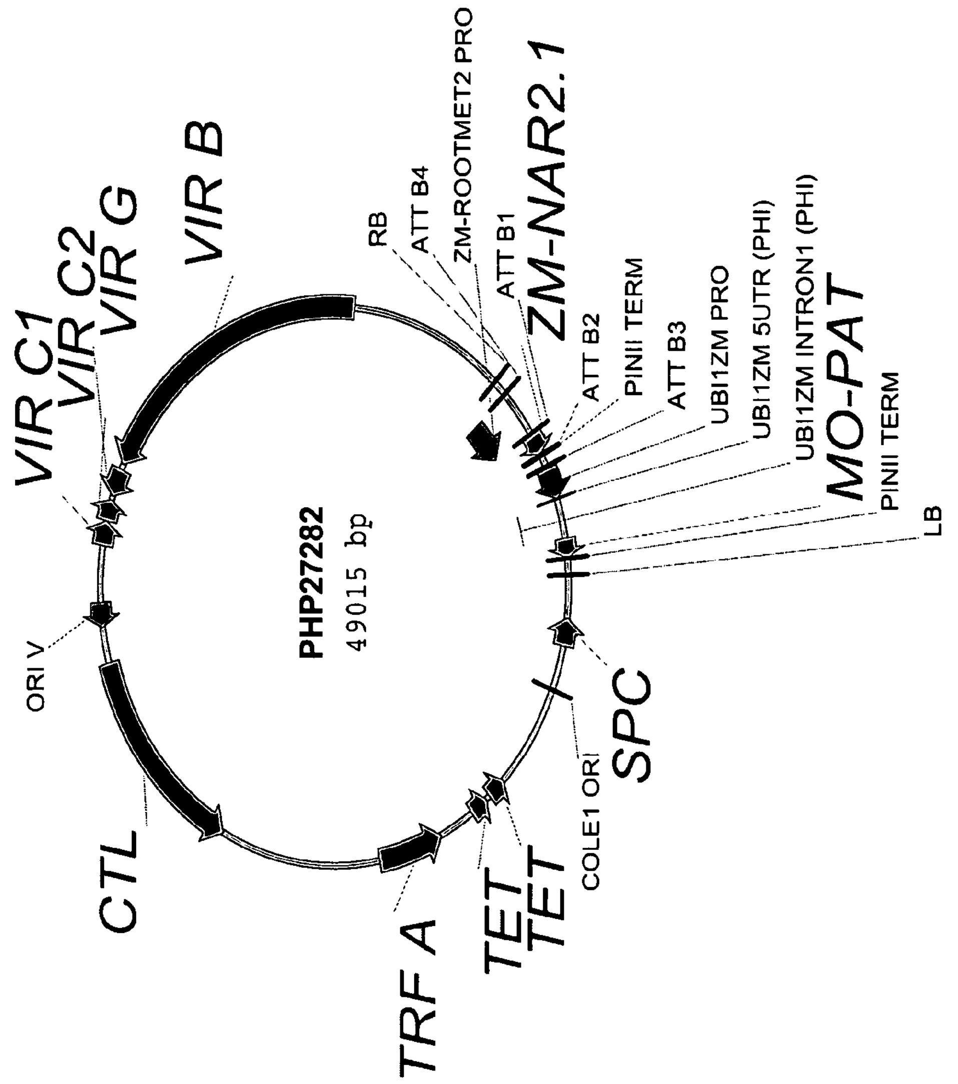
FIG. 6 is a schematic of vector PHP27282.
Figure 7:
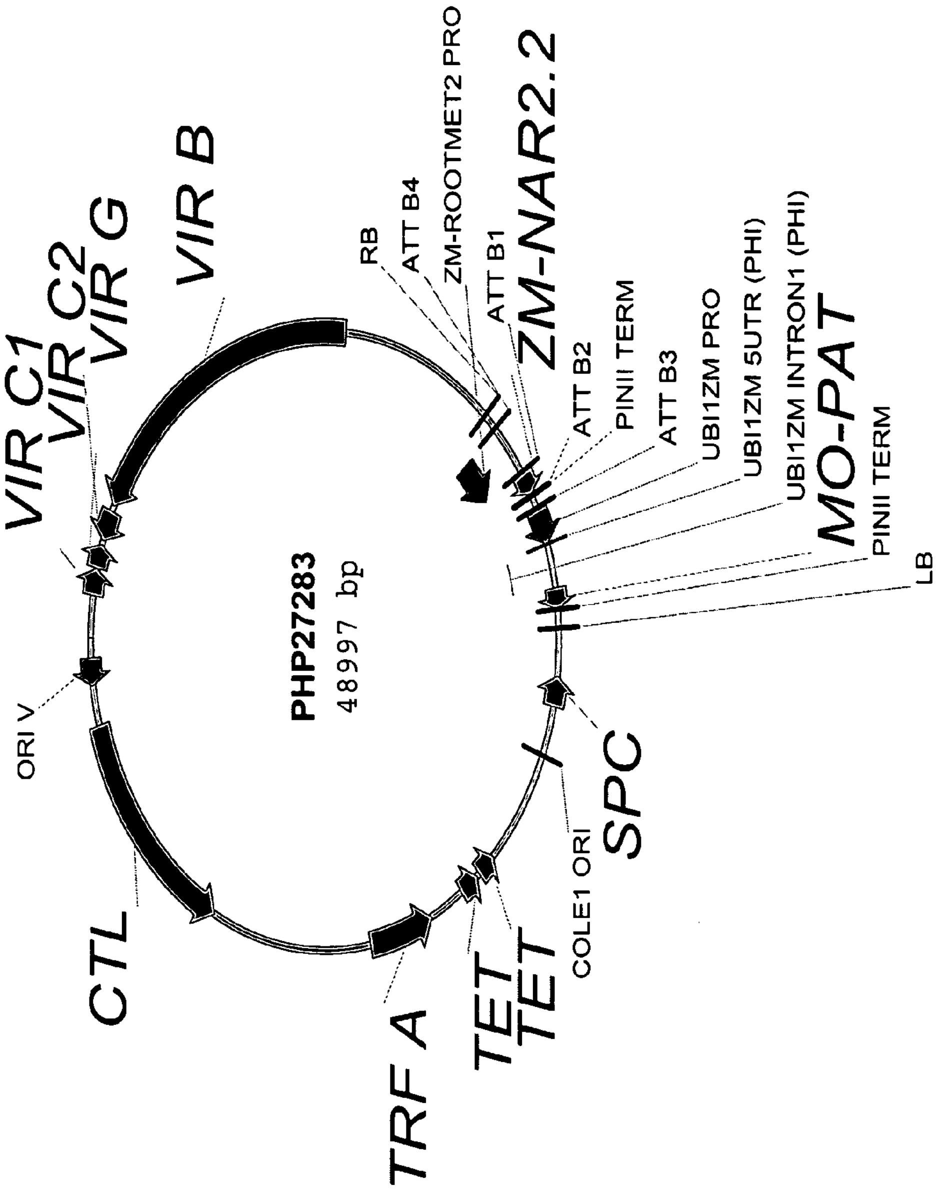
FIG. 7 is a schematic of vector PHP27283.

Evaluation of Nitrate Uptake in Maize Using HAT and NAR Sequences and Combinations Thereof The following maize expression constructs were prepared for evaluation of nitrate uptake in maize: PHP27280 (SEQ ID NO: 93 and FIG. 4), PHP27281 (SEQ ID NO:94 and FIG. 5), PHP27282 (SEQ ID NO: 95 and FIG. 6) and PHP27283 (SEQ ID NO:96 and FIG. 7).

Additional constructs comprising HAT sequences and combinations of HAT and Nar sequences will be prepared and tested for their ability to alter Nitrate transport. T0, T1 and subsequent generations will be evaualted for altered biomass and total ear weight under 1 mM nitrate conditions.

What is claimed is:

1. An isolated polynucleotide comprising:

(a) a nucleotide sequence encoding a high affinity nitrate transporter polypeptide, wherein the polypeptide has an amino acid sequence of at least 95% sequence identity, based on the Clustal V method of alignment, when compared to SEQ ID NO: 36; or (b) a complement of the nucleotide sequence, wherein the complement and the nucleotide sequence consist of the same number of nucleotides and are 100% complementary.

2. The polynucleotide of claim 1, wherein the amino acid sequence of the polypeptide has at least 99% sequence identity, based on the Clustal V method of alignment, when compared to SEQ ID NO: 36.

3. The polynucleotide of claim 1, wherein the amino acid sequence of the polypeptide comprises SEQ ID NO: 36.

4. The polynucleotide of claim 1 wherein the nucleotide sequence comprises SEQ ID NO: 35.

* * * * *

SEQUENCE LISTING

```
<160> NUMBER OF SEQ ID NOS: 96

<210> SEQ ID NO 1
<211> LENGTH: 25
<212> TYPE: DNA
<213> ORGANISM: Artificial
<220> FEATURE:
<223> OTHER INFORMATION: Primer

<400> SEQUENCE: 1

ccaactggag tccaacaccc acaaa                                          25


<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2

catgctgctc gtccactgcg g                                              21
```

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
taatacgact cactataggg 20

<210> SEQ ID NO 4
<211> LENGTH: 19
<212> TYPE: DNA
<213> ORGANISM: Artificial
<220> FEATURE:
<223> OTHER INFORMATION: Primer

<400> SEQUENCE: 4
tatttaggtg acactatag 19

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
atgttgttgg tggtgagctg 20

<210> SEQ ID NO 6
<211> LENGTH: 18
<212> TYPE: DNA
<213> ORGANISM: Artificial
<220> FEATURE:
<223> OTHER INFORMATION: Primer

<400> SEQUENCE: 6
acacgaggtt ggccatgc 18

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
gtttgacacc ccttttctag caagg 25

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
ccttgctaga aaaggggtgt caaac 25

<210> SEQ ID NO 9
<211> LENGTH: 27
<212> TYPE: DNA
<213> ORGANISM: Artificial
<220> FEATURE:
<223> OTHER INFORMATION: Primer

<400> SEQUENCE: 9
ggtcccgttt ggttagagag actaatc 27

<210> SEQ ID NO 10
<211> LENGTH: 22
<212> TYPE: DNA
<213> ORGANISM: Artificial
<220> FEATURE:
<223> OTHER INFORMATION: Primer

<400> SEQUENCE: 10
gcgcaacgaa atgcattggt ca 22

<210> SEQ ID NO 11
<211> LENGTH: 25
<212> TYPE: DNA
<213> ORGANISM: Artificial
<220> FEATURE:
<223> OTHER INFORMATION: Primer

<400> SEQUENCE: 11
aggggagaga agagaaaaag cgggt 25

<210> SEQ ID NO 12
<211> LENGTH: 28
<212> TYPE: DNA
<213> ORGANISM: Artificial
<220> FEATURE:
<223> OTHER INFORMATION: Primer

<400> SEQUENCE: 12
gctgcatgtt tacgactaca atctttgg 28

<210> SEQ ID NO 13
<211> LENGTH: 25
<212> TYPE: DNA
<213> ORGANISM: Artificial
<220> FEATURE:
<223> OTHER INFORMATION: Primer

<400> SEQUENCE: 13
tttgtgggtg ttggactcca gttgg 25

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
tttgtgggtg ttggactcca gtt 23

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
tttgtgggtg ttggactcca 20

<210> SEQ ID NO 16
<211> LENGTH: 17
<212> TYPE: DNA
<213> ORGANISM: Artificial

<220> FEATURE:
<223> OTHER INFORMATION: Primer

<400> SEQUENCE: 16
gggatgacgc cgaaggt 17

<210> SEQ ID NO 17
<211> LENGTH: 17
<212> TYPE: DNA
<213> ORGANISM: Artificial
<220> FEATURE:
<223> OTHER INFORMATION: Primer

<400> SEQUENCE: 17
cttcggcgtc atcccct 17

<210> SEQ ID NO 18
<211> LENGTH: 17
<212> TYPE: DNA
<213> ORGANISM: Artificial
<220> FEATURE:
<223> OTHER INFORMATION: Primer

<400> SEQUENCE: 18
aaggggatga cgccgaa 17

<210> SEQ ID NO 19
<211> LENGTH: 17
<212> TYPE: DNA
<213> ORGANISM: Artificial
<220> FEATURE:
<223> OTHER INFORMATION: Primer

<400> SEQUENCE: 19
ttcggcgtca tcccctt 17

<210> SEQ ID NO 20
<211> LENGTH: 21
<212> TYPE: DNA
<213> ORGANISM: Artificial
<220> FEATURE:
<223> OTHER INFORMATION: Primer

<400> SEQUENCE: 20
cacatcgccg tgggcatcct t 21

<210> SEQ ID NO 21
<211> LENGTH: 18
<212> TYPE: DNA
<213> ORGANISM: Artificial
<220> FEATURE:
<223> OTHER INFORMATION: Primer

<400> SEQUENCE: 21
aggatgccca cggcgatg 18

<210> SEQ ID NO 22
<211> LENGTH: 21
<212> TYPE: DNA
<213> ORGANISM: Artificial
<220> FEATURE:
<223> OTHER INFORMATION: Primer

<400> SEQUENCE: 22
cacatcgccg tgggcatcct t 21

<210> SEQ ID NO 23
<211> LENGTH: 21
<212> TYPE: DNA
<213> ORGANISM: Artificial
<220> FEATURE:
<223> OTHER INFORMATION: Primer

<400> SEQUENCE: 23
aaggatgccc acggcgatgt g 21

<210> SEQ ID NO 24
<211> LENGTH: 18
<212> TYPE: DNA
<213> ORGANISM: Artificial
<220> FEATURE:
<223> OTHER INFORMATION: Primer

<400> SEQUENCE: 24
tgccccgcgg ttagcaca 18

<210> SEQ ID NO 25
<211> LENGTH: 18
<212> TYPE: DNA
<213> ORGANISM: Artificial
<220> FEATURE:
<223> OTHER INFORMATION: Primer

<400> SEQUENCE: 25
tgtgctaacc gcggggca 18

<210> SEQ ID NO 26
<211> LENGTH: 18
<212> TYPE: DNA
<213> ORGANISM: Artificial
<220> FEATURE:
<223> OTHER INFORMATION: Primer

<400> SEQUENCE: 26
gcggttagca caaggatg 18

<210> SEQ ID NO 27
<211> LENGTH: 18
<212> TYPE: DNA
<213> ORGANISM: Artificial
<220> FEATURE:
<223> OTHER INFORMATION: Primer

<400> SEQUENCE: 27
catccttgtg ctaaccgc 18

<210> SEQ ID NO 28
<211> LENGTH: 25
<212> TYPE: DNA
<213> ORGANISM: Artificial
<220> FEATURE:
<223> OTHER INFORMATION: Primer

<400> SEQUENCE: 28
ggtagttggc gacggcgtgc cagag 25

<210> SEQ ID NO 29
<211> LENGTH: 22
<212> TYPE: DNA
<213> ORGANISM: Artificial
<220> FEATURE:
<223> OTHER INFORMATION: Primer

<400> SEQUENCE: 29
gcgacggcgt gccagagcac cc 22

<210> SEQ ID NO 30
<211> LENGTH: 25
<212> TYPE: DNA
<213> ORGANISM: Artificial
<220> FEATURE:
<223> OTHER INFORMATION: Primer

<400> SEQUENCE: 30
caggttctcc cggatgatgg ggatc 25

<210> SEQ ID NO 31
<211> LENGTH: 26
<212> TYPE: DNA
<213> ORGANISM: Artificial
<220> FEATURE:
<223> OTHER INFORMATION: Primer

<400> SEQUENCE: 31
gatccccatc atccgggaga acctgg 26

<210> SEQ ID NO 32
<211> LENGTH: 25
<212> TYPE: DNA
<213> ORGANISM: Artificial
<220> FEATURE:
<223> OTHER INFORMATION: Primer

<400> SEQUENCE: 32
gatccccatc atccgggaga acctg 25

<210> SEQ ID NO 33
<211> LENGTH: 26
<212> TYPE: DNA
<213> ORGANISM: Artificial
<220> FEATURE:
<223> OTHER INFORMATION: Primer

<400> SEQUENCE: 33
ccaggttctc ccggatgatg gggatc 26

<210> SEQ ID NO 34
<211> LENGTH: 3924
<212> TYPE: DNA
<213> ORGANISM: Zea mays

<400> SEQUENCE: 34
ttcgagggca atgggttcca aagaatgtca tttgaattag acacttagtt atttatgaaa 60 aggtttttttc tccccgagtt aatttgcttc caaactataa ttaaccctaa gcaaggtgtt 120
agttatttgt tttgacggtt tatatatccg tgttagcttg gtggctagct tgtatccatt 180
tgacttgacg gcacatgcat gcatgcgtgg agtgcaccgt gcggcggttt gtgacgcggt 240
gccaaacgtg caattgactc attgagtagt catcagcagg cttgcgatca ttagacacta 300
acaagcatta atatttgctg catatatata tatacacaca catgcttcac tgacgacgct 360
tgcaacttga tcttgttaat tattatatat cctaagcaca acgaacaaac cttagatatg 420
cgaccatgcc ttgagtagag cgtgaaaaat agggggtgaa aaaaagggac gagtaattat 480
agatgacact atttgatatt gtttaaagat gagataggga atgtgctgaa tagatcaatt 540
tttaatcagg gatggtaggg actagtattt cctctatgat tttccatgta acacctttga 600
atatacaata ataataagaa gccaccaacc tttgaattat tatctgttcc aatatattag 660

-continued

```
atgaggggtg tatcggaatt tgacttccga gttgttcttg cgtgtccgta cgctcgtacg    720
gtagctcgtt gggttgttgt accagccatc ctgctactgc gcaacgaaat gcattggtca    780
tctcaattaa gtccaaagat tgtagtcgta aacatgcagc caataagagc aaggataata    840
gtttagccat tgatatgtct tctaaagcta attattactg tattggaccc acctcgtact    900
ctcattctct caccacttgt ttcggaatct gtactgctac aaccagctct tagtcgactg    960
ataattaact acccgctttt tctcttctct cccctccaac tgcaaaaatc taatgtggca   1020
aaccatttag cctgcttaca tcgtcaaaaa tctaatgtgg taaagtgtga agtgtcctaa   1080
agttttagtc cttaatttct ttcaataaac taaactaaac tttagaaaac tcaaacaagt   1140
cctcatgttt gcacatttta ggtctcgttt ggtttgaggg actaaagatt agtccctcca   1200
ttttagtccc atttagttac taaattacca aacagtagga ctaaaacagg gactaaattg   1260
ttttagtccc tagtccctta agatggctaa aagggactaa accatattaa ttccacattt   1320
gcccctcatt tagttcaatt gtactaatag caggagaatg ttaaaagtca ttttaatctt   1380
cttatgagtc atttaggccc tgtttggttc cattagtcat agaactaaag tttagttgta   1440
gggactaaat agattctaaa tacattaaat gcaacacata aagaccaaaa tgcccttttt   1500
tgtttgacac cccttttcta gcaagggtat ttggagtaaa tgttgccctt tggtcccttt   1560
tagcacccat gtgagggact agagactaaa accaattagt ccctacttta gtcattccgt   1620
ttagcaaaat agagactaaa cgagactaaa aacgagaggc taaagattag tctctctaac   1680
caaacgggac ctaaaattac tatctgtatg tatctgttgg atggaaaagt cagaacgtcg   1740
tggggaccac cacgctacca catggtacgg taatgtcaga aagtcgctat cttcttcgat   1800
ctgcatctcc actccagcca gcgctgctta tcatcagcat tcacgaagcc gcccaacgat   1860
aataaaaaat gtcagcgcga tcgcgcactg cctataaaac cccggccgtc gcgtccatgg   1920
cgtttcagga tccgagcacc agaaagaagc tgagttagct agggtcaaga aagtagtcag   1980
cactcagcag gaaaagaagc agagactaca catcatggcg agtgacgccg cgcatggtag   2040
ctcgctggac ggggtgacgc cgtcgagcaa gttcgacctg ccggtggact cggagcacaa   2100
ggccaagacc atccgcctgc tctccttcgc gaacccgcac atgcgtacct tccacctctc   2160
ctggatgtcc ttcttcacct gcgtcgtctc caccttcgcg gcggcgccgc tgatccccat   2220
catccgggag aacctgggcc tgaccaaggc cgacatcggc aacgccgggg tggcctccgt   2280
ctcgggcgcc atcttctcgc gcctcgccat gggcgccgtc tgcgacctgc tgggcccgcg   2340
ctacggctgc gccttcgtcg tcatgctggc ggcgcccgcg gtgttctgca tggccgtcat   2400
cgacagcgcc gcgggctacg tcgcgtgccg cttcctcatc ggcttctccc tcgccacctt   2460
cgtctcctgc cagtactgga ccagcaccat gttcaacatc aagatcatcg gcaccgtcaa   2520
cgcgctggcg tcggggtggg gcgacatggg cggcggcgcc acgcagctca tcatgccctt   2580
cgtctacgag gccatcctcc gctgcggcgc cacgccgttc gccgcgtggc gcatcgccta   2640
cttcgtgccg gggatcatgc acatcgccgt gggcatcctt gtgctaaccg cggggcagga   2700
cctccccgac ggcaacctcc gcagcctccg gaagcagcag cagcagcagc agcagggtga   2760
cggcggcgat gccagctgct gccgcaggga cagcttctcc agggtgctct ggcacgccgt   2820
cgccaactac cgcacctggg tcttcgtctt cgtgtacggc tacagcatgg gcgtgcagct   2880
caccaccaac aacatcatcg ccgagttcta ctacgaccag ttcgagctcg acatccgcgt   2940
ggccggcatc atcgccgcct gcttcggcat ggccaacctc gtgtcgcggc ccctgggcgg   3000
cgtgctctcc gacctcggcg cgcggtactg ggcatgcgc gcgcgcctct ggaacatctg   3060
```

-continued

```
gatcctccag accgccggcg gcgcgttctg cttctggctc ggccgcgcca gcgagctccc   3120
ggcctccgtc accgccatgg tgctcttctc cttctgcgcg caggccgcct gcggcgccac   3180
cttcggcgtc atccccttcg tctcccgccg ctcgctgggc gtcatctccg ggctcacggg   3240
cgccggcggc aacgtgggcg ccgggctcac gcagctgctc ttcttcacca cgtccagcta   3300
ctccacgagg aagggcatcg agaacatggg catcatggcc atggcgtgca cgctgccgct   3360
cgtcctcgtg cacttcccgc agtggggttc catgctcctg ccgcccagcg ccgacgccga   3420
cgaggagcgg tactatgcct ccgagtggag cgaggacgag aagagcgtag gccgtcacag   3480
cgcaagccta aagttcgccg agaacagccg gtccgagcgt ggcaagcgca acgccgtcgc   3540
cgtcctcgcc acggccgcgg ccacgccgga gcacgtcgtg taacaactag cgtacgtact   3600
tgtaggttct gatcgagcat acagcaaact gtgtaatgta ctctagcagt ctagcttgct   3660
ccgatactcc tgcttccaac aaaattatga aacataggct aatatggatc ggtgtacacg   3720
tacgtcgtag tatttcctgt gcaacataca caattcagta aatgaacaaa ctttgctcat   3780
gtgcattctt ctgcaaagta caaataaaat caaatagaga ggccaggaca acgtctatga   3840
tctatcaact tggttgttaa aattaaagaa aaccaactgg agtccaacac ccacaaaaca   3900
ttttgtctct aacacgttgt tgtc                                          3924
```

<210> SEQ ID NO 35
<211> LENGTH: 1569
<212> TYPE: DNA
<213> ORGANISM: Zea mays

<400> SEQUENCE: 35

```
atggcgagtg acgccgcgca tggtagctcg ctggacgggg tgacgccgtc gagcaagttc     60
gacctgccgg tggactcgga gcacaaggcc aagaccatcc gcctgctctc cttcgcgaac    120
ccgcacatgc gtaccttcca cctctcctgg atgtccttct tcacctgcgt cgtctccacc    180
ttcgcggcgg cgccgctgat ccccatcatc cgggagaacc tgggcctgac caaggccgac    240
atcggcaacg ccggggtggc ctccgtctcg ggcgccatct tctcgcgcct cgccatgggc    300
gccgtctgcg acctgctggg cccgcgctac ggctgcgcct tcgtcgtcat gctggcggcg    360
cccgcggtgt tctgcatggc cgtcatcgac agcgccgcgg gctacgtcgc gtgccgcttc    420
ctcatcggct tctccctcgc caccttcgtc tcctgccagt actggaccag caccatgttc    480
aacatcaaga tcatcggcac cgtcaacgcg ctggcgtcgg ggtggggcga catgggcggc    540
ggcgccacgc agctcatcat gcccttcgtc tacgaggcca tcctccgctg cggcgccacg    600
ccgttcgccg cgtggcgcat cgcctacttc gtgccgggga tcatgcacat cgccgtgggc    660
atccttgtgc taaccgcggg gcaggacctc cccgacggca acctccgcag cctccggaag    720
cagcagcagc agcagcagca gggtgacggc ggcgatgcca gctgctgccg cagggacagc    780
ttctccaggg tgctctggca cgccgtcgcc aactaccgca cctgggtctt cgtcttcgtg    840
tacggctaca gcatgggcgt gcagctcacc accaacaaca tcatcgccga gttctactac    900
gaccagttcg agctcgacat ccgcgtggcc ggcatcatcg ccgcctgctt cggcatggcc    960
aacctcgtgt cgcggcccct gggcggcgtg ctctccgacc tcggcgcgcg gtactggggc   1020
atgcgcgcgc gcctctggaa catctggatc ctccagaccg ccggcggcgc gttctgcttc   1080
tggctcggcc gcgccagcga gctcccggcc tccgtcaccg ccatggtgct cttctccttc   1140
tgcgcgcagg ccgcctgcgg cgccaccttc ggcgtcatcc ccttcgtctc ccgccgctcg   1200
ctgggcgtca tctccgggct cacgggcgcc ggcggcaacg tgggcgccgg gctcacgcag   1260
```

```
ctgctcttct tcaccacgtc cagctactcc acgaggaagg gcatcgagaa catgggcatc   1320

atggccatgg cgtgcacgct gccgctcgtc ctcgtgcact tcccgcagtg ggttccatg    1380

ctcctgccgc ccagcgccga cgccgacgag gagcggtact atgcctccga gtggagcgag   1440

gacgagaaga gcgtaggccg tcacagcgca agcctaaagt tcgccgagaa cagccggtcc   1500

gagcgtggca agcgcaacgc cgtcgccgtc ctcgccacgg ccgcggccac gccggagcac   1560

gtcgtgtaa                                                           1569


<210> SEQ ID NO 36
<211> LENGTH: 522
<212> TYPE: PRT
<213> ORGANISM: Zea mays

<400> SEQUENCE: 36

Met Ala Ser Asp Ala Ala His Gly Ser Ser Leu Asp Gly Val Thr Pro
1               5                   10                  15

Ser Ser Lys Phe Asp Leu Pro Val Asp Ser Glu His Lys Ala Lys Thr
            20                  25                  30

Ile Arg Leu Leu Ser Phe Ala Asn Pro His Met Arg Thr Phe His Leu
        35                  40                  45

Ser Trp Met Ser Phe Phe Thr Cys Val Val Ser Thr Phe Ala Ala Ala
    50                  55                  60

Pro Leu Ile Pro Ile Ile Arg Glu Asn Leu Gly Leu Thr Lys Ala Asp
65                  70                  75                  80

Ile Gly Asn Ala Gly Val Ala Ser Val Ser Gly Ala Ile Phe Ser Arg
                85                  90                  95

Leu Ala Met Gly Ala Val Cys Asp Leu Leu Gly Pro Arg Tyr Gly Cys
            100                 105                 110

Ala Phe Val Val Met Leu Ala Ala Pro Ala Val Phe Cys Met Ala Val
        115                 120                 125

Ile Asp Ser Ala Ala Gly Tyr Val Ala Cys Arg Phe Leu Ile Gly Phe
    130                 135                 140

Ser Leu Ala Thr Phe Val Ser Cys Gln Tyr Trp Thr Ser Thr Met Phe
145                 150                 155                 160

Asn Ile Lys Ile Ile Gly Thr Val Asn Ala Leu Ala Ser Gly Trp Gly
                165                 170                 175

Asp Met Gly Gly Gly Ala Thr Gln Leu Ile Met Pro Phe Val Tyr Glu
            180                 185                 190

Ala Ile Leu Arg Cys Gly Ala Thr Pro Phe Ala Ala Trp Arg Ile Ala
        195                 200                 205

Tyr Phe Val Pro Gly Ile Met His Ile Ala Val Gly Ile Leu Val Leu
    210                 215                 220

Thr Ala Gly Gln Asp Leu Pro Asp Gly Asn Leu Arg Ser Leu Arg Lys
225                 230                 235                 240

Gln Gln Gln Gln Gln Gln Gln Gly Asp Gly Gly Asp Ala Ser Cys Cys
                245                 250                 255

Arg Arg Asp Ser Phe Ser Arg Val Leu Trp His Ala Val Ala Asn Tyr
            260                 265                 270

Arg Thr Trp Val Phe Val Phe Val Tyr Gly Tyr Ser Met Gly Val Gln
        275                 280                 285

Leu Thr Thr Asn Asn Ile Ile Ala Glu Phe Tyr Tyr Asp Gln Phe Glu
    290                 295                 300

Leu Asp Ile Arg Val Ala Gly Ile Ile Ala Ala Cys Phe Gly Met Ala
305                 310                 315                 320
```

-continued

```
Asn Leu Val Ser Arg Pro Leu Gly Gly Val Leu Ser Asp Leu Gly Ala
                325                 330                 335

Arg Tyr Trp Gly Met Arg Ala Arg Leu Trp Asn Ile Trp Ile Leu Gln
            340                 345                 350

Thr Ala Gly Gly Ala Phe Cys Phe Trp Leu Gly Arg Ala Ser Glu Leu
        355                 360                 365

Pro Ala Ser Val Thr Ala Met Val Leu Phe Ser Phe Cys Ala Gln Ala
    370                 375                 380

Ala Cys Gly Ala Thr Phe Gly Val Ile Pro Phe Val Ser Arg Arg Ser
385                 390                 395                 400

Leu Gly Val Ile Ser Gly Leu Thr Gly Ala Gly Gly Asn Val Gly Ala
                405                 410                 415

Gly Leu Thr Gln Leu Leu Phe Phe Thr Thr Ser Ser Tyr Ser Thr Arg
            420                 425                 430

Lys Gly Ile Glu Asn Met Gly Ile Met Ala Met Ala Cys Thr Leu Pro
        435                 440                 445

Leu Val Leu Val His Phe Pro Gln Trp Gly Ser Met Leu Leu Pro Pro
    450                 455                 460

Ser Ala Asp Ala Asp Glu Glu Arg Tyr Tyr Ala Ser Glu Trp Ser Glu
465                 470                 475                 480

Asp Glu Lys Ser Val Gly Arg His Ser Ala Ser Leu Lys Phe Ala Glu
                485                 490                 495

Asn Ser Arg Ser Glu Arg Gly Lys Arg Asn Ala Val Ala Val Leu Ala
            500                 505                 510

Thr Ala Ala Ala Thr Pro Glu His Val Val
        515                 520


<210> SEQ ID NO 37
<211> LENGTH: 2014
<212> TYPE: DNA
<213> ORGANISM: Zea mays

<400> SEQUENCE: 37

ttcgagggca atgggttcca aagaatgtca tttgaattag acacttagtt atttatgaaa     60

aggttttttc tccccgagtt aatttgcttc caaactataa ttaaccctaa gcaaggtgtt    120

agttatttgt tttgacggtt tatatatccg tgttagcttg gtggctagct tgtatccatt    180

tgacttgacg gcacatgcat gcatgcgtgg agtgcaccgt gcggcggttt gtgacgcggt    240

gccaaacgtg caattgactc attgagtagt catcagcagg cttgcgatca ttagacacta    300

acaagcatta atatttgctg catatatata tatacacaca catgcttcac tgacgacgct    360

tgcaacttga tcttgttaat tattatatat cctaagcaca acgaacaaac cttagatatg    420

cgaccatgcc ttgagtagag cgtgaaaaat agggggtgaa aaaaagggac gagtaattat    480

agatgacact atttgatatt gtttaaagat gagataggga atgtgctgaa tagatcaatt    540

tttaatcagg gatggtaggg actagtattt cctctatgat tttccatgta acacctttga    600

atatacaata ataataagaa gccaccaacc tttgaattat tatctgttcc aatatattag    660

atgaggggtg tatcggaatt tgacttccga gttgttcttg cgtgtccgta cgctcgtacg    720

gtagctcgtt gggttgttgt accagccatc ctgctactgc gcaacgaaat gcattggtca    780

tctcaattaa gtccaaagat tgtagtcgta aacatgcagc caataagagc aaggataata    840

gtttagccat tgatatgtct tctaaagcta attattactg tattggaccc acctcgtact    900

ctcattctct caccacttgt ttcggaatct gtactgctac aaccagctct tagtcgactg    960
```

-continued

```
ataattaact acccgctttt tctcttctct cccctccaac tgcaaaaatc taatgtggca   1020
aaccatttag cctgcttaca tcgtcaaaaa tctaatgtgg taaagtgtga agtgtcctaa   1080
agttttagtc cttaatttct ttcaataaac taaactaaac tttagaaaac tcaaacaagt   1140
cctcatgttt gcacatttta ggtctcgttt ggtttgaggg actaaagatt agtccctcca   1200
ttttagtccc atttagttac taaattacca aacagtagga ctaaaacagg gactaaattg   1260
ttttagtccc tagtccctta agatggctaa aagggactaa accatattaa ttccacattt   1320
gcccctcatt tagttcaatt gtactaatag caggagaatg ttaaaagtca ttttaatctt   1380
cttatgagtc atttaggccc tgtttggttc cattagtcat agaactaaag tttagttgta   1440
gggactaaat agattctaaa tacattaaat gcaacacata aagaccaaaa tgcccttttt   1500
tgtttgacac ccctttteta gcaagggtat ttggagtaaa tgttgccctt tggtcccttt   1560
tagcacccat gtgagggact agagactaaa accaattagt ccctacttta gtcattccgt   1620
ttagcaaaat agagactaaa cgagactaaa aacgagaggc taaagattag tctctctaac   1680
caaacgggac ctaaaattac tatctgtatg tatctgttgg atggaaaagt cagaacgtcg   1740
tggggaccac cacgctacca catggtacgg taatgtcaga aagtcgctat cttcttcgat   1800
ctgcatctcc actccagcca gcgctgctta tcatcagcat tcacgaagcc gcccaacgat   1860
aataaaaaat gtcagcgcga tcgcgcactg cctataaaac cccggccgtc gcgtccatgg   1920
cgtttcagga tccgagcacc agaaagaagc tgagttagct agggtcaaga aagtagtcag   1980
cactcagcag gaaaagaagc agagactaca catc                               2014
```

<210> SEQ ID NO 38
<211> LENGTH: 1014
<212> TYPE: DNA
<213> ORGANISM: Zea mays

<400> SEQUENCE: 38

```
tgcaaaaatc taatgtggca aaccatttag cctgcttaca tcgtcaaaaa tctaatgtgg     60
taaagtgtga agtgtcctaa agttttagtc cttaatttct ttcaataaac taaactaaac    120
tttagaaaac tcaaacaagt cctcatgttt gcacatttta ggtctcgttt ggtttgaggg    180
actaaagatt agtccctcca ttttagtccc atttagttac taaattacca aacagtagga    240
ctaaaacagg gactaaattg ttttagtccc tagtccctta agatggctaa aagggactaa    300
accatattaa ttccacattt gcccctcatt tagttcaatt gtactaatag caggagaatg    360
ttaaaagtca ttttaatctt cttatgagtc atttaggccc tgtttggttc cattagtcat    420
agaactaaag tttagttgta gggactaaat agattctaaa tacattaaat gcaacacata    480
aagaccaaaa tgcccttttt tgtttgacac ccctttteta gcaagggtat ttggagtaaa    540
tgttgccctt tggtcccttt tagcacccat gtgagggact agagactaaa accaattagt    600
ccctacttta gtcattccgt ttagcaaaat agagactaaa cgagactaaa aacgagaggc    660
taaagattag tctctctaac caaacgggac ctaaaattac tatctgtatg tatctgttgg    720
atggaaaagt cagaacgtcg tggggaccac cacgctacca catggtacgg taatgtcaga    780
aagtcgctat cttcttcgat ctgcatctcc actccagcca gcgctgctta tcatcagcat    840
tcacgaagcc gcccaacgat aataaaaaat gtcagcgcga tcgcgcactg cctataaaac    900
cccggccgtc gcgtccatgg cgtttcagga tccgagcacc agaaagaagc tgagttagct    960
agggtcaaga aagtagtcag cactcagcag gaaaagaagc agagactaca catc          1014
```

<210> SEQ ID NO 39

<211> LENGTH: 18
<212> TYPE: DNA
<213> ORGANISM: Artificial
<220> FEATURE:
<223> OTHER INFORMATION: Primer

<400> SEQUENCE: 39
cggggttcgc cagcctcc 18

<210> SEQ ID NO 40
<211> LENGTH: 17
<212> TYPE: DNA
<213> ORGANISM: Artificial
<220> FEATURE:
<223> OTHER INFORMATION: Primer

<400> SEQUENCE: 40
agtgggctcc ctctccg 17

<210> SEQ ID NO 41
<211> LENGTH: 18
<212> TYPE: DNA
<213> ORGANISM: Artificial
<220> FEATURE:
<223> OTHER INFORMATION: Primer

<400> SEQUENCE: 41
gctcgtcatg ccgctcgc 18

<210> SEQ ID NO 42
<211> LENGTH: 18
<212> TYPE: DNA
<213> ORGANISM: Artificial
<220> FEATURE:
<223> OTHER INFORMATION: Primer

<400> SEQUENCE: 42
gcactggatg tcgggcat 18

<210> SEQ ID NO 43
<211> LENGTH: 20
<212> TYPE: DNA
<213> ORGANISM: Artificial
<220> FEATURE:
<223> OTHER INFORMATION: Primer

<400> SEQUENCE: 43
aattaaccct cactaaaggg 20

<210> SEQ ID NO 44
<211> LENGTH: 22
<212> TYPE: DNA
<213> ORGANISM: Artificial
<220> FEATURE:
<223> OTHER INFORMATION: Primer

<400> SEQUENCE: 44
gtaatacgac tcactatagg gc 22

<210> SEQ ID NO 45
<211> LENGTH: 5812
<212> TYPE: DNA
<213> ORGANISM: Zea mays

<400> SEQUENCE: 45
ggttggcgag cgggtgtggt ctgggcagtg gcaatggcgg gggcagcgaa gaggagggcg 60

-continued

```
gtgggggagg gagtggcgag agagggagga aagagagatg aggcgtgtgc aacaacagga    120
gacgtacgtc ggcgcttgtc agggtttcgt gcaatgagat atgggtgtgt gggttgattc    180
taaagtaatg ttgggagtgt tttgaaaaaa tttgacgcag gacgaccgtt gaaactagtg    240
ctttaagtat agtagagatt taaaattaaa gtggacacat ggcccacata ctgaatatta    300
aactgcagat attacacttt atcttagcca aaaggtcgag aaatgtatga gttaaaaaag    360
gagacatgcc cttttataac tcactcggtc gcttgtccta cttcaactat taagtttgta    420
ctattcgaga acgttgtatt acatgtggtt ttgtgtcata ttgggtttgg gtgttttctc    480
actaactatc tgggtgrtaa gattgctaga cgagacgtag aggagaaaaa catatctact    540
ctacaccgtt tcatgcgtga catgatatac gaaacccaag ttttaaagga gtaaaaataa    600
aaataaagat agataaacca taaattacta tctacaaaaa cgtagacagc aggctagata    660
ccaaggaggg caagggcaag atggccgagg cacttgtgcc cgccggagct ttggatgcaa    720
gatgcaacac actagctgtt cggagacaat cggtgtatca aagaagtaaa aaaatttgga    780
tgaaacacac aagctgttac agtggctcta gaggaaagat tgggattttc attttctgat    840
gcattcttta cgcagggcaa gagtgttatt tctgctgatg tacacataat tagaagactc    900
tctttttttt taattggtgc attttcctta tgaaccacat gcgtaaaaaa ctgggccgaa    960
gttcatcacg tcgttgtgcc ctggcacgtc accaatcgca acgctcagct agaagctgct   1020
gctgaatgcg caccacagac tcttgggcga aaccagttca tctgtttttt ttttacgcgc   1080
agagcggcag agacgacaga gatatgacga tgtatattat ggattaatta aaaagcgatc   1140
cggagtttta gatgtctatt tccaccctga ggagccaaaa aggattcatc ggagattcag   1200
gaatttctgc atctgcaatc attggaccag agcggcggta gtatattccg atctacaggc   1260
ttgcccggcc gagatcctct ggggtcaacc tcgctgctac gcgggagggc gggcgcagcc   1320
cctgggcctc acggagagac tccttcacgt ctccgggccc actacagaag gccgagtagt   1380
ggcatccgac gctcctgggc ccacttgccg tctcgagtca ccatacgcgc gggcccccag   1440
cccacgtaat taaagtgtga ctgggttagt cctgtccgag gctagcgcag agtgggatgc   1500
gatgcgacaa aacggccgct agattggatt attagtatag agagtataca gattagagag   1560
ttctggaagg ttggttagct catggagttg atcgattccc gctcgtgtca aacacgtata   1620
tgttcacctt catatttatc attcgtgtaa attcacggag agtaatatac attgcttact   1680
ggagttttgt gtcaaccaat aaccgatcaa agatgttgtt atttactgca tccacactaa   1740
taaaacacat aatgtgttct aattttgtct tgggktaatt ttgtcctgga gatgacttta   1800
gcttgagggt ggtgttacga cgaaaaacaa tgccgtatag ttctaaggtt agatttttgc   1860
aattaatcaa tcacatcgat atgctaatgc taaattgcta atgctatgct ttaaattgct   1920
aatgcaatga ggtgatggca ggcagccgca gtccctttc atggcctcgg ggagccggtg   1980
gtaggcacgt acaaaagcca cacggacatg caacgcggcg ccctgcatgc acccgccgcg   2040
acaccgcttg ccctccgcct tctcgttctc ggtccaccac cttctattcc atttccacac   2100
ccatcaccac acacatttaa aaccaccagc gagtatctaa acctttcacc ccattggtcg   2160
cccacaggtc tggaactagt agccactagc tccattctct gcttggctgt ggtagatctc   2220
ttcctgcaca gccacgaggc caggcaggca gacgtcacta gctatggtgg cgatggggaa   2280
aaagcagcag ctggccgacg acgaagagaa ctgctgctac ggcgtcggca gctctgaggc   2340
ggagtgcggc gtcgatgccg agttcagggc gacggatctg cgccctctgt cactgctgtc   2400
gccgcacacg caggcgttcc acctcgcctg gctctccctc ttcgcctgct tcttcgcggc   2460
```

-continued ctttgccgcc ccgcccatcc tccctgcgct gcggccggcg ctcgtgctcg cgccctcgga 2520
cgcccccgcc gccgcagtgg gctccctctc cgccacgctg gtcggcaggc ttgccatggg 2580
gcccgcatgc gacctcctcg gcccgcgccg cgcgtcgggg ttcgccagcc tcctggccgc 2640
gctcgccgtc gcggtcaccg cggtcaccgc gtcgtcgccc gcggggttcg tcgcgctgcg 2700
cttcgtggcg ggcctctccc tcgccaactt cgtcgccaac cagcactgga tgtcgggcat 2760
cttcgcgccc tccgccgtgg ggctcgccaa cgccgtcacg gccggctggg ccaacgtcgg 2820
cagcgccgcg gcgcagctcg tcatgccgct cgcgtacgag ctcgtcctcc gcctcggcgt 2880
gcccatcacc gtcgcctggc gcgtcaccta cctcctcccc tgcgcgctcc tcatcaccac 2940
gggcctcgcc gtcctcgcct tcccytacga cctcccgcgc ggcgccggcg tcggcggcgg 3000
agccaagacc ggcaagagct tgtggaaggt ggtgcgcgga ggggtcagca actaccgcgc 3060
gtgggtgctc gcgctcacct acggctactg ctacggcgtc gagctcatca tggagaacgt 3120
ggccgccgac ttcttccgga aacgtttcca cctccccatg gaggctgcgg gcgccgcggc 3180
ggcgtgcttc ggcgcgatga acgcggtggc gcggcccgcg ggcgggttgg cgtcggacgc 3240
ggtggcgaga ctgttcggca tgcgcgggag gctgtggctt ctctgggccg tgcagaccac 3300
cggcgcggca ctgtgcgtgc tggtcggcag gatgggcgca gcggaagcgc cgtcgctggc 3360
ggccaccatg gcggtcatgg tgctgtgcgc cgcgtttgtg caggcctcgt cggggctcac 3420
cttcggcatc gtcccgttcg tgtccaagag gtgaatccaa caaacttctt acaacatcta 3480
atacagatta ttttgcgtcg gattaattca aaaatagtta tatatagatt ctaagtatat 3540
attcacatat agattttttt tccacccaaa aagttataac ttacaaggaa ggacatctat 3600
catgcatgtt tcataaacaa attaactaaa gatttttctg tgtttggtta tttagatata 3660
aatagatctt gaattatata ttgacgtaca gatcccctcc ctcaaagtta taacgtaaat 3720
aataagggca aagacgttga agctgatata tacctctcaa ttgaaagatg gccacgccag 3780
ctagcttttt gaagatattt tctaagcaca caaacaccta attactgctc cgttcattta 3840
aaattatagc tttaaaaatt aaaatcaaag cgtttaatta gaaaaatcta aaattcttca 3900
agctataagt ttaattagaa aaatcaaaac atttaataat ttaaaataga tgaaacatac 3960
ccaactaaga gggccacatc gttatcatag gccctaatat agattctata gtagaatcct 4020
ggtatactac tattgttgat gttcacctgt tttctgatat ttgtggacga aaataatcag 4080
agaggtttcc aacaataaag caactcatta attatttctc tgaacatata ggaggacgtg 4140
tttggttgcc acgctagcca tgtccaagct cacgcgcgtg tacttggtta tctgcatgta 4200
attaacaaag cgaactcgca cgcacgcgta caacctaagc accttttcca cctcctacat 4260
gcatatgtag ggaagcggcc gggtccgcgc gagtcaggag ctctcaactc acaaaccaat 4320
cacgtccata acaaccaagg actgtaaaat gtggcgtaca tattttttat gtctaagggc 4380
tagtttgaga ctccattatc ctaagagaaa gtgaattaat tagattccta aactagccct 4440
gatatgaaaa agaaacaccg gaaaaactac ggtagcaaaa tagccagtgg aaaataaact 4500
tgtcgtcaca agttactctt ctattccaat acctcttgta tatgtatttt aaagacacgg 4560
ccttaaacat tttttttaaa aaaaaaaaat ccatctaatg aattagccta ggaatatcat 4620
gcatggtttt ctcaaaataa tgtcttcgac cccatttggt cacaaattaa tttatctaaa 4680
ctagatctaa ctcgtagcat gagttttaga gcgccagagg caatttgtta ttacagaaag 4740
attaaggtca tgtttgatac acttcagctt tacaggtgaa ggtgttttaa aaaaaaataa 4800
cttcaccaat aacgattgga gaaggaaatg aggaagaaag ctacccaaag ttactttttc 4860

-continued

```
ggcttcacct ctgtctaatt ctgcgtctga gcataaaaag gagttttacc tatgaatctt   4920

tttgaaaaaa aagaatgttt acaaaaaaat aaatagctca acaacttata aagcttctga   4980

ttaatctgta ctaaaaaaga actaactata aacaaaggtc aaagaaacca tgacacattt   5040

cttacggctt gtgttgggtc acttaatttc ggtggtgtgt gtgcaggtcg ttgggcgtgg   5100

tgtccgggat gacggcgagc ggcggcgcgg tgggcgcgat cgtgacgaac cggctcttct   5160

tcagcgggtc gcggtacacc attgaggagg cyatctcgtt gaccggcgcc gccagcctcg   5220

tgtgcacgct cccgctggcc ctcgtccact tcccgcgcca cggtggcatg ctctgcggcc   5280

caaccgccgt cgtcgatggc gacgatgcag gatacgacaa cgataatagt gctggagatt   5340

acacgctcct caaatgaatt gaggaacaaa tgtatgcaac ggggggtcg catgtgaact    5400

ttgtacatag cacatccaat ggccttgata gattagcaaa cgattactca tggtttgttt   5460

caggatcagg ggtgcgatat gagcgacaca cggatagaaa tatgtcgagt ggcttcgtct   5520

gtcgatcacc tgcacataaa tagatagaga gtagagatgg ctcgtaggtt gttcacgtgt   5580

cgctgccgca ttggcaattg cgtgtcttat gtttgtgttg gttcgaagag tgagacaata   5640

ataagttgtc ggtgttcgaa tcagtaccaa cgagtaaatt gtgtatgcgt gcatgttttg   5700

gatttggatg atgtgttcag tgaacgcaag atttatactg attcggatag aacgtcccta   5760

cttctagtct tcgatggctc gcgtaatcga taacttcttg ctgaatgctc at           5812
```

<210> SEQ ID NO 46
<211> LENGTH: 2263
<212> TYPE: DNA
<213> ORGANISM: Zea mays

<400> SEQUENCE: 46

```
ggttggcgag cgggtgtggt ctgggcagtg gcaatggcgg gggcagcgaa gaggagggcg     60

gtgggggagg gagtggcgag agagggagga aagagagatg aggcgtgtgc aacaacagga    120

gacgtacgtc ggcgcttgtc agggtttcgt gcaatgagat atgggtgtgt gggttgattc    180

taaagtaatg ttgggagtgt tttgaaaaaa tttgacgcag gacgaccgtt gaaactagtg    240

ctttaagtat agtagagatt taaaattaaa gtggacacat ggcccacata ctgaatatta    300

aactgcagat attacacttt atcttagcca aaaggtcgag aaatgtatga gttaaaaaag    360

gagacatgcc cttttataac tcactcggtc gcttgtccta cttcaactat taagtttgta    420

ctattcgaga acgttgtatt acatgtggtt ttgtgtcata ttgggtttgg gtgttttctc    480

actaactatc tgggtgrtaa gattgctaga cgagacgtag aggagaaaaa catatctact    540

ctacaccgtt tcatgcgtga catgatatac gaaacccaag ttttaaagga gtaaaaataa    600

aaataaagat agataaacca taaattacta tctacaaaaa cgtagacagc aggctagata    660

ccaaggaggg caagggcaag atggccgagg cacttgtgcc cgccggagct ttggatgcaa    720

gatgcaacac actagctgtt cggagacaat cggtgtatca aagaagtaaa aaaatttgga    780

tgaaacacac aagctgttac agtggctcta gaggaaagat tgggattttc attttctgat    840

gcattcttta cgcagggcaa gagtgttatt tctgctgatg tacacataat tagaagactc    900

tctttttttt taattggtgc attttcctta tgaaccacat gcgtaaaaaa ctgggccgaa    960

gttcatcacg tcgttgtgcc ctggcacgtc accaatcgca acgctcagct agaagctgct   1020

gctgaatgcg caccacagac tcttgggcga aaccagttca tctgtttttt ttttacgcgc   1080

agagcggcag agacgacaga gatatgacga tgtatattat ggattaatta aaaagcgatc   1140

cggagtttta gatgtctatt tccaccctga ggagccaaaa aggattcatc ggagattcag   1200
```

-continued

```
gaatttctgc atctgcaatc attggaccag agcggcggta gtatattccg atctacaggc   1260

ttgcccggcc gagatcctct ggggtcaacc tcgctgctac gcgggagggc gggcgcagcc   1320

cctgggcctc acggagagac tccttcacgt ctccgggccc actacagaag gccgagtagt   1380

ggcatccgac gctcctgggc ccacttgccg tctcgagtca ccatacgcgc gggcccccag   1440

cccacgtaat taaagtgtga ctgggttagt cctgtccgag gctagcgcag agtgggatgc   1500

gatgcgacaa aacggccgct agattggatt attagtatag agagtataca gattagagag   1560

ttctggaagg ttggttagct catggagttg atcgattccc gctcgtgtca aacacgtata   1620

tgttcacctt catatttatc attcgtgtaa attcacggag agtaatatac attgcttact   1680

ggagttttgt gtcaaccaat aaccgatcaa agatgttgtt atttactgca tccacactaa   1740

taaaacacat aatgtgttct aattttgtct tgggktaatt ttgtcctgga gatgacttta   1800

gcttgagggt ggtgttacga cgaaaaacaa tgccgtatag ttctaaggtt agatttttgc   1860

aattaatcaa tcacatcgat atgctaatgc taaattgcta atgctatgct ttaaattgct   1920

aatgcaatga ggtgatggca ggcagccgca gtccctttc atggcctcgg ggagccggtg    1980

gtaggcacgt acaaaagcca cacggacatg caacgcggcg ccctgcatgc acccgccgcg   2040

acaccgcttg ccctccgcct tctcgttctc ggtccaccac cttctattcc atttccacac   2100

ccatcaccac acacatttaa aaccaccagc gagtatctaa acctttcacc ccattggtcg   2160

cccacaggtc tggaactagt agccactagc tccattctct gcttggctgt ggtagatctc   2220

ttcctgcaca gccacgaggc caggcaggca gacgtcacta gct                     2263
```

```
<210> SEQ ID NO 47
<211> LENGTH: 1263
<212> TYPE: DNA
<213> ORGANISM: Zea mays

<400> SEQUENCE: 47

acgctcagct agaagctgct gctgaatgcg caccacagac tcttgggcga aaccagttca     60

tctgtttttt ttttacgcgc agagcggcag agacgacaga gatatgacga tgtatattat    120

ggattaatta aaaagcgatc cggagtttta gatgtctatt tccaccctga ggagccaaaa    180

aggattcatc ggagattcag gaatttctgc atctgcaatc attggaccag agcggcggta    240

gtatattccg atctacaggc ttgcccggcc gagatcctct ggggtcaacc tcgctgctac    300

gcgggagggc gggcgcagcc cctgggcctc acggagagac tccttcacgt ctccgggccc    360

actacagaag gccgagtagt ggcatccgac gctcctgggc ccacttgccg tctcgagtca    420

ccatacgcgc gggcccccag cccacgtaat taaagtgtga ctgggttagt cctgtccgag    480

gctagcgcag agtgggatgc gatgcgacaa aacggccgct agattggatt attagtatag    540

agagtataca gattagagag ttctggaagg ttggttagct catggagttg atcgattccc    600

gctcgtgtca aacacgtata tgttcacctt catatttatc attcgtgtaa attcacggag    660

agtaatatac attgcttact ggagttttgt gtcaaccaat aaccgatcaa agatgttgtt    720

atttactgca tccacactaa taaaacacat aatgtgttct aattttgtct tgggktaatt    780

ttgtcctgga gatgacttta gcttgagggt ggtgttacga cgaaaaacaa tgccgtatag    840

ttctaaggtt agatttttgc aattaatcaa tcacatcgat atgctaatgc taaattgcta    900

atgctatgct ttaaattgct aatgcaatga ggtgatggca ggcagccgca gtccctttc     960

atggcctcgg ggagccggtg gtaggcacgt acaaaagcca cacggacatg caacgcggcg   1020

ccctgcatgc acccgccgcg acaccgcttg ccctccgcct tctcgttctc ggtccaccac   1080
```

-continued

```
cttctattcc atttccacac ccatcaccac acacatttaa aaccaccagc gagtatctaa   1140

acctttcacc ccattggtcg cccacaggtc tggaactagt agccactagc tccattctct   1200

gcttggctgt ggtagatctc ttcctgcaca gccacgaggc caggcaggca gacgtcacta   1260

gct                                                                 1263


<210> SEQ ID NO 48
<211> LENGTH: 1455
<212> TYPE: DNA
<213> ORGANISM: Zea mays

<400> SEQUENCE: 48

atggtggcga tggggaaaaa gcagcagctg gccgacgacg aagagaactg ctgctacggc     60

gtcggcagct ctgaggcgga gtgcggcgtc gatgccgagt tcagggcgac ggatctgcgc    120

cctctgtcac tgctgtcgcc gcacacgcag gcgttccacc tcgcctggct ctccctcttc    180

gcctgcttct tcgcggcctt tgccgccccg cccatcctcc ctgcgctgcg gccggcgctc    240

gtgctcgcgc cctcggacgc ccccgccgcc gcagtgggct ccctctccgc cacgctggtc    300

ggcaggcttg ccatggggcc cgcatgcgac ctcctcggcc cgcgccgcgc gtcggggttc    360

gccagcctcc tggccgcgct cgccgtcgcg gtcaccgcgg tcaccgcgtc gtcgcccgcg    420

gggttcgtcg cgctgcgctt cgtggcgggc ctctccctcg ccaacttcgt cgccaaccag    480

cactggatgt cgggcatctt cgcgccctcc gccgtggggc tcgccaacgc cgtcacggcc    540

ggctgggcca acgtcggcag cgccgcggcg cagctcgtca tgccgctcgc gtacgagctc    600

gtcctccgcc tcggcgtgcc catcaccgtc gcctggcgcg tcacctacct cctcccctgc    660

gcgctcctca tcaccacggg cctcgccgtc ctcgccttcc cytacgacct cccgcgcggc    720

gccggcgtcg gcggcggagc caagaccggc aagagcttgt ggaaggtggt gcgcggaggg    780

gtcagcaact accgcgcgtg ggtgctcgcg ctcacctacg gctactgcta cggcgtcgag    840

ctcatcatgg agaacgtggc cgccgacttc ttccggaaac gtttccacct ccccatggag    900

gctgcgggcg ccgcggcggc gtgcttcggc gcgatgaacg cggtggcgcg gcccgcgggc    960

gggttggcgt cggacgcggt ggcgagactg ttcggcatgc gcgggaggct gtggcttctc   1020

tgggccgtgc agaccaccgg cgcggcactg tgcgtgctgg tcggcaggat gggcgcagcg   1080

gaagcgccgt cgctggcggc caccatggcg gtcatggtgc tgtgcgccgc gtttgtgcag   1140

gcctcgtcgg ggctcacctt cggcatcgtc ccgttcgtgt ccaagaggtc gttgggcgtg   1200

gtgtccggga tgacggcgag cggcggcgcg gtgggcgcga tcgtgacgaa ccggctcttc   1260

ttcagcgggt cgcggtacac cattgaggag gcyatctcgt tgaccggcgc cgccagcctc   1320

gtgtgcacgc tcccgctggc cctcgtccac ttcccgcgcc acggtggcat gctctgcggc   1380

ccaaccgccg tcgtcgatgg cgacgatgca ggatacgaca acgataatag tgctggagat   1440

tacacgctcc tcaaa                                                    1455


<210> SEQ ID NO 49
<211> LENGTH: 485
<212> TYPE: PRT
<213> ORGANISM: Zea mays

<400> SEQUENCE: 49

Met Val Ala Met Gly Lys Lys Gln Gln Leu Ala Asp Asp Glu Glu Asn
1               5                   10                  15

Cys Cys Tyr Gly Val Gly Ser Ser Glu Ala Glu Cys Gly Val Asp Ala
            20                  25                  30
```

-continued

```
Glu Phe Arg Ala Thr Asp Leu Arg Pro Leu Ser Leu Leu Ser Pro His
        35                  40                  45

Thr Gln Ala Phe His Leu Ala Trp Leu Ser Leu Phe Ala Cys Phe Phe
    50                  55                  60

Ala Ala Phe Ala Ala Pro Pro Ile Leu Pro Ala Leu Arg Pro Ala Leu
65                  70                  75                  80

Val Leu Ala Pro Ser Asp Ala Pro Ala Ala Ala Val Gly Ser Leu Ser
                85                  90                  95

Ala Thr Leu Val Gly Arg Leu Ala Met Gly Pro Ala Cys Asp Leu Leu
            100                 105                 110

Gly Pro Arg Arg Ala Ser Gly Phe Ala Ser Leu Leu Ala Ala Leu Ala
        115                 120                 125

Val Ala Val Thr Ala Val Thr Ala Ser Ser Pro Ala Gly Phe Val Ala
    130                 135                 140

Leu Arg Phe Val Ala Gly Leu Ser Leu Ala Asn Phe Val Ala Asn Gln
145                 150                 155                 160

His Trp Met Ser Gly Ile Phe Ala Pro Ser Ala Val Gly Leu Ala Asn
                165                 170                 175

Ala Val Thr Ala Gly Trp Ala Asn Val Gly Ser Ala Ala Ala Gln Leu
            180                 185                 190

Val Met Pro Leu Ala Tyr Glu Leu Val Leu Arg Leu Gly Val Pro Ile
        195                 200                 205

Thr Val Ala Trp Arg Val Thr Tyr Leu Leu Pro Cys Ala Leu Leu Ile
    210                 215                 220

Thr Thr Gly Leu Ala Val Leu Ala Phe Pro Tyr Asp Leu Pro Arg Gly
225                 230                 235                 240

Ala Gly Val Gly Gly Gly Ala Lys Thr Gly Lys Ser Leu Trp Lys Val
                245                 250                 255

Val Arg Gly Gly Val Ser Asn Tyr Arg Ala Trp Val Leu Ala Leu Thr
            260                 265                 270

Tyr Gly Tyr Cys Tyr Gly Val Glu Leu Ile Met Glu Asn Val Ala Ala
        275                 280                 285

Asp Phe Phe Arg Lys Arg Phe His Leu Pro Met Glu Ala Ala Gly Ala
    290                 295                 300

Ala Ala Ala Cys Phe Gly Ala Met Asn Ala Val Ala Arg Pro Ala Gly
305                 310                 315                 320

Gly Leu Ala Ser Asp Ala Val Ala Arg Leu Phe Gly Met Arg Gly Arg
                325                 330                 335

Leu Trp Leu Leu Trp Ala Val Gln Thr Thr Gly Ala Ala Leu Cys Val
            340                 345                 350

Leu Val Gly Arg Met Gly Ala Ala Glu Ala Pro Ser Leu Ala Ala Thr
        355                 360                 365

Met Ala Val Met Val Leu Cys Ala Ala Phe Val Gln Ala Ser Ser Gly
    370                 375                 380

Leu Thr Phe Gly Ile Val Pro Phe Val Ser Lys Arg Ser Leu Gly Val
385                 390                 395                 400

Val Ser Gly Met Thr Ala Ser Gly Gly Ala Val Gly Ala Ile Val Thr
                405                 410                 415

Asn Arg Leu Phe Phe Ser Gly Ser Arg Tyr Thr Ile Glu Glu Ala Ile
            420                 425                 430

Ser Leu Thr Gly Ala Ala Ser Leu Val Cys Thr Leu Pro Leu Ala Leu
        435                 440                 445

Val His Phe Pro Arg His Gly Gly Met Leu Cys Gly Pro Thr Ala Val
    450                 455                 460
```

Val Asp Gly Asp Asp Ala Gly Tyr Asp Asn Asp Asn Ser Ala Gly Asp
465 470 475 480

Tyr Thr Leu Leu Lys
485

<210> SEQ ID NO 50
<211> LENGTH: 14
<212> TYPE: PRT
<213> ORGANISM: Zea maize
<220> FEATURE:
<221> NAME/KEY: UNSURE
<222> LOCATION: (1)..(14)
<223> OTHER INFORMATION: Xaa=any amino acid
<220> FEATURE:
<221> NAME/KEY: UNSURE
<222> LOCATION: (6)..(6)
<223> OTHER INFORMATION: Xaa can be any naturally occurring amino acid
<220> FEATURE:
<221> NAME/KEY: UNSURE
<222> LOCATION: (7)..(7)
<223> OTHER INFORMATION: Xaa can be any naturally occurring amino acid

<400> SEQUENCE: 50

Arg Leu Ala Met Gly Xaa Xaa Cys Asp Leu Leu Gly Pro Arg
1 5 10

<210> SEQ ID NO 51
<211> LENGTH: 28
<212> TYPE: PRT
<213> ORGANISM: Zea maize
<220> FEATURE:
<221> NAME/KEY: DOMAIN
<222> LOCATION: (1)..(28)
<223> OTHER INFORMATION: Xaa=any amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 51

Thr Phe Gly Xaa Xaa Pro Phe Val Ser Xaa Arg Ser Leu Gly Val Xaa
1 5 10 15

Ser Gly Xaa Thr Xaa Xaa Gly Gly Xaa Val Gly Ala
20 25

<210> SEQ ID NO 52
<211> LENGTH: 11
<212> TYPE: PRT
<213> ORGANISM: Zea maize
<220> FEATURE:
<221> NAME/KEY: DOMAIN
<222> LOCATION: (1)..(14)
<223> OTHER INFORMATION: Xaa=any amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 52

Cys Thr Leu Pro Leu Xaa Leu Val His Phe Pro
1 5 10

<210> SEQ ID NO 53
<211> LENGTH: 1561
<212> TYPE: DNA
<213> ORGANISM: Zea mays

<400> SEQUENCE: 53
tagctatata cacatgtctg gtctgacgac aatcaaaagg gatcgctagc tcgggctagc 60
cttcctatca ctgtcatgac atgtgctctg cctctgctgg ttgataagcc gtgcgccttc 120
tcgctaattc tttcttgtgc tagaggcgag tcaaacaaac gctgcacctc gtagccctta 180
atctgcgcta agggtcacat gaccctgttc cctatcgcta gttaccaacg acccattccc 240
cctgacagat acttacgacg cgtccgtacg cggcaggcct cggcagttcg gcatcaccag 300
caccggcgcc ggcattcgcc ccctgccagc cggttcgcag attcgcaggg cggagtcggc 360
cgcagttgcc gcatcccaaa cgcccgggaa cctttggggc ccctctacga gcaaatgaag 420
ttgctgcccc tggcttcgta aagctctgac ttttgatcac ttgattggca gtcgtactcc 480
tcgctcatag gccgacacgg ccgcaaagtc aactacccgc tccgccatcc ttcaaccccc 540
gccacgcgcc tatatatgtt cgcggccatg tccgtactag tcctccaacc cacaagccac 600
aaccccgagc tcagatccct cgcctcgtgt cgtgtctccg gtcgacgacg accaacagcc 660
agtgtgggcc agacggacac cgccgagcta tagcgcttgg tgatagcaag ggacgaccgg 720
cggccggacc ggagcacgta cgtacgtacc gcagcgatgg ctcggcagca aagcgtgcag 780
gccttgtgtg tgctggcggc gcttctcttc gccgcctccc tgccgtcgcc ggccgccgcg 840
ggggtgcacc tctcctcgct gcccaaagcg ctcgacgtca ccacctccgc caaacccggc 900
caagtcctgc acgccggcgt ggactcgctg acggtgacgt ggagcctgaa cgccacggag 960
ccggccggcg ccgacgccgg gtacaagggc gtgaaggtga agctgtgcta cgcgccggcg 1020
agccagaagg accgcgggtg gcgcaagtcc gaggacgaca tcagcaagga caaggcgtgc 1080
cagttcaagg tcaccgagca ggcgtacgcg gcggcggcgc ccggcagctt ccagtacgcc 1140
gtcgcccgcg acgtcccctc gggctcctac tacctgcgcg ccttcgccac ggacgcgtcg 1200
ggcgccgagg tggcctacgg ccagacggcg cccaccgccg ccttcgacgt cgccggcatc 1260
accggcatcc acgcctctct caagatcgcc gccggcgtct tctcggcctt ctccgtcgtc 1320
gcgctcgcct tcttcttcgt catcgagacc cgcaagaaga acaagtagaa cgagttgcgg 1380
ctgcgcgcca tacatgcata catgtaaatc gtcggcggcg atgagtggct gtcgttgctg 1440
attcattggt gcgcgcgact attttggtgt atcatgtaag ttacttttct gcagtgtgtg 1500
cgtcaaaatt accaaataat aacttaagtt tctctgctaa aaaaaaaaaa aaaaaaaaaa 1560
a 1561

<210> SEQ ID NO 54
<211> LENGTH: 612
<212> TYPE: DNA
<213> ORGANISM: Zea mays

<400> SEQUENCE: 54
atggctcggc agcaaagcgt gcaggccttg tgtgtgctgg cggcgcttct cttcgccgcc 60
tccctgccgt cgccggccgc cgcgggggtg cacctctcct cgctgcccaa agcgctcgac 120
gtcaccacct ccgccaaacc cggccaagtc ctgcacgccg gcgtggactc gctgacggtg 180
acgtggagcc tgaacgccac ggagccggcc ggcgccgacg ccgggtacaa gggcgtgaag 240
gtgaagctgt gctacgcgcc ggcgagccag aaggaccgcg ggtggcgcaa gtccgaggac 300
gacatcagca aggacaaggc gtgccagttc aaggtcaccg agcaggcgta cgcggcggcg 360
gcgcccggca gcttccagta cgccgtcgcc cgcgacgtcc cctcgggctc ctactacctg 420
cgcgccttcg ccacggacgc gtcgggcgcc gaggtggcct acggccagac ggcgcccacc 480
gccgccttcg acgtcgccgg catcaccggc atccacgcct ctctcaagat cgccgccggc 540
gtcttctcgg ccttctccgt cgtcgcgctc gccttcttct tcgtcatcga gacccgcaag 600
aagaacaagt ag 612

<210> SEQ ID NO 55
<211> LENGTH: 203
<212> TYPE: PRT
<213> ORGANISM: Zea mays

<400> SEQUENCE: 55

Met Ala Arg Gln Gln Ser Val Gln Ala Leu Cys Val Leu Ala Ala Leu
1               5                   10                  15

Leu Phe Ala Ala Ser Leu Pro Ser Pro Ala Ala Ala Gly Val His Leu
            20                  25                  30

Ser Ser Leu Pro Lys Ala Leu Asp Val Thr Thr Ser Ala Lys Pro Gly
        35                  40                  45

Gln Val Leu His Ala Gly Val Asp Ser Leu Thr Val Thr Trp Ser Leu
    50                  55                  60

Asn Ala Thr Glu Pro Ala Gly Ala Asp Ala Gly Tyr Lys Gly Val Lys
65                  70                  75                  80

Val Lys Leu Cys Tyr Ala Pro Ala Ser Gln Lys Asp Arg Gly Trp Arg
                85                  90                  95

Lys Ser Glu Asp Asp Ile Ser Lys Asp Lys Ala Cys Gln Phe Lys Val
            100                 105                 110

Thr Glu Gln Ala Tyr Ala Ala Ala Ala Pro Gly Ser Phe Gln Tyr Ala
        115                 120                 125

Val Ala Arg Asp Val Pro Ser Gly Ser Tyr Tyr Leu Arg Ala Phe Ala
    130                 135                 140

Thr Asp Ala Ser Gly Ala Glu Val Ala Tyr Gly Gln Thr Ala Pro Thr
145                 150                 155                 160

Ala Ala Phe Asp Val Ala Gly Ile Thr Gly Ile His Ala Ser Leu Lys
                165                 170                 175

Ile Ala Ala Gly Val Phe Ser Ala Phe Ser Val Val Ala Leu Ala Phe
            180                 185                 190

Phe Phe Val Ile Glu Thr Arg Lys Lys Asn Lys
        195                 200

<210> SEQ ID NO 56

<211> LENGTH: 756
<212> TYPE: DNA
<213> ORGANISM: Zea mays

<400> SEQUENCE: 56
tagctatata cacatgtctg gtctgacgac aatcaaaagg gatcgctagc tcgggctagc 60
cttcctatca ctgtcatgac atgtgctctg cctctgctgg ttgataagcc gtgcgccttc 120
tcgctaattc tttcttgtgc tagaggcgag tcaaacaaac gctgcacctc gtagccctta 180
atctgcgcta agggtcacat gaccctgttc cctatcgcta gttaccaacg acccattccc 240
cctgacagat acttacgacg cgtccgtacg cggcaggcct cggcagttcg gcatcaccag 300
caccggcgcc ggcattcgcc ccctgccagc cggttcgcag attcgcaggg cggagtcggc 360
cgcagttgcc gcatcccaaa cgcccgggaa cctttggggc ccctctacga gcaaatgaag 420
ttgctgcccc tggcttcgta aagctctgac ttttgatcac ttgattggca gtcgtactcc 480
tcgctcatag gccgacacgg ccgcaaagtc aactacccgc tccgccatcc ttcaaccccc 540
gccacgcgcc tatatatgtt cgcggccatg tccgtactag tcctccaacc cacaagccac 600
aaccccgagc tcagatccct cgcctcgtgt cgtgtctccg gtcgacgacg accaacagcc 660
agtgtgggcc agacggacac cgccgagcta tagcgcttgg tgatagcaag ggacgaccgg 720
cggccggacc ggagcacgta cgtacgtacc gcagcg 756

<210> SEQ ID NO 57
<211> LENGTH: 594
<212> TYPE: DNA
<213> ORGANISM: Zea mays

<400> SEQUENCE: 57
atgacgatgg ctcgtcctgg ggcggctttg ccgctgctgc tggtcgtggt cggcgcttgc 60
tgcgcgcgcc tggcggcggc agtgcacctc tccgcgctcg gcaggacact catcgtcgag 120
gcgtcgccga aggccggaca agtcctgcac gccggcgagg acacgataac cgtgacatgg 180
cacctcaacg cgtcggcgtc cagcgtcggg tacaaggcgc tggaggtgac cctctgctac 240
gcgccggcga gccaggagga ccgcgggtgg cgcaaggcca acgacgactt gagcaaggac 300
aaggcgtgcc agttcaggat cgcccggcat gcatacgccg gcggccaggg gacgctccgg 360
tacagggtcg cccgcgacgt ccccaccgcg tcctaccacg tgcgcgccta cgcgctggac 420
gcgtccgggg cgccggtggg ctacggccag accgcgcccg cctactactt ccacgtcgcg 480
ggcgtctcgg gcgtccacgc gtccctccgg gtcgccgccg ccgtgctctc cgcgttctcc 540
atcgccgcgc tcgccttctt tgtcgtcgtc gagaagagga ggaaggacga gtag 594

<210> SEQ ID NO 58
<211> LENGTH: 197
<212> TYPE: PRT
<213> ORGANISM: Zea mays

<400> SEQUENCE: 58

Met Thr Met Ala Arg Pro Gly Ala Ala Leu Pro Leu Leu Leu Val Val
1 5 10 15

Val Gly Ala Cys Cys Ala Arg Leu Ala Ala Ala Val His Leu Ser Ala
20 25 30

Leu Gly Arg Thr Leu Ile Val Glu Ala Ser Pro Lys Ala Gly Gln Val
35 40 45

Leu His Ala Gly Glu Asp Thr Ile Thr Val Thr Trp His Leu Asn Ala
50 55 60

```
Ser Ala Ser Ser Val Gly Tyr Lys Ala Leu Glu Val Thr Leu Cys Tyr
65                  70                  75                  80

Ala Pro Ala Ser Gln Glu Asp Arg Gly Trp Arg Lys Ala Asn Asp Asp
                85                  90                  95

Leu Ser Lys Asp Lys Ala Cys Gln Phe Arg Ile Ala Arg His Ala Tyr
            100                 105                 110

Ala Gly Gly Gln Gly Thr Leu Arg Tyr Arg Val Ala Arg Asp Val Pro
        115                 120                 125

Thr Ala Ser Tyr His Val Arg Ala Tyr Ala Leu Asp Ala Ser Gly Ala
    130                 135                 140

Pro Val Gly Tyr Gly Gln Thr Ala Pro Ala Tyr Tyr Phe His Val Ala
145                 150                 155                 160

Gly Val Ser Gly Val His Ala Ser Leu Arg Val Ala Ala Ala Val Leu
                165                 170                 175

Ser Ala Phe Ser Ile Ala Ala Leu Ala Phe Phe Val Val Val Glu Lys
            180                 185                 190

Arg Arg Lys Asp Glu
        195


<210> SEQ ID NO 59
<211> LENGTH: 30
<212> TYPE: DNA
<213> ORGANISM: Artificial
<220> FEATURE:
<223> OTHER INFORMATION: Primer

<400> SEQUENCE: 59

ggtcgttggt aactagcgat agggaacagg                                        30


<210> SEQ ID NO 60
<211> LENGTH: 27
<212> TYPE: DNA
<213> ORGANISM: Artificial
<220> FEATURE:
<223> OTHER INFORMATION: Primer

<400> SEQUENCE: 60

gtgcagcgtt tgtttgactc gcctcta                                           27


<210> SEQ ID NO 61
<211> LENGTH: 18
<212> TYPE: DNA
<213> ORGANISM: Artificial
<220> FEATURE:
<223> OTHER INFORMATION: Primer

<400> SEQUENCE: 61

caacggacca gctcttgg                                                     18


<210> SEQ ID NO 62
<211> LENGTH: 20
<212> TYPE: DNA
<213> ORGANISM: Artificial
<220> FEATURE:
<223> OTHER INFORMATION: Primer

<400> SEQUENCE: 62

tctttgtggg ttgtggaagg                                                   20


<210> SEQ ID NO 63
<211> LENGTH: 20
<212> TYPE: DNA
<213> ORGANISM: Artificial
```

<220> FEATURE:
<223> OTHER INFORMATION: Primer

<400> SEQUENCE: 63
cgagcagatc gtgcaaatag 20

<210> SEQ ID NO 64
<211> LENGTH: 22
<212> TYPE: DNA
<213> ORGANISM: Artificial
<220> FEATURE:
<223> OTHER INFORMATION: Primer

<400> SEQUENCE: 64
gggctttgat atgtttagtt gg 22

<210> SEQ ID NO 65
<211> LENGTH: 2917
<212> TYPE: DNA
<213> ORGANISM: Zea mays
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 65
ttactatagg gcacgcgtgg tcgacggccc tggctggtcc ttgtttgatt tacttccagg 60
attacataat ccagcttata tcataatcta ggtatctaga ttacataatc tatctaataa 120
tctgtgttgt tgtttaccta ctaacttatt tataagctgg gttatataat cttgaggcca 180
aataaacggg ttctaaaatg gtctagggtc cagtgttaag ctaaatcgac attatgtcta 240
gtagtgttaa gctaaatcga catttctttg tgggatgggt ccgatgtgtc gtctagtagt 300
gttaagctaa agcgacattt ctttgtgggt tgtggaaggt gtccctgctc tctaagttgt 360
tagtgttaag ctaaatgtcg ttctttgtgg gttgtggctg ctccctaagt tgttagtgtt 420
aagctaaatg tcgttctttg tgggttgtgg aaggtgttcc ttttccttaa attgttagtg 480
ttaagctaaa tcgacatttc tttgtgggtt gtggaangtg ttccttttcc ttaagttgtt 540
agttgtgcaa ggtgttcctt atagcatctc ccacatgagc cataatggan tttattttga 600
aatataggac tctaaccaac aaaaacatac tccaataggg attctatttt acaaaaaaat 660
atcaaatgat tatagggtcg attcttcggg tcctaaatat agtatctaat ataatggagc 720
tctatcctca ttttatatat tatttctaaa tttttattta ctaaataaca tgtaacatga 780
tttatttcct aatactatga tatagggctc aactgttgga gctgcaaacg ttttttggca 840
ataaatactt taaattaggt cctattttaa tttgaaagac tatatcatgc tcttagcgag 900
tgtttgtgca tgattgctat ttaggtagtt cagttggggg ctttgatatg tttagttgga 960
attctagtat ttttttttgg ttctccgctc ttttgactat cacaacgatc gctatgcgcg 1020
agcagactat ttgatctatt aaattatgat ccaaccatgt cacattaagc acttaaactc 1080
tttcaccatc agtccaagta tctttataaa aaaccctaac aaaccacaat tgcatatgtg 1140
gttagattat aatttaacgt atcagatggt tcgcttgcac tcttacacac ctagaaactg 1200
cttgcataac agtcgttctc tttgttatat aatgctttag taatcatgag ctaagggtaa 1260
acaaatggta catacaagta gtgaacacat cctcgctacc tatctatagg ggtggaacta 1320
gacatcctat tttttagaac aaatttcata ttttaaaata gatatgcttg aaaatttatg 1380
ctaatttttt tatagtatca agcatgttat tacacataag aataaaattt tgtataaatt 1440
tttatccatt atttgctccc tacaattaaa aaggtgagaa agcaaaaagg tgaagaaaca 1500
accgaacccg tatccgtttc atattcaaat ttttacatct attatttgag aatatatttg 1560
aaaaatttga ggtttagttt ttacaaatct ttacaaggtt aatgttaaat tataagactg 1620
tggatttaca tggtaaattc tatgtcttat ttgtctgcga tcgaagaaaa atgacaaaaa 1680
atctgacatt cgaataaaca tttgtttcca ctcctaccta tctcacctcc tatttcaaac 1740
tccacttcgt aatacgatac aaaatcaccc cctatctatc tcacctccta tttcaaactc 1800
cactcagtaa acaatattgt ctatggtaca aaatcaagtg ttttgtacat ctatttgcac 1860
gatctgctcg attcaggcat ccttgacaca caacatactc cttagggcta taaatgtcca 1920
aatagagcag acctaatgga tggaccgtgg catgacacga cttatcccaa cacagcacag 1980
tccgcccgat tggtcatggg gtctgggttg gtctagcctg atcatcgggt cactcttggg 2040
ccacaggtgc gccacaacag gatagcccaa cctatcctat tttttcatgc atatatctat 2100
attatagtta gtataaagta aaaaaacaaa aagtatgtgt gttatgttgg ctagatgtgt 2160
ttaaataact ctttaaagct agcaactatg gtttaaatca tacatataca catttttagt 2220
tttttttatt taaacaatat gagccttata ggcacgtcga gtgtgacggg ccagtgagat 2280
gacacattat aattactgat ctagcaggcc gtatctaggt ctttctcgcg gacctttctc 2340
gcggaccaag agctggtccg ttggctaatc tatacggtac cgatactgtc ctaattcata 2400
ctgggcctag ccgtgtctgt gactgggcat ggctagcgaa gcccgcccat ttgaacacct 2460
gtacaagagg ggaatttata aatgaggagg aatgtactca tgcggtacac caggggaatt 2520
gttttgttgt gctcagcgat agatttcaac gcaacggtga gccagtttca ccaaaaaaaa 2580
gggggaaaag gccacatcaa aggcgaggtg cagacgagca gaagatgcta gcagtgcagc 2640
taagtccagc agctagcaat gaaagggtac tcaggattta acaatgccta gagacggcat 2700
catcccctca atgatccggt gctctctttt tgtttattca cccgttggcg taactatata 2760
cacatgtctg gtctgacgaa cgaatcaagg gatcgctagc tcgggcgagc cttcctatca 2820
ctgtcatgac atgtgctctg cctctgctgg ttgataagcc gtgcgccttc tcgctaattc 2880
tttcttgtgc tagaggcgag tcaaacaaac gctgcac 2917

<210> SEQ ID NO 66
<211> LENGTH: 4498
<212> TYPE: DNA
<213> ORGANISM: Zea mays
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 66
ttactatagg gcacgcgtgg tcgacggccc tggctggtcc ttgtttgatt tacttccagg 60
attacataat ccagcttata tcataatcta ggtatctaga ttacataatc tatctaataa 120
tctgtgttgt tgtttaccta ctaacttatt tataagctgg gttatataat cttgaggcca 180
aataaacggg ttctaaaatg gtctagggtc cagtgttaag ctaaatcgac attatgtcta 240
gtagtgttaa gctaaatcga catttctttg tgggatgggt ccgatgtgtc gtctagtagt 300
gttaagctaa agcgacattt ctttgtgggt tgtggaaggt gtccctgctc tctaagttgt 360

-continued

```
tagtgttaag ctaaatgtcg ttctttgtgg gttgtggctg ctccctaagt tgttagtgtt    420
aagctaaatg tcgttctttg tgggttgtgg aaggtgttcc ttttccttaa attgttagtg    480
ttaagctaaa tcgacatttc tttgtgggtt gtggaangtg ttccttttcc ttaagttgtt    540
agttgtgcaa ggtgttcctt atagcatctc ccacatgagc cataatggan tttattttga    600
aatataggac tctaaccaac aaaaacatac tccaataggg attctatttt acaaaaaaat    660
atcaaatgat tatagggtcg attcttcggg tcctaaatat agtatctaat ataatggagc    720
tctatcctca ttttatatat tatttctaaa tttttattta ctaaataaca tgtaacatga    780
tttatttcct aatactatga tatagggctc aactgttgga gctgcaaacg tttttggca     840
ataaatactt taaattaggt cctattttaa tttgaaagac tatatcatgc tcttagcgag    900
tgtttgtgca tgattgctat ttaggtagtt cagttggggg ctttgatatg tttagttgga    960
attctagtat ttttttttgg ttctccgctc ttttgactat cacaacgatc gctatgcgcg   1020
agcagactat ttgatctatt aaattatgat ccaaccatgt cacattaagc acttaaactc   1080
tttcaccatc agtccaagta tctttataaa aaaccctaac aaaccacaat tgcatatgtg   1140
gttagattat aatttaacgt atcagatggt tcgcttgcac tcttacacac ctagaaactg   1200
cttgcataac agtcgttctc tttgttatat aatgctttag taatcatgag ctaagggtaa   1260
acaaatggta catacaagta gtgaacacat cctcgctacc tatctatagg ggtggaacta   1320
gacatcctat tttttagaac aaatttcata ttttaaaata gatatgcttg aaaatttatg   1380
ctaatttttt tatagtatca agcatgttat tacacataag aataaaattt tgtataaatt   1440
tttatccatt atttgctccc tacaattaaa aaggtgagaa agcaaaaagg tgaagaaaca   1500
accgaacccg tatccgtttc atattcaaat ttttacatct attatttgag aatatatttg   1560
aaaaatttga ggtttagttt ttacaaatct ttacaaggtt aatgttaaat tataagactg   1620
tggatttaca tggtaaattc tatgtcttat ttgtctgcga tcgaagaaaa atgacaaaaa   1680
atctgacatt cgaataaaca tttgtttcca ctcctaccta tctcacctcc tatttcaaac   1740
tccacttcgt aatacgatac aaaatcaccc cctatctatc tcacctccta tttcaaactc   1800
cactcagtaa acaatattgt ctatggtaca aaatcaagtg ttttgtacat ctatttgcac   1860
gatctgctcg attcaggcat ccttgacaca caacatactc cttagggcta taaatgtcca   1920
aatagagcag acctaatgga tggaccgtgg catgacacga cttatcccaa cacagcacag   1980
tccgcccgat tggtcatggg gtctgggttg gtctagcctg atcatcgggt cactcttggg   2040
ccacaggtgc gccacaacag gatagcccaa cctatcctat tttttcatgc atatatctat   2100
attatagtta gtataaagta aaaaaacaaa aagtatgtgt gttatgttgg ctagatgtgt   2160
ttaaataact ctttaaagct agcaactatg gtttaaatca tacatataca catttttagt   2220
ttttttttatt taaacaatat gagccttata ggcacgtcga gtgtgacggg ccagtgagat   2280
gacacattat aattactgat ctagcaggcc gtatctaggt ctttctcgcg gacctttctc   2340
gcggaccaag agctggtccg ttggctaatc tatacggtac cgatactgtc ctaattcata   2400
ctgggcctag ccgtgtctgt gactgggcat ggctagcgaa gcccgcccat ttgaacacct   2460
gtacaagagg ggaatttata aatgaggagg aatgtactca tgcggtacac caggggaatt   2520
gttttgttgt gctcagcgat agatttcaac gcaacggtga gccagtttca ccaaaaaaaa   2580
gggggaaaag gccacatcaa aggcgaggtg cagacgagca gaagatgcta gcagtgcagc   2640
taagtccagc agctagcaat gaaagggtac tcaggattta acaatgccta gagacggcat   2700
catcccctca atgatccggt gctctctttt tgtttattca cccgttggcg taactatata   2760
```

cacatgtctg gtctgacgaa cgaatcaagg gatcgctagc tcgggcgagc cttcctatca 2820
ctgtcatgac atgtgctctg cctctgctgg ttgataagcc gtgcgccttc tcgctaattc 2880
tttcttgtgc tagaggcgag tcaaacaaac gctgcacctc gtagccctta atctgcgcta 2940
agggtcacat gaccctgttc cctatcgcta gttaccaacg acccattccc cctgacagat 3000
acttacgacg cgtccgtacg cggcaggcct cggcagttcg gcatcaccag caccggcgcc 3060
ggcattcgcc ccctgccagc cggttcgcag attcgcaggg cggagtcggc cgcagttgcc 3120
gcatcccaaa cgcccgggaa cctttggggc ccctctacga gcaaatgaag ttgctgcccc 3180
tggcttcgta aagctctgac ttttgatcac ttgattggca gtcgtactcc tcgctcatag 3240
gccgacacgg ccgcaaagtc aactacccgc tccgccatcc ttcaaccccc gccacgcgcc 3300
tatatatgtt cgcggccatg tccgtactag tcctccaacc cacaagccac aaccccgagc 3360
tcagatccct cgcctcgtgt cgtgtctccg gtcgacgacg accaacagcc agtgtgggcc 3420
agacggacac cgccgagcta tagcgcttgg tgatagcaag ggacgaccgg cggccggacc 3480
ggagcacgta cgtacgtacc gcagcgatgg ctcggcagca aagcgtgcag gccttgtgtg 3540
tgctggcggc gcttctcttc gccgcctccc tgccgtcgcc ggccgccgcg ggggtgcacc 3600
tctcctcgct gcccaaagcg ctcgacgtca ccacctccgc caaacccggc caaggtgcgc 3660
gcgcgttccg gcccggctca tagtcatagc caaaggatta gcactttgat tacttgctcg 3720
gttaattcat agtcctattc ttctctatgt ttgaaacccc cctttagatt tgttcattca 3780
caatcaagga gctagctgat taaaatacac acgattgcca taaaatatat gcttctcgca 3840
gtcctgcacg ccggcgtgga ctcgctgacg gtgacgtgga gcctgaacgc cacggagccg 3900
gccggcgccg acgccgggta caagggcgtg aaggtgaagc tgtgctacgc gccggcgagc 3960
cagaaggacc gcgggtggcg caagtccgag gacgacatca gcaaggacaa ggcgtgccag 4020
ttcaaggtca ccgagcaggc gtacgcggcg gcggcgcccg gcagcttcca gtacgccgtc 4080
gcccgcgacg tcccctcggg ctcctactac ctgcgcgcct tcgccacgga cgcgtcgggc 4140
gccgaggtgg cctacggcca gacggcgccc accgccgcct tcgacgtcgc cggcatcacc 4200
ggcatccacg cctctctcaa gatcgccgcc ggcgtcttct cggccttctc cgtcgtcgcg 4260
ctcgccttct tcttcgtcat cgagacccgc aagaagaaca agtagaacga gttgcggctg 4320
cgcgccatac atgcatacat gtaaatcgtc ggcggcgatg agtggctgtc gttgctgatt 4380
cattggtgcg cgcgactatt ttggtgtatc atgtaagtta cttttctgca gtgtgtgcgt 4440
caaaattacc aaataataac ttaagtttct ctgctaaaaa aaaaaaaaaa aaaaaaaa 4498

<210> SEQ ID NO 67
<211> LENGTH: 3506
<212> TYPE: DNA
<213> ORGANISM: Zea mays
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (590)..(590)
<223> OTHER INFORMATION: n is a, c, g, or t

<400> SEQUENCE: 67
ttactatagg gcacgcgtgg tcgacggccc tggctggtcc ttgtttgatt tacttccagg 60
attacataat ccagcttata tcataatcta ggtatctaga ttacataatc tatctaataa 120
tctgtgttgt tgtttaccta ctaacttatt tataagctgg gttatataat cttgaggcca 180

-continued

```
aataaacggg ttctaaaatg gtctagggtc cagtgttaag ctaaatcgac attatgtcta    240
gtagtgttaa gctaaatcga catttctttg tgggatgggt ccgatgtgtc gtctagtagt    300
gttaagctaa agcgacattt ctttgtgggt tgtggaaggt gtccctgctc tctaagttgt    360
tagtgttaag ctaaatgtcg ttctttgtgg gttgtggctg ctccctaagt tgttagtgtt    420
aagctaaatg tcgttctttg tgggttgtgg aaggtgttcc ttttccttaa attgttagtg    480
ttaagctaaa tcgacatttc tttgtgggtt gtggaangtg ttccttttcc ttaagttgtt    540
agttgtgcaa ggtgttcctt atagcatctc ccacatgagc cataatggan tttattttga    600
aatataggac tctaaccaac aaaaacatac tccaataggg attctatttt acaaaaaaat    660
atcaaatgat tatagggtcg attcttcggg tcctaaatat agtatctaat ataatggagc    720
tctatcctca ttttatatat tatttctaaa tttttattta ctaaataaca tgtaacatga    780
tttatttcct aatactatga tatagggctc aactgttgga gctgcaaacg tttttggca     840
ataaatactt taaattaggt cctattttaa tttgaaagac tatatcatgc tcttagcgag    900
tgtttgtgca tgattgctat ttaggtagtt cagttggggg ctttgatatg tttagttgga    960
attctagtat ttttttttgg ttctccgctc ttttgactat cacaacgatc gctatgcgcg   1020
agcagactat ttgatctatt aaattatgat ccaaccatgt cacattaagc acttaaactc   1080
tttcaccatc agtccaagta tctttataaa aaaccctaac aaaccacaat tgcatatgtg   1140
gttagattat aatttaacgt atcagatggt tcgcttgcac tcttacacac ctagaaactg   1200
cttgcataac agtcgttctc tttgttatat aatgctttag taatcatgag ctaagggtaa   1260
acaaatggta catacaagta gtgaacacat cctcgctacc tatctatagg ggtggaacta   1320
gacatcctat tttttagaac aaatttcata ttttaaaata gatatgcttg aaaatttatg   1380
ctaatttttt tatagtatca agcatgttat tacacataag aataaaattt tgtataaatt   1440
tttatccatt atttgctccc tacaattaaa aaggtgagaa agcaaaaagg tgaagaaaca   1500
accgaacccg tatccgtttc atattcaaat ttttacatct attatttgag aatatatttg   1560
aaaaatttga ggtttagttt ttacaaatct ttacaaggtt aatgttaaat tataagactg   1620
tggatttaca tggtaaattc tatgtcttat ttgtctgcga tcgaagaaaa atgacaaaaa   1680
atctgacatt cgaataaaca tttgtttcca ctcctaccta tctcacctcc tatttcaaac   1740
tccacttcgt aatacgatac aaaatcaccc cctatctatc tcacctccta tttcaaactc   1800
cactcagtaa acaatattgt ctatggtaca aaatcaagtg ttttgtacat ctatttgcac   1860
gatctgctcg attcaggcat ccttgacaca caacatactc cttagggcta taaatgtcca   1920
aatagagcag acctaatgga tggaccgtgg catgacacga cttatcccaa cacagcacag   1980
tccgcccgat tggtcatggg gtctgggttg gtctagcctg atcatcgggt cactcttggg   2040
ccacaggtgc gccacaacag gatagcccaa cctatcctat tttttcatgc atatatctat   2100
attatagtta gtataaagta aaaaaacaaa aagtatgtgt gttatgttgg ctagatgtgt   2160
ttaaataact ctttaaagct agcaactatg gtttaaatca tacatataca catttttagt   2220
tttttttatt taaacaatat gagccttata ggcacgtcga gtgtgacggg ccagtgagat   2280
gacacattat aattactgat ctagcaggcc gtatctaggt ctttctcgcg gacctttctc   2340
gcggaccaag agctggtccg ttggctaatc tatacggtac cgatactgtc ctaattcata   2400
ctgggcctag ccgtgtctgt gactgggcat ggctagcgaa gcccgcccat ttgaacacct   2460
gtacaagagg ggaatttata aatgaggagg aatgtactca tgcggtacac caggggaatt   2520
gttttgttgt gctcagcgat agatttcaac gcaacggtga gccagtttca ccaaaaaaaa   2580
```

```
gggggaaaag gccacatcaa aggcgaggtg cagacgagca gaagatgcta gcagtgcagc   2640

taagtccagc agctagcaat gaaagggtac tcaggattta acaatgccta gagacggcat   2700

catcccctca atgatccggt gctctctttt tgtttattca cccgttggcg taactatata   2760

cacatgtctg gtctgacgaa cgaatcaagg gatcgctagc tcgggcgagc cttcctatca   2820

ctgtcatgac atgtgctctg cctctgctgg ttgataagcc gtgcgccttc tcgctaattc   2880

tttcttgtgc tagaggcgag tcaaacaaac gctgcacctc gtagccctta atctgcgcta   2940

agggtcacat gaccctgttc cctatcgcta gttaccaacg acccattccc cctgacagat   3000

acttacgacg cgtccgtacg cggcaggcct cggcagttcg gcatcaccag caccggcgcc   3060

ggcattcgcc ccctgccagc cggttcgcag attcgcaggg cggagtcggc cgcagttgcc   3120

gcatcccaaa cgcccgggaa cctttggggc ccctctacga gcaaatgaag ttgctgcccc   3180

tggcttcgta aagctctgac ttttgatcac ttgattggca gtcgtactcc tcgctcatag   3240

gccgacacgg ccgcaaagtc aactacccgc tccgccatcc ttcaaccccc gccacgcgcc   3300

tatatatgtt cgcggccatg tccgtactag tcctccaacc cacaagccac aaccccgagc   3360

tcagatccct cgcctcgtgt cgtgtctccg gtcgacgacg accaacagcc agtgtgggcc   3420

agacggacac cgccgagcta tagcgcttgg tgatagcaag ggacgaccgg cggccggacc   3480

ggagcacgta cgtacgtacc gcagcg                                        3506
```

<210> SEQ ID NO 68
<211> LENGTH: 1014
<212> TYPE: DNA
<213> ORGANISM: Zea mays

<400> SEQUENCE: 68

```
cacaacgatc gctatgcgcg agcagactat ttgatctatt aaattatgat ccaaccatgt     60

cacattaagc acttaaactc tttcaccatc agtccaagta tctttataaa aaaccctaac    120

aaaccacaat tgcatatgtg gttagattat aatttaacgt atcagatggt tcgcttgcac    180

tcttacacac ctagaaactg cttgcataac agtcgttctc tttgttatat aatgctttag    240

taatcatgag ctaagggtaa acaaatggta catacaagta gtgaacacat cctcgctacc    300

tatctatagg ggtggaacta gacatcctat tttttagaac aaatttcata ttttaaaata    360

gatatgcttg aaaatttatg ctaatttttt tatagtatca agcatgttat tacacataag    420

aataaaattt tgtataaatt tttatccatt atttgctccc tacaattaaa aaggtgagaa    480

agcaaaaagg tgaagaaaca accgaacccg tatccgtttc atattcaaat ttttacatct    540

attatttgag aatatatttg aaaaatttga ggtttagttt ttacaaatct ttacaaggtt    600

aatgttaaat tataagactg tggatttaca tggtaaattc tatgtcttat ttgtctgcga    660

tcgaagaaaa atgacaaaaa atctgacatt cgaataaaca tttgtttcca ctcctaccta    720

tctcacctcc tatttcaaac tccacttcgt aatacgatac aaaatcaccc cctatctatc    780

tcacctccta tttcaaactc cactcagtaa acaatattgt ctatggtaca aaatcaagtg    840

ttttgtacat ctatttgcac gatctgctcg attcaggcat ccttgacaca caacatactc    900

cttagggcta taaatgtcca aatagagcag acctaatgga tggaccgtgg catgacacga    960

cttatcccaa cacagcacag tccgcccgat tggtcatggg gtctgggttg gtct         1014
```

<210> SEQ ID NO 69
<211> LENGTH: 1492
<212> TYPE: DNA
<213> ORGANISM: Zea mays

<400> SEQUENCE: 69
agcctgatca tcgggtcact cttgggccac aggtgcgcca caacaggata gcccaaccta 60
tcctattttt tcatgcatat atctatatta tagttagtat aaagtaaaaa aacaaaaagt 120
atgtgtgtta tgttggctag atgtgtttaa ataactcttt aaagctagca actatggttt 180
aaatcataca tatacacatt tttagttttt tttatttaaa caatatgagc cttataggca 240
cgtcgagtgt gacgggccag tgagatgaca cattataatt actgatctag caggccgtat 300
ctaggtcttt ctcgcggacc tttctcgcgg accaagagct ggtccgttgg ctaatctata 360
cggtaccgat actgtcctaa ttcatactgg gcctagccgt gtctgtgact gggcatggct 420
agcgaagccc gcccatttga acacctgtac aagaggggaa tttataaatg aggaggaatg 480
tactcatgcg gtacaccagg ggaattgttt tgttgtgctc agcgatagat ttcaacgcaa 540
cggtgagcca gtttcaccaa aaaaaagggg gaaaaggcca catcaaaggc gaggtgcaga 600
cgagcagaag atgctagcag tgcagctaag tccagcagct agcaatgaaa gggtactcag 660
gatttaacaa tgcctagaga cggcatcatc ccctcaatga tccggtgctc tctttttgtt 720
tattcacccg ttggcgtaac tatatacaca tgtctggtct gacgaacgaa tcaagggatc 780
gctagctcgg gcgagccttc ctatcactgt catgacatgt gctctgcctc tgctggttga 840
taagccgtgc gccttctcgc taattctttc ttgtgctaga ggcgagtcaa acaaacgctg 900
cacctcgtag cccttaatct gcgctaaggg tcacatgacc ctgttcccta tcgctagtta 960
ccaacgaccc attccccctg acagatactt acgacgcgtc cgtacgcggc aggcctcggc 1020
agttcggcat caccagcacc ggcgccggca ttcgcccccct gccagccggt tcgcagattc 1080
gcagggcgga gtcggccgca gttgccgcat cccaaacgcc cgggaacctt tggggcccct 1140
ctacgagcaa atgaagttgc tgcccctggc ttcgtaaagc tctgactttt gatcacttga 1200
ttggcagtcg tactcctcgc tcataggccg acacggccgc aaagtcaact acccgctccg 1260
ccatccttca acccccgcca cgcgcctata tatgttcgcg gccatgtccg tactagtcct 1320
ccaacccaca agccacaacc ccgagctcag atccctcgcc tcgtgtcgtg tctccggtcg 1380
acgacgacca acagccagtg tgggccagac ggacaccgcc gagctatagc gcttggtgat 1440
agcaagggac gaccggcggc cggaccggag cacgtacgta cgtaccgcag cg 1492

<210> SEQ ID NO 70
<211> LENGTH: 3621
<212> TYPE: DNA
<213> ORGANISM: Zea mays

<400> SEQUENCE: 70
tggtccttgt ttgatttact tccaggatta tataatccag cttatggatt atataagtac 60
ctattgacgt cacgtgctta tgtattataa taatctaggt atatagatta tataatctat 120
ctaataataa tctgtgttgt ttgtttatct ctcaaaacaa acaggtccta aaatggtccc 180
gggcgtccaa tgtgtcgtca agtagtgtta agctaaatcg acatttcttt gtgggttgtg 240
tggaaggtgt tccttttcct taagttgtta gttgtgcaag gtgttcctta gagcatctcc 300
aataggacct ataatggatt ctattttgaa ttataagact ctaacaacaa aagcatactt 360
taatggggat tctattttac aaaaaaatat caaatgatta tatggtcgat tcctcgggtc 420
ctaaatatag tatctcatat aatagagctc tatcctcatt ttatatacta tttttaagtt 480
tttatttact aaataacatg atttattttc taatactatg aactcaacta ttagagctgt 540
aaacgttttt gtggtactaa acactttaaa tcaggtccta ttttaatttg aaggacttaa 600

-continued

```
atataagact tctggttaga gatgctctta gcgagtgttt gtgcatgatt gctatttagt    660
ctttgtggat tgtggaaggt gttacttttc ctcaagttgt tagttgtgca aggtgtttct    720
tagagcatct ctaacaggag ccttaacgga atctattttg aagtatagta ctttaacacc    780
aaaaacatac tttaataggg gtcctatttt acaaaaaaat tatcaaatga ttataaggtc    840
cactcctcgg gtcctaaata taatatctca tatactagag ctctatcctc attttatata    900
ctatccctag gtttttattc cctaaataac atgatttatt tcctaatact aagatatagg    960
gctcaactat tggagttgca aatgtttttt ggcactaaac actttatatc aggtcctatt   1020
ttaattttaa tttgaaggac tcaaatatag gacttctcgt tagagatgct cttagcgagt   1080
gtttgtgcat gattgctatt tatgtctgta gtttagttgg gggctttaat atgtttagtt   1140
gaagttctag tattttttag gttctccact ctttggatta tgacaacgac cactatccaa   1200
gcagtctttg agtgcaaacg cgcgagcaaa ctatctgatc tattaaatta tgatccaacc   1260
gttatgtcat attgaagact taaacccttt caccaccagc ccaagtatct ttatgaaaaa   1320
ccctaacaaa ccacaattgc atctatggtt ggattataat ttaacgtatc agatggttcg   1380
cttgcatgct tacatatcta gaaactgttt gcataacagt cgttctcttt ggttatataa   1440
tgctttagta atcatcagcc aagtgtaaac aaatggtaca aactagtagt gaacacatcc   1500
tccctaccta tctctagggg tgtaactaga tatccgaatt cttagaacaa atttcatatt   1560
ttaaaataga tatgcttcaa aatttatgct aatctttttt atattatcaa gcatattatt   1620
acacataaga ataaaatttt gtatagaatt ttatccatta tttgttccct agaatttaaa   1680
aagtgaaaaa acattcgaat ctgtatcagt ttcgtattca aatttttaca tctattattt   1740
gagaatatat atgataaatt tgaggtttag tttttatgaa tctttacaag gttaatgtta   1800
aatacatgac tatggattta catagtaaat tctatgtctt atttgtccgc gattgaagaa   1860
aaatgacaaa aagatctgac attcgaataa acatctgttt ccactcctac ctatctgacc   1920
tcctatttca aactccactt tgtaacacgg tacaaaatca ctccctacct atctgacctc   1980
ctatttcaaa ctccactcag taaacaatat tgtctatggt acaaaaccaa gtgttttata   2040
catctatttg cacgatctgc tcgagtcagg catccttgac acacaacata ctccttgtgg   2100
ctataaatgt ccaaatagag cagacctaat gggtggaccg ttgcatgaca cgacttatcc   2160
caagacgagc acagttcgcc ccattggtca tgggggtccg ggctagtcta gcctgatcat   2220
cgggtcacac ttaggccaca ggtgtgccac aacgggatag cccaacatgt cccttttttgt   2280
catgcatata tctatattat agttagtata atgtaaaaaa acaaaaggta tgtgtgttat   2340
gttggttaga tgtgtttaaa taactcttta aagctagcaa ctatggttta aatcatacat   2400
atacacattt ttattttatt tttatttaaa cgatatgggc cttctaggca cgtcgagtgt   2460
gacgggccag tgagatgaca cattataatt actggtctag caggccgtac ctaggtcttt   2520
ctcgtgggcc aagactaagg gttggcccgt tggctaatct gtacggtacc gatactgtcc   2580
taattcattt gaacacctgt agaagagggg aatttataat tgaggaggaa tgtactcatg   2640
cggtacacca ggggaattgt tttgttgtgc tcagcgatag atttcaacgc aacggtgagc   2700
cagtttcact aaaaaaaggg gggggggggg gggggggga aggccacatc aaaggcgagg   2760
tgctgacgag cagaagatgc tagcagtgac gccaagtcca gcagctagca atgaaagggt   2820
actcgggatt taacaatgcc tagagacggc atcatcccct caataatccg gtgctctctt   2880
tttgtttatt caccagttgg cgtagctata tacacatgtc tggtctgacg aacaaatcaa   2940
gggatcgcta gctcgggcta gccttcctat cactgtcatg acatgtgctc tgcctctgct   3000
```

ggttgataag ccgtgcgcct tctcgctaat tctttcttgt gctagaggcg agtcaaacaa 3060
acgctgcacc tcgtagccct taatctgcgc taagggtcac atgaccctgt tccctatcgc 3120
tagttaccaa cgacccattc cccctgacag atacttacga cgcgtccgta cgcggcaggc 3180
ctcggcagtt cggcatcacc agcaccggcg ccggcattcg ccccctgcca gccggttcgc 3240
agattcgcag ggcggagtcg gccgcagttg ccgcatccca aacgcccggg aacctttggg 3300
gcccctctac gagcaaatga agttgctgcc cctggcttcg taaagctctg acttttgatc 3360
acttgattgg cagtcgtact cctcgctcat aggccgacac ggccgcaaag tcaactaccc 3420
gctccgccat ccttcaaccc ccgccacgcg cctatatatg ttcgcggcca tgtccgtact 3480
agtcctccaa cccacaagcc acaaccccga gctcagatcc ctcgcctcgt gtcgtgtctc 3540
cggtcgacga cgaccaacag ccagtgtggg ccagacggac accgccgagc tatagcgctt 3600
ggtgatagca agggacgacc g 3621

<210> SEQ ID NO 71
<211> LENGTH: 3236
<212> TYPE: DNA
<213> ORGANISM: Zea mays

<400> SEQUENCE: 71
tggtccttgt ttgatttact tccaggatta tataatccag cttatggatt atataagtac 60
ctattgacgt cacgtgctta tgtattataa taatctaggt atatagatta tataatctat 120
ctaataataa tctgtgttgt ttgtttatct ctcaaaacaa acaggtccta aaatggtccc 180
gggcgtccaa tgtgtcgtca agtagtgtta agctaaatcg acatttcttt gtgggttgtg 240
tggaaggtgt tccttttcct taagttgtta gttgtgcaag gtgttcctta gagcatctcc 300
aataggacct ataatggatt ctattttgaa ttataagact ctaacaacaa aagcatactt 360
taatggggat tctattttac aaaaaaatat caaatgatta tatggtcgat tcctcgggtc 420
ctaaatatag tatctcatat aatagagctc tatcctcatt ttatatacta tttttaagtt 480
tttatttact aaataacatg atttattttc taatactatg aactcaacta ttagagctgt 540
aaacgttttt gtggtactaa acactttaaa tcaggtccta ttttaatttg aaggacttaa 600
atataagact tctggttaga gatgctctta gcgagtgttt gtgcatgatt gctatttagt 660
ctttgtggat tgtggaaggt gttacttttc ctcaagttgt tagttgtgca aggtgtttct 720
tagagcatct ctaacaggag ccttaacgga atctattttg aagtatagta ctttaacacc 780
aaaaacatac tttaataggg gtcctatttt acaaaaaaat tatcaaatga ttataaggtc 840
cactcctcgg gtcctaaata taatatctca tatactagag ctctatcctc attttatata 900
ctatccctag gtttttattc cctaaataac atgatttatt tcctaatact aagatatagg 960
gctcaactat tggagttgca aatgtttttt ggcactaaac actttatatc aggtcctatt 1020
ttaattttaa tttgaaggac tcaaatatag gacttctcgt tagagatgct cttagcgagt 1080
gtttgtgcat gattgctatt tatgtctgta gtttagttgg gggctttaat atgtttagtt 1140
gaagttctag tattttttag gttctccact ctttggatta tgacaacgac cactatccaa 1200
gcagtctttg agtgcaaacg cgcgagcaaa ctatctgatc tattaaatta tgatccaacc 1260
gttatgtcat attgaagact taaacccttt caccaccagc ccaagtatct ttatgaaaaa 1320
ccctaacaaa ccacaattgc atctatggtt ggattataat ttaacgtatc agatggttcg 1380
cttgcatgct tacatatcta gaaactgttt gcataacagt cgttctcttt ggttatataa 1440
tgctttagta atcatcagcc aagtgtaaac aaatggtaca aactagtagt gaacacatcc 1500
tccctaccta tctctagggg tgtaactaga tatccgaatt cttagaacaa atttcatatt 1560
ttaaaataga tatgcttcaa aatttatgct aatctttttt atattatcaa gcatattatt 1620
acacataaga ataaaatttt gtatagaatt ttatccatta tttgttccct agaatttaaa 1680
aagtgaaaaa acattcgaat ctgtatcagt ttcgtattca aatttttaca tctattattt 1740
gagaatatat atgataaatt tgaggtttag tttttatgaa tctttacaag gttaatgtta 1800
aatacatgac tatggattta catagtaaat tctatgtctt atttgtccgc gattgaagaa 1860
aaatgacaaa aagatctgac attcgaataa acatctgttt ccactcctac ctatctgacc 1920
tcctatttca aactccactt tgtaacacgg tacaaaatca ctccctacct atctgacctc 1980
ctatttcaaa ctccactcag taaacaatat tgtctatggt acaaaaccaa gtgttttata 2040
catctatttg cacgatctgc tcgagtcagg catccttgac acacaacata ctccttgtgg 2100
ctataaatgt ccaaatagag cagacctaat gggtggaccg ttgcatgaca cgacttatcc 2160
caagacgagc acagttcgcc ccattggtca tgggggtccg ggctagtcta gcctgatcat 2220
cgggtcacac ttaggccaca ggtgtgccac aacgggatag cccaacatgt cccttttttgt 2280 catgcatata tctatattat agttagtata atgtaaaaaa acaaaaggta tgtgtgttat 2340
gttggttaga tgtgtttaaa taactcttta aagctagcaa ctatggttta aatcatacat 2400
atacacattt ttattttatt tttatttaaa cgatatgggc cttctaggca cgtcgagtgt 2460
gacgggccag tgagatgaca cattataatt actggtctag caggccgtac ctaggtcttt 2520
ctcgtgggcc aagactaagg gttggcccgt tggctaatct gtacggtacc gatactgtcc 2580
taattcattt gaacacctgt agaagagggg aatttataat tgaggaggaa tgtactcatg 2640
cggtacacca ggggaattgt tttgttgtgc tcagcgatag atttcaacgc aacggtgagc 2700
cagtttcact aaaaaaaggg gggggggggg gggggggga aggccacatc aaaggcgagg 2760
tgctgacgag cagaagatgc tagcagtgac gccaagtcca gcagctagca atgaaagggt 2820
actcgggatt taacaatgcc tagagacggc atcatcccct caataatccg gtgctctctt 2880
tttgtttatt caccagttgg cgtagctata tacacatgtc tggtctgacg aacaaatcaa 2940
gggatcgcta gctcgggcta gccttcctat cactgtcatg acatgtgctc tgcctctgct 3000
ggttgataag ccgtgcgcct tctcgctaat tctttcttgt gctagaggcg agtcaaacaa 3060
acgctgcacc tcgtagccct taatctgcgc taagggtcac atgaccctgt tccctatcgc 3120
tagttaccaa cgacccattc cccctgacag atacttacga cgcgtccgta cgcggcaggc 3180
ctcggcagtt cggcatcacc agcaccggcg ccggcattcg ccccctgcca gccggt 3236

<210> SEQ ID NO 72
<211> LENGTH: 1000
<212> TYPE: DNA
<213> ORGANISM: Zea mays

<400> SEQUENCE: 72
tggtccttgt ttgatttact tccaggatta tataatccag cttatggatt atataagtac 60
ctattgacgt cacgtgctta tgtattataa taatctaggt atatagatta tataatctat 120
ctaataataa tctgtgttgt ttgtttatct ctcaaaacaa acaggtccta aaatggtccc 180
gggcgtccaa tgtgtcgtca agtagtgtta agctaaatcg acatttcttt gtgggttgtg 240
tggaaggtgt tccttttcct taagttgtta gttgtgcaag gtgttcctta gagcatctcc 300
aataggacct ataatggatt ctattttgaa ttataagact ctaacaacaa aagcatactt 360
taatggggat tctattttac aaaaaaatat caaatgatta tatggtcgat tcctcgggtc 420
ctaaatatag tatctcatat aatagagctc tatcctcatt ttatatacta tttttaagtt 480
tttatttact aaataacatg atttattttc taatactatg aactcaacta ttagagctgt 540
aaacgttttt gtggtactaa acactttaaa tcaggtccta ttttaatttg aaggacttaa 600
atataagact tctggttaga gatgctctta gcgagtgttt gtgcatgatt gctatttagt 660
ctttgtggat tgtggaaggt gttacttttc ctcaagttgt tagttgtgca aggtgtttct 720
tagagcatct ctaacaggag ccttaacgga atctattttg aagtatagta ctttaacacc 780
aaaaacatac tttaataggg gtcctatttt acaaaaaaat tatcaaatga ttataaggtc 840
cactcctcgg gtcctaaata taatatctca tatactagag ctctatcctc attttatata 900
ctatccctag gtttttattc cctaaataac atgatttatt tcctaatact aagatatagg 960
gctcaactat tggagttgca aatgtttttt ggcactaaac 1000

<210> SEQ ID NO 73
<211> LENGTH: 2236
<212> TYPE: DNA
<213> ORGANISM: Zea mays

<400> SEQUENCE: 73
actttatatc aggtcctatt ttaattttaa tttgaaggac tcaaatatag gacttctcgt 60
tagagatgct cttagcgagt gtttgtgcat gattgctatt tatgtctgta gtttagttgg 120
gggctttaat atgtttagtt gaagttctag tattttttag gttctccact ctttggatta 180
tgacaacgac cactatccaa gcagtctttg agtgcaaacg cgcgagcaaa ctatctgatc 240
tattaaatta tgatccaacc gttatgtcat attgaagact taaacccttt caccaccagc 300
ccaagtatct ttatgaaaaa ccctaacaaa ccacaattgc atctatggtt ggattataat 360
ttaacgtatc agatggttcg cttgcatgct tacatatcta gaaactgttt gcataacagt 420
cgttctcttt ggttatataa tgctttagta atcatcagcc aagtgtaaac aaatggtaca 480
aactagtagt gaacacatcc tccctaccta tctctagggg tgtaactaga tatccgaatt 540
cttagaacaa atttcatatt ttaaaataga tatgcttcaa aatttatgct aatctttttt 600
atattatcaa gcatattatt acacataaga ataaaatttt gtatagaatt ttatccatta 660
tttgttccct agaatttaaa aagtgaaaaa acattcgaat ctgtatcagt ttcgtattca 720
aatttttaca tctattattt gagaatatat atgataaatt tgaggtttag tttttatgaa 780
tctttacaag gttaatgtta aatacatgac tatggattta catagtaaat tctatgtctt 840
atttgtccgc gattgaagaa aaatgacaaa aagatctgac attcgaataa acatctgttt 900
ccactcctac ctatctgacc tcctatttca aactccactt tgtaacacgg tacaaaatca 960
ctccctacct atctgacctc ctatttcaaa ctccactcag taaacaatat tgtctatggt 1020
acaaaaccaa gtgttttata catctatttg cacgatctgc tcgagtcagg catccttgac 1080
acacaacata ctccttgtgg ctataaatgt ccaaatagag cagacctaat gggtggaccg 1140
ttgcatgaca cgacttatcc caagacgagc acagttcgcc ccattggtca tgggggtccg 1200
ggctagtcta gcctgatcat cgggtcacac ttaggccaca ggtgtgccac aacgggatag 1260
cccaacatgt ccctttttgt catgcatata tctatattat agttagtata atgtaaaaaa 1320
acaaaaggta tgtgtgttat gttggttaga tgtgtttaaa taactcttta aagctagcaa 1380
ctatggttta aatcatacat atacacattt ttattttatt tttatttaaa cgatatgggc 1440
cttctaggca cgtcgagtgt gacgggccag tgagatgaca cattataatt actggtctag 1500
caggccgtac ctaggtcttt ctcgtgggcc aagactaagg gttggcccgt tggctaatct 1560

```
gtacggtacc gatactgtcc taattcattt gaacacctgt agaagagggg aatttataat   1620

tgaggaggaa tgtactcatg cggtacacca ggggaattgt tttgttgtgc tcagcgatag   1680

atttcaacgc aacggtgagc cagtttcact aaaaaaaggg gggggggggg gggggggga   1740

aggccacatc aaaggcgagg tgctgacgag cagaagatgc tagcagtgac gccaagtcca   1800

gcagctagca atgaaagggt actcgggatt taacaatgcc tagagacggc atcatcccct   1860

caataatccg gtgctctctt tttgtttatt caccagttgg cgtagctata tacacatgtc   1920

tggtctgacg aacaaatcaa gggatcgcta gctcgggcta gccttcctat cactgtcatg   1980

acatgtgctc tgcctctgct ggttgataag ccgtgcgcct tctcgctaat tctttcttgt   2040

gctagaggcg agtcaaacaa acgctgcacc tcgtagccct taatctgcgc taagggtcac   2100

atgaccctgt tccctatcgc tagttaccaa cgacccattc cccctgacag atacttacga   2160

cgcgtccgta cgcggcaggc ctcggcagtt cggcatcacc agcaccggcg ccggcattcg   2220

ccccctgcca gccggt                                                   2236
```

<210> SEQ ID NO 74
<211> LENGTH: 1237
<212> TYPE: DNA
<213> ORGANISM: Zea Mays

<400> SEQUENCE: 74

```
gtaaacaata ttgtctatgg tacaaaacca agtgttttat acatctattt gcacgatctg     60

ctcgagtcag gcatccttga cacacaacat actccttgtg gctataaatg tccaaataga    120

gcagacctaa tgggtggacc gttgcatgac acgacttatc ccaagacgag cacagttcgc    180

cccattggtc atgggggtcc gggctagtct agcctgatca tcgggtcaca cttaggccac    240

aggtgtgcca caacgggata gcccaacatg tccctttttg tcatgcatat atctatatta    300

tagttagtat aatgtaaaaa aacaaaaggt atgtgtgtta tgttggttag atgtgtttaa    360

ataactcttt aaagctagca actatggttt aaatcataca tatacacatt tttattttat    420

ttttatttaa acgatatggg ccttctaggc acgtcgagtg tgacgggcca gtgagatgac    480

acattataat tactggtcta gcaggccgta cctaggtctt tctcgtgggc caagactaag    540

ggttggcccg ttggctaatc tgtacggtac cgatactgtc ctaattcatt tgaacacctg    600

tagaagaggg gaatttataa ttgaggagga atgtactcat gcggtacacc aggggaattg    660

ttttgttgtg ctcagcgata gatttcaacg caacggtgag ccagtttcac taaaaaaagg    720

gggggggggg gggggggggg aaggccacat caaaggcgag gtgctgacga gcagaagatg    780

ctagcagtga cgccaagtcc agcagctagc aatgaaaggg tactcgggat ttaacaatgc    840

ctagagacgg catcatcccc tcaataatcc ggtgctctct ttttgtttat tcaccagttg    900

gcgtagctat atacacatgt ctggtctgac gaacaaatca agggatcgct agctcgggct    960

agccttccta tcactgtcat gacatgtgct ctgcctctgc tggttgataa gccgtgcgcc   1020

ttctcgctaa ttctttcttg tgctagaggc gagtcaaaca aacgctgcac ctcgtagccc   1080

ttaatctgcg ctaagggtca catgaccctg ttccctatcg ctagttacca acgacccatt   1140

ccccctgaca gatacttacg acgcgtccgt acgcggcagg cctcggcagt tcggcatcac   1200

cagcaccggc gccggcattc gccccctgcc agccggt                            1237
```

<210> SEQ ID NO 75
<211> LENGTH: 21
<212> TYPE: DNA
<213> ORGANISM: Artificial

<220> FEATURE:
<223> OTHER INFORMATION: Primer

<400> SEQUENCE: 75
gccgtgcgcc ttctcgctaa t 21

<210> SEQ ID NO 76
<211> LENGTH: 24
<212> TYPE: DNA
<213> ORGANISM: Artificial
<220> FEATURE:
<223> OTHER INFORMATION: Primer

<400> SEQUENCE: 76
gcgaggagta cgactgccaa tcaa 24

<210> SEQ ID NO 77
<211> LENGTH: 32
<212> TYPE: DNA
<213> ORGANISM: Artificial
<220> FEATURE:
<223> OTHER INFORMATION: Primer

<400> SEQUENCE: 77
ttcggatcct ggtccttgtt tgatttactt cc 32

<210> SEQ ID NO 78
<211> LENGTH: 27
<212> TYPE: DNA
<213> ORGANISM: Artificial
<220> FEATURE:
<223> OTHER INFORMATION: Primer

<400> SEQUENCE: 78
ggcaagcttc ggtcgtccct tgctatc 27

<210> SEQ ID NO 79
<211> LENGTH: 18
<212> TYPE: DNA
<213> ORGANISM: Artificial
<220> FEATURE:
<223> OTHER INFORMATION: Primer

<400> SEQUENCE: 79
tgtaaaacga cggccagt 18

<210> SEQ ID NO 80
<211> LENGTH: 19
<212> TYPE: DNA
<213> ORGANISM: Artificial
<220> FEATURE:
<223> OTHER INFORMATION: Primer

<400> SEQUENCE: 80
ggaaacagct atgaccatg 19

<210> SEQ ID NO 81
<211> LENGTH: 24
<212> TYPE: DNA
<213> ORGANISM: Artificial
<220> FEATURE:
<223> OTHER INFORMATION: Primer

<400> SEQUENCE: 81
tcaaatgatt atatggtcga ttcc 24

<210> SEQ ID NO 82
<211> LENGTH: 20
<212> TYPE: DNA
<213> ORGANISM: Artificial
<220> FEATURE:
<223> OTHER INFORMATION: Primer

<400> SEQUENCE: 82
cgagcagatc gtgcaaatag 20

<210> SEQ ID NO 83
<211> LENGTH: 18
<212> TYPE: DNA
<213> ORGANISM: Artificial
<220> FEATURE:
<223> OTHER INFORMATION: Primer

<400> SEQUENCE: 83
tgctagctgc tggacttg 18

<210> SEQ ID NO 84
<211> LENGTH: 24
<212> TYPE: DNA
<213> ORGANISM: Artificial
<220> FEATURE:
<223> OTHER INFORMATION: Primer

<400> SEQUENCE: 84
ttgattggca gtcgtactcc tcgc 24

<210> SEQ ID NO 85
<211> LENGTH: 2777
<212> TYPE: DNA
<213> ORGANISM: vector

<400> SEQUENCE: 85
gaaaggccca gtcttccgac tgagcctttc gttttatttg atgcctggca gttccctact 60
ctcgcgttaa cgctagcatg gatgttttcc cagtcacgac gttgtaaaac gacggccagt 120
cttaagctcg ggcccgcgtt aacgctacca tggagctcca aataatgatt ttattttgac 180
tgatagtgac ctgttcgttg caacaaattg ataagcaatg ctttttata atgccaactt 240 tgtatagaaa agttgggccg aattcgagct cggtacggcc agaatggccc ggaccgggtt 300
accgaattcg agctcggtac cctgggatcc gatatcgatg ggccctggcc gaagcttggt 360
cacccggtcc gggcctagaa ggccagcttc aagtttgtac aaaaaagttg aacgagaaac 420
gtaaaatgat ataaatatca atatattaaa ttagattttg cataaaaaac agactacata 480
atactgtaaa acacaacata tgcagtcact atgaatcaac tacttagatg gtattagtga 540
cctgtagaat tcgagctcta gagctgcagg gcggccgcga tatcccctat agtgagtcgt 600
attacatggt catagctgtt tcctggcagc tctggcccgt gtctcaaaat ctctgatgtt 660
acattgcaca agataaaaat atatcatcat gaacaataaa actgtctgct tacataaaca 720
gtaatacaag gggtgttatg agccatattc aacgggaaac gtcgaggccg cgattaaatt 780
ccaacatgga tgctgattta tatgggtata aatgggctcg cgataatgtc gggcaatcag 840
gtgcgacaat ctatcgcttg tatgggaagc ccgatgcgcc agagttgttt ctgaaacatg 900
gcaaaggtag cgttgccaat gatgttacag atgagatggt cagactaaac tggctgacgg 960
aatttatgcc tcttccgacc atcaagcatt ttatccgtac tcctgatgat gcatggttac 1020
tcaccactgc gatccccgga aaaacagcat tccaggtatt agaagaatat cctgattcag 1080
gtgaaaatat tgttgatgcg ctggcagtgt tcctgcgccg gttgcattcg attcctgttt 1140

```
gtaattgtcc ttttaacagc gatcgcgtat ttcgtctcgc tcaggcgcaa tcacgaatga   1200
ataacggttt ggttgatgcg agtgattttg atgacgagcg taatggctgg cctgttgaac   1260
aagtctggaa agaaatgcat aaacttttgc cattctcacc ggattcagtc gtcactcatg   1320
gtgatttctc acttgataac cttatttttg acgaggggaa attaataggt tgtattgatg   1380
ttggacgagt cggaatcgca gaccgatacc aggatcttgc catcctatgg aactgcctcg   1440
gtgagttttc tccttcatta cagaaacggc tttttcaaaa atatggtatt gataatcctg   1500
atatgaataa attgcagttt catttgatgc tcgatgagtt tttctaatca gaattggtta   1560
attggttgta acactggcag agcattacgc tgacttgacg ggacggcgca agctcatgac   1620
caaaatccct taacgtgagt tacgcgtcgt tccactgagc gtcagacccc gtagaaaaga   1680
tcaaaggatc ttcttgagat cctttttttc tgcgcgtaat ctgctgcttg caaacaaaaa   1740
aaccaccgct accagcggtg gtttgtttgc cggatcaaga gctaccaact ctttttccga   1800
aggtaactgg cttcagcaga gcgcagatac caaatactgt ccttctagtg tagccgtagt   1860
taggccacca cttcaagaac tctgtagcac cgcctacata cctcgctctg ctaatcctgt   1920
taccagtggc tgctgccagt ggcgataagt cgtgtcttac cgggttggac tcaagacgat   1980
agttaccgga taaggcgcag cggtcgggct gaacgggggg ttcgtgcaca cagcccagct   2040
tggagcgaac gacctacacc gaactgagat acctacagcg tgagcattga gaaagcgcca   2100
cgcttcccga agggagaaag gcggacaggt atccggtaag cggcagggtc ggaacaggag   2160
agcgcacgag ggagcttcca gggggaaacg cctggtatct ttatagtcct gtcgggtttc   2220
gccacctctg acttgagcgt cgatttttgt gatgctcgtc aggggggcgg agcctatgga   2280
aaaacgccag caacgcggcc tttttacggt tcctggcctt ttgctggcct tttgctcaca   2340
tgttctttcc tgcgttatcc cctgattctg tggataaccg tattaccgcc tttgagtgag   2400
ctgataccgc tcgccgcagc cgaacgaccg agcgcagcga gtcagtgagc gaggaagcgg   2460
aagagcgccc aatacgcaaa ccgcctctcc ccgcgcgttg gccgattcat taatgcagct   2520
ggcacgacag gtttcccgac tggaaagcgg gcagtgagcg caacgcaatt aatacgcgta   2580
ccgctagcca ggaagagttt gtagaaacgc aaaaaggcca tccgtcagga tggccttctg   2640
cttagtttga tgcctggcag tttatggcgg gcgtcctgcc cgccaccctc cgggccgttg   2700
cttcacaacg ttcaaatccg ctcccggcgg atttgtccta ctcaggagag cgttcaccga   2760
caaacaacag ataaaac                                                  2777
```

<210> SEQ ID NO 86
<211> LENGTH: 6377
<212> TYPE: DNA
<213> ORGANISM: vector

<400> SEQUENCE: 86

```
gaaaggccca gtcttccgac tgagcctttc gttttatttg atgcctggca gttccctact     60
ctcgcgttaa cgctagcatg gatgttttcc cagtcacgac gttgtaaaac gacggccagt    120
cttaagctcg ggcccgcgtt aacgctacca tggagctcca aataatgatt ttattttgac    180
tgatagtgac ctgttcgttg caacaaattg ataagcaatg ctttttttata atgccaactt    240
tgtatagaaa agttgggccg aattcgagct cggtacggcc agaatggccc ggaccgggtt    300
accgaattcg agctcggtac cctgggatcc gcaagggacg accgtggtcc ttgtttgatt    360
tacttccagg attatataat ccagcttatg gattatataa gtacctattg acgtcacgtg    420
cttatgtatt ataataatct aggtatatag attatataat ctatctaata ataatctgtg    480
```

```
ttgtttgttt atctctcaaa acaaacaggt cctaaaatgg tcccgggcgt ccaatgtgtc    540
gtcaagtagt gttaagctaa atcgacattt ctttgtgggt tgtgtggaag gtgttccttt    600
tccttaagtt gttagttgtg caaggtgttc cttagagcat ctccaatagg acctataatg    660
gattctattt tgaattataa gactctaaca acaaaagcat actttaatgg ggattctatt    720
ttacaaaaaa atatcaaatg attatatggt cgattcctcg ggtcctaaat atagtatctc    780
atataataga gctctatcct cattttatat actattttta agtttttatt tactaaataa    840
catgatttat tttctaatac tatgaactca actattagag ctgtaaacgt ttttgtggta    900
ctaaacactt taaatcaggt cctattttaa tttgaaggac ttaaatataa gacttctggt    960
tagagatgct cttagcgagt gtttgtgcat gattgctatt tagtctttgt ggattgtgga   1020
aggtgttact tttcctcaag ttgttagttg tgcaaggtgt ttcttagagc atctctaaca   1080
ggagccttaa cggaatctat tttgaagtat agtactttaa caccaaaaac atactttaat   1140
aggggtccta ttttacaaaa aaattatcaa atgattataa ggtccactcc tcgggtccta   1200
aatataatat ctcatatact agagctctat cctcatttta tatactatcc ctaggttttt   1260
attccctaaa taacatgatt tatttcctaa tactaagata tagggctcaa ctattggagt   1320
tgcaaatgtt ttttggcact aaacacttta tatcaggtcc tattttaatt ttaatttgaa   1380
ggactcaaat ataggacttc tcgttagaga tgctcttagc gagtgtttgt gcatgattgc   1440
tatttatgtc tgtagtttag ttgggggctt taatatgttt agttgaagtt ctagtatttt   1500
ttaggttctc cactctttgg attatgacaa cgaccactat ccaagcagtc tttgagtgca   1560
aacgcgcgag caaactatct gatctattaa attatgatcc aaccgttatg tcatattgaa   1620
gacttaaacc ctttcaccac cagcccaagt atctttatga aaaaccctaa caaaccacaa   1680
ttgcatctat ggttggatta taatttaacg tatcagatgg ttcgcttgca tgcttacata   1740
tctagaaact gtttgcataa cagtcgttct ctttggttat ataatgcttt agtaatcatc   1800
agccaagtgt aaacaaatgg tacaaactag tagtgaacac atcctcccta cctatctcta   1860
ggggtgtaac tagatatccg aattcttaga acaaatttca tattttaaaa tagatatgct   1920
tcaaaattta tgctaatctt ttttatatta tcaagcatat tattacacat aagaataaaa   1980
ttttgtatag aattttatcc attatttgtt ccctagaatt taaaaagtga aaaaacattc   2040
gaatctgtat cagtttcgta ttcaaatttt tacatctatt atttgagaat atatatgata   2100
aatttgaggt ttagttttta tgaatcttta caaggttaat gttaaataca tgactatgga   2160
tttacatagt aaattctatg tcttatttgt ccgcgattga agaaaaatga caaaaagatc   2220
tgacattcga ataaacatct gtttccactc ctacctatct gacctcctat ttcaaactcc   2280
actttgtaac acggtacaaa atcactccct acctatctga cctcctattt caaactccac   2340
tcagtaaaca atattgtcta tggtacaaaa ccaagtgttt tatacatcta tttgcacgat   2400
ctgctcgagt caggcatcct tgacacacaa catactcctt gtggctataa atgtccaaat   2460
agagcagacc taatgggtgg accgttgcat gacacgactt atcccaagac gagcacagtt   2520
cgccccattg gtcatggggg tccgggctag tctagcctga tcatcgggtc acacttaggc   2580
cacaggtgtg ccacaacggg atagcccaac atgtcccttt ttgtcatgca tatatctata   2640
ttatagttag tataatgtaa aaaaacaaaa ggtatgtgtg ttatgttggt tagatgtgtt   2700
taaataactc tttaaagcta gcaactatgg tttaaatcat acatatacac atttttattt   2760
tatttttatt taaacgatat gggccttcta ggcacgtcga gtgtgacggg ccagtgagat   2820
gacacattat aattactggt ctagcaggcc gtacctaggt ctttctcgtg ggccaagact   2880
```

-continued

```
aagggttggc ccgttggcta atctgtacgg taccgatact gtcctaattc atttgaacac   2940
ctgtagaaga ggggaattta taattgagga ggaatgtact catgcggtac accaggggaa   3000
ttgttttgtt gtgctcagcg atagatttca acgcaacggt gagccagttt cactaaaaaa   3060
aggggggggg gggggggggg gggaaggcca catcaaaggc gaggtgctga cgagcagaag   3120
atgctagcag tgacgccaag tccagcagct agcaatgaaa gggtactcgg gatttaacaa   3180
tgcctagaga cggcatcatc ccctcaataa tccggtgctc tctttttgtt tattcaccag   3240
ttggcgtagc tatatacaca tgtctggtct gacgaacaaa tcaagggatc gctagctcgg   3300
gctagccttc ctatcactgt catgacatgt gctctgcctc tgctggttga taagccgtgc   3360
gccttctcgc taattctttc ttgtgctaga ggcgagtcaa acaaacgctg cacctcgtag   3420
cccttaatct gcgctaaggg tcacatgacc ctgttcccta tcgctagtta ccaacgaccc   3480
attccccctg acagatactt acgacgcgtc cgtacgcggc aggcctcggc agttcggcat   3540
caccagcacc ggcgccggca ttcgccccct gccagccggt tcgcagattc gcagggcgga   3600
gtcggccgca gttgccgcat cccaaacgcc cgggaacctt tggggcccct ctacgagcaa   3660
atgaagttgc tgcccctggc ttcgtaaagc tctgactttt gatcacttga ttggcagtcg   3720
tactcctcgc tcataggccg acacggccgc aaagtcaact acccgctccg ccatccttca   3780
acccccgcca cgcgcctata tatgttcgcg gccatgtccg tactagtcct ccaacccaca   3840
agccacaacc ccgagctcag atccctcgcc tcgtgtcgtg tctccggtcg acgacgacca   3900
acagccagtg tgggccagac ggacaccgcc gagctatagc gcttggtgat aaagcttggt   3960
cacccggtcc gggcctagaa ggccagcttc aagtttgtac aaaaaagttg aacgagaaac   4020
gtaaaatgat ataaatatca atatattaaa ttagattttg cataaaaaac agactacata   4080
atactgtaaa acacaacata tgcagtcact atgaatcaac tacttagatg gtattagtga   4140
cctgtagaat tcgagctcta gagctgcagg gcggccgcga tatcccctat agtgagtcgt   4200
attacatggt catagctgtt tcctggcagc tctggcccgt gtctcaaaat ctctgatgtt   4260
acattgcaca agataaaaat atatcatcat gaacaataaa actgtctgct tacataaaca   4320
gtaatacaag gggtgttatg agccatattc aacgggaaac gtcgaggccg cgattaaatt   4380
ccaacatgga tgctgattta tatgggtata aatgggctcg cgataatgtc gggcaatcag   4440
gtgcgacaat ctatcgcttg tatgggaagc ccgatgcgcc agagttgttt ctgaaacatg   4500
gcaaaggtag cgttgccaat gatgttacag atgagatggt cagactaaac tggctgacgg   4560
aatttatgcc tcttccgacc atcaagcatt ttatccgtac tcctgatgat gcatggttac   4620
tcaccactgc gatccccgga aaaacagcat tccaggtatt agaagaatat cctgattcag   4680
gtgaaaatat tgttgatgcg ctggcagtgt tcctgcgccg gttgcattcg attcctgttt   4740
gtaattgtcc ttttaacagc gatcgcgtat ttcgtctcgc tcaggcgcaa tcacgaatga   4800
ataacggttt ggttgatgcg agtgattttg atgacgagcg taatggctgg cctgttgaac   4860
aagtctggaa agaaatgcat aaacttttgc cattctcacc ggattcagtc gtcactcatg   4920
gtgatttctc acttgataac cttatttttg acgaggggaa attaataggt tgtattgatg   4980
ttggacgagt cggaatcgca gaccgatacc aggatcttgc catcctatgg aactgcctcg   5040
gtgagttttc tccttcatta cagaaacggc tttttcaaaa atatggtatt gataatcctg   5100
atatgaataa attgcagttt catttgatgc tcgatgagtt tttctaatca gaattggtta   5160
attggttgta acactggcag agcattacgc tgacttgacg ggacggcgca agctcatgac   5220
caaaatccct taacgtgagt tacgcgtcgt tccactgagc gtcagacccc gtagaaaaga   5280
```

```
tcaaaggatc ttcttgagat cctttttttc tgcgcgtaat ctgctgcttg caaacaaaaa   5340

aaccaccgct accagcggtg gtttgtttgc cggatcaaga gctaccaact ctttttccga   5400

aggtaactgg cttcagcaga gcgcagatac caaatactgt ccttctagtg tagccgtagt   5460

taggccacca cttcaagaac tctgtagcac cgcctacata cctcgctctg ctaatcctgt   5520

taccagtggc tgctgccagt ggcgataagt cgtgtcttac cgggttggac tcaagacgat   5580

agttaccgga taaggcgcag cggtcgggct gaacgggggg ttcgtgcaca cagcccagct   5640

tggagcgaac gacctacacc gaactgagat acctacagcg tgagcattga gaaagcgcca   5700

cgcttcccga agggagaaag gcggacaggt atccggtaag cggcagggtc ggaacaggag   5760

agcgcacgag ggagcttcca gggggaaacg cctggtatct ttatagtcct gtcgggtttc   5820

gccacctctg acttgagcgt cgatttttgt gatgctcgtc aggggggcgg agcctatgga   5880

aaaacgccag caacgcggcc tttttacggt tcctggcctt ttgctggcct tttgctcaca   5940

tgttctttcc tgcgttatcc cctgattctg tggataaccg tattaccgcc tttgagtgag   6000

ctgataccgc tcgccgcagc cgaacgaccg agcgcagcga gtcagtgagc gaggaagcgg   6060

aagagcgccc aatacgcaaa ccgcctctcc ccgcgcgttg gccgattcat taatgcagct   6120

ggcacgacag gtttcccgac tggaaagcgg gcagtgagcg caacgcaatt aatacgcgta   6180

ccgctagcca ggaagagttt gtagaaacgc aaaaaggcca tccgtcagga tggccttctg   6240

cttagtttga tgcctggcag tttatggcgg gcgtcctgcc cgccaccctc cgggccgttg   6300

cttcacaacg ttcaaatccg ctcccggcgg atttgtccta ctcaggagag cgttcaccga   6360

caaacaacag ataaaac                                                   6377
```

```
<210> SEQ ID NO 87
<211> LENGTH: 17777
<212> TYPE: DNA
<213> ORGANISM: vector

<400> SEQUENCE: 87
```

```
attatacaaa gttgatagat atcggaccga ttaaacttta attcggtccg aagcttgcat     60

gcctgcagtg cagcgtgacc cggtcgtgcc cctctctaga gataatgagc attgcatgtc    120

taagttataa aaaattacca catatttttt ttgtcacact tgtttgaagt gcagtttatc    180

tatctttata catatattta aactttactc tacgaataat ataatctata gtactacaat    240

aatatcagtg ttttagagaa tcatataaat gaacagttag acatggtcta aaggacaatt    300

gagtattttg acaacaggac tctacagttt tatcttttta gtgtgcatgt gttctccttt    360

tttttttgcaa atagcttcac ctatataata cttcatccat tttattagta catccattta    420

gggtttaggg ttaatggttt ttatagacta atttttttag tacatctatt ttattctatt    480

ttagcctcta aattaagaaa actaaaactc tattttagtt tttttattta ataatttaga    540

tataaaatag aataaaataa agtgactaaa aattaaacaa ataccccttta agaaattaaa    600

aaaactaagg aaacattttt cttgtttcga gtagataatg ccagcctgtt aaacgccgtc    660

gacgagtcta acggacacca accagcgaac cagcagcgtc gcgtcgggcc aagcgaagca    720

gacggcacgg catctctgtc gctgcctctg gacccctctc gagagttccg ctccaccgtt    780

ggacttgctc cgctgtcggc atccagaaat tgcgtggcgg agcggcagac gtgagccggc    840

acggcaggcg gcctcctcct cctctcacgg caccggcagc tacgggggat tcctttccca    900

ccgctccttc gctttccctt cctcgcccgc cgtaataaat agacaccccc tccacaccct    960

ctttccccaa cctcgtgttg ttcggagcgc acacacacac aaccagatct cccccaaatc   1020
```

-continued

```
cacccgtcgg cacctccgct tcaaggtacg ccgctcgtcc tccccccccc ccctctctac   1080
cttctctaga tcggcgttcc ggtccatgca tggttagggc ccggtagttc tacttctgtt   1140
catgtttgtg ttagatccgt gtttgtgtta gatccgtgct gctagcgttc gtacacggat   1200
gcgacctgta cgtcagacac gttctgattg ctaacttgcc agtgtttctc tttggggaat   1260
cctgggatgg ctctagccgt tccgcagacg ggatcgattt catgattttt tttgtttcgt   1320
tgcatagggt ttggtttgcc cttttccttt atttcaatat atgccgtgca cttgtttgtc   1380
gggtcatctt ttcatgcttt tttttgtctt ggttgtgatg atgtggtctg gttgggcggt   1440
cgttctagat cggagtagaa ttctgtttca aactacctgg tggatttatt aattttggat   1500
ctgtatgtgt gtgccataca tattcatagt tacgaattga agatgatgga tggaaatatc   1560
gatctaggat aggtatacat gttgatgcgg gttttactga tgcatataca gagatgcttt   1620
ttgttcgctt ggttgtgatg atgtggtgtg gttgggcggt cgttcattcg ttctagatcg   1680
gagtagaata ctgtttcaaa ctacctggtg tatttattaa ttttggaact gtatgtgtgt   1740
gtcatacatc ttcatagtta cgagtttaag atggatggaa atatcgatct aggataggta   1800
tacatgttga tgtgggtttt actgatgcat atacatgatg gcatatgcag catctattca   1860
tatgctctaa ccttgagtac ctatctatta taataaacaa gtatgtttta taattatttt   1920
gatcttgata tacttggatg atggcatatg cagcagctat atgtggattt ttttagccct   1980
gccttcatac gctatttatt tgcttggtac tgtttctttt gtcgatgctc accctgttgt   2040
ttggtgttac ttctgcaggt cgactttaac ttagcctagg atccacacga caccatgtcc   2100
cccgagcgcc gccccgtcga gatccgcccg gccaccgccg ccgacatggc cgccgtgtgc   2160
gacatcgtga accactacat cgagacctcc accgtgaact tccgcaccga gccgcagacc   2220
ccgcaggagt ggatcgacga cctggagcgc ctccaggacc gctacccgtg gctcgtggcc   2280
gaggtggagg gcgtggtggc cggcatcgcc tacgccggcc cgtggaaggc ccgcaacgcc   2340
tacgactgga ccgtggagtc caccgtgtac gtgtcccacc gccaccagcg cctcggcctc   2400
ggctccaccc tctacaccca cctcctcaag agcatggagg cccagggctt caagtccgtg   2460
gtggccgtga tcggcctccc gaacgacccg tccgtgcgcc tccacgaggc cctcggctac   2520
accgcccgcg gcaccctccg cgccgccggc tacaagcacg gcggctggca cgacgtcggc   2580
ttctggcagc gcgacttcga gctgccggcc ccgccgcgcc cggtgcgccc ggtgacgcag   2640
atctgagtcg aaacctagac ttgtccatct tctggattgg ccaacttaat taatgtatga   2700
aataaaagga tgcacacata gtgacatgct aatcactata atgtgggcat caaagttgtg   2760
tgttatgtgt aattactagt tatctgaata aaagagaaag agatcatcca tatttcttat   2820
cctaaatgaa tgtcacgtgt ctttataatt ctttgatgaa ccagatgcat ttcattaacc   2880
aaatccatat acatataaat attaatcata tataattaat atcaattggg ttagcaaaac   2940
aaatctagtc taggtgtgtt ttgcgaattg cggccgccac cgcggtggag ctcgaattca   3000
ttccgattaa tcgtggcctc ttgctcttca ggatgaagag ctatgtttaa acgtgcaagc   3060
gctactagac aattcagtac attaaaaacg tccgcaatgt gttattaagt tgtctaagcg   3120
tcaatttgtt tacaccacaa tatatcctgc caccagccag ccaacagctc cccgaccggc   3180
agctcggcac aaaatcacca ctcgatacag gcagcccatc agtccgggac ggcgtcagcg   3240
ggagagccgt tgtaaggcgg cagactttgc tcatgttacc gatgctattc ggaagaacgg   3300
caactaagct gccgggtttg aaacacggat gatctcgcgg agggtagcat gttgattgta   3360
acgatgacag agcgttgctg cctgtgatca aatatcatct ccctcgcaga gatccgaatt   3420
```

-continued

```
atcagccttc ttattcattt ctcgcttaac cgtgacaggc tgtcgatctt gagaactatg   3480
ccgacataat aggaaatcgc tggataaagc cgctgaggaa gctgagtggc gctatttctt   3540
tagaagtgaa cgttgacgat cgtcgaccgt accccgatga attaattcgg acgtacgttc   3600
tgaacacagc tggatactta cttgggcgat tgtcatacat gacatcaaca atgtacccgt   3660
ttgtgtaacc gtctcttgga ggttcgtatg acactagtgg ttcccctcag cttgcgacta   3720
gatgttgagg cctaacattt tattagagag caggctagtt gcttagatac atgatcttca   3780
ggccgttatc tgtcagggca agcgaaaatt ggccatttat gacgaccaat gccccgcaga   3840
agctcccatc tttgccgcca tagacgccgc gcccccctt tggggtgtag aacatccttt   3900
tgccagatgt ggaaaagaag ttcgttgtcc cattgttggc aatgacgtag tagccggcga   3960
aagtgcgaga cccatttgcg ctatatataa gcctacgatt tccgttgcga ctattgtcgt   4020
aattggatga actattatcg tagttgctct cagagttgtc gtaatttgat ggactattgt   4080
cgtaattgct tatggagttg tcgtagttgc ttggagaaat gtcgtagttg gatggggagt   4140
agtcataggg aagacgagct tcatccacta aaacaattgg caggtcagca agtgcctgcc   4200
ccgatgccat cgcaagtacg aggcttagaa ccaccttcaa cagatcgcgc atagtcttcc   4260
ccagctctct aacgcttgag ttaagccgcg ccgcgaagcg gcgtcggctt gaacgaattg   4320
ttagacatta tttgccgact accttggtga tctcgccttt cacgtagtga acaaattctt   4380
ccaactgatc tgcgcgcgag gccaagcgat cttcttgtcc aagataagcc tgcctagctt   4440
caagtatgac gggctgatac tgggccggca ggcgctccat tgcccagtcg gcagcgacat   4500
ccttcggcgc gattttgccg gttactgcgc tgtaccaaat gcgggacaac gtaagcacta   4560
catttcgctc atcgccagcc cagtcgggcg gcgagttcca tagcgttaag gtttcattta   4620
gcgcctcaaa tagatcctgt tcaggaaccg gatcaaagag ttcctccgcc gctggaccta   4680
ccaaggcaac gctatgttct cttgcttttg tcagcaagat agccagatca atgtcgatcg   4740
tggctggctc gaagatacct gcaagaatgt cattgcgctg ccattctcca aattgcagtt   4800
cgcgcttagc tggataacgc cacggaatga tgtcgtcgtg cacaacaatg gtgacttcta   4860
cagcgcggag aatctcgctc tctccagggg aagccgaagt ttccaaaagg tcgttgatca   4920
aagctcgccg cgttgtttca tcaagcctta cagtcaccgt aaccagcaaa tcaatatcac   4980
tgtgtggctt caggccgcca tccactgcgg agccgtacaa atgtacggcc agcaacgtcg   5040
gttcgagatg gcgctcgatg acgccaacta cctctgatag ttgagtcgat acttcggcga   5100
tcaccgcttc cctcatgatg tttaactcct gaattaagcc gcgccgcgaa gcggtgtcgg   5160
cttgaatgaa ttgttaggcg tcatcctgtg ctcccgagaa ccagtaccag tacatcgctg   5220
tttcgttcga gacttgaggt ctagttttat acgtgaacag gtcaatgccg ccgagagtaa   5280
agccacattt tgcgtacaaa ttgcaggcag gtacattgtt cgtttgtgtc tctaatcgta   5340
tgccaaggag ctgtctgctt agtgcccact tttcgcaaa ttcgatgaga ctgtgcgcga   5400
ctcctttgcc tcggtgcgtg tgcgacacaa caatgtgttc gatagaggct agatcgttcc   5460
atgttgagtt gagttcaatc ttcccgacaa gctcttggtc gatgaatgcg ccatagcaag   5520
cagagtcttc atcagagtca tcatccgaga tgtaatcctt ccggtagggg ctcacacttc   5580
tggtagatag ttcaaagcct tggtcggata ggtgcacatc gaacacttca cgaacaatga   5640
aatggttctc agcatccaat gtttccgcca cctgctcagg gatcaccgaa atcttcatat   5700
gacgcctaac gcctggcaca gcggatcgca aacctggcgc ggcttttggc acaaaaggcg   5760
tgacaggttt gcgaatccgt tgctgccact tgttaaccct tttgccagat ttggtaacta   5820
```

```
taatttatgt tagaggcgaa gtcttgggta aaaactggcc taaaattgct ggggatttca   5880
ggaaagtaaa catcaccttc cggctcgatg tctattgtag atatatgtag tgtatctact   5940
tgatcggggg atctgctgcc tcgcgcgttt cggtgatgac ggtgaaaacc tctgacacat   6000
gcagctcccg gagacggtca cagcttgtct gtaagcggat gccgggagca gacaagcccg   6060
tcagggcgcg tcagcgggtg ttggcgggtg tcggggcgca gccatgaccc agtcacgtag   6120
cgatagcgga gtgtatactg gcttaactat gcggcatcag agcagattgt actgagagtg   6180
caccatatgc ggtgtgaaat accgcacaga tgcgtaagga gaaaataccg catcaggcgc   6240
tcttccgctt cctcgctcac tgactcgctg cgctcggtcg ttcggctgcg gcgagcggta   6300
tcagctcact caaaggcggt aatacggtta tccacagaat caggggataa cgcaggaaag   6360
aacatgtgag caaaaggcca gcaaaaggcc aggaaccgta aaaaggccgc gttgctggcg   6420
tttttccata ggctccgccc ccctgacgag catcacaaaa atcgacgctc aagtcagagg   6480
tggcgaaacc cgacaggact ataaagatac caggcgtttc cccctggaag ctccctcgtg   6540
cgctctcctg ttccgaccct gccgcttacc ggatacctgt ccgcctttct cccttcggga   6600
agcgtggcgc tttctcatag ctcacgctgt aggtatctca gttcggtgta ggtcgttcgc   6660
tccaagctgg gctgtgtgca cgaacccccc gttcagcccg accgctgcgc cttatccggt   6720
aactatcgtc ttgagtccaa cccggtaaga cacgacttat cgccactggc agcagccact   6780
ggtaacagga ttagcagagc gaggtatgta ggcggtgcta cagagttctt gaagtggtgg   6840
cctaactacg gctacactag aaggacagta tttggtatct gcgctctgct gaagccagtt   6900
accttcggaa aaagagttgg tagctcttga tccggcaaac aaaccaccgc tggtagcggt   6960
ggtttttttg tttgcaagca gcagattacg cgcagaaaaa aaggatctca agaagatcct   7020
ttgatctttt ctacggggtc tgacgctcag tggaacgaaa actcacgtta agggattttg   7080
gtcatgagat tatcaaaaag gatcttcacc tagatccttt taaattaaaa atgaagtttt   7140
aaatcaatct aaagtatata tgagtaaact tggtctgaca gttaccaatg cttaatcagt   7200
gaggcaccta tctcagcgat ctgtctattt cgttcatcca tagttgcctg actccccgtc   7260
gtgtagataa ctacgatacg ggagggctta ccatctggcc ccagtgctgc aatgataccg   7320
cgagacccac gctcaccggc tccagattta tcagcaataa accagccagc cggaagggcc   7380
gagcgcagaa gtggtcctgc aactttatcc gcctccatcc agtctattaa ttgttgccgg   7440
gaagctagag taagtagttc gccagttaat agtttgcgca acgttgttgc cattgctgca   7500
gggggggggg gggggggga cttccattgt tcattccacg gacaaaaaca gagaaaggaa   7560
acgacagagg ccaaaaagcc tcgctttcag cacctgtcgt ttcctttctt ttcagagggt   7620
attttaaata aaaacattaa gttatgacga agaagaacgg aaacgcctta aaccggaaaa   7680
ttttcataaa tagcgaaaac ccgcgaggtc gccgccccgt aacctgtcgg atcaccggaa   7740
aggacccgta aagtgataat gattatcatc tacatatcac aacgtgcgtg gaggccatca   7800
aaccacgtca aataatcaat tatgacgcag gtatcgtatt aattgatctg catcaactta   7860
acgtaaaaac aacttcagac aatacaaatc agcgacactg aatacggggc aacctcatgt   7920
cccccccccc ccccccctg caggcatcgt ggtgtcacgc tcgtcgtttg gtatggcttc   7980
attcagctcc ggttcccaac gatcaaggcg agttacatga tcccccatgt tgtgcaaaaa   8040
agcggttagc tccttcggtc ctccgatcgt tgtcagaagt aagttggccg cagtgttatc   8100
actcatggtt atggcagcac tgcataattc tcttactgtc atgccatccg taagatgctt   8160
ttctgtgact ggtgagtact caaccaagtc attctgagaa tagtgtatgc ggcgaccgag   8220
```

```
ttgctcttgc ccggcgtcaa cacgggataa taccgcgcca catagcagaa ctttaaaagt   8280
gctcatcatt ggaaaacgtt cttcggggcg aaaactctca aggatcttac cgctgttgag   8340
atccagttcg atgtaaccca ctcgtgcacc caactgatct tcagcatctt ttactttcac   8400
cagcgtttct gggtgagcaa aaacaggaag gcaaaatgcc gcaaaaaagg gaataagggc   8460
gacacggaaa tgttgaatac tcatactctt cctttttcaa tattattgaa gcatttatca   8520
gggttattgt ctcatgagcg gatacatatt tgaatgtatt tagaaaaata aacaaatagg   8580
ggttccgcgc acatttcccc gaaaagtgcc acctgacgtc taagaaacca ttattatcat   8640
gacattaacc tataaaaata ggcgtatcac gaggcccttt cgtcttcaag aattggtcga   8700
cgatcttgct gcgttcggat attttcgtgg agttcccgcc acagacccgg attgaaggcg   8760
agatccagca actcgcgcca gatcatcctg tgacggaact ttggcgcgtg atgactggcc   8820
aggacgtcgg ccgaaagagc gacaagcaga tcacgctttt cgacagcgtc ggatttgcga   8880
tcgaggattt ttcggcgctg cgctacgtcc gcgaccgcgt tgagggatca agccacagca   8940
gcccactcga ccttctagcc gacccagacg agccaaggga tctttttgga atgctgctcc   9000
gtcgtcaggc tttccgacgt ttgggtggtt gaacagaagt cattatcgta cggaatgcca   9060
agcactcccg aggggaaccc tgtggttggc atgcacatac aaatggacga acggataaac   9120
cttttcacgc ccttttaaat atccgttatt ctaataaacg ctcttttctc ttaggtttac   9180
ccgccaatat atcctgtcaa acactgatag tttaaactga aggcgggaaa cgacaatctg   9240
atcatgagcg gagaattaag ggagtcacgt tatgaccccc gccgatgacg cgggacaagc   9300
cgttttacgt ttggaactga cagaaccgca acgttgaagg agccactcag caagctggta   9360
cgattgtaat acgactcact atagggcgaa ttgagcgctg tttaaacgct cttcaactgg   9420
aagagcggtt accagagctg gtcacctttg tccaccaaga tggaactgcg gccgctcatt   9480
aattaagtca ggcgcgcctc tagttgaaga cacgttcatg tcttcatcgt aagaagacac   9540
tcagtagtct tcggccagaa tggcccggac cgaagctggc cgctctagaa ctagtggatc   9600
tcgatgtgta gtctacgaga agggttaacc gtctcttcgt gagaataacc gtggcctaaa   9660
aataagccga tgaggataaa taaaatgtgg tggtacagta cttcaagagg tttactcatc   9720
aagaggatgc ttttccgatg agctctagta gtacatcgga cctcacatac ctccattgtg   9780
gtgaaatatt ttgtgctcat ttagtgatgg gtaaattttg tttatgtcac tctaggtttt   9840
gacatttcag ttttgccact cttaggtttt gacaaataat ttccattccg cggcaaaagc   9900
aaaacaattt tattttactt ttaccactct tagctttcac aatgtatcac aaatgccact   9960
ctagaaattc tgtttatgcc acagaatgtg aaaaaaaaca ctcacttatt tgaagccaag  10020
gtgttcatgg catggaaatg tgacataaag taacgttcgt gtataagaaa aaattgtact  10080
cctcgtaaca agagacggaa acatcatgag acaatcgcgt ttggaaggct ttgcatcacc  10140
tttggatgat gcgcatgaat ggagtcgtct gcttgctagc cttcgcctac cgcccactga  10200
gtccgggcgg caactaccat cggcgaacga cccagctgac ctctaccgac cggacttgaa  10260
tgcgctacct tcgtcagcga cgatggccgc gtacgctggc gacgtgcccc cgcatgcatg  10320
gcggcacatg gcgagctcag accgtgcgtg gctggctaca aatacgtacc ccgtgagtgc  10380
cctagctaga aacttacacc tgcaactgcg agagcgagcg tgtgagtgta gccgagtaga  10440
tccccggtc gccaccatgg cctcctccga gaacgtcatc accgagttca tgcgcttcaa  10500
ggtgcgcatg gagggcaccg tgaacggcca cgagttcgag atcgagggcg agggcgaggg  10560
ccgcccctac gagggccaca acaccgtgaa gctgaaggtg accaagggcg gcccctgcc  10620
```

-continued

```
cttcgcctgg gacatcctgt ccccccagtt ccagtacggc tccaaggtgt acgtgaagca  10680
ccccgccgac atccccgact acaagaagct gtccttcccc gagggcttca agtgggagcg  10740
cgtgatgaac ttcgaggacg gcggcgtggc gaccgtgacc caggactcct ccctgcagga  10800
cggctgcttc atctacaagg tgaagttcat cggcgtgaac ttcccctccg acggccccgt  10860
gatgcagaag aagaccatgg gctgggaggc ctccaccgag cgcctgtacc cccgcgacgg  10920
cgtgctgaag ggcgagaccc acaaggccct gaagctgaag gacggcggcc actacctggt  10980
ggagttcaag tccatctaca tggccaagaa gcccgtgcag ctgcccggct actactacgt  11040
ggacgccaag ctggacatca cctcccacaa cgaggactac accatcgtgg agcagtacga  11100
gcgcaccgag ggccgccacc acctgttcct gtagcggccc atggatattc gaacgcgtag  11160
gtaccacatg gttaacctag acttgtccat cttctggatt ggccaactta attaatgtat  11220
gaaataaaag gatgcacaca tagtgacatg ctaatcacta taatgtgggc atcaaagttg  11280
tgtgttatgt gtaattacta gttatctgaa taaaagagaa agagatcatc catatttctt  11340
atcctaaatg aatgtcacgt gtctttataa ttctttgatg aaccagatgc atttcattaa  11400
ccaaatccat atacatataa atattaatca tatataatta atatcaattg ggttagcaaa  11460
acaaatctag tctaggtgtg ttttgcgaat gcggccgcca ccgcggtgga gctcgaattc  11520
cggtccgggc ctagaaggcc atttaaatcc tgaggatctg gtcttcctaa ggacccggga  11580
tatcgctatc aactttgtat agaaaagttg ggccgaattc gagctcggta cggccagaat  11640
ggcccggacc gggttaccga attcgagctc ggtaccctgg gatccgcaag ggacgaccgt  11700
ggtccttgtt tgatttactt ccaggattat ataatccagc ttatggatta tataagtacc  11760
tattgacgtc acgtgcttat gtattataat aatctaggta tatagattat ataatctatc  11820
taataataat ctgtgttgtt tgtttatctc tcaaaacaaa caggtcctaa aatggtcccg  11880
ggcgtccaat gtgtcgtcaa gtagtgttaa gctaaatcga catttctttg tgggttgtgt  11940
ggaaggtgtt ccttttcctt aagttgttag ttgtgcaagg tgttccttag agcatctcca  12000
ataggaccta taatggattc tattttgaat tataagactc taacaacaaa agcatacttt  12060
aatggggatt ctattttaca aaaaaatatc aaatgattat atggtcgatt cctcgggtcc  12120
taaatatagt atctcatata atagagctct atcctcattt tatatactat ttttaagttt  12180
ttatttacta aataacatga tttattttct aatactatga actcaactat tagagctgta  12240
aacgtttttg tggtactaaa cactttaaat caggtcctat tttaatttga aggacttaaa  12300
tataagactt ctggttagag atgctcttag cgagtgtttg tgcatgattg ctatttagtc  12360
tttgtggatt gtggaaggtg ttacttttcc tcaagttgtt agttgtgcaa ggtgtttctt  12420
agagcatctc taacaggagc cttaacggaa tctattttga agtatagtac tttaacacca  12480
aaaacatact ttaatagggg tcctatttta caaaaaaatt atcaaatgat tataaggtcc  12540
actcctcggg tcctaaatat aatatctcat atactagagc tctatcctca ttttatatac  12600
tatccctagg tttttattcc ctaaataaca tgatttattt cctaatacta agatataggg  12660
ctcaactatt ggagttgcaa atgtttttttg gcactaaaca ctttatatca ggtcctattt  12720
taattttaat ttgaaggact caaatatagg acttctcgtt agagatgctc ttagcgagtg  12780
tttgtgcatg attgctattt atgtctgtag tttagttggg ggctttaata tgtttagttg  12840
aagttctagt attttttagg ttctccactc tttggattat gacaacgacc actatccaag  12900
cagtctttga gtgcaaacgc gcgagcaaac tatctgatct attaaattat gatccaaccg  12960
ttatgtcata ttgaagactt aaacccttc accaccagcc caagtatctt tatgaaaaac  13020
```

```
cctaacaaac cacaattgca tctatggttg gattataatt taacgtatca gatggttcgc  13080
ttgcatgctt acatatctag aaactgtttg cataacagtc gttctctttg gttatataat  13140
gctttagtaa tcatcagcca agtgtaaaca aatggtacaa actagtagtg aacacatcct  13200
ccctacctat ctctaggggt gtaactagat atccgaattc ttagaacaaa tttcatattt  13260
taaaatagat atgcttcaaa atttatgcta atctttttta tattatcaag catattatta  13320
cacataagaa taaaattttg tatagaattt tatccattat ttgttcccta gaatttaaaa  13380
agtgaaaaaa cattcgaatc tgtatcagtt tcgtattcaa atttttacat ctattatttg  13440
agaatatata tgataaattt gaggtttagt ttttatgaat ctttacaagg ttaatgttaa  13500
atacatgact atggatttac atagtaaatt ctatgtctta tttgtccgcg attgaagaaa  13560
aatgacaaaa agatctgaca ttcgaataaa catctgtttc cactcctacc tatctgacct  13620
cctatttcaa actccacttt gtaacacggt acaaaatcac tccctaccta tctgacctcc  13680
tatttcaaac tccactcagt aaacaatatt gtctatggta caaaaccaag tgttttatac  13740
atctatttgc acgatctgct cgagtcaggc atccttgaca cacaacatac tccttgtggc  13800
tataaatgtc caaatagagc agacctaatg ggtggaccgt tgcatgacac gacttatccc  13860
aagacgagca cagttcgccc cattggtcat gggggtccgg gctagtctag cctgatcatc  13920
gggtcacact taggccacag gtgtgccaca acgggatagc ccaacatgtc cctttttgtc  13980
atgcatatat ctatattata gttagtataa tgtaaaaaaa caaaaggtat gtgtgttatg  14040
ttggttagat gtgtttaaat aactctttaa agctagcaac tatggtttaa atcatacata  14100
tacacatttt tattttattt ttatttaaac gatatgggcc ttctaggcac gtcgagtgtg  14160
acgggccagt gagatgacac attataatta ctggtctagc aggccgtacc taggtctttc  14220
tcgtgggcca agactaaggg ttggcccgtt ggctaatctg tacggtaccg atactgtcct  14280
aattcatttg aacacctgta gaagagggga atttataatt gaggaggaat gtactcatgc  14340
ggtacaccag gggaattgtt ttgttgtgct cagcgataga tttcaacgca acggtgagcc  14400
agtttcacta aaaaaagggg gggggggggg gggggggaa ggccacatca aaggcgaggt  14460
gctgacgagc agaagatgct agcagtgacg ccaagtccag cagctagcaa tgaaagggta  14520
ctcgggattt aacaatgcct agagacggca tcatcccctc aataatccgg tgctctcttt  14580
ttgtttattc accagttggc gtagctatat acacatgtct ggtctgacga acaaatcaag  14640
ggatcgctag ctcgggctag ccttcctatc actgtcatga catgtgctct gcctctgctg  14700
gttgataagc cgtgcgcctt ctcgctaatt ctttcttgtg ctagaggcga gtcaaacaaa  14760
cgctgcacct cgtagccctt aatctgcgct aagggtcaca tgaccctgtt ccctatcgct  14820
agttaccaac gacccattcc ccctgacaga tacttacgac gcgtccgtac gcggcaggcc  14880
tcggcagttc ggcatcacca gcaccggcgc cggcattcgc cccctgccag ccggttcgca  14940
gattcgcagg gcggagtcgg ccgcagttgc cgcatcccaa acgcccggga acctttgggg  15000
cccctctacg agcaaatgaa gttgctgccc ctggcttcgt aaagctctga cttttgatca  15060
cttgattggc agtcgtactc ctcgctcata ggccgacacg gccgcaaagt caactacccg  15120
ctccgccatc cttcaacccc cgccacgcgc ctatatatgt tcgcggccat gtccgtacta  15180
gtcctccaac ccacaagcca caaccccgag ctcagatccc tcgcctcgtg tcgtgtctcc  15240
ggtcgacgac gaccaacagc cagtgtgggc cagacggaca ccgccgagct atagcgcttg  15300
gtgataaagc ttggtcaccc ggtccgggcc tagaaggcca gcttcaagtt tgtacaaaaa  15360
agcaggctcc agcgctcacc atggtccgtc ctgtagaaac cccaacccgt gaaatcaaaa  15420
```

-continued

```
aactcgacgg cctgtgggca ttcagtctgg atcgcgaaaa ctgtggaatt gatcagcgtt  15480
ggtgggaaag cgcgttacaa gaaagccggg caattgctgt gccaggcagt tttaacgatc  15540
agttcgccga tgcagatatt cgtaattatg cgggcaacgt ctggtatcag cgcgaagtct  15600
ttataccgaa aggttgggca ggccagcgta tcgtgctgcg tttcgatgcg gtcactcatt  15660
acggcaaagt gtgggtcaat aatcaggaag tgatggagca tcagggcggc tatacgccat  15720
ttgaagccga tgtcacgccg tatgttattg ccgggaaaag tgtacgtaag tttctgcttc  15780
tacctttgat atatatataa taattatcat taattagtag taatataata tttcaaatat  15840
tttttcaaa ataaaagaat gtagtatata gcaattgctt ttctgtagtt tataagtgtg  15900
tatattttaa tttataactt ttctaatata tgaccaaaat ttgttgatgt gcaggtatca  15960
ccgtttgtgt gaacaacgaa ctgaactggc agactatccc gccgggaatg gtgattaccg  16020
acgaaaacgg caagaaaaag cagtcttact tccatgattt ctttaactat gccggaatcc  16080
atcgcagcgt aatgctctac accacgccga acacctgggt ggacgatatc accgtggtga  16140
cgcatgtcgc gcaagactgt aaccacgcgt ctgttgactg gcaggtggtg gccaatggtg  16200
atgtcagcgt tgaactgcgt gatgcggatc aacaggtggt tgcaactgga caaggcacta  16260
gcgggacttt gcaagtggtg aatccgcacc tctggcaacc gggtgaaggt tatctctatg  16320
aactgtgcgt cacagccaaa agccagacag agtgtgatat ctacccgctt cgcgtcggca  16380
tccggtcagt ggcagtgaag ggcgaacagt tcctgattaa ccacaaaccg ttctacttta  16440
ctggctttgg tcgtcatgaa gatgcggact tgcgtggcaa aggattcgat aacgtgctga  16500
tggtgcacga ccacgcatta atggactgga ttggggccaa ctcctaccgt acctcgcatt  16560
acccttacgc tgaagagatg ctcgactggg cagatgaaca tggcatcgtg gtgattgatg  16620
aaactgctgc tgtcggcttt aacctctctt taggcattgg tttcgaagcg ggcaacaagc  16680
cgaaagaact gtacagcgaa gaggcagtca acggggaaac tcagcaagcg cacttacagg  16740
cgattaaaga gctgatagcg cgtgacaaaa accacccaag cgtggtgatg tggagtattg  16800
ccaacgaacc ggatacccgt ccgcaaggtg cacgggaata tttcgcgcca ctggcggaag  16860
caacgcgtaa actcgacccg acgcgtccga tcacctgcgt caatgtaatg ttctgcgacg  16920
ctcacaccga taccatcagc gatctctttg atgtgctgtg cctgaaccgt tattacggat  16980
ggtatgtcca aagcggcgat ttggaaacgg cagagaaggt actggaaaaa gaacttctgg  17040
cctggcagga gaaactgcat cagccgatta tcatcaccga atacggcgtg gatacgttag  17100
ccgggctgca ctcaatgtac accgacatgt ggagtgaaga gtatcagtgt gcatggctgg  17160
atatgtatca ccgcgtcttt gatcgcgtca gcgccgtcgt cggtgaacag gtatggaatt  17220
tcgccgattt tgcgacctcg caaggcatat tgcgcgttgg cggtaacaag aaagggatct  17280
tcactcgcga ccgcaaaccg aagtcggcgg cttttctgct gcaaaaacgc tggactggca  17340
tgaacttcgg tgaaaaaccg cagcagggag gcaaacaatg aagatctccc gggcacccag  17400
ctttcttgta caaagtggcc gttaacggat ccagacttgt ccatcttctg gattggccaa  17460
cttaattaat gtatgaaata aaaggatgca cacatagtga catgctaatc actataatgt  17520
gggcatcaaa gttgtgtgtt atgtgtaatt actagttatc tgaataaaag agaaagagat  17580
catccatatt tcttatccta aatgaatgtc acgtgtcttt ataattcttt gatgaaccag  17640
atgcatttca ttaaccaaat ccatatacat ataaatatta atcatatata attaatatca  17700
attgggttag caaaacaaat ctagtctagg tgtgttttgc gaattgcggc aagcttgcgg  17760
ccgccccggg caacttt                                                 17777
```

<210> SEQ ID NO 88
<211> LENGTH: 54686
<212> TYPE: DNA
<213> ORGANISM: vector

<400> SEQUENCE: 88
tctagagctc gttcctcgag gcctcgaggc ctcgaggaac ggtacctgcg gggaagctta 60
caataatgtg tgttgttaag tcttgttgcc tgtcatcgtc tgactgactt tcgtcataaa 120
tcccggcctc cgtaacccag ctttgggcaa gctcacggat ttgatccggc ggaacgggaa 180
tatcgagatg ccgggctgaa cgctgcagtt ccagctttcc ctttcgggac aggtactcca 240
gctgattgat tatctgctga agggtcttgg ttccacctcc tggcacaatg cgaatgatta 300
cttgagcgcg atcgggcatc caattttctc ccgtcaggtg cgtggtcaag tgctacaagg 360
cacctttcag taacgagcga ccgtcgatcc gtcgccggga tacggacaaa atggagcgca 420
gtagtccatc gagggcggcg aaagcctcgc caaaagcaat acgttcatct cgcacagcct 480
ccagatccga tcgagggtct tcggcgtagg cagatagaag catggataca ttgcttgaga 540
gtattccgat ggactgaagt atggcttcca tcttttctcg tgtgtctgca tctatttcga 600
gaaagccccc gatgcggcgc accgcaacgc gaattgccat actatccgaa agtcccagca 660
ggcgcgcttg ataggaaaag gtttcatact cggccgatcg cagacgggca ctcacgacct 720
tgaacccttc aactttcagg gatcgatgct ggttgatggt agtctcactc gacgtggctc 780
tggtgtgttt tgacatagct tcctccaaag aaagcggaag gtctggatac tccagcacga 840
aatgtgcccg ggtagacgga tggaagtcta gccctgctca atatgaaatc aacagtacat 900
ttacagtcaa tactgaatat acttgctaca tttgcaattg tcttataacg aatgtgaaat 960
aaaaatagtg taacaacgct tttactcatc gataatcaca aaaacattta tacgaacaaa 1020
aatacaaatg cactccggtt tcacaggata ggcgggatca gaatatgcaa cttttgacgt 1080
tttgttcttt caaagggggt gctggcaaaa ccaccgcact catgggcctt tgcgctgctt 1140
tggcaaatga cggtaaacga gtggccctct ttgatgccga cgaaaaccgg cctctgacgc 1200
gatggagaga aaacgcctta caaagcagta ctgggatcct cgctgtgaag tctattccgc 1260
cgacgaaatg ccccttcttg aagcagccta tgaaaatgcc gagctcgaag gatttgatta 1320
tgcgttggcc gatacgcgtg gcggctcgag cgagctcaac aacacaatca tcgctagctc 1380
aaacctgctt ctgatcccca ccatgctaac gccgctcgac atcgatgagg cactatctac 1440
ctaccgctac gtcatcgagc tgctgttgag tgaaaatttg gcaattccta cagctgtttt 1500
gcgccaacgc gtcccggtcg gccgattgac aacatcgcaa cgcaggatgt cagagacgct 1560
agagagcctt ccagttgtac cgtctcccat gcatgaaaga gatgcatttg ccgcgatgaa 1620
agaacgcggc atgttgcatc ttacattact aaacacggga actgatccga cgatgcgcct 1680
catagagagg aatcttcgga ttgcgatgga ggaagtcgtg gtcatttcga aactgatcag 1740
caaaatcttg gaggcttgaa gatggcaatt cgcaagcccg cattgtcggt cggcgaagca 1800
cggcggcttg ctggtgctcg acccgagatc caccatccca acccgacact tgttccccag 1860
aagctggacc tccagcactt gcctgaaaaa gccgacgaga aagaccagca acgtgagcct 1920
ctcgtcgccg atcacattta cagtcccgat cgacaactta agctaactgt ggatgccctt 1980
agtccacctc cgtccccgaa aaagctccag gtttttcttt cagcgcgacc gcccgcgcct 2040
caagtgtcga aaacatatga caacctcgtt cggcaataca gtccctcgaa gtcgctacaa 2100
atgattttaa ggcgcgcgtt ggacgatttc gaaagcatgc tggcagatgg atcatttcgc 2160

-continued gtggccccga aaagttatcc gatcccttca actacagaaa aatccgttct cgttcagacc 2220
tcacgcatgt tcccggttgc gttgctcgag gtcgctcgaa gtcattttga tccgttgggg 2280
ttggagaccg ctcgagcttt cggccacaag ctggctaccg ccgcgctcgc gtcattcttt 2340
gctggagaga agccatcgag caattggtga agagggacct atcggaaccc ctcaccaaat 2400
attgagtgta ggtttgaggc cgctggccgc gtcctcagtc acctttttgag ccagataatt 2460
aagagccaaa tgcaattggc tcaggctgcc atcgtccccc cgtgcgaaac ctgcacgtcc 2520
gcgtcaaaga aataaccggc acctcttgct gtttttatca gttgagggct tgacggatcc 2580
gcctcaagtt tgcggcgcag ccgcaaaatg agaacatcta tactcctgtc gtaaacctcc 2640
tcgtcgcgta ctcgactggc aatgagaagt tgctcgcgcg atagaacgtc gcggggtttc 2700
tctaaaaacg cgaggagaag attgaactca cctgccgtaa gtttcacctc accgccagct 2760
tcggacatca agcgacgttg cctgagatta agtgtccagt cagtaaaaca aaaagaccgt 2820
cggtctttgg agcggacaac gttggggcgc acgcgcaagg caacccgaat gcgtgcaaga 2880
aactctctcg tactaaacgg cttagcgata aaatcacttg ctcctagctc gagtgcaaca 2940
actttatccg tctcctcaag gcggtcgcca ctgataatta tgattggaat atcagacttt 3000
gccgccagat ttcgaacgat ctcaagccca tcttcacgac ctaaatttag atcaacaacc 3060
acgacatcga ccgtcgcgga agagagtact ctagtgaact gggtgctgtc ggctaccgcg 3120
gtcactttga aggcgtggat cgtaaggtat tcgataataa gatgccgcat agcgacatcg 3180
tcatcgataa gaagaacgtg tttcaacggc tcacctttca atctaaaatc tgaacccttg 3240
ttcacagcgc ttgagaaatt ttcacgtgaa ggatgtacaa tcatctccag ctaaatgggc 3300
agttcgtcag aattgcggct gaccgcggat gacgaaaatg cgaaccaagt atttcaattt 3360
tatgacaaaa gttctcaatc gttgttacaa gtgaaacgct tcgaggttac agctactatt 3420
gattaaggag atcgcctatg gtctcgcccc ggcgtcgtgc gtccgccgcg agccagatct 3480
cgcctacttc ataaacgtcc tcataggcac ggaatggaat gatgacatcg atcgccgtag 3540
agagcatgtc aatcagtgtg cgatcttcca agctagcacc ttgggcgcta cttttgacaa 3600
gggaaaacag tttcttgaat ccttggattg gattcgcgcc gtgtattgtt gaaatcgatc 3660
ccggatgtcc cgagacgact tcactcagat aagcccatgc tgcatcgtcg cgcatctcgc 3720
caagcaatat ccggtccggc cgcatacgca gacttgcttg gagcaagtgc tcggcgctca 3780
cagcacccag cccagcaccg ttcttggagt agagtagtct aacatgatta tcgtgtggaa 3840
tgacgagttc gagcgtatct tctatggtga ttagcctttc ctgggggggg atggcgctga 3900
tcaaggtctt gctcattgtt gtcttgccgc ttccggtagg gccacatagc aacatcgtca 3960
gtcggctgac gacgcatgcg tgcagaaacg cttccaaatc cccgttgtca aaatgctgaa 4020
ggatagcttc atcatcctga ttttggcgtt tccttcgtgt ctgccactgg ttccacctcg 4080
aagcatcata acgggaggag acttctttaa gaccagaaac acgcgagctt ggccgtcgaa 4140
tggtcaagct gacggtgccc gagggaacgg tcggcggcag acagatttgt agtcgttcac 4200
caccaggaag ttcagtggcg cagagggggt tacgtggtcc gacatcctgc tttctcagcg 4260
cgcccgctaa aatagcgata tcttcaagat catcataaga gacgggcaaa ggcatcttgg 4320
taaaaatgcc ggcttggcgc acaaatgcct ctccaggtcg attgatcgca atttcttcag 4380
tcttcgggtc atcgagccat tccaaaatcg gcttcagaag aaagcgtagt tgcggatcca 4440
cttccattta caatgtatcc tatctctaag cggaaatttg aattcattaa gagcggcggt 4500
tcctcccccg cgtggcgccg ccagtcaggc ggagctggta aacaccaaag aaatcgaggt 4560

-continued

```
cccgtgctac gaaaatggaa acggtgtcac cctgattctt cttcagggtt ggcggtatgt   4620
tgatggttgc cttaagggct gtctcagttg tctgctcacc gttattttga aagctgttga   4680
agctcatccc gccacccgag ctgccggcgt aggtgctagc tgcctggaag gcgccttgaa   4740
caacactcaa gagcatagct ccgctaaaac gctgccagaa gtggctgtcg accgagcccg   4800
gcaatcctga gcgaccgagt tcgtccgcgc ttggcgatgt taacgagatc atcgcatggt   4860
caggtgtctc ggcgcgatcc cacaacacaa aaacgcgccc atctccctgt tgcaagccac   4920
gctgtatttc gccaacaacg gtggtgccac gatcaagaag cacgatattg ttcgttgttc   4980
cacgaatatc ctgaggcaag acacacttta catagcctgc caaatttgtg tcgattgcgg   5040
tttgcaagat gcacggaatt attgtccctt gcgttaccat aaaatcgggg tgcggcaaga   5100
gcgtggcgct gctgggctgc agctcggtgg gtttcatacg tatcgacaaa tcgttctcgc   5160
cggacacttc gccattcggc aaggagttgt cgtcacgctt gccttcttgt cttcggcccg   5220
tgtcgccctg aatggcgcgt ttgctgaccc cttgatcgcc gctgctatat gcaaaaatcg   5280
gtgtttcttc cggccgtggc tcatgccgct ccggttcgcc cctcggcggt agaggagcag   5340
caggctgaac agcctcttga accgctggag gatccggcgg cacctcaatc ggagctggat   5400
gaaatggctt ggtgtttgtt gcgatcaaag ttgacggcga tgcgttctca ttcaccttct   5460
tttggcgccc acctagccaa atgaggctta atgataacgc gagaacgaca cctccgacga   5520
tcaatttctg agaccccgaa agacgccggc gatgtttgtc ggagaccagg gatccagatg   5580
catcaacctc atgtgccgct tgctgactat cgttattcat cccttcgccc ccttcaggac   5640
gcgtttcaca tcgggcctca ccgtgcccgt ttgcggcctt tggccaacgg gatcgtaagc   5700
ggtgttccag atacatagta ctgtgtggcc atccctcaga cgccaacctc gggaaaccga   5760
agaaatctcg acatcgctcc ctttaactga atagttggca acagcttcct tgccatcagg   5820
attgatggtg tagatggagg gtatgcgtac attgcccgga aagtggaata ccgtcgtaaa   5880
tccattgtcg aagacttcga gtggcaacag cgaacgatcg ccttgggcga cgtagtgcca   5940
attactgtcc gccgcaccaa gggctgtgac aggctgatcc aataaattct cagctttccg   6000
ttgatattgt gcttccgcgt gtagtctgtc cacaacagcc ttctgttgtg cctcccttcg   6060
ccgagccgcc gcatcgtcgg cggggtaggc gaattggacg ctgtaataga gatcgggctg   6120
ctctttatcg aggtgggaca gagtcttgga acttatactg aaaacataac ggcgcatccc   6180
ggagtcgctt gcggttagca cgattactgg ctgaggcgtg aggacctggc ttgccttgaa   6240
aaatagataa tttccccgcg gtagggctgc tagatctttg ctatttgaaa cggcaaccgc   6300
tgtcaccgtt tcgttcgtgg cgaatgttac gaccaaagta gctccaaccg ccgtcgagag   6360
gcgcaccact tgatcgggat tgtaagccaa ataacgcatg cgcggatcta gcttgcccgc   6420
cattggagtg tcttcagcct ccgcaccagt cgcagcggca aataaacatg ctaaaatgaa   6480
aagtgctttt ctgatcatgg ttcgctgtgg cctacgtttg aaacggtatc ttccgatgtc   6540
tgataggagg tgacaaccag acctgccggg ttggttagtc tcaatctgcc gggcaagctg   6600
gtcacctttt cgtagcgaac tgtcgcggtc cacgtactca ccacaggcat tttgccgtca   6660
acgacgaggg tccttttata gcgaatttgc tgcgtgcttg gagttacatc atttgaagcg   6720
atgtgctcga cctccaccct gccgcgtttg ccaagaatga cttgaggcga actgggattg   6780
ggatagttga agaattgctg gtaatcctgg cgcactgttg gggcactgaa gttcgatacc   6840
aggtcgtagg cgtactgagc ggtgtcggca tcataactct cgcgcaggcg aacgtactcc   6900
cacaatgagg cgttaacgac ggcctcctct tgagttgcag gcaatcgcga gacagacacc   6960
```

```
tcgctgtcaa cggtgccgtc cggccgtatc catagatata cgggcacaag cctgctcaac   7020
ggcaccattg tggctatagc gaacgcttga gcaacatttc ccaaaatcgc gatagctgcg   7080
acagctgcaa tgagtttgga gagacgtcgc gccgatttcg ctcgcgcggt ttgaaaggct   7140
tctacttcct tatagtgctc ggcaaggctt tcgcgcgcca ctagcatggc atattcaggc   7200
cccgtcatag cgtccacccg aattgccgag ctgaagatct gacggagtag gctgccatcg   7260
ccccacattc agcgggaaga tcgggccttt gcagctcgct aatgtgtcgt ttgtctggca   7320
gccgctcaaa gcgacaacta ggcacagcag gcaatacttc atagaattct ccattgaggc   7380
gaatttttgc gcgacctagc ctcgctcaac ctgagcgaag cgacggtaca agctgctggc   7440
agattgggtt gcgccgctcc agtaactgcc tccaatgttg ccggcgatcg ccggcaaagc   7500
gacaatgagc gcatcccctg tcagaaaaaa catatcgagt tcgtaaagac caatgatctt   7560
ggccgcggtc gtaccggcga aggtgattac accaagcata agggtgagcg cagtcgcttc   7620
ggttaggatg acgatcgttg ccacgaggtt taagaggaga agcaagagac cgtaggtgat   7680
aagttgcccg atccacttag ctgcgatgtc ccgcgtgcga tcaaaaatat atccgacgag   7740
gatcagaggc ccgatcgcga gaagcacttt cgtgagaatt ccaacggcgt cgtaaactcc   7800
gaaggcagac cagagcgtgc cgtaaaggac ccactgtgcc ccttggaaag caaggatgtc   7860
ctggtcgttc atcggaccga tttcggatgc gattttctga aaaacggcct gggtcacggc   7920
gaacattgta tccaactgtg ccggaacagt ctgcagaggc aagccggtta cactaaactg   7980
ctgaacaaag tttgggaccg tcttttcgaa gatggaaacc acatagtctt ggtagttagc   8040
ctgcccaaca attagagcaa caacgatggt gaccgtgatc acccgagtga taccgctacg   8100
ggtatcgact tcgccgcgta tgactaaaat accctgaaca ataatccaaa gagtgacaca   8160
ggcgatcaat ggcgcactca ccgcctcctg gatagtctca agcatcgagt ccaagcctgt   8220
cgtgaaggct acatcgaaga tcgtatgaat ggccgtaaac ggcgccggaa tcgtgaaatt   8280
catcgattgg acctgaactt gactggtttg tcgcataatg ttggataaaa tgagctcgca   8340
ttcggcgagg atgcgggcgg atgaacaaat cgcccagcct taggggaggg caccaaagat   8400
gacagcggtc ttttgatgct ccttgcgttg agcggccgcc tcttccgcct cgtgaaggcc   8460
ggcctgcgcg gtagtcatcg ttaataggct tgtcgcctgt acattttgaa tcattgcgtc   8520
atggatctgc ttgagaagca aaccattggt cacggttgcc tgcatgatat tgcgagatcg   8580
ggaaagctga gcagacgtat cagcattcgc cgtcaagcgt ttgtccatcg tttccagatt   8640
gtcagccgca atgccagcgc tgtttgcgga accggtgatc tgcgatcgca acaggtccgc   8700
ttcagcatca ctacccacga ctgcacgatc tgtatcgctg gtgatcgcac gtgccgtggt   8760
cgacattggc attcgcggcg aaaacatttc attgtctagg tccttcgtcg aaggatactg   8820
atttttctgg ttgagcgaag tcagtagtcc agtaacgccg taggccgacg tcaacatcgt   8880
aaccatcgct atagtctgag tgagattctc cgcagtcgcg agcgcagtcg cgagcgtctc   8940
agcctccgtt gccgggtcgc taacaacaaa ctgcgcccgc gcgggctgaa tatatagaaa   9000
gctgcaggtc aaaactgttg caataagttg cgtcgtcttc atcgtttcct accttatcaa   9060
tcttctgcct cgtggtgacg ggccatgaat tcgctgagcc agccagatga gttgccttct   9120
tgtgcctcgc gtagtcgagt tgcaaagcgc accgtgttgg cacgccccga aagcacggcg   9180
acatattcac gcatatcccg cagatcaaat tcgcagatga cgcttccact ttctcgttta   9240
agaagaaact tacggctgcc gaccgtcatg tcttcacgga tcgcctgaaa ttccttttcg   9300
gtacatttca gtccatcgac ataagccgat cgatctgcgg ttggtgatgg atagaaaatc   9360
```

-continued

```
ttcgtcatac attgcgcaac caagctggct cctagcggcg attccagaac atgctctggt   9420
tgctgcgttg ccagtattag catcccgttg ttttttcgaa cggtcaggag gaatttgtcg   9480
acgacagtcg aaaatttagg gtttaacaaa taggcgcgaa actcatcgca gctcatcaca   9540
aaacggcggc cgtcgatcat ggctccaatc cgatgcagga gatatgctgc agcgggagcg   9600
catacttcct cgtattcgag aagatgcgtc atgtcgaagc cggtaatcga cggatctaac   9660
tttacttcgt caacttcgcc gtcaaatgcc cagccaagcg catggccccg gcaccagcgt   9720
tggagccgcg ctcctgcgcc ttcggcgggc ccatgcaaca aaaattcacg taaccccgcg   9780
attgaacgca tttgtggatc aaacgagagc tgacgatgga taccacggac cagacggcgg   9840
ttctcttccg gagaaatccc accccgacca tcactctcga tgagagccac gatccattcg   9900
cgcagaaaat cgtgtgaggc tgctgtgttt tctaggccac gcaacggcgc caacccgctg   9960
ggtgtgcctc tgtgaagtgc caaatatgtt cctcctgtgg cgcgaaccag caattcgcca  10020
ccccggtcct tgtcaaagaa cacgaccgta cctgcacggt cgaccatgct ctgttcgagc  10080
atggctagaa caaacatcat gagcgtcgtc ttacccctcc cgataggccc gaatattgcc  10140
gtcatgccaa catcgtgctc atgcgggata tagtcgaaag gcgttccgcc attggtacga  10200
aatcgggcaa tcgcgttgcc ccagtggcct gagctggcgc cctctggaaa gttttcgaaa  10260
gagacaaacc ctgcgaaatt gcgtgaagtg attgcgccag ggcgtgtgcg ccacttaaaa  10320
ttccccggca attgggacca ataggccgct tccataccaa taccttcttg gacaaccacg  10380
gcacctgcat ccgccattcg tgtccgagcc cgcgcgcccc tgtccccaag actattgaga  10440
tcgtctgcat agacgcaaag gctcaaatga tgtgagccca taacgaattc gttgctcgca  10500
agtgcgtcct cagcctcgga taatttgccg atttgagtca cggctttatc gccggaactc  10560
agcatctggc tcgatttgag gctaagtttc gcgtgcgctt gcgggcgagt caggaacgaa  10620
aaactctgcg tgagaacaag tggaaaatcg agggatagca gcgcgttgag catgcccggc  10680
cgtgtttttg cagggtattc gcgaaacgaa tagatggatc caacgtaact gtcttttggc  10740
gttctgatct cgagtcctcg cttgccgcaa atgactctgt cggtataaat cgaagcgccg  10800
agtgagccgc tgacgaccgg aaccggtgtg aaccgaccag tcatgatcaa ccgtagcgct  10860
tcgccaattt cggtgaagag cacaccctgc ttctcgcgga tgccaagacg atgcaggcca  10920
tacgctttaa gagagccagc gacaacatgc caaagatctt ccatgttcct gatctggccc  10980
gtgagatcgt tttccctttt tccgcttagc ttggtgaacc tcctctttac cttccctaaa  11040
gccgcctgtg ggtagacaat caacgtaagg aagtgttcat tgcggaggag ttggccggag  11100
agcacgcgct gttcaaaagc ttcgttcagg ctagcggcga aaacactacg gaagtgtcgc  11160
ggcgccgatg atggcacgtc ggcatgacgt acgaggtgag catatattga cacatgatca  11220
tcagcgatat tgcgcaacag cgtgttgaac gcacgacaac gcgcattgcg catttcagtt  11280
tcctcaagct cgaatgcaac gccatcaatt ctcgcaatgg tcatgatcga tccgtcttca  11340
agaaggacga tatggtcgct gaggtggcca atataaggga gatagatctc accggatctt  11400
tcggtcgttc cactcgcgcc gagcatcaca ccattcctct ccctcgtggg ggaaccctaa  11460
ttggatttgg gctaacagta gcgccccccc aaactgcact atcaatgctt cttcccgcgg  11520
tccgcaaaaa tagcaggacg acgctcgccg cattgtagtc tcgctccacg atgagccggg  11580
ctgcaaacca taacggcacg agaacgactt cgtagagcgg gttctgaacg ataacgatga  11640
caaagccggc gaacatcatg aataaccctg ccaatgtcag tggcacccca agaaacaatg  11700
cgggccgtgt ggctgcgagg taaagggtcg attcttccaa acgatcagcc atcaactacc  11760
```

gccagtgagc gtttggccga ggaagctcgc cccaaacatg ataacaatgc cgccgacgac 11820
gccggcaacc agcccaagcg aagcccgccc gaacatccag gagatcccga tagcgacaat 11880
gccgagaaca gcgagtgact ggccgaacgg accaaggata aacgtgcata tattgttaac 11940
cattgtggcg gggtcagtgc cgccacccgc agattgcgct gcggcgggtc cggatgagga 12000
aatgctccat gcaattgcac cgcacaagct tggggcgcag ctcgatatca cgcgcatcat 12060
cgcattcgag agcgagaggc gatttagatg taaacggtat ctctcaaagc atcgcatcaa 12120
tgcgcacctc cttagtataa gtcgaataag acttgattgt cgtctgcgga tttgccgttg 12180
tcctggtgtg gcggtggcgg agcgattaaa ccgccagcgc catcctcctg cgagcggcgc 12240
tgatatgacc cccaaacatc ccacgtctct tcggatttta gcgcctcgtg atcgtctttt 12300
ggaggctcga ttaacgcggg caccagcgat tgagcagctg tttcaacttt tcgcacgtag 12360
ccgtttgcaa aaccgccgat gaaattaccg gtgttgtaag cggagatcgc ccgacgaagc 12420
gcaaattgct tctcgtcaat cgtttcgccg cctgcataac gacttttcag catgtttgca 12480
gcggcagata atgatgtgca cgcctggagc gcaccgtcag gtgtcagacc gagcatagaa 12540
aaatttcgag agtttatttg catgaggcca acatccagcg aatgccgtgc atcgagacgg 12600
tgcctgacga cttgggttgc ttggctgtga tcttgccagt gaagcgtttc gccggtcgtg 12660
ttgtcatgaa tcgctaaagg atcaaagcga ctctccacct tagctatcgc cgcaagcgta 12720
gatgtcgcaa ctgatggggc acacttgcga gcaacatggt caaactcagc agatgagagt 12780
ggcgtggcaa ggctcgacga acagaaggag accatcaagg caagagaaag cgaccccgat 12840
ctcttaagca taccttatct ccttagctcg caactaacac cgcctctccc gttggaagaa 12900
gtgcgttgtt ttatgttgaa gattatcggg agggtcggtt actcgaaaat tttcaattgc 12960
ttctttatga tttcaattga agcgagaaac ctcgcccggc gtcttggaac gcaacatgga 13020
ccgagaaccg cgcatccatg actaagcaac cggatcgacc tattcaggcc gcagttggtc 13080
aggtcaggct cagaacgaaa atgctcggcg aggttacgct gtctgtaaac ccattcgatg 13140
aacgggaagc ttccttccga ttgctcttgg caggaatatt ggcccatgcc tgcttgcgct 13200
ttgcaaatgc tcttatcgcg ttggtatcat atgccttgtc cgccagcaga aacgcactct 13260
aagcgattat ttgtaaaaat gtttcggtca tgcggcggtc atgggcttga cccgctgtca 13320
gcgcaagacg gatcggtcaa ccgtcggcat cgacaacagc gtgaatcttg gtggtcaaac 13380
cgccacggga acgtcccata cagccatcgt cttgatcccg ctgtttcccg tcgccgcatg 13440
ttggtggacg cggacacagg aactgtcaat catgacgaca ttctatcgaa agccttggaa 13500
atcacactca gaatatgatc ccagacgtct gcctcacgcc atcgtacaaa gcgattgtag 13560
caggttgtac aggaaccgta tcgatcagga acgtctgccc agggcgggcc cgtccggaag 13620
cgccacaaga tgacattgat cacccgcgtc aacgcgcggc acgcgacgcg gcttatttgg 13680
gaacaaagga ctgaacaaca gtccattcga aatcggtgac atcaaagcgg ggacgggtta 13740
tcagtggcct ccaagtcaag cctcaatgaa tcaaaatcag accgatttgc aaacctgatt 13800
tatgagtgtg cggcctaaat gatgaaatcg tccttctaga tcgcctccgt ggtgtagcaa 13860
cacctcgcag tatcgccgtg ctgaccttgg ccagggaatt gactggcaag ggtgctttca 13920
catgaccgct cttttggccg cgatagatga tttcgttgct gctttgggca cgtagaagga 13980
gagaagtcat atcggagaaa ttcctcctgg cgcgagagcc tgctctatcg cgacggcatc 14040
ccactgtcgg gaacagaccg gatcattcac gaggcgaaag tcgtcaacac atgcgttata 14100
ggcatcttcc cttgaaggat gatcttgttg ctgccaatct ggaggtgcgg cagccgcagg 14160

-continued

```
cagatgcgat ctcagcgcaa cttgcggcaa aacatctcac tcacctgaaa accactagcg  14220
agtctcgcga tcagacgaag gccttttact taacgacaca atatccgatg tctgcatcac  14280
aggcgtcgct atcccagtca atactaaagc ggtgcaggaa ctaaagatta ctgatgactt  14340
aggcgtgcca cgaggcctga gacgacgcgc gtagacagtt ttttgaaatc attatcaaag  14400
tgatggcctc cgctgaagcc tatcacctct gcgccggtct gtcggagaga tgggcaagca  14460
ttattacggt cttcgcgccc gtacatgcat tggacgattg cagggtcaat ggatctgaga  14520
tcatccagag gattgccgcc cttaccttcc gtttcgagtt ggagccagcc cctaaatgag  14580
acgacatagt cgacttgatg tgacaatgcc aagagagaga tttgcttaac ccgatttttt  14640
tgctcaagcg taagcctatt gaagcttgcc ggcatgacgt ccgcgccgaa agaatatcct  14700
acaagtaaaa cattctgcac accgaaatgc ttggtgtaga catcgattat gtgaccaaga  14760
tccttagcag tttcgcttgg ggaccgctcc gaccagaaat accgaagtga actgacgcca  14820
atgacaggaa tcccttccgt ctgcagatag gtaccatcga tagatctgct gcctcgcgcg  14880
tttcggtgat gacggtgaaa acctctgaca catgcagctc ccggagacgg tcacagcttg  14940
tctgtaagcg gatgccggga gcagacaagc ccgtcagggc gcgtcagcgg gtgttggcgg  15000
gtgtcggggc gcagccatga cccagtcacg tagcgatagc ggagtgtata ctggcttaac  15060
tatgcggcat cagagcagat tgtactgaga gtgcaccata tgcggtgtga aataccgcac  15120
agatgcgtaa ggagaaaata ccgcatcagg cgctcttccg cttcctcgct cactgactcg  15180
ctgcgctcgg tcgttcggct gcggcgagcg gtatcagctc actcaaaggc ggtaatacgg  15240
ttatccacag aatcagggga taacgcagga aagaacatgt gagcaaaagg ccagcaaaag  15300
gccaggaacc gtaaaaaggc cgcgttgctg gcgtttttcc ataggctccg cccccctgac  15360
gagcatcaca aaaatcgacg ctcaagtcag aggtggcgaa acccgacagg actataaaga  15420
taccaggcgt ttccccctgg aagctccctc gtgcgctctc ctgttccgac cctgccgctt  15480
accggatacc tgtccgcctt tctcccttcg ggaagcgtgg cgctttctca tagctcacgc  15540
tgtaggtatc tcagttcggt gtaggtcgtt cgctccaagc tgggctgtgt gcacgaaccc  15600
cccgttcagc ccgaccgctg cgccttatcc ggtaactatc gtcttgagtc caacccggta  15660
agacacgact tatcgccact ggcagcagcc actggtaaca ggattagcag agcgaggtat  15720
gtaggcggtg ctacagagtt cttgaagtgg tggcctaact acggctacac tagaaggaca  15780
gtatttggta tctgcgctct gctgaagcca gttaccttcg gaaaaagagt tggtagctct  15840
tgatccggca aacaaaccac cgctggtagc ggtggttttt ttgtttgcaa gcagcagatt  15900
acgcgcagaa aaaaaggatc tcaagaagat cctttgatct tttctacggg gtctgacgct  15960
cagtggaacg aaaactcacg ttaagggatt ttggtcatga gattatcaaa aaggatcttc  16020
acctagatcc ttttaaatta aaaatgaagt tttaaatcaa tctaaagtat atatgagtaa  16080
acttggtctg acagttacca atgcttaatc agtgaggcac ctatctcagc gatctgtcta  16140
tttcgttcat ccatagttgc ctgactcccc gtcgtgtaga taactacgat acgggagggc  16200
ttaccatctg gccccagtgc tgcaatgata ccgcgagacc cacgctcacc ggctccagat  16260
ttatcagcaa taaaccagcc agccggaagg gccgagcgca gaagtggtcc tgcaacttta  16320
tccgcctcca tccagtctat taattgttgc cgggaagcta gagtaagtag ttcgccagtt  16380
aatagtttgc gcaacgttgt tgccattgct gcaggggggg gggggggggg gttccattgt  16440
tcattccacg gacaaaaaca gagaaaggaa acgacagagg ccaaaaagct cgctttcagc  16500
acctgtcgtt tcctttcttt tcagagggta ttttaaataa aaacattaag ttatgacgaa  16560
```

```
gaagaacgga aacgccttaa accggaaaat tttcataaat agcgaaaacc cgcgaggtcg  16620
ccgccccgta acctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc cccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
aggccctttc gtcttcaaga attggtcgac gatcttgctg cgttcggata ttttcgtgga  17640
gttcccgcca cagacccgga ttgaaggcga gatccagcaa ctcgcgccag atcatcctgt  17700
gacggaactt tggcgcgtga tgactggcca ggacgtcggc cgaaagagcg acaagcagat  17760
cacgcttttc gacagcgtcg gatttgcgat cgaggatttt tcggcgctgc gctacgtccg  17820
cgaccgcgtt gagggatcaa gccacagcag cccactcgac cttctagccg acccagacga  17880
gccaagggat ctttttggaa tgctgctccg tcgtcaggct ttccgacgtt tgggtggttg  17940
aacagaagtc attatcgtac ggaatgccaa gcactcccga ggggaaccct gtggttggca  18000
tgcacataca aatggacgaa cggataaacc ttttcacgcc cttttaaata tccgttattc  18060
taataaacgc tcttttctct taggtttacc cgccaatata tcctgtcaaa cactgatagt  18120
ttaaactgaa ggcgggaaac gacaatctga tcatgagcgg agaattaagg gagtcacgtt  18180
atgacccccg ccgatgacgc gggacaagcc gttttacgtt tggaactgac agaaccgcaa  18240
cgttgaagga gccactcagc aagctggtac gattgtaata cgactcacta tagggcgaat  18300
tgagcgctgt ttaaacgctc ttcaactgga agagcggtta ccagagctgg tcacctttgt  18360
ccaccaagat ggaactgcgg ccgctcatta attaagtcag gcgcgcctct agttgaagac  18420
acgttcatgt cttcatcgta agaagacact cagtagtctt cggccagaat ggcccggacc  18480
gaagctggcc gctctagaac tagtggatct cgatgtgtag tctacgagaa gggttaaccg  18540
tctcttcgtg agaataaccg tggcctaaaa ataagccgat gaggataaat aaaatgtggt  18600
ggtacagtac ttcaagaggt ttactcatca agaggatgct tttccgatga gctctagtag  18660
tacatcggac ctcacatacc tccattgtgg tgaaatattt tgtgctcatt tagtgatggg  18720
taaattttgt ttatgtcact ctaggttttg acatttcagt tttgccactc ttaggttttg  18780
acaaataatt tccattccgc ggcaaaagca aaacaatttt attttacttt taccactctt  18840
agctttcaca atgtatcaca aatgccactc tagaaattct gtttatgcca cagaatgtga  18900
aaaaaaacac tcacttattt gaagccaagg tgttcatggc atggaaatgt gacataaagt  18960
```

-continued

```
aacgttcgtg tataagaaaa aattgtactc ctcgtaacaa gagacggaaa catcatgaga  19020
caatcgcgtt tggaaggctt tgcatcacct ttggatgatg cgcatgaatg gagtcgtctg  19080
cttgctagcc ttcgcctacc gcccactgag tccgggcggc aactaccatc ggcgaacgac  19140
ccagctgacc tctaccgacc ggacttgaat gcgctacctt cgtcagcgac gatggccgcg  19200
tacgctggcg acgtgccccc gcatgcatgg cggcacatgg cgagctcaga ccgtgcgtgg  19260
ctggctacaa atacgtaccc cgtgagtgcc ctagctagaa acttacacct gcaactgcga  19320
gagcgagcgt gtgagtgtag ccgagtagat cccccggtcg ccaccatggc ctcctccgag  19380
aacgtcatca ccgagttcat gcgcttcaag gtgcgcatgg agggcaccgt gaacggccac  19440
gagttcgaga tcgagggcga gggcgagggc cgcccctacg agggccacaa caccgtgaag  19500
ctgaaggtga ccaagggcgg cccccctgccc ttcgcctggg acatcctgtc cccccagttc  19560
cagtacggct ccaaggtgta cgtgaagcac cccgccgaca tccccgacta caagaagctg  19620
tccttccccg agggcttcaa gtgggagcgc gtgatgaact tcgaggacgg cggcgtggcg  19680
accgtgaccc aggactcctc cctgcaggac ggctgcttca tctacaaggt gaagttcatc  19740
ggcgtgaact tcccctccga cggccccgtg atgcagaaga agaccatggg ctgggaggcc  19800
tccaccgagc gcctgtaccc ccgcgacggc gtgctgaagg gcgagaccca caaggccctg  19860
aagctgaagg acggcggcca ctacctggtg gagttcaagt ccatctacat ggccaagaag  19920
cccgtgcagc tgcccggcta ctactacgtg gacgccaagc tggacatcac ctcccacaac  19980
gaggactaca ccatcgtgga gcagtacgag cgcaccgagg gccgccacca cctgttcctg  20040
tagcggccca tggatattcg aacgcgtagg taccacatgg ttaacctaga cttgtccatc  20100
ttctggattg gccaacttaa ttaatgtatg aaataaaagg atgcacacat agtgacatgc  20160
taatcactat aatgtgggca tcaaagttgt gtgttatgtg taattactag ttatctgaat  20220
aaaagagaaa gagatcatcc atatttctta tcctaaatga atgtcacgtg tctttataat  20280
tctttgatga accagatgca tttcattaac caaatccata tacatataaa tattaatcat  20340
atataattaa tatcaattgg gttagcaaaa caaatctagt ctaggtgtgt tttgcgaatg  20400
cggccgccac cgcggtggag ctcgaattcc ggtccgggcc tagaaggcca tttaaatcct  20460
gaggatctgg tcttcctaag gacccgggat atcgctatca actttgtata gaaaagttgg  20520
gccgaattcg agctcggtac ggccagaatg gcccggaccg ggttaccgaa ttcgagctcg  20580
gtaccctggg atccgcaagg gacgaccgtg gtccttgttt gatttacttc caggattata  20640
taatccagct tatggattat ataagtacct attgacgtca cgtgcttatg tattataata  20700
atctaggtat atagattata taatctatct aataataatc tgtgttgttt gtttatctct  20760
caaaacaaac aggtcctaaa atggtcccgg gcgtccaatg tgtcgtcaag tagtgttaag  20820
ctaaatcgac atttctttgt gggttgtgtg gaaggtgttc cttttcctta agttgttagt  20880
tgtgcaaggt gttccttaga gcatctccaa taggacctat aatggattct attttgaatt  20940
ataagactct aacaacaaaa gcatacttta atggggattc tattttacaa aaaaatatca  21000
aatgattata tggtcgattc ctcgggtcct aaatatagta tctcatataa tagagctcta  21060
tcctcatttt atatactatt tttaagtttt tatttactaa ataacatgat ttattttcta  21120
atactatgaa ctcaactatt agagctgtaa acgtttttgt ggtactaaac actttaaatc  21180
aggtcctatt ttaatttgaa ggacttaaat ataagacttc tggttagaga tgctcttagc  21240
gagtgtttgt gcatgattgc tatttagtct ttgtggattg tggaaggtgt tacttttcct  21300
caagttgtta gttgtgcaag gtgtttctta gagcatctct aacaggagcc ttaacggaat  21360
```

ctattttgaa gtatagtact ttaacaccaa aaacatactt taataggggt cctattttac 21420
aaaaaaatta tcaaatgatt ataaggtcca ctcctcgggt cctaaatata atatctcata 21480
tactagagct ctatcctcat tttatatact atccctaggt ttttattccc taaataacat 21540
gatttatttc ctaatactaa gatatagggc tcaactattg gagttgcaaa tgttttttgg 21600
cactaaacac tttatatcag gtcctatttt aattttaatt tgaaggactc aaatatagga 21660
cttctcgtta gagatgctct tagcgagtgt ttgtgcatga ttgctattta tgtctgtagt 21720
ttagttgggg gctttaatat gtttagttga agttctagta ttttttaggt tctccactct 21780
ttggattatg acaacgacca ctatccaagc agtctttgag tgcaaacgcg cgagcaaact 21840
atctgatcta ttaaattatg atccaaccgt tatgtcatat tgaagactta aaccctttca 21900
ccaccagccc aagtatcttt atgaaaaacc ctaacaaacc acaattgcat ctatggttgg 21960
attataattt aacgtatcag atggttcgct tgcatgctta catatctaga aactgtttgc 22020
ataacagtcg ttctctttgg ttatataatg ctttagtaat catcagccaa gtgtaaacaa 22080
atggtacaaa ctagtagtga acacatcctc cctacctatc tctaggggtg taactagata 22140
tccgaattct tagaacaaat ttcatatttt aaaatagata tgcttcaaaa tttatgctaa 22200 tctttttat attatcaagc atattattac acataagaat aaaattttgt atagaatttt 22260
atccattatt tgttccctag aatttaaaaa gtgaaaaaac attcgaatct gtatcagttt 22320
cgtattcaaa tttttacatc tattatttga gaatatatat gataaatttg aggtttagtt 22380
tttatgaatc tttacaaggt taatgttaaa tacatgacta tggatttaca tagtaaattc 22440
tatgtcttat ttgtccgcga ttgaagaaaa atgacaaaaa gatctgacat tcgaataaac 22500
atctgtttcc actcctacct atctgacctc ctatttcaaa ctccactttg taacacggta 22560
caaaatcact ccctacctat ctgacctcct atttcaaact ccactcagta aacaatattg 22620
tctatggtac aaaaccaagt gttttataca tctatttgca cgatctgctc gagtcaggca 22680
tccttgacac acaacatact ccttgtggct ataaatgtcc aaatagagca gacctaatgg 22740
gtggaccgtt gcatgacacg acttatccca agacgagcac agttcgcccc attggtcatg 22800
ggggtccggg ctagtctagc ctgatcatcg ggtcacactt aggccacagg tgtgccacaa 22860
cgggatagcc caacatgtcc ctttttgtca tgcatatatc tatattatag ttagtataat 22920
gtaaaaaaac aaaaggtatg tgtgttatgt tggttagatg tgtttaaata actctttaaa 22980
gctagcaact atggtttaaa tcatacatat acacattttt attttatttt tatttaaacg 23040
atatgggcct tctaggcacg tcgagtgtga cgggccagtg agatgacaca ttataattac 23100
tggtctagca ggccgtacct aggtctttct cgtgggccaa gactaagggt tggcccgttg 23160
gctaatctgt acggtaccga tactgtccta attcatttga acacctgtag aagaggggaa 23220
tttataattg aggaggaatg tactcatgcg gtacaccagg ggaattgttt tgttgtgctc 23280
agcgatagat ttcaacgcaa cggtgagcca gtttcactaa aaaaaggggg gggggggggg 23340 ggggggaag gccacatcaa aggcgaggtg ctgacgagca gaagatgcta gcagtgacgc 23400
caagtccagc agctagcaat gaaagggtac tcgggattta acaatgccta gagacggcat 23460
catcccctca ataatccggt gctctctttt tgtttattca ccagttggcg tagctatata 23520
cacatgtctg gtctgacgaa caaatcaagg gatcgctagc tcgggctagc cttcctatca 23580
ctgtcatgac atgtgctctg cctctgctgg ttgataagcc gtgcgccttc tcgctaattc 23640
tttcttgtgc tagaggcgag tcaaacaaac gctgcacctc gtagccctta atctgcgcta 23700
agggtcacat gaccctgttc cctatcgcta gttaccaacg acccattccc cctgacagat 23760
acttacgacg cgtccgtacg cggcaggcct cggcagttcg gcatcaccag caccggcgcc 23820
ggcattcgcc ccctgccagc cggttcgcag attcgcaggg cggagtcggc cgcagttgcc 23880
gcatcccaaa cgcccgggaa cctttggggc ccctctacga gcaaatgaag ttgctgcccc 23940
tggcttcgta aagctctgac ttttgatcac ttgattggca gtcgtactcc tcgctcatag 24000
gccgacacgg ccgcaaagtc aactacccgc tccgccatcc ttcaaccccc gccacgcgcc 24060
tatatatgtt cgcggccatg tccgtactag tcctccaacc cacaagccac aaccccgagc 24120
tcagatccct cgcctcgtgt cgtgtctccg gtcgacgacg accaacagcc agtgtgggcc 24180
agacggacac cgccgagcta tagcgcttgg tgataaagct tggtcacccg gtccgggcct 24240
agaaggccag cttcaagttt gtacaaaaaa gcaggctcca gcgctcacca tggtccgtcc 24300
tgtagaaacc ccaacccgtg aaatcaaaaa actcgacggc ctgtgggcat tcagtctgga 24360
tcgcgaaaac tgtggaattg atcagcgttg gtgggaaagc gcgttacaag aaagccgggc 24420
aattgctgtg ccaggcagtt ttaacgatca gttcgccgat gcagatattc gtaattatgc 24480
gggcaacgtc tggtatcagc gcgaagtctt tataccgaaa ggttgggcag gccagcgtat 24540
cgtgctgcgt ttcgatgcgg tcactcatta cggcaaagtg tgggtcaata atcaggaagt 24600
gatggagcat cagggcggct atacgccatt tgaagccgat gtcacgccgt atgttattgc 24660
cgggaaaagt gtacgtaagt ttctgcttct acctttgata tatatataat aattatcatt 24720
aattagtagt aatataatat ttcaaatatt tttttcaaaa taaaagaatg tagtatatag 24780
caattgcttt tctgtagttt ataagtgtgt atattttaat ttataacttt tctaatatat 24840
gaccaaaatt tgttgatgtg caggtatcac cgtttgtgtg aacaacgaac tgaactggca 24900
gactatcccg ccgggaatgg tgattaccga cgaaaacggc aagaaaaagc agtcttactt 24960
ccatgatttc tttaactatg ccggaatcca tcgcagcgta atgctctaca ccacgccgaa 25020
cacctgggtg gacgatatca ccgtggtgac gcatgtcgcg caagactgta accacgcgtc 25080
tgttgactgg caggtggtgg ccaatggtga tgtcagcgtt gaactgcgtg atgcggatca 25140
acaggtggtt gcaactggac aaggcactag cgggactttg caagtggtga atccgcacct 25200
ctggcaaccg ggtgaaggtt atctctatga actgtgcgtc acagccaaaa gccagacaga 25260
gtgtgatatc tacccgcttc gcgtcggcat ccggtcagtg gcagtgaagg gcgaacagtt 25320
cctgattaac cacaaaccgt tctactttac tggctttggt cgtcatgaag atgcggactt 25380
gcgtggcaaa ggattcgata acgtgctgat ggtgcacgac cacgcattaa tggactggat 25440
tggggccaac tcctaccgta cctcgcatta cccttacgct gaagagatgc tcgactgggc 25500
agatgaacat ggcatcgtgg tgattgatga aactgctgct gtcggcttta acctctcttt 25560
aggcattggt ttcgaagcgg gcaacaagcc gaaagaactg tacagcgaag aggcagtcaa 25620
cggggaaact cagcaagcgc acttacaggc gattaaagag ctgatagcgc gtgacaaaaa 25680
ccacccaagc gtggtgatgt ggagtattgc caacgaaccg gatacccgtc cgcaaggtgc 25740
acgggaatat ttcgcgccac tggcggaagc aacgcgtaaa ctcgacccga cgcgtccgat 25800
cacctgcgtc aatgtaatgt tctgcgacgc tcacaccgat accatcagcg atctctttga 25860
tgtgctgtgc ctgaaccgtt attacggatg gtatgtccaa agcggcgatt tggaaacggc 25920
agagaaggta ctggaaaaag aacttctggc ctggcaggag aaactgcatc agccgattat 25980
catcaccgaa tacggcgtgg atacgttagc cgggctgcac tcaatgtaca ccgacatgtg 26040
gagtgaagag tatcagtgtg catggctgga tatgtatcac cgcgtctttg atcgcgtcag 26100
cgccgtcgtc ggtgaacagg tatggaattt cgccgatttt gcgacctcgc aaggcatatt 26160
gcgcgttggc ggtaacaaga aagggatctt cactcgcgac cgcaaaccga agtcggcggc 26220
ttttctgctg caaaaacgct ggactggcat gaacttcggt gaaaaaccgc agcagggagg 26280
caaacaatga agatctcccg ggcacccagc tttcttgtac aaagtggccg ttaacggatc 26340
cagacttgtc catcttctgg attggccaac ttaattaatg tatgaaataa aaggatgcac 26400
acatagtgac atgctaatca ctataatgtg ggcatcaaag ttgtgtgtta tgtgtaatta 26460
ctagttatct gaataaaaga gaaagagatc atccatattt cttatcctaa atgaatgtca 26520
cgtgtcttta taattctttg atgaaccaga tgcatttcat taaccaaatc catatacata 26580
taaatattaa tcatatataa ttaatatcaa ttgggttagc aaaacaaatc tagtctaggt 26640
gtgttttgcg aattgcggca agcttgcggc cgccccgggc aactttatta tacaaagttg 26700
atagatatcg gaccgattaa actttaattc ggtccgaagc ttgcatgcct gcagtgcagc 26760
gtgacccggt cgtgcccctc tctagagata atgagcattg catgtctaag ttataaaaaa 26820
ttaccacata tttttttgt cacacttgtt tgaagtgcag tttatctatc tttatacata 26880
tatttaaact ttactctacg aataatataa tctatagtac tacaataata tcagtgtttt 26940
agagaatcat ataaatgaac agttagacat ggtctaaagg acaattgagt attttgacaa 27000
caggactcta cagttttatc tttttagtgt gcatgtgttc tcctttttt ttgcaaatag 27060 cttcacctat ataatacttc atccatttta ttagtacatc catttagggt ttagggttaa 27120
tggtttttat agactaattt ttttagtaca tctattttat tctattttag cctctaaatt 27180
aagaaaacta aaactctatt ttagtttttt tatttaataa tttagatata aaatagaata 27240
aaataaagtg actaaaaatt aaacaaatac cctttaagaa attaaaaaaa ctaaggaaac 27300
atttttcttg tttcgagtag ataatgccag cctgttaaac gccgtcgacg agtctaacgg 27360
acaccaacca gcgaaccagc agcgtcgcgt cgggccaagc gaagcagacg gcacggcatc 27420
tctgtcgctg cctctggacc cctctcgaga gttccgctcc accgttggac ttgctccgct 27480
gtcggcatcc agaaattgcg tggcggagcg gcagacgtga gccggcacgg caggcggcct 27540
cctcctcctc tcacggcacc ggcagctacg ggggattcct ttcccaccgc tccttcgctt 27600
tcccttcctc gcccgccgta ataaatagac accccctcca caccctcttt ccccaacctc 27660
gtgttgttcg gagcgcacac acacacaacc agatctcccc caaatccacc cgtcggcacc 27720
tccgcttcaa ggtacgccgc tcgtcctccc cccccccct ctctaccttc tctagatcgg 27780
cgttccggtc catgcatggt tagggcccgg tagttctact tctgttcatg tttgtgttag 27840
atccgtgttt gtgttagatc cgtgctgcta gcgttcgtac acggatgcga cctgtacgtc 27900
agacacgttc tgattgctaa cttgccagtg tttctctttg gggaatcctg ggatggctct 27960
agccgttccg cagacgggat cgatttcatg attttttttg tttcgttgca tagggtttgg 28020
tttgcccttt tcctttattt caatatatgc cgtgcacttg tttgtcgggt catcttttca 28080
tgcttttttt tgtcttggtt gtgatgatgt ggtctggttg ggcggtcgtt ctagatcgga 28140
gtagaattct gtttcaaact acctggtgga tttattaatt ttggatctgt atgtgtgtgc 28200
catacatatt catagttacg aattgaagat gatggatgga aatatcgatc taggataggt 28260
atacatgttg atgcgggttt tactgatgca tatacagaga tgctttttgt tcgcttggtt 28320
gtgatgatgt ggtgtggttg ggcggtcgtt cattcgttct agatcggagt agaatactgt 28380
ttcaaactac ctggtgtatt tattaatttt ggaactgtat gtgtgtgtca tacatcttca 28440
tagttacgag tttaagatgg atggaaatat cgatctagga taggtataca tgttgatgtg 28500
ggttttactg atgcatatac atgatggcat atgcagcatc tattcatatg ctctaacctt 28560
gagtacctat ctattataat aaacaagtat gttttataat tattttgatc ttgatatact 28620
tggatgatgg catatgcagc agctatatgt ggattttttt agccctgcct tcatacgcta 28680
tttatttgct tggtactgtt tcttttgtcg atgctcaccc tgttgtttgg tgttacttct 28740
gcaggtcgac tttaacttag cctaggatcc acacgacacc atgtccccccg agcgccgccc 28800
cgtcgagatc cgcccggcca ccgccgccga catggccgcc gtgtgcgaca tcgtgaacca 28860
ctacatcgag acctccaccg tgaacttccg caccgagccg cagaccccgc aggagtggat 28920
cgacgacctg gagcgcctcc aggaccgcta cccgtggctc gtggccgagg tggagggcgt 28980
ggtggccggc atcgcctacg ccggcccgtg gaaggcccgc aacgcctacg actggaccgt 29040
ggagtccacc gtgtacgtgt cccaccgcca ccagcgcctc ggcctcggct ccaccctcta 29100
cacccacctc ctcaagagca tggaggccca gggcttcaag tccgtggtgg ccgtgatcgg 29160
cctcccgaac gacccgtccg tgcgcctcca cgaggccctc ggctacaccg cccgcggcac 29220
cctccgcgcc gccggctaca agcacggcgg ctggcacgac gtcggcttct ggcagcgcga 29280
cttcgagctg ccggccccgc cgcgcccggt gcgcccggtg acgcagatct gagtcgaaac 29340
ctagacttgt ccatcttctg gattggccaa cttaattaat gtatgaaata aaaggatgca 29400
cacatagtga catgctaatc actataatgt gggcatcaaa gttgtgtgtt atgtgtaatt 29460
actagttatc tgaataaaag agaaagagat catccatatt tcttatccta aatgaatgtc 29520
acgtgtcttt ataattcttt gatgaaccag atgcatttca ttaaccaaat ccatatacat 29580
ataaatatta atcatatata attaatatca attgggttag caaaacaaat ctagtctagg 29640
tgtgttttgc gaattgcggc cgccaccgcg gtggagctcg aattcattcc gattaatcgt 29700
ggcctcttgc tcttcaggat gaagagctat gtttaaacgt gcaagcgcta ctagacaatt 29760
cagtacatta aaaacgtccg caatgtgtta ttaagttgtc taagcgtcaa tttgtttaca 29820
ccacaatata tcctgccacc agccagccaa cagctccccg accggcagct cggcacaaaa 29880
tcaccactcg atacaggcag cccatcagtc cgggacggcg tcagcgggag agccgttgta 29940
aggcggcaga ctttgctcat gttaccgatg ctattcggaa gaacggcaac taagctgccg 30000
ggtttgaaac acggatgatc tcgcggaggg tagcatgttg attgtaacga tgacagagcg 30060
ttgctgcctg tgatcaaata tcatctccct cgcagagatc cgaattatca gccttcttat 30120
tcatttctcg cttaaccgtg acaggctgtc gatcttgaga actatgccga cataatagga 30180
aatcgctgga taaagccgct gaggaagctg agtggcgcta tttctttaga agtgaacgtt 30240
gacgatcgtc gaccgtaccc cgatgaatta attcggacgt acgttctgaa cacagctgga 30300
tacttacttg ggcgattgtc atacatgaca tcaacaatgt acccgtttgt gtaaccgtct 30360
cttggaggtt cgtatgacac tagtggttcc cctcagcttg cgactagatg ttgaggccta 30420
acattttatt agagagcagg ctagttgctt agatacatga tcttcaggcc gttatctgtc 30480
agggcaagcg aaaattggcc atttatgacg accaatgccc cgcagaagct cccatctttg 30540
ccgccataga cgccgcgccc ccccttttggg gtgtagaaca tccttttgcc agatgtggaa 30600
aagaagttcg ttgtcccatt gttggcaatg acgtagtagc cggcgaaagt gcgagaccca 30660
tttgcgctat atataagcct acgatttccg ttgcgactat tgtcgtaatt ggatgaacta 30720
ttatcgtagt tgctctcaga gttgtcgtaa tttgatggac tattgtcgta attgcttatg 30780
gagttgtcgt agttgcttgg agaaatgtcg tagttggatg gggagtagtc atagggaaga 30840
cgagcttcat ccactaaaac aattggcagg tcagcaagtg cctgccccga tgccatcgca 30900
agtacgaggc ttagaaccac cttcaacaga tcgcgcatag tcttccccag ctctctaacg 30960
cttgagttaa gccgcgccgc gaagcggcgt cggcttgaac gaattgttag acattatttg 31020
ccgactacct tggtgatctc gcctttcacg tagtgaacaa attcttccaa ctgatctgcg 31080
cgcgaggcca agcgatcttc ttgtccaaga taagcctgcc tagcttcaag tatgacgggc 31140
tgatactggg ccggcaggcg ctccattgcc cagtcggcag cgacatcctt cggcgcgatt 31200
ttgccggtta ctgcgctgta ccaaatgcgg gacaacgtaa gcactacatt tcgctcatcg 31260
ccagcccagt cgggcggcga gttccatagc gttaaggttt catttagcgc ctcaaataga 31320
tcctgttcag gaaccggatc aaagagttcc tccgccgctg gacctaccaa ggcaacgcta 31380
tgttctcttg cttttgtcag caagatagcc agatcaatgt cgatcgtggc tggctcgaag 31440
atacctgcaa gaatgtcatt gcgctgccat tctccaaatt gcagttcgcg cttagctgga 31500
taacgccacg gaatgatgtc gtcgtgcaca acaatggtga cttctacagc gcggagaatc 31560
tcgctctctc caggggaagc cgaagtttcc aaaaggtcgt tgatcaaagc tcgccgcgtt 31620
gtttcatcaa gccttacagt caccgtaacc agcaaatcaa tatcactgtg tggcttcagg 31680
ccgccatcca ctgcggagcc gtacaaatgt acggccagca acgtcggttc gagatggcgc 31740
tcgatgacgc caactacctc tgatagttga gtcgatactt cggcgatcac cgcttccctc 31800
atgatgttta actcctgaat taagccgcgc cgcgaagcgg tgtcggcttg aatgaattgt 31860
taggcgtcat cctgtgctcc cgagaaccag taccagtaca tcgctgtttc gttcgagact 31920
tgaggtctag ttttatacgt gaacaggtca atgccgccga gagtaaagcc acattttgcg 31980
tacaaattgc aggcaggtac attgttcgtt tgtgtctcta atcgtatgcc aaggagctgt 32040
ctgcttagtg cccacttttt cgcaaattcg atgagactgt gcgcgactcc tttgcctcgg 32100
tgcgtgtgcg acacaacaat gtgttcgata gaggctagat cgttccatgt tgagttgagt 32160
tcaatcttcc cgacaagctc ttggtcgatg aatgcgccat agcaagcaga gtcttcatca 32220
gagtcatcat ccgagatgta atccttccgg taggggctca cacttctggt agatagttca 32280
aagccttggt cggataggtg cacatcgaac acttcacgaa caatgaaatg gttctcagca 32340
tccaatgttt ccgccacctg ctcagggatc accgaaatct tcatatgacg cctaacgcct 32400
ggcacagcgg atcgcaaacc tggcgcggct tttggcacaa aaggcgtgac aggtttgcga 32460
atccgttgct gccacttgtt aaccctttttg ccagatttgg taactataat ttatgttaga 32520
ggcgaagtct tgggtaaaaa ctggcctaaa attgctgggg atttcaggaa agtaaacatc 32580
accttccggc tcgatgtcta ttgtagatat atgtagtgta tctacttgat cgggggatct 32640
gctgcctcgc gcgtttcggt gatgacggtg aaaacctctg acacatgcag ctcccggaga 32700
cggtcacagc ttgtctgtaa gcggatgccg ggagcagaca agcccgtcag ggcgcgtcag 32760
cgggtgttgg cgggtgtcgg ggcgcagcca tgacccagtc acgtagcgat agcggagtgt 32820
atactggctt aactatgcgg catcagagca gattgtactg agagtgcacc atatgcggtg 32880
tgaaataccg cacagatgcg taaggagaaa ataccgcatc aggcgctctt ccgcttcctc 32940
gctcactgac tcgctgcgct cggtcgttcg gctgcggcga gcggtatcag ctcactcaaa 33000
ggcggtaata cggttatcca cagaatcagg ggataacgca ggaaagaaca tgtgagcaaa 33060
aggccagcaa aaggccagga accgtaaaaa ggccgcgttg ctggcgtttt tccataggct 33120
ccgcccccct gacgagcatc acaaaaatcg acgctcaagt cagaggtggc gaaacccgac 33180
aggactataa agataccagg cgtttccccc tggaagctcc ctcgtgcgct ctcctgttcc 33240
gaccctgccg cttaccggat acctgtccgc ctttctccct tcgggaagcg tggcgctttc 33300
tcatagctca cgctgtaggt atctcagttc ggtgtaggtc gttcgctcca agctgggctg 33360
tgtgcacgaa ccccccgttc agcccgaccg ctgcgcctta tccggtaact atcgtcttga 33420
gtccaacccg gtaagacacg acttatcgcc actggcagca gccactggta acaggattag 33480
cagagcgagg tatgtaggcg gtgctacaga gttcttgaag tggtggccta actacggcta 33540
cactagaagg acagtatttg gtatctgcgc tctgctgaag ccagttacct tcggaaaaag 33600
agttggtagc tcttgatccg gcaaacaaac caccgctggt agcggtggtt tttttgtttg 33660
caagcagcag attacgcgca gaaaaaaagg atctcaagaa gatcctttga tcttttctac 33720
ggggtctgac gctcagtgga acgaaaactc acgttaaggg attttggtca tgagattatc 33780
aaaaaggatc ttcacctaga tccttttaaa ttaaaaatga agttttaaat caatctaaag 33840
tatatatgag taaacttggt ctgacagtta ccaatgctta atcagtgagg cacctatctc 33900
agcgatctgt ctatttcgtt catccatagt tgcctgactc cccgtcgtgt agataactac 33960
gatacgggag ggcttaccat ctggccccag tgctgcaatg ataccgcgag acccacgctc 34020
accggctcca gatttatcag caataaacca gccagccgga agggccgagc gcagaagtgg 34080
tcctgcaact ttatccgcct ccatccagtc tattaattgt tgccgggaag ctagagtaag 34140
tagttcgcca gttaatagtt tgcgcaacgt tgttgccatt gctgcagggg gggggggggg 34200
gggggacttc cattgttcat tccacggaca aaaacagaga aaggaaacga cagaggccaa 34260
aaagcctcgc tttcagcacc tgtcgtttcc tttcttttca gagggtattt taaataaaaa 34320
cattaagtta tgacgaagaa gaacggaaac gccttaaacc ggaaaatttt cataaatagc 34380
gaaaacccgc gaggtcgccg ccccgtaacc tgtcggatca ccggaaagga cccgtaaagt 34440
gataatgatt atcatctaca tatcacaacg tgcgtggagg ccatcaaacc acgtcaaata 34500
atcaattatg acgcaggtat cgtattaatt gatctgcatc aacttaacgt aaaaacaact 34560
tcagacaata caaatcagcg acactgaata cggggcaacc tcatgtcccc cccccccccc 34620
cccctgcagg catcgtggtg tcacgctcgt cgtttggtat ggcttcattc agctccggtt 34680
cccaacgatc aaggcgagtt acatgatccc ccatgttgtg caaaaaagcg gttagctcct 34740
tcggtcctcc gatcgttgtc agaagtaagt tggccgcagt gttatcactc atggttatgg 34800
cagcactgca taattctctt actgtcatgc catccgtaag atgcttttct gtgactggtg 34860
agtactcaac caagtcattc tgagaatagt gtatgcggcg accgagttgc tcttgcccgg 34920
cgtcaacacg ggataatacc gcgccacata gcagaacttt aaaagtgctc atcattggaa 34980
aacgttcttc ggggcgaaaa ctctcaagga tcttaccgct gttgagatcc agttcgatgt 35040
aacccactcg tgcacccaac tgatcttcag catcttttac tttcaccagc gtttctgggt 35100
gagcaaaaac aggaaggcaa aatgccgcaa aaaagggaat aagggcgaca cggaaatgtt 35160
gaatactcat actcttcctt tttcaatatt attgaagcat ttatcagggt tattgtctca 35220
tgagcggata catatttgaa tgtatttaga aaaataaaca aataggggtt ccgcgcacat 35280
ttccccgaaa agtgccacct gacgtctaag aaaccattat tatcatgaca ttaacctata 35340
aaaataggcg tatcacgagg ccctttcgtc ttcaagaatt cggagctttt gccattctca 35400
ccggattcag tcgtcactca tggtgatttc tcacttgata accttatttt tgacgagggg 35460
aaattaatag gttgtattga tgttggacga gtcggaatcg cagaccgata ccaggatctt 35520
gccatcctat ggaactgcct cggtgagttt tctccttcat tacagaaacg gctttttcaa 35580
aaatatggta ttgataatcc tgatatgaat aaattgcagt ttcatttgat gctcgatgag 35640
tttttctaat cagaattggt taattggttg taacactggc agagcattac gctgacttga 35700
cgggacggcg gctttgttga ataaatcgaa cttttgctga gttgaaggat cagatcacgc 35760

-continued

```
atcttcccga caacgcagac cgttccgtgg caaagcaaaa gttcaaaatc accaactggt  35820
ccacctacaa caaagctctc atcaaccgtg gctccctcac tttctggctg gatgatgggg  35880
cgattcaggc ctggtatgag tcagcaacac cttcttcacg aggcagacct cagcgccaga  35940
aggccgccag agaggccgag cgcggccgtg aggcttggac gctagggcag ggcatgaaaa  36000
agcccgtagc gggctgctac gggcgtctga cgcggtggaa agggggaggg gatgttgtct  36060
acatggctct gctgtagtga gtgggttgcg ctccggcagc ggtcctgatc aatcgtcacc  36120
ctttctcggt ccttcaacgt tcctgacaac gagcctcctt ttcgccaatc catcgacaat  36180
caccgcgagt ccctgctcga acgctgcgtc cggaccggct tcgtcgaagg cgtctatcgc  36240
ggcccgcaac agcggcgaga gcggagcctg ttcaacggtg ccgccgcgct cgccggcatc  36300
gctgtcgccg gcctgctcct caagcacggc cccaacagtg aagtagctga ttgtcatcag  36360
cgcattgacg gcgtccccgg ccgaaaaacc cgcctcgcag aggaagcgaa gctgcgcgtc  36420
ggccgtttcc atctgcggtg cgcccggtcg cgtgccggca tggatgcgcg cgccatcgcg  36480
gtaggcgagc agcgcctgcc tgaagctgcg ggcattcccg atcagaaatg agcgccagtc  36540
gtcgtcggct ctcggcaccg aatgcgtatg attctccgcc agcatggctt cggccagtgc  36600
gtcgagcagc gcccgcttgt tcctgaagtg ccagtaaagc gccggctgct gaacccccaa  36660
ccgttccgcc agtttgcgtg tcgtcagacc gtctacgccg acctcgttca acaggtccag  36720
ggcggcacgg atcactgtat tcggctgcaa ctttgtcatg cttgacactt tatcactgat  36780
aaacataata tgtccaccaa cttatcagtg ataaagaatc cgcgcgttca atcggaccag  36840
cggaggctgg tccggaggcc agacgtgaaa cccaacatac ccctgatcgt aattctgagc  36900
actgtcgcgc tcgacgctgt cggcatcggc ctgattatgc cggtgctgcc gggcctcctg  36960
cgcgatctgg ttcactcgaa cgacgtcacc gcccactatg gcattctgct ggcgctgtat  37020
gcgttggtgc aatttgcctg cgcacctgtg ctgggcgcgc tgtcggatcg tttcgggcgg  37080
cggccaatct tgctcgtctc gctggccggc gccactgtcg actacgccat catggcgaca  37140
gcgcctttcc tttgggttct ctatatcggg cggatcgtgg ccggcatcac cggggcgact  37200
ggggcggtag ccggcgctta tattgccgat atcactgatg gcgatgagcg cgcgcggcac  37260
ttcggcttca tgagcgcctg tttcgggttc gggatggtcg cgggacctgt gctcggtggg  37320
ctgatgggcg gtttctcccc ccacgctccg ttcttcgccg cggcagcctt gaacggcctc  37380
aatttcctga cgggctgttt ccttttgccg gagtcgcaca aaggcgaacg ccggccgtta  37440
cgccgggagg ctctcaaccc gctcgcttcg ttccggtggg cccggggcat gaccgtcgtc  37500
gccgccctga tggcggtctt cttcatcatg caacttgtcg gacaggtgcc ggccgcgctt  37560
tgggtcattt tcggcgagga tcgctttcac tgggacgcga ccacgatcgg catttcgctt  37620
gccgcatttg gcattctgca ttcactcgcc caggcaatga tcaccggccc tgtagccgcc  37680
cggctcggcg aaaggcgggc actcatgctc ggaatgattg ccgacggcac aggctacatc  37740
ctgcttgcct tcgcgacacg gggatggatg gcgttcccga tcatggtcct gcttgcttcg  37800
ggtggcatcg gaatgccggc gctgcaagca atgttgtcca ggcaggtgga tgaggaacgt  37860
caggggcagc tgcaaggctc actggcggcg ctcaccagcc tgacctcgat cgtcggaccc  37920
ctcctcttca cggcgatcta tgcggcttct ataacaacgt ggaacgggtg ggcatggatt  37980
gcaggcgctg ccctctactt gctctgcctg ccggcgctgc gtcgcgggct ttggagcggc  38040
gcagggcaac gagccgatcg ctgatcgtgg aaacgatagg cctatgccat gcgggtcaag  38100
gcgacttccg gcaagctata cgcgccctag gagtgcggtt ggaacgttgg cccagccaga  38160
```

```
tactcccgat cacgagcagg acgccgatga tttgaagcgc actcagcgtc tgatccaaga  38220
acaaccatcc tagcaacacg gcggtccccg ggctgagaaa gcccagtaag gaaacaactg  38280
taggttcgag tcgcgagatc ccccggaacc aaaggaagta ggttaaaccc gctccgatca  38340
ggccgagcca cgccaggccg agaacattgg ttcctgtagg catcgggatt ggcggatcaa  38400
acactaaagc tactggaacg agcagaagtc ctccggccgc cagttgccag gcggtaaagg  38460
tgagcagagg cacgggaggt tgccacttgc gggtcagcac ggttccgaac gccatggaaa  38520
ccgcccccgc caggcccgct gcgacgccga caggatctag cgctgcgttt ggtgtcaaca  38580
ccaacagcgc cacgcccgca gttccgcaaa tagcccccag gaccgccatc aatcgtatcg  38640
ggctacctag cagagcggca gagatgaaca cgaccatcag cggctgcaca gcgcctaccg  38700
tcgccgcgac cccgcccggc aggcggtaga ccgaaataaa caacaagctc cagaatagcg  38760
aaatattaag tgcgccgagg atgaagatgc gcatccacca gattcccgtt ggaatctgtc  38820
ggacgatcat cacgagcaat aaacccgccg gcaacgcccg cagcagcata ccggcgaccc  38880
ctcggcctcg ctgttcgggc tccacgaaaa cgccggacag atgcgccttg tgagcgtcct  38940
tggggccgtc ctcctgtttg aagaccgaca gcccaatgat ctcgccgtcg atgtaggcgc  39000
cgaatgccac ggcatctcgc aaccgttcag cgaacgcctc catgggcttt ttctcctcgt  39060
gctcgtaaac ggacccgaac atctctggag ctttcttcag ggccgacaat cggatctcgc  39120
ggaaatcctg cacgtcggcc gctccaagcc gtcgaatctg agccttaatc acaattgtca  39180
attttaatcc tctgtttatc ggcagttcgt agagcgcgcc gtgcgtcccg agcgatactg  39240
agcgaagcaa gtgcgtcgag cagtgcccgc ttgttcctga aatgccagta aagcgctggc  39300
tgctgaaccc ccagccggaa ctgaccccac aaggccctag cgtttgcaat gcaccaggtc  39360
atcattgacc caggcgtgtt ccaccaggcc gctgcctcgc aactcttcgc aggcttcgcc  39420
gacctgctcg cgccacttct tcacgcgggt ggaatccgat ccgcacatga ggcggaaggt  39480
ttccagcttg agcgggtacg gctcccggtg cgagctgaaa tagtcgaaca tccgtcgggc  39540
cgtcggcgac agcttgcggt acttctccca tatgaatttc gtgtagtggt cgccagcaaa  39600
cagcacgacg atttcctcgt cgatcaggac ctggcaacgg gacgttttct tgccacggtc  39660
caggacgcgg aagcggtgca gcagcgacac cgattccagg tgcccaacgc ggtcggacgt  39720
gaagcccatc gccgtcgcct gtaggcgcga caggcattcc tcggccttcg tgtaataccg  39780
gccattgatc gaccagccca ggtcctggca aagctcgtag aacgtgaagg tgatcggctc  39840
gccgataggg gtgcgcttcg cgtactccaa cacctgctgc cacaccagtt cgtcatcgtc  39900
ggcccgcagc tcgacgccgg tgtaggtgat cttcacgtcc ttgttgacgt ggaaaatgac  39960
cttgttttgc agcgcctcgc gcgggatttt cttgttgcgc gtggtgaaca gggcagagcg  40020
ggccgtgtcg tttggcatcg ctcgcatcgt gtccggccac ggcgcaatat cgaacaagga  40080
aagctgcatt tccttgatct gctgcttcgt gtgtttcagc aacgcggcct gcttggcctc  40140
gctgacctgt tttgccaggt cctcgccggc ggtttttcgc ttcttggtcg tcatagttcc  40200
tcgcgtgtcg atggtcatcg acttcgccaa acctgccgcc tcctgttcga gacgacgcga  40260
acgctccacg gcggccgatg gcgcgggcag ggcagggggga gccagttgca cgctgtcgcg  40320
ctcgatcttg gccgtagctt gctggaccat cgagccgacg gactggaagg tttcgcgggg  40380
cgcacgcatg acggtgcggc ttgcgatggt ttcggcatcc tcggcggaaa accccgcgtc  40440
gatcagttct tgcctgtatg ccttccggtc aaacgtccga ttcattcacc ctccttgcgg  40500
gattgccccg actcacgccg gggcaatgtg cccttattcc tgatttgacc cgcctggtgc  40560
```

-continued

```
cttggtgtcc agataatcca ccttatcggc aatgaagtcg gtcccgtaga ccgtctggcc  40620
gtccttctcg tacttggtat tccgaatctt gccctgcacg aataccagcg accccttgcc  40680
caaatacttg ccgtgggcct cggcctgaga gccaaaacac ttgatgcgga agaagtcggt  40740
gcgctcctgc ttgtcgccgg catcgttgcg ccactcttca ttaaccgcta tatcgaaaat  40800
tgcttgcggc ttgttagaat tgccatgacg tacctcggtg tcacgggtaa gattaccgat  40860
aaactggaac tgattatggc tcatatcgaa agtctccttg agaaaggaga ctctagttta  40920
gctaaacatt ggttccgctg tcaagaactt tagcggctaa aattttgcgg gccgcgacca  40980
aaggtgcgag gggcggcttc cgctgtgtac aaccagatat ttttcaccaa catccttcgt  41040
ctgctcgatg agcggggcat gacgaaacat gagctgtcgg agagggcagg ggtttcaatt  41100
tcgtttttat cagacttaac caacggtaag gccaacccct cgttgaaggt gatggaggcc  41160
attgccgacg ccctggaaac tcccctacct cttctcctgg agtccaccga ccttgaccgc  41220
gaggcactcg cggagattgc gggtcatcct ttcaagagca gcgtgccgcc cggatacgaa  41280
cgcatcagtg tggttttgcc gtcacataag gcgtttatcg taaagaaatg gggcgacgac  41340
acccgaaaaa agctgcgtgg aaggctctga cgccaagggt tagggcttgc acttccttct  41400
ttagccgcta aaacggcccc ttctctgcgg gccgtcggct cgcgcatcat atcgacatcc  41460
tcaacggaag ccgtgccgcg aatggcatcg ggcgggtgcg ctttgacagt tgttttctat  41520
cagaacccct acgtcgtgcg gttcgattag ctgtttgtct tgcaggctaa acactttcgg  41580
tatatcgttt gcctgtgcga taatgttgct aatgatttgt tgcgtagggg ttactgaaaa  41640
gtgagcggga aagaagagtt tcagaccatc aaggagcggg ccaagcgcaa gctggaacgc  41700
gacatgggtg cggacctgtt ggccgcgctc aacgacccga aaaccgttga agtcatgctc  41760
aacgcggacg gcaaggtgtg gcacgaacgc cttggcgagc cgatgcggta catctgcgac  41820
atgcggccca gccagtcgca ggcgattata gaaacggtgg ccggattcca cggcaaagag  41880
gtcacgcggc attcgcccat cctggaaggc gagttcccct tggatggcag ccgctttgcc  41940
ggccaattgc cgccggtcgt ggccgcgcca acctttgcga tccgcaagcg cgcggtcgcc  42000
atcttcacgc tggaacagta cgtcgaggcg ggcatcatga cccgcgagca atacgaggtc  42060
attaaaagcg ccgtcgcggc gcatcgaaac atcctcgtca ttggcggtac tggctcgggc  42120
aagaccacgc tcgtcaacgc gatcatcaat gaaatggtcg ccttcaaccc gtctgagcgc  42180
gtcgtcatca tcgaggacac cggcgaaatc cagtgcgccg cagagaacgc cgtccaatac  42240
cacaccagca tcgacgtctc gatgacgctg ctgctcaaga caacgctgcg tatgcgcccc  42300
gaccgcatcc tggtcggtga ggtacgtggc cccgaagccc ttgatctgtt gatggcctgg  42360
aacaccgggc atgaaggagg tgccgccacc ctgcacgcaa acaaccccaa agcgggcctg  42420
agccggctcg ccatgcttat cagcatgcac ccggattcac cgaaacccat tgagccgctg  42480
attggcgagg cggttcatgt ggtcgtccat atcgccagga cccctagcgg ccgtcgagtg  42540
caagaaattc tcgaagttct tggttacgag aacggccagt acatcaccaa aaccctgtaa  42600
ggagtatttc caatgacaac ggctgttccg ttccgtctga ccatgaatcg cggcattttg  42660
ttctaccttg ccgtgttctt cgttctcgct ctcgcgttat ccgcgcatcc ggcgatggcc  42720
tcggaaggca ccggcggcag cttgccatat gagagctggc tgacgaacct gcgcaactcc  42780
gtaaccggcc cggtggcctt cgcgctgtcc atcatcggca tcgtcgtcgc cggcggcgtg  42840
ctgatcttcg gcggcgaact caacgccttc ttccgaaccc tgatcttcct ggttctggtg  42900
atggcgctgc tggtcggcgc gcagaacgtg atgagcacct tcttcggtcg tggtgccgaa  42960
```

-continued atcgcggccc tcggcaacgg ggcgctgcac caggtgcaag tcgcggcggc ggatgccgtg 43020
cgtgcggtag cggctggacg gctcgcctaa tcatggctct gcgcacgatc cccatccgtc 43080
gcgcaggcaa ccgagaaaac ctgttcatgg gtggtgatcg tgaactggtg atgttctcgg 43140
gcctgatggc gtttgcgctg attttcagcg cccaagagct gcgggccacc gtggtcggtc 43200
tgatcctgtg gttcggggcg ctctatgcgt tccgaatcat ggcgaaggcc gatccgaaga 43260
tgcggttcgt gtacctgcgt caccgccggt acaagccgta ttacccggcc cgctcgaccc 43320
cgttccgcga gaacaccaat agccaaggga agcaataccg atgatccaag caattgcgat 43380
tgcaatcgcg ggcctcggcg cgcttctgtt gttcatcctc tttgcccgca tccgcgcggt 43440
cgatgccgaa ctgaaactga aaaagcatcg ttccaaggac gccggcctgg ccgatctgct 43500
caactacgcc gctgtcgtcg atgacggcgt aatcgtgggc aagaacggca gctttatggc 43560
tgcctggctg tacaagggcg atgacaacgc aagcagcacc gaccagcagc gcgaagtagt 43620
gtccgcccgc atcaaccagg ccctcgcggg cctgggaagt gggtggatga tccatgtgga 43680
cgccgtgcgg cgtcctgctc cgaactacgc ggagcggggc ctgtcggcgt tccctgaccg 43740
tctgacggca gcgattgaag aagagcgctc ggtcttgcct tgctcgtcgg tgatgtactt 43800
caccagctcc gcgaagtcgc tcttcttgat ggagcgcatg gggacgtgct tggcaatcac 43860
gcgcaccccc cggccgtttt agcggctaaa aaagtcatgg ctctgccctc gggcggacca 43920
cgcccatcat gaccttgcca agctcgtcct gcttctcttc gatcttcgcc agcagggcga 43980
ggatcgtggc atcaccgaac cgcgccgtgc gcgggtcgtc ggtgagccag agtttcagca 44040
ggccgcccag gcggcccagg tcgccattga tgcgggccag ctcgcggacg tgctcatagt 44100
ccacgacgcc cgtgattttg tagccctggc cgacggccag caggtaggcc gacaggctca 44160
tgccggccgc cgccgccttt tcctcaatcg ctcttcgttc gtctggaagg cagtacacct 44220
tgataggtgg gctgcccttc ctggttggct tggtttcatc agccatccgc ttgccctcat 44280
ctgttacgcc ggcggtagcc ggccagcctc gcagagcagg attcccgttg agcaccgcca 44340
ggtgcgaata agggacagtg aagaaggaac acccgctcgc gggtgggcct acttcaccta 44400
tcctgcccgg ctgacgccgt tggatacacc aaggaaagtc tacacgaacc ctttggcaaa 44460
atcctgtata tcgtgcgaaa aaggatggat ataccgaaaa aatcgctata atgaccccga 44520
agcagggtta tgcagcggaa aagcgctgct tccctgctgt tttgtggaat atctaccgac 44580
tggaaacagg caaatgcagg aaattactga actgagggga caggcgagag acgatgccaa 44640
agagctacac cgacgagctg gccgagtggg ttgaatcccg cgcggccaag aagcgccggc 44700
gtgatgaggc tgcggttgcg ttcctggcgg tgagggcgga tgtcgaggcg gcgttagcgt 44760
ccggctatgc gctcgtcacc atttgggagc acatgcggga aacggggaag gtcaagttct 44820
cctacgagac gttccgctcg cacgccaggc ggcacatcaa ggccaagccc gccgatgtgc 44880
ccgcaccgca ggccaaggct gcggaacccg cgccggcacc caagacgccg gagccacggc 44940
ggccgaagca ggggggcaag gctgaaaagc cggcccccgc tgcggccccg accggcttca 45000
ccttcaaccc aacaccggac aaaaaggatc tactgtaatg gcgaaaattc acatggtttt 45060
gcagggcaag ggcggggtcg gcaagtcggc catcgccgcg atcattgcgc agtacaagat 45120
ggacaagggg cagacaccct tgtgcatcga caccgacccg gtgaacgcga cgttcgaggg 45180
ctacaaggcc ctgaacgtcc gccggctgaa catcatggcc ggcgacgaaa ttaactcgcg 45240
caacttcgac accctggtcg agctgattgc gccgaccaag gatgacgtgg tgatcgacaa 45300
cggtgccagc tcgttcgtgc ctctgtcgca ttacctcatc agcaaccagg tgccggctct 45360

-continued

```
gctgcaagaa atggggcatg agctggtcat ccataccgtc gtcaccggcg gccaggctct  45420
cctggacacg gtgagcggct tcgcccagct cgccagccag ttcccggccg aagcgctttt  45480
cgtggtctgg ctgaacccgt attgggggcc tatcgagcat gagggcaaga gctttgagca  45540
gatgaaggcg tacacggcca acaaggcccg cgtgtcgtcc atcatccaga ttccggccct  45600
caaggaagaa acctacggcc gcgatttcag cgacatgctg caagagcggc tgacgttcga  45660
ccaggcgctg gccgatgaat cgctcacgat catgacgcgg caacgcctca agatcgtgcg  45720
gcgcggcctg tttgaacagc tcgacgcggc ggccgtgcta tgagcgacca gattgaagag  45780
ctgatccggg agattgcggc caagcacggc atcgccgtcg gccgcgacga cccggtgctg  45840
atcctgcata ccatcaacgc ccggctcatg gccgacagtg cggccaagca agaggaaatc  45900
cttgccgcgt tcaaggaaga gctggaaggg atcgcccatc gttggggcga ggacgccaag  45960
gccaaagcgg agcggatgct gaacgcggcc ctggcggcca gcaaggacgc aatggcgaag  46020
gtaatgaagg acagcgccgc gcaggcggcc gaagcgatcc gcagggaaat cgacgacggc  46080
cttggccgcc agctcgcggc caaggtcgcg gacgcgcggc gcgtggcgat gatgaacatg  46140
atcgccggcg gcatggtgtt gttcgcggcc gccctggtgg tgtgggcctc gttatgaatc  46200
gcagaggcgc agatgaaaaa gcccggcgtt gccgggcttt gtttttgcgt tagctgggct  46260
tgtttgacag gcccaagctc tgactgcgcc cgcgctcgcg ctcctgggcc tgtttcttct  46320
cctgctcctg cttgcgcatc agggcctggt gccgtcgggc tgcttcacgc atcgaatccc  46380
agtcgccggc cagctcggga tgctccgcgc gcatcttgcg cgtcgccagt tcctcgatct  46440
tgggcgcgtg aatgcccatg ccttccttga tttcgcgcac catgtccagc cgcgtgtgca  46500
gggtctgcaa gcgggcttgc tgttgggcct gctgctgctg ccaggcggcc tttgtacgcg  46560
gcagggacag caagccgggg gcattggact gtagctgctg caaacgcgcc tgctgacggt  46620
ctacgagctg ttctaggcgg tcctcgatgc gctccacctg gtcatgcttt gcctgcacgt  46680
agagcgcaag ggtctgctgg taggtctgct cgatgggcgc ggattctaag agggcctgct  46740
gttccgtctc ggcctcctgg gccgcctgta gcaaatcctc gccgctgttg ccgctggact  46800
gctttactgc cggggactgc tgttgccctg ctcgcgccgt cgtcgcagtt cggcttgccc  46860
ccactcgatt gactgcttca tttcgagccg cagcgatgcg atctcggatt gcgtcaacgg  46920
acggggcagc gcggaggtgt ccggcttctc cttgggtgag tcggtcgatg ccatagccaa  46980
aggtttcctt ccaaaatgcg tccattgctg gaccgtgttt ctcattgatg cccgcaagca  47040
tcttcggctt gaccgccagg tcaagcgcgc cttcatgggc ggtcatgacg gacgccgcca  47100
tgaccttgcc gccgttgttc tcgatgtagc cgcgtaatga ggcaatggtg ccgcccatcg  47160
tcagcgtgtc atcgacaacg atgtacttct ggccggggat cacctccccc tcgaaagtcg  47220
ggttgaacgc caggcgatga tctgaaccgg ctccggttcg ggcgaccttc tcccgctgca  47280
caatgtccgt ttcgacctca aggccaaggc ggtcggccag aacgaccgcc atcatggccg  47340
gaatcttgtt gttccccgcc gcctcgacgg cgaggactgg aacgatgcgg ggcttgtcgt  47400
cgccgatcag cgtcttgagc tgggcaacag tgtcgtccga aatcaggcgc tcgaccaaat  47460
taagcgccgc ttccgcgtcg ccctgcttcg cagcctggta ttcaggctcg ttggtcaaag  47520
aaccaaggtc gccgttgcga accaccttcg ggaagtctcc ccacggtgcg cgctcggctc  47580
tgctgtagct gctcaagacg cctccctttt tagccgctaa aactctaacg agtgcgcccg  47640
cgactcaact tgacgctttc ggcacttacc tgtgccttgc cacttgcgtc ataggtgatg  47700
cttttcgcac tcccgatttc aggtacttta tcgaaatctg accgggcgtg cattacaaag  47760
```

ttcttcccca cctgttggta aatgctgccg ctatctgcgt ggacgatgct gccgtcgtgg 47820
cgctgcgact tatcggcctt ttgggccata tagatgttgt aaatgccagg tttcagggcc 47880
ccggctttat ctaccttctg gttcgtccat gcgccttggt tctcggtctg gacaattctt 47940
tgcccattca tgaccaggag gcggtgtttc attgggtgac tcctgacggt tgcctctggt 48000
gttaaacgtg tcctggtcgc ttgccggcta aaaaaaagcc gacctcggca gttcgaggcc 48060
ggctttccct agagccgggc gcgtcaaggt tgttccatct attttagtga actgcgttcg 48120
atttatcagt tactttcctc ccgctttgtg tttcctccca ctcgtttccg cgtctagccg 48180
acccctcaac atagcggcct cttcttgggc tgcctttgcc tcttgccgcg cttcgtcacg 48240
ctcggcttgc accgtcgtaa agcgctcggc ctgcctggcc gcctcttgcg ccgccaactt 48300
cctttgctcc tggtgggcct cggcgtcggc ctgcgccttc gctttcaccg ctgccaactc 48360
cgtgcgcaaa ctctccgctt cgcgcctggt ggcgtcgcgc tcgccgcgaa gcgcctgcat 48420
ttcctggttg gccgcgtcca gggtcttgcg gctctcttct ttgaatgcgc gggcgtcctg 48480
gtgagcgtag tccagctcgg cgcgcagctc ctgcgctcga cgctccacct cgtcggcccg 48540
ctgcgtcgcc agcgcggccc gctgctcggc tcctgccagg gcggtgcgtg cttcggccag 48600
ggcttgccgc tggcgtgcgg ccagctcggc cgcctcggcg gcctgctgct ctagcaatgt 48660
aacgcgcgcc tgggcttctt ccagctcgcg ggcctgcgcc tcgaaggcgt cggccagctc 48720
cccgcgcacg gcttccaact cgttgcgctc acgatcccag ccggcttgcg ctgcctgcaa 48780
cgattcattg gcaagggcct gggcggcttg ccagagggcg gccacggcct ggttgccggc 48840
ctgctgcacc gcgtccggca cctggactgc cagcggggcg gcctgcgccg tgcgctggcg 48900
tcgccattcg cgcatgccgg cgctggcgtc gttcatgttg acgcgggcgg ccttacgcac 48960
tgcatccacg gtcgggaagt tctcccggtc gccttgctcg aacagctcgt ccgcagccgc 49020
aaaaatgcgg tcgcgcgtct ctttgttcag ttccatgttg gctccggtaa ttggtaagaa 49080
taataatact cttacctacc ttatcagcgc aagagtttag ctgaacagtt ctcgacttaa 49140
cggcaggttt tttagcggct gaagggcagg caaaaaaagc cccgcacggt cggcgggggc 49200
aaagggtcag cgggaagggg attagcgggc gtcgggcttc ttcatgcgtc ggggccgcgc 49260
ttcttgggat ggagcacgac gaagcgcgca cgcgcatcgt cctcggccct atcggcccgc 49320
gtcgcggtca ggaacttgtc gcgcgctagg tcctccctgg tgggcaccag gggcatgaac 49380
tcggcctgct cgatgtaggt ccactccatg accgcatcgc agtcgaggcc gcgttccttc 49440
accgtctctt gcaggtcgcg gtacgcccgc tcgttgagcg gctggtaacg ggccaattgg 49500
tcgtaaatgg ctgtcggcca tgagcggcct ttcctgttga gccagcagcc gacgacgaag 49560
ccggcaatgc aggcccctgg cacaaccagg ccgacgccgg gggcagggga tggcagcagc 49620
tcgccaacca ggaaccccgc cgcgatgatg ccgatgccgg tcaaccagcc cttgaaacta 49680
tccggccccg aaacacccct gcgcattgcc tggatgctgc gccggatagc ttgcaacatc 49740
aggagccgtt tcttttgttc gtcagtcatg gtccgccctc accagttgtt cgtatcggtg 49800
tcggacgaac tgaaatcgca agagctgccg gtatcggtcc agccgctgtc cgtgtcgctg 49860
ctgccgaagc acggcgaggg gtccgcgaac gccgcagacg gcgtatccgg ccgcagcgca 49920
tcgcccagca tggccccggt cagcgagccg ccggccaggt agcccagcat ggtgctgttg 49980
gtcgccccgg ccaccagggc cgacgtgacg aaatcgccgt cattccctct ggattgttcg 50040
ctgctcggcg gggcagtgcg ccgcgccggc ggcgtcgtgg atggctcggg ttggctggcc 50100
tgcgacggcc ggcgaaaggt gcgcagcagc tcgttatcga ccggctgcgg cgtcggggcc 50160

```
gccgccttgc gctgcggtcg gtgttccttc ttcggctcgc gcagcttgaa cagcatgatc  50220
gcggaaacca gcagcaacgc cgcgcctacg cctcccgcga tgtagaacag catcggattc  50280
attcttcggt cctccttgta gcggaaccgt tgtctgtgcg gcgcgggtgg cccgcgccgc  50340
tgtctttggg gatcagccct cgatgagcgc gaccagtttc acgtcggcaa ggttcgcctc  50400
gaactcctgg ccgtcgtcct cgtacttcaa ccaggcatag ccttccgccg gcggccgacg  50460
gttgaggata aggcgggcag ggcgctcgtc gtgctcgacc tggacgatgg cctttttcag  50520
cttgtccggg tccggctcct tcgcgccctt ttccttggcg tccttaccgt cctggtcgcc  50580
gtcctcgccg tcctggccgt cgccggcctc cgcgtcacgc tcggcatcag tctggccgtt  50640
gaaggcatcg acggtgttgg gatcgcggcc cttctcgtcc aggaactcgc gcagcagctt  50700
gaccgtgccg cgcgtgattt cctgggtgtc gtcgtcaagc cacgcctcga cttcctccgg  50760
gcgcttcttg aaggccgtca ccagctcgtt caccacggtc acgtcgcgca cgcggccggt  50820
gttgaacgca tcggcgatct tctccggcag gtccagcagc gtgacgtgct gggtgatgaa  50880
cgccggcgac ttgccgattt ccttggcgat atcgcctttc ttcttgccct tcgccagctc  50940
gcggccaatg aagtcggcaa tttcgcgcgg ggtcagctcg ttgcgttgca ggttctcgat  51000
aacctggtcg gcttcgttgt agtcgttgtc gatgaacgcc gggatggact tcttgccggc  51060
ccacttcgag ccacggtagc ggcgggcgcc gtgattgatg atatagcggc ccggctgctc  51120
ctggttctcg cgcaccgaaa tgggtgactt caccccgcgc tctttgatcg tggcaccgat  51180
ttccgcgatg ctctccgggg aaaagccggg gttgtcggcc gtccgcggct gatgcggatc  51240
ttcgtcgatc aggtccaggt ccagctcgat agggccggaa ccgccctgag acgccgcagg  51300
agcgtccagg aggctcgaca ggtcgccgat gctatccaac cccaggccgg acggctgcgc  51360
cgcgcctgcg gcttcctgag cggccgcagc ggtgtttttc ttggtggtct tggcttgagc  51420
cgcagtcatt gggaaatctc catcttcgtg aacacgtaat cagccagggc gcgaacctct  51480
ttcgatgcct tgcgcgcggc cgttttcttg atcttccaga ccggcacacc ggatgcgagg  51540
gcatcggcga tgctgctgcg caggccaacg gtggccggaa tcatcatctt ggggtacgcg  51600
gccagcagct cggcttggtg gcgcgcgtgg cgcggattcc gcgcatcgac cttgctgggc  51660
accatgccaa ggaattgcag cttggcgttc ttctggcgca cgttcgcaat ggtcgtgacc  51720
atcttcttga tgccctggat gctgtacgcc tcaagctcga tgggggacag cacatagtcg  51780
gccgcgaaga gggcggccgc caggccgacg ccaagggtcg gggccgtgtc gatcaggcac  51840
acgtcgaagc cttggttcgc cagggccttg atgttcgccc cgaacagctc gcgggcgtcg  51900
tccagcgaca gccgttcggc gttcgccagt accgggttgg actcgatgag ggcgaggcgc  51960
gcggcctggc cgtcgccggc tgcgggtgcg gtttcggtcc agccgccggc agggacagcg  52020
ccgaacagct tgcttgcatg caggccggta gcaaagtcct tgagcgtgta ggacgcattg  52080
ccctgggggt ccaggtcgat cacggcaacc cgcaagccgc gctcgaaaaa gtcgaaggca  52140
agatgcacaa gggtcgaagt cttgccgacg ccgcctttct ggttggccgt gaccaaagtt  52200
ttcatcgttt ggtttcctgt tttttcttgg cgtccgcttc ccacttccgg acgatgtacg  52260
cctgatgttc cggcagaacc gccgttaccc gcgcgtaccc ctcgggcaag ttcttgtcct  52320
cgaacgcggc ccacacgcga tgcaccgctt gcgacactgc gcccctggtc agtcccagcg  52380
acgttgcgaa cgtcgcctgt ggcttcccat cgactaagac gccccgcgct atctcgatgg  52440
tctgctgccc cacttccagc ccctggatcg cctcctggaa ctggctttcg gtaagccgtt  52500
tcttcatgga taacacccat aatttgctcc gcgccttggt tgaacatagc ggtgacagcc  52560
```

```
gccagcacat gagagaagtt tagctaaaca tttctcgcac gtcaacacct ttagccgcta  52620
aaactcgtcc ttggcgtaac aaaacaaaag cccggaaacc gggctttcgt ctcttgccgc  52680
ttatggctct gcacccggct ccatcaccaa caggtcgcgc acgcgcttca ctcggttgcg  52740
gatcgacact gccagcccaa caaagccggt tgccgccgcc gccaggatcg cgccgatgat  52800
gccggccaca ccggccatcg cccaccaggt cgccgccttc cggttccatt cctgctggta  52860
ctgcttcgca atgctggacc tcggctcacc ataggctgac cgctcgatgg cgtatgccgc  52920
ttctcccctt ggcgtaaaac ccagcgccgc aggcggcatt gccatgctgc ccgccgcttt  52980
cccgaccacg acgcgcgcac caggcttgcg gtccagacct tcggccacgg cgagctgcgc  53040
aaggacataa tcagccgccg acttggctcc acgcgcctcg atcagctctt gcactcgcgc  53100
gaaatccttg gcctccacgg ccgccatgaa tcgcgcacgc ggcgaaggct ccgcagggcc  53160
ggcgtcgtga tcgccgccga gaatgccctt caccaagttc gacgacacga aaatcatgct  53220
gacggctatc accatcatgc agacggatcg cacgaacccg ctgaattgaa cacgagcacg  53280
gcacccgcga ccactatgcc aagaatgccc aaggtaaaaa ttgccggccc cgccatgaag  53340
tccgtgaatg ccccgacggc cgaagtgaag ggcaggccgc cacccaggcc gccgccctca  53400
ctgcccggca cctggtcgct gaatgtcgat gccagcacct gcggcacgtc aatgcttccg  53460
ggcgtcgcgc tcgggctgat cgcccatccc gttactgccc cgatcccggc aatggcaagg  53520
actgccagcg ctgccatttt tggggtgagg ccgttcgcgg ccgaggggcg cagcccctgg  53580
ggggatggga ggcccgcgtt agcgggccgg gagggttcga gaagggggggg caccccccctt  53640
cggcgtgcgc ggtcacgcgc acagggcgca gccctggtta aaaacaaggt ttataaatat  53700
tggtttaaaa gcaggttaaa agacaggtta gcggtggccg aaaaacgggc ggaaaccctt  53760
gcaaatgctg gattttctgc ctgtggacag cccctcaaat gtcaataggt gcgcccctca  53820
tctgtcagca ctctgcccct caagtgtcaa ggatcgcgcc cctcatctgt cagtagtcgc  53880
gcccctcaag tgtcaatacc gcagggcact tatccccagg cttgtccaca tcatctgtgg  53940
gaaactcgcg taaaatcagg cgttttcgcc gatttgcgag gctggccagc tccacgtcgc  54000
cggccgaaat cgagcctgcc cctcatctgt caacgccgcg ccgggtgagt cggcccctca  54060
agtgtcaacg tccgcccctc atctgtcagt gagggccaag ttttccgcga ggtatccaca  54120
acgccggcgg ccgcggtgtc tcgcacacgg cttcgacggc gtttctggcg cgtttgcagg  54180
gccatagacg gccgccagcc cagcggcgag ggcaaccagc ccggtgagcg tcggaaaggc  54240
gctggaagcc ccgtagcgac gcggagaggg gcgagacaag ccaagggcgc aggctcgatg  54300
cgcagcacga catagccggt tctcgcaagg acgagaattt ccctgcggtg cccctcaagt  54360
gtcaatgaaa gtttccaacg cgagccattc gcgagagcct tgagtccacg ctagatgaga  54420
gctttgttgt aggtggacca gttggtgatt ttgaactttt gctttgccac ggaacggtct  54480
gcgttgtcgg gaagatgcgt gatctgatcc ttcaactcag caaaagttcg atttattcaa  54540
caaagccacg ttgtgtctca aaatctctga tgttacattg cacaagataa aaatatatca  54600
tcatgaacaa taaaactgtc tgcttacata aacagtaata caaggggtgt tatgagccat  54660
attcaacggg aaacgtcttg ctcgac                                         54686
```

<210> SEQ ID NO 89
<211> LENGTH: 3324
<212> TYPE: DNA
<213> ORGANISM: Zea mays

<400> SEQUENCE: 89

-continued

```
tggtccttgt ttgatttact tccaggatta tataatccag cttatggatt atataagtac     60
ctattgacgt cacgtgctta tgtattataa taatctaggt atatagatta tataatctat    120
ctaataataa tctgtgttgt ttgtttatct ctcaaaacaa acaggtccta aaatggtccc    180
gggcgtccaa tgtgtcgtca agtagtgtta agctaaatcg acatttcttt gtgggttgtg    240
tggaaggtgt tccttttcct taagttgtta gttgtgcaag gtgttcctta gagcatctcc    300
aataggacct ataatggatt ctattttgaa ttataagact ctaacaacaa aagcatactt    360
taatggggat tctattttac aaaaaaatat caaatgatta tatggtcgat tcctcgggtc    420
ctaaatatag tatctcatat aatagagctc tatcctcatt ttatatacta tttttaagtt    480
tttatttact aaataacatg atttatttc taatactatg aactcaacta ttagagctgt     540
aaacgttttt gtggtactaa acactttaaa tcaggtccta ttttaatttg aaggacttaa    600
atataagact tctggttaga gatgctctta gcgagtgttt gtgcatgatt gctatttagt    660
ctttgtggat tgtggaaggt gttacttttc ctcaagttgt tagttgtgca aggtgtttct    720
tagagcatct ctaacaggag ccttaacgga atctattttg aagtatagta ctttaacacc    780
aaaaacatac tttaataggg gtcctatttt acaaaaaaat tatcaaatga ttataaggtc    840
cactcctcgg gtcctaaata taatatctca tatactagag ctctatcctc attttatata    900
ctatccctag gtttttattc cctaaataac atgatttatt tcctaatact aagatatagg    960
gctcaactat tggagttgca aatgtttttt ggcactaaac actttatatc aggtcctatt   1020
ttaattttaa tttgaaggac tcaaatatag gacttctcgt tagagatgct cttagcgagt   1080
gtttgtgcat gattgctatt tatgtctgta gtttagttgg gggctttaat atgtttagtt   1140
gaagttctag tattttttag gttctccact ctttggatta tgacaacgac cactatccaa   1200
gcagtctttg agtgcaaacg cgcgagcaaa ctatctgatc tattaaatta tgatccaacc   1260
gttatgtcat attgaagact taaacccttt caccaccagc ccaagtatct ttatgaaaaa   1320
ccctaacaaa ccacaattgc atctatggtt ggattataat ttaacgtatc agatggttcg   1380
cttgcatgct tacatatcta gaaactgttt gcataacagt cgttctcttt ggttatataa   1440
tgctttagta atcatcagcc aagtgtaaac aaatggtaca aactagtagt gaacacatcc   1500
tccctaccta tctctagggg tgtcatagta aattctatgt cttatttgtc cgcgattgaa   1560
gaaaaatgac aaaaagatct gacattcgaa taaacatctg tttccactcc tacctatctg   1620
acctcctatt tcaaactcca ctttgtaaca cggtacaaaa tcactcccta cctatctgac   1680
ctcctatttc aaactccact cagtaaacaa tattgtctat ggtacaaaac caagtgtttt   1740
atacatctat ttgcacgatc tgctcgagtc aggcatcctt gacacacaac atactccttg   1800
tggctataaa tgtccaaata gagcagacct aatgggtgga ccgttgcatg acacgactta   1860
tcccaagacg agcacagttc gccccattgg tcatgggggt ccgggctagt ctagcctgat   1920
catcgggtca cacttaggcc acaggtgtgc cacaacggga tagcccaaca tgtccctttt   1980
tgtcatgcat atatctatat tatagttagt ataatgtaaa aaaacaaaag gtatgtgtgt   2040
tatgttggtt agatgtgttt aaataactct ttaaagctag caactatggt ttaaatcata   2100
catatacaca tttttatttt atttttattt aaacgatatg ggccttctag gcacgtcgag   2160
tgtgacgggc cagtgagatg acacattata attactggtc tagcaggccg tacctaggtc   2220
tttctcgtgg gccaagacta agggttggcc cgttggctaa tctgtacggt accgatactg   2280
tcctaattca tttgaacacc tgtagaagag gggaatttat aattgaggag gaatgtactc   2340
atgcggtaca ccaggggaat tgttttgttg tgctcagcga tagatttcaa cgcaacggtg   2400
```

agccagtttc actaaaaaaa gggggggggg gggggggggg ggaaggccac atcaaaggcg 2460
aggtgctgac gagcagaaga tgctagcagt gacgccaagt ccagcagcta gcaatgaaag 2520
ggtactcggg atttaacaat gcctagagac ggcatcatcc cctcaataat ccggtgctct 2580
ctttttgttt attcaccagt tggcgtagct atatacacat gtctggtctg acgaacaaat 2640
caagggatcg ctagctcggg ctagccttcc tatcactgtc atgacatgtg ctctgcctct 2700
gctggttgat aagccgtgcg ccttctcgct aattctttct tgtgctagag gcgagtcaaa 2760
caaacgctgc acctcgtagc ccttaatctg cgctaagggt cacatgaccc tgttccctat 2820
cgctagttac caacgaccca ttccccctga cagatactta cgacgcgtcc gtacgcggca 2880
ggcctcggca gttcggcatc accagcaccg gcgccggcat tcgcccccctg ccagccggtt 2940 cgcagattcg cagggcggag tcggccgcag ttgccgcatc ccaaacgccc gggaaccttt 3000
ggggcccctc tacgagcaaa tgaagttgct gcccctggct tcgtaaagct ctgacttttg 3060
atcacttgat tggcagtcgt actcctcgct catagggccga cacggccgca aagtcaacta 3120
cccgctccgc catccttcaa cccccgccac gcgcctatat atgttcgcgg ccatgtccgt 3180
actagtcctc caacccacaa gccacaaccc cgagctcaga tccctcgcct cgtgtcgtgt 3240
ctccggtcga cgacgaccaa cagccagtgt gggccagacg gacaccgccg agctatagcg 3300
cttggtgata gcaagggacg accg 3324

<210> SEQ ID NO 90
<211> LENGTH: 500
<212> TYPE: DNA
<213> ORGANISM: Zea mays

<400> SEQUENCE: 90
agttaccaac gacccattcc ccctgacaga tacttacgac gcgtccgtac gcggcaggcc 60
tcggcagttc ggcatcacca gcaccggcgc cggcattcgc cccctgccag ccggttcgca 120
gattcgcagg gcggagtcgg ccgcagttgc cgcatcccaa acgcccggga acctttgggg 180
cccctctacg agcaaatgaa gttgctgccc ctggcttcgt aaagctctga cttttgatca 240
cttgattggc agtcgtactc ctcgctcata ggccgacacg gccgcaaagt caactacccg 300
ctccgccatc cttcaacccc cgccacgcgc ctatatatgt tcgcggccat gtccgtacta 360
gtcctccaac ccacaagcca caaccccgag ctcagatccc tcgcctcgtg tcgtgtctcc 420
ggtcgacgac gaccaacagc cagtgtgggc cagacggaca ccgccgagct atagcgcttg 480
gtgatagcaa gggacgaccg 500

<210> SEQ ID NO 91
<211> LENGTH: 2025
<212> TYPE: DNA
<213> ORGANISM: Zea mays

<400> SEQUENCE: 91
gagcgctccg ctgccgtgcg cgcccccgcg ccggcctccc actggatcgc tccacctcat 60
gctccaaatc tttattggtt tccacgttgc cccctcgccg tccccaacca tcgaccgcgc 120
cgcgcccgct gccgcctccc agctcgctct atataaacac cacgtacgcg ccgaagcatc 180
agcacagcca cgtacgtacg accggcttcc ggcaggtgag agaacagtga gaagcaggcg 240
agcggtgaca tggcggaggg ggagttcaag cccgcggcga tgcaggtgga ggctcctgcc 300
gaggcggcgg cggcgccgtc caagccgcgg ttcaggatgc ccgtcgactc cgacaacaag 360
gccaccgagt tctggctctt ctccttcgcg aggccgcaca tgagcgcctt ccacatgtcg 420

```
tggttctcct tcttctgctg cttcctctcc accttcgcgg cgccgccgct gctcccgctc    480
atccgggaca cgctggggct cacggccacg gacatcggca acgccgggat cgcctccgtg    540
tccggcgcgg tcttcgcgcg cgtggccatg ggcacggcgt gcgacctggt gggcccgcgc    600
ctggcgtccg cggccatcat actcctcacc acgcccgccg tctactactc cgccgtcatc    660
gactccgcct cgtcctacct gctcgtgcgc ttcttcacgg gcttctcgct cgcgtccttc    720
gtgtccacgc agttctggat gagctccatg ttctcgccgc ccaaggtggg gctggccaac    780
ggcgtcgccg gggggtgggg caacctcggc ggcggcgccg tgcagctcat catgccgctc    840
gtgttcgagg ccatccgcaa ggccggggcc acgccgttca cggcgtggcg cgtcgccttc    900
ttcgtcccgg gcctgctgca gacgctgtcg gccgtcgccg tgctggcgtt cggccaggac    960
atgcccgacg gcaactaccg caagctgcac aggtccggcg acatgcacaa ggacagcttc   1020
ggcaacgtgc tccgccacgc cgtcaccaac taccgcgcct ggatcctggc gctcacctac   1080
ggatactgct tcggcgtgga gctcgccgtg gacaacatcg tcgcgcagta cttctacgac   1140
cgcttcggcg tcaagctcag caccgccggc ttcatcgccg ccagcttcgg gatggccaac   1200
atcgtctccc gccccggcgg cggcctcctg tcggactggc tctccagccg cttcggcatg   1260
cgcggcaggc tgtggggcct gtgggtggtg cagaccatcg gggcgtcct ctgcgtcgtg   1320
ctcggcgccg tcgactactc cttcgccgcg tccgtggccg tcatgatact cttctccatg   1380
ttcgtgcagg cggcctgcgg gctcaccttt ggcatcgtcc cgttcgtctc ccgaaggtcg   1440
ctggggctca tctccggcat gaccggcggc ggcggcaacg tgggcgccgt gctcacgcag   1500
ctcatcttct tccacggatc caagtacaag acggagacgg ggatcaagta catggggttc   1560
atgatcatcg cctgcacgtt gcccatcacg ctcatctact tcccgcagtg gggcggcatg   1620
ttcctggggc cgcggcccgg ggcgacggcg gaggactact acaaccggga gtggacagcg   1680
cacgagtgcg acaagggttt caacaccgcg agcgtacgct ttgcggagaa cagcgtgcgg   1740
gaagggggac gctcgggcag ccagtccaag cacactactg tgcccgtcga gtcctcgccg   1800
gccgacgtgt gaaacacaca caagcatacg gtactgcccg tataatcagc ggtccctccc   1860
gtgtcagcaa atcatatgta gtgttcctaa gtcgtgatga ctccgtacgt gtggtaattt   1920
ctgtgtgaag gaaaaaccgg gggtgaattt cagcgaggag tgacattata agcagggctc   1980
gtttgcataa aaaaaaaaaa aaaaaaaaaa aaaaaaaaaa aaaaa                   2025
```

```
<210> SEQ ID NO 92
<211> LENGTH: 520
<212> TYPE: PRT
<213> ORGANISM: Zea mays

<400> SEQUENCE: 92

Met Ala Glu Gly Glu Phe Lys Pro Ala Ala Met Gln Val Glu Ala Pro
1               5                   10                  15

Ala Glu Ala Ala Ala Ala Pro Ser Lys Pro Arg Phe Arg Met Pro Val
            20                  25                  30

Asp Ser Asp Asn Lys Ala Thr Glu Phe Trp Leu Phe Ser Phe Ala Arg
        35                  40                  45

Pro His Met Ser Ala Phe His Met Ser Trp Phe Ser Phe Phe Cys Cys
    50                  55                  60

Phe Leu Ser Thr Phe Ala Ala Pro Pro Leu Leu Pro Leu Ile Arg Asp
65                  70                  75                  80

Thr Leu Gly Leu Thr Ala Thr Asp Ile Gly Asn Ala Gly Ile Ala Ser
                85                  90                  95
```

-continued

```
Val Ser Gly Ala Val Phe Ala Arg Val Ala Met Gly Thr Ala Cys Asp
            100                 105                 110

Leu Val Gly Pro Arg Leu Ala Ser Ala Ala Ile Ile Leu Leu Thr Thr
        115                 120                 125

Pro Ala Val Tyr Tyr Ser Ala Val Ile Asp Ser Ala Ser Ser Tyr Leu
    130                 135                 140

Leu Val Arg Phe Phe Thr Gly Phe Ser Leu Ala Ser Phe Val Ser Thr
145                 150                 155                 160

Gln Phe Trp Met Ser Ser Met Phe Ser Pro Pro Lys Val Gly Leu Ala
                165                 170                 175

Asn Gly Val Ala Gly Gly Trp Gly Asn Leu Gly Gly Gly Ala Val Gln
            180                 185                 190

Leu Ile Met Pro Leu Val Phe Glu Ala Ile Arg Lys Ala Gly Ala Thr
        195                 200                 205

Pro Phe Thr Ala Trp Arg Val Ala Phe Phe Val Pro Gly Leu Leu Gln
    210                 215                 220

Thr Leu Ser Ala Val Ala Val Leu Ala Phe Gly Gln Asp Met Pro Asp
225                 230                 235                 240

Gly Asn Tyr Arg Lys Leu His Arg Ser Gly Asp Met His Lys Asp Ser
                245                 250                 255

Phe Gly Asn Val Leu Arg His Ala Val Thr Asn Tyr Arg Ala Trp Ile
            260                 265                 270

Leu Ala Leu Thr Tyr Gly Tyr Cys Phe Gly Val Glu Leu Ala Val Asp
        275                 280                 285

Asn Ile Val Ala Gln Tyr Phe Tyr Asp Arg Phe Gly Val Lys Leu Ser
    290                 295                 300

Thr Ala Gly Phe Ile Ala Ala Ser Phe Gly Met Ala Asn Ile Val Ser
305                 310                 315                 320

Arg Pro Gly Gly Gly Leu Leu Ser Asp Trp Leu Ser Ser Arg Phe Gly
                325                 330                 335

Met Arg Gly Arg Leu Trp Gly Leu Trp Val Val Gln Thr Ile Gly Gly
            340                 345                 350

Val Leu Cys Val Val Leu Gly Ala Val Asp Tyr Ser Phe Ala Ala Ser
        355                 360                 365

Val Ala Val Met Ile Leu Phe Ser Met Phe Val Gln Ala Ala Cys Gly
    370                 375                 380

Leu Thr Phe Gly Ile Val Pro Phe Val Ser Arg Arg Ser Leu Gly Leu
385                 390                 395                 400

Ile Ser Gly Met Thr Gly Gly Gly Gly Asn Val Gly Ala Val Leu Thr
                405                 410                 415

Gln Leu Ile Phe Phe His Gly Ser Lys Tyr Lys Thr Glu Thr Gly Ile
            420                 425                 430

Lys Tyr Met Gly Phe Met Ile Ile Ala Cys Thr Leu Pro Ile Thr Leu
        435                 440                 445

Ile Tyr Phe Pro Gln Trp Gly Gly Met Phe Leu Gly Pro Arg Pro Gly
    450                 455                 460

Ala Thr Ala Glu Asp Tyr Tyr Asn Arg Glu Trp Thr Ala His Glu Cys
465                 470                 475                 480

Asp Lys Gly Phe Asn Thr Ala Ser Val Arg Phe Ala Glu Asn Ser Val
                485                 490                 495

Arg Glu Gly Gly Arg Ser Gly Ser Gln Ser Lys His Thr Thr Val Pro
            500                 505                 510

Val Glu Ser Ser Pro Ala Asp Val
```

515 520

<210> SEQ ID NO 93
<211> LENGTH: 49597
<212> TYPE: DNA
<213> ORGANISM: vector

<400> SEQUENCE: 93
gtcttgctcg actctagagc tcgttcctcg aggcctcgag gcctcgagga acggtacctg 60
cggggaagct tacaataatg tgtgttgtta agtcttgttg cctgtcatcg tctgactgac 120
tttcgtcata aatcccggcc tccgtaaccc agctttgggc aagctcacgg atttgatccg 180
gcggaacggg aatatcgaga tgccgggctg aacgctgcag ttccagcttt ccctttcggg 240
acaggtactc cagctgattg attatctgct gaagggtctt ggttccacct cctggcacaa 300
tgcgaatgat tacttgagcg cgatcgggca tccaattttc tcccgtcagg tgcgtggtca 360
agtgctacaa ggcacctttc agtaacgagc gaccgtcgat ccgtcgccgg gatacggaca 420
aaatggagcg cagtagtcca tcgagggcgg cgaaagcctc gccaaaagca atacgttcat 480
ctcgcacagc ctccagatcc gatcgagggt cttcggcgta ggcagataga agcatggata 540
cattgcttga gagtattccg atggactgaa gtatggcttc catcttttct cgtgtgtctg 600
catctatttc gagaaagccc ccgatgcggc gcaccgcaac gcgaattgcc atactatccg 660
aaagtcccag caggcgcgct tgataggaaa aggtttcata ctcggccgat cgcagacggg 720
cactcacgac cttgaaccct tcaactttca gggatcgatg ctggttgatg gtagtctcac 780
tcgacgtggc tctggtgtgt tttgacatag cttcctccaa agaaagcgga aggtctggat 840
actccagcac gaaatgtgcc cgggtagacg gatggaagtc tagccctgct caatatgaaa 900
tcaacagtac atttacagtc aatactgaat atacttgcta catttgcaat tgtcttataa 960
cgaatgtgaa ataaaaatag tgtaacaacg cttttactca tcgataatca caaaaacatt 1020
tatacgaaca aaaatacaaa tgcactccgg tttcacagga taggcgggat cagaatatgc 1080 aactttgac gttttgttct ttcaaagggg gtgctggcaa aaccaccgca ctcatgggcc 1140
tttgcgctgc tttggcaaat gacggtaaac gagtggccct ctttgatgcc gacgaaaacc 1200
ggcctctgac gcgatggaga gaaaacgcct tacaaagcag tactgggatc ctcgctgtga 1260
agtctattcc gccgacgaaa tgccccttct tgaagcagcc tatgaaaatg ccgagctcga 1320
aggatttgat tatgcgttgg ccgatacgcg tggcggctcg agcgagctca acaacacaat 1380
catcgctagc tcaaacctgc ttctgatccc caccatgcta acgccgctcg acatcgatga 1440
ggcactatct acctaccgct acgtcatcga gctgctgttg agtgaaaatt tggcaattcc 1500
tacagctgtt ttgcgccaac gcgtcccggt cggccgattg acaacatcgc aacgcaggat 1560
gtcagagacg ctagagagcc ttccagttgt accgtctccc atgcatgaaa gagatgcatt 1620
tgccgcgatg aaagaacgcg gcatgttgca tcttacatta ctaaacacgg gaactgatcc 1680
gacgatgcgc ctcatagaga ggaatcttcg gattgcgatg gaggaagtcg tggtcatttc 1740
gaaactgatc agcaaaatct tggaggcttg aagatggcaa ttcgcaagcc cgcattgtcg 1800
gtcggcgaag cacggcggct tgctggtgct cgacccgaga tccaccatcc caacccgaca 1860
cttgttcccc agaagctgga cctccagcac ttgcctgaaa aagccgacga gaaagaccag 1920
caacgtgagc ctctcgtcgc cgatcacatt tacagtcccg atcgacaact taagctaact 1980
gtggatgccc ttagtccacc tccgtccccg aaaaagctcc aggtttttct ttcagcgcga 2040
ccgcccgcgc ctcaagtgtc gaaaacatat gacaacctcg ttcggcaata cagtccctcg 2100

-continued

```
aagtcgctac aaatgatttt aaggcgcgcg ttggacgatt tcgaaagcat gctggcagat   2160
ggatcatttc gcgtggcccc gaaaagttat ccgatccctt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg taggtttgag gccgctggcc gcgtcctcag tcaccttttg   2460
agccagataa ttaagagcca aatgcaattg gctcaggctg ccatcgtccc cccgtgcgaa   2520
acctgcacgt ccgcgtcaaa gaaataaccg gcacctcttg ctgtttttat cagttgaggg   2580
cttgacggat ccgcctcaag tttgcggcgc agccgcaaaa tgagaacatc tatactcctg   2640
tcgtaaacct cctcgtcgcg tactcgactg gcaatgagaa gttgctcgcg cgatagaacg   2700
tcgcggggtt tctctaaaaa cgcgaggaga agattgaact cacctgccgt aagtttcacc   2760
tcaccgccag cttcggacat caagcgacgt tgcctgagat taagtgtcca gtcagtaaaa   2820
caaaaagacc gtcggtcttt ggagcggaca acgttggggc gcacgcgcaa ggcaacccga   2880
atgcgtgcaa gaaactctct cgtactaaac ggcttagcga taaaatcact tgctcctagc   2940
tcgagtgcaa caactttatc cgtctcctca aggcggtcgc cactgataat tatgattgga   3000
atatcagact ttgccgccag atttcgaacg atctcaagcc catcttcacg acctaaattt   3060
agatcaacaa ccacgacatc gaccgtcgcg gaagagagta ctctagtgaa ctgggtgctg   3120
tcggctaccg cggtcacttt gaaggcgtgg atcgtaaggt attcgataat aagatgccgc   3180
atagcgacat cgtcatcgat aagaagaacg tgtttcaacg gctcaccttt caatctaaaa   3240
tctgaaccct tgttcacagc gcttgagaaa ttttcacgtg aaggatgtac aatcatctcc   3300
agctaaatgg gcagttcgtc agaattgcgg ctgaccgcgg atgacgaaaa tgcgaaccaa   3360
gtatttcaat tttatgacaa aagttctcaa tcgttgttac aagtgaaacg cttcgaggtt   3420
acagctacta ttgattaagg agatcgccta tggtctcgcc ccggcgtcgt gcgtccgccg   3480
cgagccagat ctcgcctact tcataaacgt cctcataggc acggaatgga atgatgacat   3540
cgatcgccgt agagagcatg tcaatcagtg tgcgatcttc caagctagca ccttgggcgc   3600
tacttttgac aagggaaaac agtttcttga atccttggat tggattcgcg ccgtgtattg   3660
ttgaaatcga tcccggatgt cccgagacga cttcactcag ataagcccat gctgcatcgt   3720
cgcgcatctc gccaagcaat atccggtccg gccgcatacg cagacttgct tggagcaagt   3780
gctcggcgct cacagcaccc agcccagcac cgttcttgga gtagagtagt ctaacatgat   3840
tatcgtgtgg aatgacgagt tcgagcgtat cttctatggt gattagcctt tcctgggggg   3900
ggatggcgct gatcaaggtc ttgctcattg ttgtcttgcc gcttccggta gggccacata   3960
gcaacatcgt cagtcggctg acgacgcatg cgtgcagaaa cgcttccaaa tccccgttgt   4020
caaaatgctg aaggatagct tcatcatcct gattttggcg tttccttcgt gtctgccact   4080
ggttccacct cgaagcatca taacgggagg agacttcttt aagaccagaa acacgcgagc   4140
ttggccgtcg aatggtcaag ctgacggtgc ccgagggaac ggtcggcggc agacagattt   4200
gtagtcgttc accaccagga agttcagtgg cgcagagggg gttacgtggt ccgacatcct   4260
gctttctcag cgcgcccgct aaaatagcga tatcttcaag atcatcataa gagacgggca   4320
aaggcatctt ggtaaaaatg ccggcttggc gcacaaatgc ctctccaggt cgattgatcg   4380
caatttcttc agtcttcggg tcatcgagcc attccaaaat cggcttcaga agaaagcgta   4440
gttgcggatc cacttccatt tacaatgtat cctatctcta agcggaaatt tgaattcatt   4500
```

-continued aagagcggcg gttcctcccc cgcgtggcgc cgccagtcag gcggagctgg taaacaccaa 4560
agaaatcgag gtcccgtgct acgaaaatgg aaacggtgtc accctgattc ttcttcaggg 4620
ttggcggtat gttgatggtt gccttaaggg ctgtctcagt tgtctgctca ccgttatttt 4680
gaaagctgtt gaagctcatc ccgccacccg agctgccggc gtaggtgcta gctgcctgga 4740
aggcgccttg aacaacactc aagagcatag ctccgctaaa acgctgccag aagtggctgt 4800
cgaccgagcc cggcaatcct gagcgaccga gttcgtccgc gcttggcgat gttaacgaga 4860
tcatcgcatg gtcaggtgtc tcggcgcgat cccacaacac aaaaacgcgc ccatctccct 4920
gttgcaagcc acgctgtatt tcgccaacaa cggtggtgcc acgatcaaga agcacgatat 4980
tgttcgttgt tccacgaata tcctgaggca agacacactt tacatagcct gccaaatttg 5040
tgtcgattgc ggtttgcaag atgcacggaa ttattgtccc ttgcgttacc ataaaatcgg 5100
ggtgcggcaa gagcgtggcg ctgctgggct gcagctcggt gggtttcata cgtatcgaca 5160
aatcgttctc gccggacact tcgccattcg gcaaggagtt gtcgtcacgc ttgccttctt 5220
gtcttcggcc cgtgtcgccc tgaatggcgc gtttgctgac cccttgatcg ccgctgctat 5280
atgcaaaaat cggtgtttct tccggccgtg gctcatgccg ctccggttcg cccctcggcg 5340
gtagaggagc agcaggctga acagcctctt gaaccgctgg aggatccggc ggcacctcaa 5400
tcggagctgg atgaaatggc ttggtgtttg ttgcgatcaa agttgacggc gatgcgttct 5460
cattcacctt cttttggcgc ccacctagcc aaatgaggct taatgataac gcgagaacga 5520
cacctccgac gatcaatttc tgagaccccg aaagacgccg gcgatgtttg tcggagacca 5580
gggatccaga tgcatcaacc tcatgtgccg cttgctgact atcgttattc atcccttcgc 5640
ccccttcagg acgcgtttca catcgggcct caccgtgccc gtttgcggcc tttggccaac 5700
gggatcgtaa gcggtgttcc agatacatag tactgtgtgg ccatccctca gacgccaacc 5760
tcgggaaacc gaagaaatct cgacatcgct ccctttaact gaatagttgg caacagcttc 5820
cttgccatca ggattgatgg tgtagatgga gggtatgcgt acattgcccg gaaagtggaa 5880
taccgtcgta aatccattgt cgaagacttc gagtggcaac agcgaacgat cgccttgggc 5940
gacgtagtgc caattactgt ccgccgcacc aagggctgtg acaggctgat ccaataaatt 6000
ctcagctttc cgttgatatt gtgcttccgc gtgtagtctg tccacaacag ccttctgttg 6060
tgcctccctt cgccgagccg ccgcatcgtc ggcggggtag gcgaattgga cgctgtaata 6120
gagatcgggc tgctctttat cgaggtggga cagagtcttg gaacttatac tgaaaacata 6180
acggcgcatc ccggagtcgc ttgcggttag cacgattact ggctgaggcg tgaggacctg 6240
gcttgccttg aaaaatagat aatttccccg cggtagggct gctagatctt tgctatttga 6300
aacggcaacc gctgtcaccg tttcgttcgt ggcgaatgtt acgaccaaag tagctccaac 6360
cgccgtcgag aggcgcacca cttgatcggg attgtaagcc aaataacgca tgcgcggatc 6420
tagcttgccc gccattggag tgtcttcagc ctccgcacca gtcgcagcgg caaataaaca 6480
tgctaaaatg aaaagtgctt ttctgatcat ggttcgctgt ggcctacgtt tgaaacggta 6540
tcttccgatg tctgatagga ggtgacaacc agacctgccg ggttggttag tctcaatctg 6600
ccgggcaagc tggtcacctt ttcgtagcga actgtcgcgg tccacgtact caccacaggc 6660
attttgccgt caacgacgag ggtcctttta tagcgaattt gctgcgtgct tggagttaca 6720
tcatttgaag cgatgtgctc gacctccacc ctgccgcgtt tgccaagaat gacttgaggc 6780
gaactgggat tgggatagtt gaagaattgc tggtaatcct ggcgcactgt tggggcactg 6840
aagttcgata ccaggtcgta ggcgtactga gcggtgtcgg catcataact ctcgcgcagg 6900

-continued

```
cgaacgtact cccacaatga ggcgttaacg acggcctcct cttgagttgc aggcaatcgc   6960
gagacagaca cctcgctgtc aacggtgccg tccggccgta tccatagata tacgggcaca   7020
agcctgctca acggcaccat tgtggctata gcgaacgctt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgccccacat tcagcgggaa gatcgggcct ttgcagctcg ctaatgtgtc   7320
gtttgtctgg cagccgctca aagcgacaac taggcacagc aggcaatact tcatagaatt   7380
ctccattgag gcgaattttt gcgcgaccta gcctcgctca acctgagcga agcgacggta   7440
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact ttcgtgagaa ttccaacggc   7800
gtcgtaaact ccgaaggcag accagagcgt gccgtaaagg acccactgtg ccccttggaa   7860
agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccggcctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgatttttct ggttgagcga agtcagtagt ccagtaacgc cgtaggccga   8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
gagttgcctt cttgtgcctc gcgtagtcga gttgcaaagc gcaccgtgtt ggcacgcccc   9180
gaaagcacgg cgacatattc acgcatatcc cgcagatcaa attcgcagat gacgcttcca   9240
ctttctcgtt taagaagaaa cttacggctg ccgaccgtca tgtcttcacg gatcgcctga   9300
```

-continued

```
aattcctttt cggtacattt cagtccatcg acataagccg atcgatctgc ggttggtgat    9360
ggatagaaaa tcttcgtcat acattgcgca accaagctgg ctcctagcgg cgattccaga    9420
acatgctctg gttgctgcgt tgccagtatt agcatcccgt tgttttttcg aacggtcagg    9480
aggaatttgt cgacgacagt cgaaaattta gggtttaaca aataggcgcg aaactcatcg    9540
cagctcatca caaaacggcg gccgtcgatc atggctccaa tccgatgcag gagatatgct    9600
gcagcgggag cgcatacttc ctcgtattcg agaagatgcg tcatgtcgaa gccggtaatc    9660
gacggatcta actttacttc gtcaacttcg ccgtcaaatg cccagccaag cgcatggccc    9720
cggcaccagc gttggagccg cgctcctgcg ccttcggcgg gcccatgcaa caaaaattca    9780
cgtaaccccg cgattgaacg catttgtgga tcaaacgaga gctgacgatg gataccacgg    9840
accagacggc ggttctcttc cggagaaatc ccaccccgac catcactctc gatgagagcc    9900
acgatccatt cgcgcagaaa atcgtgtgag gctgctgtgt tttctaggcc acgcaacggc    9960
gccaacccgc tgggtgtgcc tctgtgaagt gccaaatatg ttcctcctgt ggcgcgaacc   10020
agcaattcgc caccccggtc cttgtcaaag aacacgaccg tacctgcacg gtcgaccatg   10080
ctctgttcga gcatggctag aacaaacatc atgagcgtcg tcttacccct cccgataggc   10140
ccgaatattg ccgtcatgcc aacatcgtgc tcatgcggga tatagtcgaa aggcgttccg   10200
ccattggtac gaaatcgggc aatcgcgttg ccccagtggc ctgagctggc gccctctgga   10260
aagttttcga aagagacaaa ccctgcgaaa ttgcgtgaag tgattgcgcc agggcgtgtg   10320
cgccacttaa aattccccgg caattgggac caataggccg cttccatacc aataccttct   10380
tggacaacca cggcacctgc atccgccatt cgtgtccgag cccgcgcgcc cctgtcccca   10440
agactattga gatcgtctgc atagacgcaa aggctcaaat gatgtgagcc cataacgaat   10500
tcgttgctcg caagtgcgtc ctcagcctcg gataatttgc cgatttgagt cacggcttta   10560
tcgccggaac tcagcatctg gctcgatttg aggctaagtt tcgcgtgcgc ttgcgggcga   10620
gtcaggaacg aaaaactctg cgtgagaaca agtggaaaat cgagggatag cagcgcgttg   10680
agcatgcccg gccgtgtttt tgcagggtat tcgcgaaacg aatagatgga tccaacgtaa   10740
ctgtcttttg gcgttctgat ctcgagtcct cgcttgccgc aaatgactct gtcggtataa   10800
atcgaagcgc cgagtgagcc gctgacgacc ggaaccggtg tgaaccgacc agtcatgatc   10860
aaccgtagcg cttcgccaat ttcggtgaag agcacaccct gcttctcgcg gatgccaaga   10920
cgatgcaggc catacgcttt aagagagcca gcgacaacat gccaaagatc ttccatgttc   10980
ctgatctggc ccgtgagatc gttttccctt tttccgctta gcttggtgaa cctcctcttt   11040
accttcccta aagccgcctg tgggtagaca atcaacgtaa ggaagtgttc attgcggagg   11100
agttggccgg agagcacgcg ctgttcaaaa gcttcgttca ggctagcggc gaaaacacta   11160
cggaagtgtc gcggcgccga tgatggcacg tcggcatgac gtacgaggtg agcatatatt   11220
gacacatgat catcagcgat attgcgcaac agcgtgttga acgcacgaca acgcgcattg   11280
cgcatttcag tttcctcaag ctcgaatgca acgccatcaa ttctcgcaat ggtcatgatc   11340
gatccgtctt caagaaggac gatatggtcg ctgaggtggc caatataagg gagatagatc   11400
tcaccggatc tttcggtcgt tccactcgcg ccgagcatca caccattcct ctccctcgtg   11460
ggggaaccct aattggattt gggctaacag tagcgccccc ccaaactgca ctatcaatgc   11520
ttcttcccgc ggtccgcaaa aatagcagga cgacgctcgc cgcattgtag tctcgctcca   11580
cgatgagccg ggctgcaaac cataacggca cgagaacgac ttcgtagagc gggttctgaa   11640
cgataacgat gacaaagccg gcgaacatca tgaataaccc tgccaatgtc agtggcaccc   11700
```

-continued caagaaacaa tgcgggccgt gtggctgcga ggtaaagggt cgattcttcc aaacgatcag 11760
ccatcaacta ccgccagtga gcgtttggcc gaggaagctc gccccaaaca tgataacaat 11820
gccgccgacg acgccggcaa ccagcccaag cgaagcccgc ccgaacatcc aggagatccc 11880
gatagcgaca atgccgagaa cagcgagtga ctggccgaac ggaccaagga taaacgtgca 11940
tatattgtta accattgtgg cggggtcagt gccgccaccc gcagattgcg ctgcggcggg 12000
tccggatgag gaaatgctcc atgcaattgc accgcacaag cttggggcgc agctcgatat 12060
cacgcgcatc atcgcattcg agagcgagag gcgatttaga tgtaaacggt atctctcaaa 12120
gcatcgcatc aatgcgcacc tccttagtat aagtcgaata agacttgatt gtcgtctgcg 12180
gatttgccgt tgtcctggtg tggcggtggc ggagcgatta aaccgccagc gccatcctcc 12240
tgcgagcggc gctgatatga cccccaaaca tcccacgtct cttcggattt tagcgcctcg 12300
tgatcgtctt ttggaggctc gattaacgcg ggcaccagcg attgagcagc tgtttcaact 12360
tttcgcacgt agccgtttgc aaaaccgccg atgaaattac cggtgttgta agcggagatc 12420
gcccgacgaa gcgcaaattg cttctcgtca atcgtttcgc cgcctgcata acgacttttc 12480
agcatgtttg cagcggcaga taatgatgtg cacgcctgga gcgcaccgtc aggtgtcaga 12540
ccgagcatag aaaaatttcg agagtttatt tgcatgaggc caacatccag cgaatgccgt 12600
gcatcgagac ggtgcctgac gacttgggtt gcttggctgt gatcttgcca gtgaagcgtt 12660
tcgccggtcg tgttgtcatg aatcgctaaa ggatcaaagc gactctccac cttagctatc 12720
gccgcaagcg tagatgtcgc aactgatggg gcacacttgc gagcaacatg gtcaaactca 12780
gcagatgaga gtggcgtggc aaggctcgac gaacagaagg agaccatcaa ggcaagagaa 12840
agcgaccccg atctcttaag cataccttat ctccttagct cgcaactaac accgcctctc 12900
ccgttggaag aagtgcgttg ttttatgttg aagattatcg ggagggtcgg ttactcgaaa 12960
attttcaatt gcttctttat gatttcaatt gaagcgagaa acctcgcccg gcgtcttgga 13020
acgcaacatg gaccgagaac cgcgcatcca tgactaagca accggatcga cctattcagg 13080
ccgcagttgg tcaggtcagg ctcagaacga aaatgctcgg cgaggttacg ctgtctgtaa 13140
acccattcga tgaacgggaa gcttccttcc gattgctctt ggcaggaata ttggcccatg 13200
cctgcttgcg ctttgcaaat gctcttatcg cgttggtatc atatgccttg tccgccagca 13260
gaaacgcact ctaagcgatt atttgtaaaa atgtttcggt catgcggcgg tcatgggctt 13320
gacccgctgt cagcgcaaga cggatcggtc aaccgtcggc atcgacaaca gcgtgaatct 13380
tggtggtcaa accgccacgg gaacgtccca tacagccatc gtcttgatcc cgctgtttcc 13440
cgtcgccgca tgttggtgga cgcggacaca ggaactgtca atcatgacga cattctatcg 13500
aaagccttgg aaatcacact cagaatatga tcccagacgt ctgcctcacg ccatcgtaca 13560
aagcgattgt agcaggttgt acaggaaccg tatcgatcag gaacgtctgc ccagggcggg 13620
cccgtccgga agcgccacaa gatgacattg atcacccgcg tcaacgcgcg gcacgcgacg 13680
cggcttattt gggaacaaag gactgaacaa cagtccattc gaaatcggtg acatcaaagc 13740
ggggacgggt tatcagtggc ctccaagtca agcctcaatg aatcaaaatc agaccgattt 13800
gcaaacctga tttatgagtg tgcggcctaa atgatgaaat cgtccttcta gatcgcctcc 13860
gtggtgtagc aacacctcgc agtatcgccg tgctgacctt ggccagggaa ttgactggca 13920
agggtgcttt cacatgaccg ctcttttggc cgcgatagat gatttcgttg ctgctttggg 13980
cacgtagaag gagagaagtc atatcggaga aattcctcct ggcgcgagag cctgctctat 14040
cgcgacggca tcccactgtc gggaacagac cggatcattc acgaggcgaa agtcgtcaac 14100

-continued

```
acatgcgtta taggcatctt cccttgaagg atgatcttgt tgctgccaat ctggaggtgc  14160
ggcagccgca ggcagatgcg atctcagcgc aacttgcggc aaaacatctc actcacctga  14220
aaaccactag cgagtctcgc gatcagacga aggcctttta cttaacgaca caatatccga  14280
tgtctgcatc acaggcgtcg ctatcccagt caatactaaa gcggtgcagg aactaaagat  14340
tactgatgac ttaggcgtgc cacgaggcct gagacgacgc gcgtagacag tttttgaaa  14400
tcattatcaa agtgatggcc tccgctgaag cctatcacct ctgcgccggt ctgtcggaga  14460
gatgggcaag cattattacg gtcttcgcgc ccgtacatgc attggacgat tgcagggtca  14520
atggatctga gatcatccag aggattgccg cccttacctt ccgtttcgag ttggagccag  14580
cccctaaatg agacgacata gtcgacttga tgtgacaatg ccaagagaga gatttgctta  14640
acccgatttt tttgctcaag cgtaagccta ttgaagcttg ccggcatgac gtccgcgccg  14700
aaagaatatc ctacaagtaa aacattctgc acaccgaaat gcttggtgta gacatcgatt  14760
atgtgaccaa gatccttagc agtttcgctt ggggaccgct ccgaccagaa ataccgaagt  14820
gaactgacgc caatgacagg aatcccttcc gtctgcagat aggtaccatc gatagatctg  14880
ctgcctcgcg cgtttcggtg atgacggtga aaacctctga cacatgcagc tcccggagac  14940
ggtcacagct tgtctgtaag cggatgccgg gagcagacaa gcccgtcagg gcgcgtcagc  15000
gggtgttggc gggtgtcggg gcgcagccat gacccagtca cgtagcgata gcggagtgta  15060
tactggctta actatgcggc atcagagcag attgtactga gagtgcacca tatgcggtgt  15120
gaaataccgc acagatgcgt aaggagaaaa taccgcatca ggcgctcttc cgcttcctcg  15180
ctcactgact cgctgcgctc ggtcgttcgg ctgcggcgag cggtatcagc tcactcaaag  15240
gcggtaatac ggttatccac agaatcaggg gataacgcag gaaagaacat gtgagcaaaa  15300
ggccagcaaa aggccaggaa ccgtaaaaag gccgcgttgc tggcgttttt ccataggctc  15360
cgcccccctg acgagcatca caaaaatcga cgctcaagtc agaggtggcg aaacccgaca  15420
ggactataaa gataccaggc gtttccccct ggaagctccc tcgtgcgctc tcctgttccg  15480
accctgccgc ttaccggata cctgtccgcc tttctccctt cgggaagcgt ggcgctttct  15540
catagctcac gctgtaggta tctcagttcg gtgtaggtcg ttcgctccaa gctgggctgt  15600
gtgcacgaac cccccgttca gcccgaccgc tgcgccttat ccggtaacta tcgtcttgag  15660
tccaacccgg taagacacga cttatcgcca ctggcagcag ccactggtaa caggattagc  15720
agagcgaggt atgtaggcgg tgctacagag ttcttgaagt ggtggcctaa ctacggctac  15780
actagaagga cagtatttgg tatctgcgct ctgctgaagc cagttacctt cggaaaaaga  15840
gttggtagct cttgatccgg caaacaaacc accgctggta gcggtggttt ttttgtttgc  15900
aagcagcaga ttacgcgcag aaaaaaagga tctcaagaag atcctttgat cttttctacg  15960
gggtctgacg ctcagtggaa cgaaaactca cgttaaggga ttttggtcat gagattatca  16020
aaaaggatct tcacctagat ccttttaaat taaaaatgaa gttttaaatc aatctaaagt  16080
atatatgagt aaacttggtc tgacagttac caatgcttaa tcagtgaggc acctatctca  16140
gcgatctgtc tatttcgttc atccatagtt gcctgactcc ccgtcgtgta gataactacg  16200
atacgggagg gcttaccatc tggccccagt gctgcaatga taccgcgaga cccacgctca  16260
ccggctccag atttatcagc aataaaccag ccagccggaa gggccgagcg cagaagtggt  16320
cctgcaactt tatccgcctc catccagtct attaattgtt gccgggaagc tagagtaagt  16380
agttcgccag ttaatagttt gcgcaacgtt gttgccattg ctgcaggggg gggggggggg  16440
gggttccatt gttcattcca cggacaaaaa cagagaaagg aaacgacaga ggccaaaaag  16500
```

-continued

```
ctcgctttca gcacctgtcg tttcctttct tttcagaggg tattttaaat aaaaacatta  16560
agttatgacg aagaagaacg gaaacgcctt aaaccggaaa attttcataa atagcgaaaa  16620
cccgcgaggt ccctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc cccccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
aggccctttc gtcttcaaga attggtcgac gatcttgctg cgttcggata ttttcgtgga  17640
gttcccgcca cagacccgga ttgaaggcga gatccagcaa ctcgcgccag atcatcctgt  17700
gacggaactt tggcgcgtga tgactggcca ggacgtcggc cgaaagagcg acaagcagat  17760
cacgcttttc gacagcgtcg gatttgcgat cgaggatttt tcggcgctgc gctacgtccg  17820
cgaccgcgtt gagggatcaa gccacagcag cccactcgac cttctagccg acccagacga  17880
gccaagggat ctttttggaa tgctgctccg tcgtcaggct ttccgacgtt tgggtggttg  17940
aacagaagtc attatcgtac ggaatgccaa gcactcccga ggggaaccct gtggttggca  18000
tgcacataca aatggacgaa cggataaacc ttttcacgcc cttttaaata tccgttattc  18060
taataaacgc tcttttctct taggtttacc cgccaatata tcctgtcaaa cactgatagt  18120
ttaaactgaa ggcgggaaac gacaatctga tcatgagcgg agaattaagg gagtcacgtt  18180
atgacccccg ccgatgacgc gggacaagcc gttttacgtt tggaactgac agaaccgcaa  18240
cgttgaagga gccactcagc aagctggtac gattgtaata cgactcacta tagggcgaat  18300
tgagcgctgt ttaaacgctc ttcaactgga agagcggtta cccggaccga agcttgcatg  18360
cctgcagtgc agcgtgaccc ggtcgtgccc ctctctagag ataatgagca ttgcatgtct  18420
aagttataaa aaattaccac atattttttt tgtcacactt gtttgaagtg cagtttatct  18480
atctttatac atatatttaa actttactct acgaataata taatctatag tactacaata  18540
atatcagtgt tttagagaat catataaatg aacagttaga catggtctaa aggacaattg  18600
agtattttga caacaggact ctacagtttt atctttttag tgtgcatgtg ttctcctttt  18660
tttttgcaaa tagcttcacc tatataatac ttcatccatt ttattagtac atccatttag  18720
ggtttagggt taatggtttt tatagactaa ttttttttagt acatctattt tattctattt  18780
tagcctctaa attaagaaaa ctaaaactct attttagttt ttttatttaa taatttagat  18840
ataaaataga ataaaataaa gtgactaaaa attaaacaaa taccctttaa gaaattaaaa  18900
```

-continued

```
aaactaagga aacatttttc ttgtttcgag tagataatgc cagcctgtta aacgccgtcg  18960
acgagtctaa cggacaccaa ccagcgaacc agcagcgtcg cgtcgggcca agcgaagcag  19020
acggcacggc atctctgtcg ctgcctctgg acccctctcg agagttccgc tccaccgttg  19080
gacttgctcc gctgtcggca tccagaaatt gcgtggcgga gcggcagacg tgagccggca  19140
cggcaggcgg cctcctcctc ctctcacggc acggcagcta cgggggattc ctttcccacc  19200
gctccttcgc tttcccttcc tcgcccgccg taataaatag acacccccctc cacaccctct  19260
ttccccaacc tcgtgttgtt cggagcgcac acacacacaa ccagatctcc cccaaatcca  19320
cccgtcggca cctccgcttc aaggtacgcc gctcgtcctc cccccccccc cctctctacc  19380
ttctctagat cggcgttccg gtccatggtt agggcccggt agttctactt ctgttcatgt  19440
ttgtgttaga tccgtgtttg tgttagatcc gtgctgctag cgttcgtaca cggatgcgac  19500
ctgtacgtca gacacgttct gattgctaac ttgccagtgt ttctctttgg ggaatcctgg  19560
gatggctcta gccgttccgc agacgggatc gatttcatga ttttttttgt ttcgttgcat  19620
agggtttggt ttgccctttt cctttatttc aatatatgcc gtgcacttgt ttgtcgggtc  19680
atcttttcat gctttttttt gtcttggttg tgatgatgtg gtctggttgg gcggtcgttc  19740
tagatcggag tagaattctg tttcaaacta cctggtggat ttattaattt tggatctgta  19800
tgtgtgtgcc atacatattc atagttacga attgaagatg atggatggaa atatcgatct  19860
aggataggta tacatgttga tgcgggtttt actgatgcat atacagagat gctttttgtt  19920
cgcttggttg tgatgatgtg gtgtggttgg gcggtcgttc attcgttcta gatcggagta  19980
gaatactgtt tcaaactacc tggtgtattt attaattttg gaactgtatg tgtgtgtcat  20040
acatcttcat agttacgagt ttaagatgga tggaaatatc gatctaggat aggtatacat  20100
gttgatgtgg gttttactga tgcatataca tgatggcata tgcagcatct attcatatgc  20160
tctaaccttg agtacctatc tattataata aacaagtatg ttttataatt attttgatct  20220
tgatatactt ggatgatggc atatgcagca gctatatgtg gattttttta gccctgcctt  20280
catacgctat ttatttgctt ggtactgttt cttttgtcga tgctcaccct gttgtttggt  20340
gttacttctg caggtcgact ctagaggatc tacaagtttg tacaaaaaag caggctccgc  20400
ggccgccccc ttcaccatgg ctcggcagca aagcgtgcag gccttgtgtg tgctggcggc  20460
gcttctcttc gccgcctccc tgccgtcgcc ggccgccgcg ggggtgcacc tctcctcgct  20520
gcccaaagcg ctcgacgtca ccacctccgc caaacccggc caagtcctgc acgccggcgt  20580
ggactcgctg acggtgacgt ggagcctgaa cgccacggag ccggccggcg ccgacgccgg  20640
gtacaagggc gtgaaggtga agctgtgcta cgcgccggcg agccagaagg accgcgggtg  20700
gcgcaagtcc gaggacgaca tcagcaagga caaggcgtgc cagttcaagg tcaccgagca  20760
ggcgtacgcg gcggcggcgc ccggcagctt ccagtacgcc gtcgcccgcg acgtcccctc  20820
gggctcctac tacctgcgcg ccttcgccac ggacgcgtcg ggcgccgagg tggcctacgg  20880
ccagacggcg cccaccgccg ccttcgacgt cgccggcatc accggcatcc acgcctctct  20940
caagatcgcc gccggcgtct tctcggcctt ctccgtcgtc gcgctcgcct tcttcttcgt  21000
catcgagacc cgcaagaaga acaagtagaa gggtgggcgc gccgacccag ctttcttgta  21060
caaagtggtg ttaacctaga cttgtccatc ttctggattg gccaacttaa ttaatgtatg  21120
aaataaaagg atgcacacat agtgacatgc taatcactat aatgtgggca tcaaagttgt  21180
gtgttatgtg taattactag ttatctgaat aaaagagaaa gagatcatcc atatttctta  21240
tcctaaatga atgtcacgtg tctttataat tctttgatga accagatgca tttcattaac  21300
```

caaatccata tacatataaa tattaatcat atataattaa tatcaattgg gttagcaaaa 21360
caaatctagt ctaggtgtgt tttgcgaatt gcggccgcca ccgcggtgga gctcgaattc 21420
cggtccgggt cacctttgtc caccaagatg gaactgcggc cgctcattaa ttaagtcagg 21480
cgcgcctcta gttgaagaca cgttcatgtc ttcatcgtaa gaagacactc agtagtcttc 21540
ggccagaatg gccatctgga ttcagcaggc ctagaaggcc atttaaatcc tgaggatctg 21600
gtcttcctaa ggacccgggc ggtccgatta aactttaatt cggaccgaag cttgcatgcc 21660
tgcagtgcag cgtgacccgg tcgtgcccct ctctagagat aatgagcatt gcatgtctaa 21720
gttataaaaa attaccacat attttttttg tcacacttgt ttgaagtgca gtttatctat 21780
ctttatacat atatttaaac tttactctac gaataatata atctatagta ctacaataat 21840
atcagtgttt tagagaatca tataaatgaa cagttagaca tggtctaaag gacaattgag 21900
tattttgaca acaggactct acagttttat ctttttagtg tgcatgtgtt ctcctttttt 21960
tttgcaaata gcttcaccta tataatactt catccatttt attagtacat ccatttaggg 22020
tttagggtta atggttttta tagactaatt tttttagtac atctatttta ttctatttta 22080
gcctctaaat taagaaaact aaaactctat tttagttttt ttatttaata atttagatat 22140
aaaatagaat aaaataaagt gactaaaaat taaacaaata ccctttaaga aattaaaaaa 22200
actaaggaaa catttttctt gtttcgagta gataatgcca gcctgttaaa cgccgtcgac 22260
gagtctaacg gacaccaacc agcgaaccag cagcgtcgcg tcgggccaag cgaagcagac 22320
ggcacggcat ctctgtcgct gcctctggac ccctctcgag agttccgctc caccgttgga 22380
cttgctccgc tgtcggcatc cagaaattgc gtggcggagc ggcagacgtg agccggcacg 22440
gcaggcggcc tcctcctcct ctcacggcac cggcagctac gggggattcc tttcccaccg 22500
ctccttcgct ttcccttcct cgcccgccgt aataaataga caccccctcc acaccctctt 22560
tccccaacct cgtgttgttc ggagcgcaca cacacacaac cagatctccc ccaaatccac 22620
ccgtcggcac ctccgcttca aggtacgccg ctcgtcctcc cccccccccc tctctacctt 22680
ctctagatcg gcgttccggt ccatgcatgg ttagggcccg gtagttctac ttctgttcat 22740
gtttgtgtta gatccgtgtt tgtgttagat ccgtgctgct agcgttcgta cacggatgcg 22800
acctgtacgt cagacacgtt ctgattgcta acttgccagt gtttctcttt ggggaatcct 22860
gggatggctc tagccgttcc gcagacggga tcgatttcat gatttttttt gtttcgttgc 22920
atagggtttg gtttgccctt ttcctttatt tcaatatatg ccgtgcactt gtttgtcggg 22980
tcatcttttc atgctttttt ttgtcttggt tgtgatgatg tggtctggtt gggcggtcgt 23040
tctagatcgg agtagaattc tgtttcaaac tacctggtgg atttattaat tttggatctg 23100
tatgtgtgtg ccatacatat tcatagttac gaattgaaga tgatggatgg aaatatcgat 23160
ctaggatagg tatacatgtt gatgcgggtt ttactgatgc atatacagag atgctttttg 23220
ttcgcttggt tgtgatgatg tggtgtggtt gggcggtcgt tcattcgttc tagatcggag 23280
tagaatactg tttcaaacta cctggtgtat ttattaattt tggaactgta tgtgtgtgtc 23340
atacatcttc atagttacga gtttaagatg gatggaaata tcgatctagg ataggtatac 23400
atgttgatgt gggttttact gatgcatata catgatggca tatgcagcat ctattcatat 23460
gctctaacct tgagtaccta tctattataa taaacaagta tgttttataa ttattttgat 23520
cttgatatac ttggatgatg gcatatgcag cagctatatg tggatttttt tagccctgcc 23580
ttcatacgct atttatttgc ttggtactgt ttcttttgtc gatgctcacc ctgttgtttg 23640
gtgttacttc tgcaggtcga ctttaactta gcctaggatc cacacgacac catgtccccc 23700

```
gagcgccgcc ccgtcgagat ccgcccggcc accgccgccg acatggccgc cgtgtgcgac    23760

atcgtgaacc actacatcga gacctccacc gtgaacttcc gcaccgagcc gcagaccccg    23820

caggagtgga tcgacgacct ggagcgcctc caggaccgct acccgtggct cgtggccgag    23880

gtggagggcg tggtggccgg catcgcctac gccggcccgt ggaaggcccg caacgcctac    23940

gactggaccg tggagtccac cgtgtacgtg tcccaccgcc accagcgcct cggcctcggc    24000

tccaccctct acacccacct cctcaagagc atggaggccc agggcttcaa gtccgtggtg    24060

gccgtgatcg gcctcccgaa cgacccgtcc gtgcgcctcc acgaggccct cggctacacc    24120

gcccgcggca ccctccgcgc cgccggctac aagcacggcg gctggcacga cgtcggcttc    24180

tggcagcgcg acttcgagct gccggccccg ccgcgcccgg tgcgcccggt gacgcagatc    24240

tgagtcgaaa cctagacttg tccatcttct ggattggcca acttaattaa tgtatgaaat    24300

aaaaggatgc acacatagtg acatgctaat cactataatg tgggcatcaa agttgtgtgt    24360

tatgtgtaat tactagttat ctgaataaaa gagaaagaga tcatccatat ttcttatcct    24420

aaatgaatgt cacgtgtctt tataattctt tgatgaacca gatgcatttc attaaccaaa    24480

tccatataca tataaatatt aatcatatat aattaatatc aattgggtta gcaaaacaaa    24540

tctagtctag gtgtgttttg cgaattgcgg ccgccaccgc ggtggagctc gaattcattc    24600

cgattaatcg tggcctcttg ctcttcagga tgaagagcta tgtttaaacg tgcaagcgct    24660

actagacaat tcagtacatt aaaaacgtcc gcaatgtgtt attaagttgt ctaagcgtca    24720

atttgtttac accacaatat atcctgccac cagccagcca acagctcccc gaccggcagc    24780

tcggcacaaa atcaccactc gatacaggca gcccatcagt ccgggacggc gtcagcggga    24840

gagccgttgt aaggcggcag actttgctca tgttaccgat gctattcgga agaacggcaa    24900

ctaagctgcc gggtttgaaa cacgatgat ctcgcggagg gtagcatgtt gattgtaacg    24960

atgacagagc gttgctgcct gtgatcaaat atcatctccc tcgcagagat ccgaattatc    25020

agccttctta ttcatttctc gcttaaccgt gacaggctgt cgatcttgag aactatgccg    25080

acataatagg aaatcgctgg ataaagccgc tgaggaagct gagtggcgct atttctttag    25140

aagtgaacgt tgacgatcgt cgaccgtacc ccgatgaatt aattcggacg tacgttctga    25200

acacagctgg atacttactt gggcgattgt catacatgac atcaacaatg tacccgtttg    25260

tgtaaccgtc tcttggaggt tcgtatgaca ctagtggttc ccctcagctt gcgactagat    25320

gttgaggcct aacattttat tagagagcag gctagttgct tagatacatg atcttcaggc    25380

cgttatctgt cagggcaagc gaaaattggc catttatgac gaccaatgcc ccgcagaagc    25440

tcccatcttt gccgccatag acgccgcgcc ccccttttgg ggtgtagaac atccttttgc    25500

cagatgtgga aaagaagttc gttgtcccat tgttggcaat gacgtagtag ccggcgaaag    25560

tgcgagaccc atttgcgcta tatataagcc tacgatttcc gttgcgacta ttgtcgtaat    25620

tggatgaact attatcgtag ttgctctcag agttgtcgta atttgatgga ctattgtcgt    25680

aattgcttat ggagttgtcg tagttgcttg gagaaatgtc gtagttggat ggggagtagt    25740

catagggaag acgagcttca tccactaaaa caattggcag gtcagcaagt gcctgccccg    25800

atgccatcgc aagtacgagg cttagaacca ccttcaacag atcgcgcata gtcttcccca    25860

gctctctaac gcttgagtta agccgcgccg cgaagcggcg tcggcttgaa cgaattgtta    25920

gacattattt gccgactacc ttggtgatct cgcctttcac gtagtgaaca aattcttcca    25980

actgatctgc gcgcgaggcc aagcgatctt cttgtccaag ataagcctgc ctagcttcaa    26040

gtatgacggg ctgatactgg gccggcaggc gctccattgc ccagtcggca gcgacatcct    26100
```

tcggcgcgat tttgccggtt actgcgctgt accaaatgcg ggacaacgta agcactacat 26160
ttcgctcatc gccagcccag tcgggcggcg agttccatag cgttaaggtt tcatttagcg 26220
cctcaaatag atcctgttca ggaaccggat caaagagttc ctccgccgct ggacctacca 26280
aggcaacgct atgttctctt gcttttgtca gcaagatagc cagatcaatg tcgatcgtgg 26340
ctggctcgaa gatacctgca agaatgtcat tgcgctgcca ttctccaaat tgcagttcgc 26400
gcttagctgg ataacgccac ggaatgatgt cgtcgtgcac aacaatggtg acttctacag 26460
cgcggagaat ctcgctctct ccaggggaag ccgaagtttc caaaaggtcg ttgatcaaag 26520
ctcgccgcgt tgtttcatca agccttacag tcaccgtaac cagcaaatca atatcactgt 26580
gtggcttcag gccgccatcc actgcggagc cgtacaaatg tacggccagc aacgtcggtt 26640
cgagatggcg ctcgatgacg ccaactacct ctgatagttg agtcgatact tcggcgatca 26700
ccgcttccct catgatgttt aactcctgaa ttaagccgcg ccgcgaagcg gtgtcggctt 26760
gaatgaattg ttaggcgtca tcctgtgctc ccgagaacca gtaccagtac atcgctgttt 26820
cgttcgagac ttgaggtcta gttttatacg tgaacaggtc aatgccgccg agagtaaagc 26880
cacattttgc gtacaaattg caggcaggta cattgttcgt ttgtgtctct aatcgtatgc 26940
caaggagctg tctgcttagt gcccactttt tcgcaaattc gatgagactg tgcgcgactc 27000
ctttgcctcg gtgcgtgtgc gacacaacaa tgtgttcgat agaggctaga tcgttccatg 27060
ttgagttgag ttcaatcttc ccgacaagct cttggtcgat gaatgcgcca tagcaagcag 27120
agtcttcatc agagtcatca tccgagatgt aatccttccg gtaggggctc acacttctgg 27180
tagatagttc aaagccttgg tcggataggt gcacatcgaa cacttcacga acaatgaaat 27240
ggttctcagc atccaatgtt tccgccacct gctcagggat caccgaaatc ttcatatgac 27300
gcctaacgcc tggcacagcg gatcgcaaac ctggcgcggc ttttggcaca aaaggcgtga 27360
caggtttgcg aatccgttgc tgccacttgt taaccctttt gccagatttg gtaactataa 27420
tttatgttag aggcgaagtc ttgggtaaaa actggcctaa aattgctggg gatttcagga 27480
aagtaaacat caccttccgg ctcgatgtct attgtagata tatgtagtgt atctacttga 27540
tcgggggatc tgctgcctcg cgcgtttcgg tgatgacggt gaaaacctct gacacatgca 27600
gctcccggag acggtcacag cttgtctgta agcggatgcc gggagcagac aagcccgtca 27660
gggcgcgtca gcgggtgttg gcgggtgtcg gggcgcagcc atgacccagt cacgtagcga 27720
tagcggagtg tatactggct taactatgcg gcatcagagc agattgtact gagagtgcac 27780
catatgcggt gtgaaatacc gcacagatgc gtaaggagaa aataccgcat caggcgctct 27840
tccgcttcct cgctcactga ctcgctgcgc tcggtcgttc ggctgcggcg agcggtatca 27900
gctcactcaa aggcggtaat acggttatcc acagaatcag gggataacgc aggaaagaac 27960
atgtgagcaa aaggccagca aaaggccagg aaccgtaaaa aggccgcgtt gctggcgttt 28020
ttccataggc tccgcccccc tgacgagcat cacaaaaatc gacgctcaag tcagaggtgg 28080
cgaaacccga caggactata aagataccag gcgtttcccc ctggaagctc cctcgtgcgc 28140
tctcctgttc cgaccctgcc gcttaccgga tacctgtccg cctttctccc ttcgggaagc 28200
gtggcgcttt ctcatagctc acgctgtagg tatctcagtt cggtgtaggt cgttcgctcc 28260
aagctgggct gtgtgcacga accccccgtt cagcccgacc gctgcgcctt atccggtaac 28320
tatcgtcttg agtccaaccc ggtaagacac gacttatcgc cactggcagc agccactggt 28380
aacaggatta gcagagcgag gtatgtaggc ggtgctacag agttcttgaa gtggtggcct 28440
aactacggct acactagaag gacagtattt ggtatctgcg ctctgctgaa gccagttacc 28500

-continued

```
ttcggaaaaa gagttggtag ctcttgatcc ggcaaacaaa ccaccgctgg tagcggtggt  28560
tttttgtttt gcaagcagca gattacgcgc agaaaaaaag gatctcaaga agatcctttg  28620
atcttttcta cggggtctga cgctcagtgg aacgaaaact cacgttaagg gattttggtc  28680
atgagattat caaaaaggat cttcacctag atccttttaa attaaaaatg aagttttaaa  28740
tcaatctaaa gtatatatga gtaaacttgg tctgacagtt accaatgctt aatcagtgag  28800
gcacctatct cagcgatctg tctatttcgt tcatccatag ttgcctgact ccccgtcgtg  28860
tagataacta cgatacggga gggcttacca tctggcccca gtgctgcaat gataccgcga  28920
gacccacgct caccggctcc agatttatca gcaataaacc agccagccgg aagggccgag  28980
cgcagaagtg gtcctgcaac tttatccgcc tccatccagt ctattaattg ttgccgggaa  29040
gctagagtaa gtagttcgcc agttaatagt ttgcgcaacg ttgttgccat tgctgcaggg  29100
gggggggggg ggggggactt ccattgttca ttccacggac aaaaacagag aaaggaaacg  29160
acagaggcca aaaagcctcg ctttcagcac ctgtcgtttc ctttcttttc agagggtatt  29220
ttaaataaaa acattaagtt atgacgaaga agaacggaaa cgccttaaac cggaaaattt  29280
tcataaatag cgaaaacccg cgaggtcgcc gccccgtaag ccgccccgta acctgtcgga  29340
tcaccggaaa ggacccgtaa agtgataatg attatcatct acatatcaca acgtgcgtgg  29400
aggccatcaa accacgtcaa ataatcaatt atgacgcagg tatcgtatta attgatctgc  29460
atcaacttaa cgtaaaaaca acttcagaca atacaaatca gcgacactga atacggggca  29520
acctcatgtc cccccccccc cccccccctgc aggcatcgtg gtgtcacgct cgtcgtttgg  29580
tatggcttca ttcagctccg gttcccaacg atcaaggcga gttacatgat cccccatgtt  29640
gtgcaaaaaa gcggttagct ccttcggtcc tccgatcgtt gtcagaagta agttggccgc  29700
agtgttatca ctcatggtta tggcagcact gcataattct cttactgtca tgccatccgt  29760
aagatgcttt tctgtgactg gtgagtactc aaccaagtca ttctgagaat agtgtatgcg  29820
gcgaccgagt tgctcttgcc cggcgtcaac acgggataat accgcgccac atagcagaac  29880
tttaaaagtg ctcatcattg gaaaacgttc ttcggggcga aaactctcaa ggatcttacc  29940
gctgttgaga tccagttcga tgtaacccac tcgtgcaccc aactgatctt cagcatcttt  30000
tactttcacc agcgtttctg ggtgagcaaa aacaggaagg caaaatgccg caaaaaaggg  30060
aataagggcg acacggaaat gttgaatact catactcttc ctttttcaat attattgaag  30120
catttatcag ggttattgtc tcatgagcgg atacatattt gaatgtattt agaaaaataa  30180
acaaataggg gttccgcgca catttccccg aaaagtgcca cctgacgtct aagaaaccat  30240
tattatcatg acattaacct ataaaaatag gcgtatcacg aggccctttc gtcttcaaga  30300
attcggagct tttgccattc tcaccggatt cagtcgtcac tcatggtgat ttctcacttg  30360
ataaccttat ttttgacgag gggaaattaa taggttgtat tgatgttgga cgagtcggaa  30420
tcgcagaccg ataccaggat cttgccatcc tatggaactg cctcggtgag ttttctcctt  30480
cattacagaa acggcttttt caaaaatatg gtattgataa tcctgatatg aataaattgc  30540
agtttcattt gatgctcgat gagtttttct aatcagaatt ggttaattgg ttgtaacact  30600
ggcagagcat tacgctgact tgacgggacg gcggctttgt tgaataaatc gaacttttgc  30660
tgagttgaag gatcagatca cgcatcttcc cgacaacgca gaccgttccg tggcaaagca  30720
aaagttcaaa atcaccaact ggtccaccta caacaaagct ctcatcaacc gtggctccct  30780
cactttctgg ctggatgatg gggcgattca ggcctggtat gagtcagcaa caccttcttc  30840
acgaggcaga cctcagcgcc agaaggccgc cagagaggcc gagcgcggcc gtgaggcttg  30900
```

-continued

```
gacgctaggg cagggcatga aaaagcccgt agcgggctgc tacgggcgtc tgacgcggtg  30960
gaaaggggga ggggatgttg tctacatggc tctgctgtag tgagtgggtt gcgctccggc  31020
agcggtcctg atcaatcgtc accctttctc ggtccttcaa cgttcctgac aacgagcctc  31080
cttttcgcca atccatcgac aatcaccgcg agtccctgct cgaacgctgc gtccggaccg  31140
gcttcgtcga aggcgtctat cgcggcccgc aacagcggcg agagcggagc ctgttcaacg  31200
gtgccgccgc gctcgccggc atcgctgtcg ccggcctgct cctcaagcac ggccccaaca  31260
gtgaagtagc tgattgtcat cagcgcattg acggcgtccc cggccgaaaa acccgcctcg  31320
cagaggaagc gaagctgcgc gtcggccgtt tccatctgcg gtgcgcccgg tcgcgtgccg  31380
gcatggatgc gcgcgccatc gcggtaggcg agcagcgcct gcctgaagct gcgggcattc  31440
ccgatcagaa atgagcgcca gtcgtcgtcg gctctcggca ccgaatgcgt atgattctcc  31500
gccagcatgg cttcggccag tgcgtcgagc agcgcccgct tgttcctgaa gtgccagtaa  31560
agcgccggct gctgaacccc caaccgttcc gccagtttgc gtgtcgtcag accgtctacg  31620
ccgacctcgt tcaacaggtc cagggcggca cggatcactg tattcggctg caactttgtc  31680
atgcttgaca ctttatcact gataaacata atatgtccac caacttatca gtgataaaga  31740
atccgcgcgt tcaatcggac cagcggaggc tggtccggag gccagacgtg aaacccaaca  31800
taccccctgat cgtaattctg agcactgtcg cgctcgacgc tgtcggcatc ggcctgatta  31860
tgccggtgct gccgggcctc ctgcgcgatc tggttcactc gaacgacgtc accgcccact  31920
atggcattct gctggcgctg tatgcgttgg tgcaatttgc ctgcgcacct gtgctgggcg  31980
cgctgtcgga tcgtttcggg cggcggccaa tcttgctcgt ctcgctggcc ggcgccactg  32040
tcgactacgc catcatggcg acagcgcctt tcctttgggt tctctatatc gggcggatcg  32100
tggccggcat caccggggcg actggggcgg tagccggcgc ttatattgcc gatatcactg  32160
atggcgatga gcgcgcgcgg cacttcggct tcatgagcgc ctgtttcggg ttcgggatgg  32220
tcgcgggacc tgtgctcggt gggctgatgg gcggtttctc cccccacgct ccgttcttcg  32280
ccgcggcagc cttgaacggc ctcaatttcc tgacgggctg tttccttttg ccggagtcgc  32340
acaaaggcga acgccggccg ttacgccggg aggctctcaa cccgctcgct tcgttccggt  32400
gggcccgggg catgaccgtc gtcgccgccc tgatggcggt cttcttcatc atgcaacttg  32460
tcggacaggt gccggccgcg ctttgggtca ttttcggcga ggatcgcttt cactgggacg  32520
cgaccacgat cggcatttcg cttgccgcat ttggcattct gcattcactc gcccaggcaa  32580
tgatcaccgg ccctgtagcc gcccggctcg gcgaaaggcg ggcactcatg ctcggaatga  32640
ttgccgacgg cacaggctac atcctgcttg ccttcgcgac acggggatgg atggcgttcc  32700
cgatcatggt cctgcttgct tcgggtggca tcggaatgcc ggcgctgcaa gcaatgttgt  32760
ccaggcaggt ggatgaggaa cgtcaggggc agctgcaagg ctcactggcg gcgctcacca  32820
gcctgacctc gatcgtcgga cccctcctct tcacggcgat ctatgcggct tctataacaa  32880
cgtggaacgg gtgggcatgg attgcaggcg ctgccctcta cttgctctgc ctgccggcgc  32940
tgcgtcgcgg gctttggagc ggcgcagggc aacgagccga tcgctgatcg tggaaacgat  33000
aggcctatgc catgcgggtc aaggcgactt ccggcaagct atacgcgccc taggagtgcg  33060
gttggaacgt tggcccagcc agatactccc gatcacgagc aggacgccga tgatttgaag  33120
cgcactcagc gtctgatcca agaacaacca tcctagcaac acggcggtcc ccgggctgag  33180
aaagcccagt aaggaaacaa ctgtaggttc gagtcgcgag atcccccgga accaaaggaa  33240
gtaggttaaa cccgctccga tcaggccgag ccacgccagg ccgagaacat tggttcctgt  33300
```

-continued

```
aggcatcggg attggcggat caaacactaa agctactgga acgagcagaa gtcctccggc  33360
cgccagttgc caggcggtaa aggtgagcag aggcacggga ggttgccact tgcgggtcag  33420
cacggttccg aacgccatgg aaaccgcccc cgccaggccc gctgcgacgc cgacaggatc  33480
tagcgctgcg tttggtgtca acaccaacag cgccacgccc gcagttccgc aaatagcccc  33540
caggaccgcc atcaatcgta tcgggctacc tagcagagcg gcagagatga acacgaccat  33600
cagcggctgc acagcgccta ccgtcgccgc gaccccgccc ggcaggcggt agaccgaaat  33660
aaacaacaag ctccagaata gcgaaatatt aagtgcgccg aggatgaaga tgcgcatcca  33720
ccagattccc gttggaatct gtcggacgat catcacgagc aataaacccg ccggcaacgc  33780
ccgcagcagc ataccggcga cccctcggcc tcgctgttcg ggctccacga aaacgccgga  33840
cagatgcgcc ttgtgagcgt ccttggggcc gtcctcctgt ttgaagaccg acagcccaat  33900
gatctcgccg tcgatgtagg cgccgaatgc cacggcatct cgcaaccgtt cagcgaacgc  33960
ctccatgggc tttttctcct cgtgctcgta aacggacccg aacatctctg gagctttctt  34020
cagggccgac aatcggatct cgcggaaatc ctgcacgtcg gccgctccaa gccgtcgaat  34080
ctgagcctta atcacaattg tcaattttaa tcctctgttt atcggcagtt cgtagagcgc  34140
gccgtgcgtc ccgagcgata ctgagcgaag caagtgcgtc gagcagtgcc cgcttgttcc  34200
tgaaatgcca gtaaagcgct ggctgctgaa cccccagccg gaactgaccc cacaaggccc  34260
tagcgtttgc aatgcaccag gtcatcattg acccaggcgt gttccaccag gccgctgcct  34320
cgcaactctt cgcaggcttc gccgacctgc tcgcgccact tcttcacgcg ggtggaatcc  34380
gatccgcaca tgaggcggaa ggtttccagc ttgagcgggt acggctcccg gtgcgagctg  34440
aaatagtcga acatccgtcg ggccgtcggc gacagcttgc ggtacttctc ccatatgaat  34500
ttcgtgtagt ggtcgccagc aaacagcacg acgatttcct cgtcgatcag gacctggcaa  34560
cgggacgttt tcttgccacg gtccaggacg cggaagcggt gcagcagcga caccgattcc  34620
aggtgcccaa cgcggtcgga cgtgaagccc atcgccgtcg cctgtaggcg cgacaggcat  34680
tcctcggcct tcgtgtaata ccggccattg atcgaccagc ccaggtcctg gcaaagctcg  34740
tagaacgtga aggtgatcgg ctcgccgata ggggtgcgct tcgcgtactc caacacctgc  34800
tgccacacca gttcgtcatc gtcggcccgc agctcgacgc cggtgtaggt gatcttcacg  34860
tccttgttga cgtggaaaat gaccttgttt tgcagcgcct cgcgcgggat tttcttgttg  34920
cgcgtggtga acagggcaga gcgggccgtg tcgtttggca tcgctcgcat cgtgtccggc  34980
cacggcgcaa tatcgaacaa ggaaagctgc atttccttga tctgctgctt cgtgtgtttc  35040
agcaacgcgg cctgcttggc ctcgctgacc tgttttgcca ggtcctcgcc ggcggttttt  35100
cgcttcttgg tcgtcatagt tcctcgcgtg tcgatggtca tcgacttcgc caaacctgcc  35160
gcctcctgtt cgagacgacg cgaacgctcc acggcggccg atggcgcggg cagggcaggg  35220
ggagccagtt gcacgctgtc gcgctcgatc ttggccgtag cttgctggac catcgagccg  35280
acggactgga aggtttcgcg gggcgcacgc atgacggtgc ggcttgcgat ggtttcggca  35340
tcctcggcgg aaaaccccgc gtcgatcagt tcttgcctgt atgccttccg gtcaaacgtc  35400
cgattcattc accctccttg cgggattgcc ccgactcacg ccggggcaat gtgcccttat  35460
tcctgatttg acccgcctgg tgccttggtg tccagataat ccaccttatc ggcaatgaag  35520
tcggtcccgt agaccgtctg gccgtccttc tcgtacttgg tattccgaat cttgccctgc  35580
acgaatacca gcgacccctt gcccaaatac ttgccgtggg cctcggcctg agagccaaaa  35640
cacttgatgc ggaagaagtc ggtgcgctcc tgcttgtcgc cggcatcgtt gcgccactct  35700
```

-continued

```
tcattaaccg ctatatcgaa aattgcttgc ggcttgttag aattgccatg acgtacctcg  35760
gtgtcacggg taagattacc gataaactgg aactgattat ggctcatatc gaaagtctcc  35820
ttgagaaagg agactctagt ttagctaaac attggttccg ctgtcaagaa ctttagcggc  35880
taaaattttg cgggccgcga ccaaaggtgc gaggggcggc ttccgctgtg tacaaccaga  35940
tatttttcac caacatcctt cgtctgctcg atgagcgggg catgacgaaa catgagctgt  36000
cggagagggc aggggtttca atttcgtttt tatcagactt aaccaacggt aaggccaacc  36060
cctcgttgaa ggtgatggag gccattgccg acgccctgga aactccccta cctcttctcc  36120
tggagtccac cgaccttgac cgcgaggcac tcgcggagat tgcgggtcat cctttcaaga  36180
gcagcgtgcc gcccggatac gaacgcatca gtgtggtttt gccgtcacat aaggcgttta  36240
tcgtaaagaa atggggcgac gacacccgaa aaaagctgcg tggaaggctc tgacgccaag  36300
ggttagggct tgcacttcct tctttagccg ctaaaacggc cccttctctg cgggccgtcg  36360
gctcgcgcat catatcgaca tcctcaacgg aagccgtgcc gcgaatggca tcgggcgggt  36420
gcgctttgac agttgttttc tatcagaacc cctacgtcgt gcggttcgat tagctgtttg  36480
tcttgcaggc taaacacttt cggtatatcg tttgcctgtg cgataatgtt gctaatgatt  36540
tgttgcgtag ggttactgaa aaagtgagcg ggaaagaaga gtttcagacc atcaaggagc  36600
gggccaagcg caagctggaa cgcgacatgg gtgcggacct gttggccgcg ctcaacgacc  36660
cgaaaaccgt tgaagtcatg ctcaacgcgg acggcaaggt gtggcacgaa cgccttggcg  36720
agccgatgcg gtacatctgc gacatgcggc ccagccagtc gcaggcgatt atagaaacgg  36780
tggccggatt ccacggcaaa gaggtcacgc ggcattcgcc catcctggaa ggcgagttcc  36840
ccttggatgg cagccgcttt gccggccaat tgccgccggt cgtggccgcg ccaacctttg  36900
cgatccgcaa gcgcgcggtc gccatcttca cgctggaaca gtacgtcgag gcgggcatca  36960
tgacccgcga gcaatacgag gtcattaaaa gcgccgtcgc ggcgcatcga aacatcctcg  37020
tcattggcgg tactggctcg ggcaagacca cgctcgtcaa cgcgatcatc aatgaaatgg  37080
tcgccttcaa cccgtctgag cgcgtcgtca tcatcgagga caccggcgaa atccagtgcg  37140
ccgcagagaa cgccgtccaa taccacacca gcatcgacgt ctcgatgacg ctgctgctca  37200
agacaacgct gcgtatgcgc cccgaccgca tcctggtcgg tgaggtacgt ggccccgaag  37260
cccttgatct gttgatggcc tggaacaccg ggcatgaagg aggtgccgcc accctgcacg  37320
caaacaaccc caaagcgggc ctgagccggc tcgccatgct tatcagcatg cacccggatt  37380
caccgaaacc cattgagccg ctgattggcg aggcggttca tgtggtcgtc catatcgcca  37440
ggacccctag cggccgtcga gtgcaagaaa ttctcgaagt tcttggttac gagaacggcc  37500
agtacatcac caaaaccctg taaggagtat ttccaatgac aacggctgtt ccgttccgtc  37560
tgaccatgaa tcgcggcatt ttgttctacc ttgccgtgtt cttcgttctc gctctcgcgt  37620
tatccgcgca tccggcgatg gcctcggaag gcaccggcgg cagcttgcca tatgagagct  37680
ggctgacgaa cctgcgcaac tccgtaaccg gcccggtggc cttcgcgctg tccatcatcg  37740
gcatcgtcgt cgccggcggc gtgctgatct tcggcggcga actcaacgcc ttcttccgaa  37800
ccctgatctt cctggttctg gtgatggcgc tgctggtcgg cgcgcagaac gtgatgagca  37860
ccttcttcgg tcgtggtgcc gaaatcgcgg ccctcggcaa cggggcgctg caccaggtgc  37920
aagtcgcggc ggcggatgcc gtgcgtgcgg tagcggctgg acggctcgcc taatcatggc  37980
tctgcgcacg atccccatcc gtcgcgcagg caaccgagaa aacctgttca tgggtggtga  38040
tcgtgaactg gtgatgttct cgggcctgat ggcgtttgcg ctgattttca gcgcccaaga  38100
```

```
gctgcgggcc accgtggtcg gtctgatcct gtggttcggg gcgctctatg cgttccgaat  38160
catggcgaag gccgatccga agatgcggtt cgtgtacctg cgtcaccgcc ggtacaagcc  38220
gtattacccg gcccgctcga ccccgttccg cgagaacacc aatagccaag ggaagcaata  38280
ccgatgatcc aagcaattgc gattgcaatc gcgggcctcg gcgcgcttct gttgttcatc  38340
ctctttgccc gcatccgcgc ggtcgatgcc gaactgaaac tgaaaaagca tcgttccaag  38400
gacgccggcc tggccgatct gctcaactac gccgctgtcg tcgatgacgg cgtaatcgtg  38460
ggcaagaacg gcagctttat ggctgcctgg ctgtacaagg gcgatgacaa cgcaagcagc  38520
accgaccagc agcgcgaagt agtgtccgcc cgcatcaacc aggccctcgc gggcctggga  38580
agtgggtgga tgatccatgt ggacgccgtg cggcgtcctg ctccgaacta cgcggagcgg  38640
ggcctgtcgg cgttccctga ccgtctgacg gcagcgattg aagaagagcg ctcggtcttg  38700
ccttgctcgt cggtgatgta cttcaccagc tccgcgaagt cgctcttctt gatggagcgc  38760
atggggacgt gcttggcaat cacgcgcacc ccccggccgt tttagcggct aaaaaagtca  38820
tggctctgcc ctcgggcgga ccacgcccat catgaccttg ccaagctcgt cctgcttctc  38880
ttcgatcttc gccagcaggg cgaggatcgt ggcatcaccg aaccgcgccg tgcgcgggtc  38940
gtcggtgagc cagagtttca gcaggccgcc caggcggccc aggtcgccat tgatgcgggc  39000
cagctcgcgg acgtgctcat agtccacgac gcccgtgatt ttgtagccct ggccgacggc  39060
cagcaggtag gccgacaggc tcatgccggc cgccgccgcc ttttcctcaa tcgctcttcg  39120
ttcgtctgga aggcagtaca ccttgatagg tgggctgccc ttcctggttg gcttggtttc  39180
atcagccatc cgcttgccct catctgttac gccggcggta gccggccagc ctcgcagagc  39240
aggattcccg ttgagcaccg ccaggtgcga ataagggaca gtgaagaagg aacacccgct  39300
cgcgggtggg cctacttcac ctatcctgcc cggctgacgc cgttggatac accaaggaaa  39360
gtctacacga accctttggc aaaatcctgt atatcgtgcg aaaaaggatg gatataccga  39420
aaaaatcgct ataatgaccc cgaagcaggg ttatgcagcg gaaaagcgct gcttccctgc  39480
tgttttgtgg aatatctacc gactggaaac aggcaaatgc aggaaattac tgaactgagg  39540
ggacaggcga gagacgatgc caaagagcta caccgacgag ctggccgagt gggttgaatc  39600
ccgcgcggcc aagaagcgcc ggcgtgatga ggctgcggtt gcgttcctgg cggtgagggc  39660
ggatgtcgag gcggcgttag cgtccggcta tgcgctcgtc accatttggg agcacatgcg  39720
ggaaacgggg aaggtcaagt tctcctacga gacgttccgc tcgcacgcca ggcggcacat  39780
caaggccaag cccgccgatg tgcccgcacc gcaggccaag gctgcggaac ccgcgccggc  39840
acccaagacg ccggagccac ggcggccgaa gcaggggggc aaggctgaaa agccggcccc  39900
cgctgcggcc ccgaccggct tcaccttcaa cccaacaccg gacaaaaagg atctactgta  39960
atggcgaaaa ttcacatggt tttgcagggc aagggcgggg tcggcaagtc ggccatcgcc  40020
gcgatcattg cgcagtacaa gatggacaag gggcagacac ccttgtgcat cgacaccgac  40080
ccggtgaacg cgacgttcga gggctacaag gccctgaacg tccgccggct gaacatcatg  40140
gccggcgacg aaattaactc gcgcaacttc gacaccctgg tcgagctgat tgcgccgacc  40200
aaggatgacg tggtgatcga caacggtgcc agctcgttcg tgcctctgtc gcattacctc  40260
atcagcaacc aggtgccggc tctgctgcaa gaaatggggc atgagctggt catccatacc  40320
gtcgtcaccg gcggccaggc tctcctggac acggtgagcg gcttcgccca gctcgccagc  40380
cagttcccgg ccgaagcgct tttcgtggtc tggctgaacc cgtattgggg gcctatcgag  40440
catgagggca agagctttga gcagatgaag gcgtacacgg ccaacaaggc ccgcgtgtcg  40500
```

-continued tccatcatcc agattccggc cctcaaggaa gaaacctacg gccgcgattt cagcgacatg 40560
ctgcaagagc ggctgacgtt cgaccaggcg ctggccgatg aatcgctcac gatcatgacg 40620
cggcaacgcc tcaagatcgt gcggcgcggc ctgtttgaac agctcgacgc ggcggccgtg 40680
ctatgagcga ccagattgaa gagctgatcc gggagattgc ggccaagcac ggcatcgccg 40740
tcggccgcga cgacccggtg ctgatcctgc ataccatcaa cgcccggctc atggccgaca 40800
gtgcggccaa gcaagaggaa atccttgccg cgttcaagga agagctggaa gggatcgccc 40860
atcgttgggg cgaggacgcc aaggccaaag cggagcggat gctgaacgcg gccctggcgg 40920
ccagcaagga cgcaatggcg aaggtaatga aggacagcgc cgcgcaggcg gccgaagcga 40980
tccgcaggga aatcgacgac ggccttggcc gccagctcgc ggccaaggtc gcggacgcgc 41040
ggcgcgtggc gatgatgaac atgatcgccg gcggcatggt gttgttcgcg gccgccctgg 41100
tggtgtgggc ctcgttatga atcgcagagg cgcagatgaa aaagcccggc gttgccgggc 41160
tttgtttttg cgttagctgg gcttgtttga caggcccaag ctctgactgc gcccgcgctc 41220
gcgctcctgg gcctgtttct tctcctgctc ctgcttgcgc atcagggcct ggtgccgtcg 41280
ggctgcttca cgcatcgaat cccagtcgcc ggccagctcg ggatgctccg cgcgcatctt 41340
gcgcgtcgcc agttcctcga tcttgggcgc gtgaatgccc atgccttcct tgatttcgcg 41400
caccatgtcc agccgcgtgt gcagggtctg caagcgggct tgctgttggg cctgctgctg 41460
ctgccaggcg gcctttgtac gcggcaggga cagcaagccg ggggcattgg actgtagctg 41520
ctgcaaacgc gcctgctgac ggtctacgag ctgttctagg cggtcctcga tgcgctccac 41580
ctggtcatgc tttgcctgca cgtagagcgc aagggtctgc tggtaggtct gctcgatggg 41640
cgcggattct aagagggcct gctgttccgt ctcggcctcc tgggccgcct gtagcaaatc 41700
ctcgccgctg ttgccgctgg actgctttac tgccggggac tgctgttgcc ctgctcgcgc 41760
cgtcgtcgca gttcggcttg cccccactcg attgactgct tcatttcgag ccgcagcgat 41820
gcgatctcgg attgcgtcaa cggacggggc agcgcggagg tgtccggctt ctccttgggt 41880
gagtcggtcg atgccatagc caaaggtttc cttccaaaat gcgtccattg ctggaccgtg 41940
tttctcattg atgcccgcaa gcatcttcgg cttgaccgcc aggtcaagcg cgccttcatg 42000
ggcggtcatg acggacgccg ccatgacctt gccgccgttg ttctcgatgt agccgcgtaa 42060
tgaggcaatg gtgccgccca tcgtcagcgt gtcatcgaca acgatgtact tctggccggg 42120
gatcacctcc ccctcgaaag tcgggttgaa cgccaggcga tgatctgaac cggctccggt 42180
tcgggcgacc ttctcccgct gcacaatgtc cgtttcgacc tcaaggccaa ggcggtcggc 42240
cagaacgacc gccatcatgg ccggaatctt gttgttcccc gccgcctcga cggcgaggac 42300
tggaacgatg cggggcttgt cgtcgccgat cagcgtcttg agctgggcaa cagtgtcgtc 42360
cgaaatcagg cgctcgacca aattaagcgc cgcttccgcg tcgccctgct tcgcagcctg 42420
gtattcaggc tcgttggtca aagaaccaag gtcgccgttg cgaaccacct tcgggaagtc 42480
tccccacggt gcgcgctcgg ctctgctgta gctgctcaag acgcctccct ttttagccgc 42540
taaaactcta acgagtgcgc ccgcgactca acttgacgct ttcggcactt acctgtgcct 42600
tgccacttgc gtcataggtg atgcttttcg cactcccgat ttcaggtact ttatcgaaat 42660
ctgaccgggc gtgcattaca aagttcttcc ccacctgttg gtaaatgctg ccgctatctg 42720
cgtggacgat gctgccgtcg tggcgctgcg acttatcggc cttttgggcc atatagatgt 42780
tgtaaatgcc aggtttcagg gccccggctt tatctacctt ctggttcgtc catgcgcctt 42840
ggttctcggt ctggacaatt ctttgcccat tcatgaccag gaggcggtgt ttcattgggt 42900

-continued

```
gactcctgac ggttgcctct ggtgttaaac gtgtcctggt cgcttgccgg ctaaaaaaaa  42960
gccgacctcg gcagttcgag gccggctttc cctagagccg ggcgcgtcaa ggttgttcca  43020
tctattttag tgaactgcgt tcgatttatc agttactttc ctcccgcttt gtgtttcctc  43080
ccactcgttt ccgcgtctag ccgacccctc aacatagcgg cctcttcttg ggctgccttt  43140
gcctcttgcc gcgcttcgtc acgctcggct tgcaccgtcg taaagcgctc ggcctgcctg  43200
gccgcctctt gcgccgccaa cttcctttgc tcctggtggg cctcggcgtc ggcctgcgcc  43260
ttcgctttca ccgctgccaa ctccgtgcgc aaactctccg cttcgcgcct ggtggcgtcg  43320
cgctcgccgc gaagcgcctg catttcctgg ttggccgcgt ccagggtctt gcggctctct  43380
tctttgaatg cgcgggcgtc ctggtgagcg tagtccagct cggcgcgcag ctcctgcgct  43440
cgacgctcca cctcgtcggc ccgctgcgtc gccagcgcgg cccgctgctc ggctcctgcc  43500
agggcggtgc gtgcttcggc cagggcttgc cgctggcgtg cggccagctc ggccgcctcg  43560
gcggcctgct gctctagcaa tgtaacgcgc gcctgggctt cttccagctc gcgggcctgc  43620
gcctcgaagg cgtcggccag ctccccgcgc acggcttcca actcgttgcg ctcacgatcc  43680
cagccggctt gcgctgcctg caacgattca ttggcaaggg cctgggcggc ttgccagagg  43740
gcggccacgg cctggttgcc ggcctgctgc accgcgtccg gcacctggac tgccagcggg  43800
gcggcctgcg ccgtgcgctg gcgtcgccat tcgcgcatgc cggcgctggc gtcgttcatg  43860
ttgacgcggg cggccttacg cactgcatcc acggtcggga agttctcccg gtcgccttgc  43920
tcgaacagct cgtccgcagc cgcaaaaatg cggtcgcgcg tctctttgtt cagttccatg  43980
ttggctccgg taattggtaa gaataataat actcttacct accttatcag cgcaagagtt  44040
tagctgaaca gttctcgact taacggcagg ttttttagcg gctgaagggc aggcaaaaaa  44100
agccccgcac ggtcggcggg ggcaaagggt cagcgggaag ggattagcg ggcgtcgggc  44160
ttcttcatgc gtcggggccg cgcttcttgg gatggagcac gacgaagcgc gcacgcgcat  44220
cgtcctcggc cctatcggcc cgcgtcgcgg tcaggaactt gtcgcgcgct aggtcctccc  44280
tggtgggcac caggggcatg aactcggcct gctcgatgta ggtccactcc atgaccgcat  44340
cgcagtcgag gccgcgttcc ttcaccgtct cttgcaggtc gcggtacgcc cgctcgttga  44400
gcggctggta acgggccaat tggtcgtaaa tggctgtcgg ccatgagcgg cctttcctgt  44460
tgagccagca gccgacgacg aagccggcaa tgcaggcccc tggcacaacc aggccgacgc  44520
cgggggcagg ggatggcagc agctcgccaa ccaggaaccc cgccgcgatg atgccgatgc  44580
cggtcaacca gcccttgaaa ctatccggcc ccgaaacacc cctgcgcatt gcctggatgc  44640
tgcgccggat agcttgcaac atcaggagcc gtttcttttg ttcgtcagtc atggtccgcc  44700
ctcaccagtt gttcgtatcg gtgtcggacg aactgaaatc gcaagagctg ccggtatcgg  44760
tccagccgct gtccgtgtcg ctgctgccga agcacggcga ggggtccgcg aacgccgcag  44820
acggcgtatc cggccgcagc gcatcgccca gcatggcccc ggtcagcgag ccgccggcca  44880
ggtagcccag catggtgctg ttggtcgccc cggccaccag ggccgacgtg acgaaatcgc  44940
cgtcattccc tctggattgt tcgctgctcg gcggggcagt gcgccgcgcc ggcggcgtcg  45000
tggatggctc gggttggctg gcctgcgacg gccggcgaaa ggtgcgcagc agctcgttat  45060
cgaccggctg cggcgtcggg gccgccgcct tgcgctgcgg tcggtgttcc ttcttcggct  45120
cgcgcagctt gaacagcatg atcgcggaaa ccagcagcaa cgccgcgcct acgcctcccg  45180
cgatgtagaa cagcatcgga ttcattcttc ggtcctcctt gtagcggaac cgttgtctgt  45240
gcggcgcggg tggcccgcgc cgctgtcttt ggggatcagc cctcgatgag cgcgaccagt  45300
```

-continued

```
ttcacgtcgg caaggttcgc ctcgaactcc tggccgtcgt cctcgtactt caaccaggca  45360
tagccttccg ccggcggccg acggttgagg ataaggcggg cagggcgctc gtcgtgctcg  45420
acctggacga tggccttttt cagcttgtcc gggtccggct ccttcgcgcc cttttccttg  45480
gcgtccttac cgtcctggtc gccgtcctcg ccgtcctggc cgtcgccggc ctccgcgtca  45540
cgctcggcat cagtctggcc gttgaaggca tcgacggtgt tgggatcgcg gcccttctcg  45600
tccaggaact cgcgcagcag cttgaccgtg ccgcgcgtga tttcctgggt gtcgtcgtca  45660
agccacgcct cgacttcctc cgggcgcttc ttgaaggccg tcaccagctc gttcaccacg  45720
gtcacgtcgc gcacgcggcc ggtgttgaac gcatcggcga tcttctccgg caggtccagc  45780
agcgtgacgt gctgggtgat gaacgccggc gacttgccga tttccttggc gatatcgcct  45840
ttcttcttgc ccttcgccag ctcgcggcca atgaagtcgg caatttcgcg cggggtcagc  45900
tcgttgcgtt gcaggttctc gataacctgg tcggcttcgt tgtagtcgtt gtcgatgaac  45960
gccgggatgg acttcttgcc ggcccacttc gagccacggt agcggcgggc gccgtgattg  46020
atgatatagc ggcccggctg ctcctggttc tcgcgcaccg aaatgggtga cttcaccccg  46080
cgctctttga tcgtggcacc gatttccgcg atgctctccg gggaaaagcc ggggttgtcg  46140
gccgtccgcg gctgatgcgg atcttcgtcg atcaggtcca ggtccagctc gatagggccg  46200
gaaccgccct gagacgccgc aggagcgtcc aggaggctcg acaggtcgcc gatgctatcc  46260
aaccccaggc cggacggctg cgccgcgcct gcggcttcct gagcggccgc agcggtgttt  46320
ttcttggtgg tcttggcttg agccgcagtc attgggaaat ctccatcttc gtgaacacgt  46380
aatcagccag ggcgcgaacc tctttcgatg ccttgcgcgc ggccgttttc ttgatcttcc  46440
agaccggcac accggatgcg agggcatcgg cgatgctgct gcgcaggcca acggtggccg  46500
gaatcatcat cttggggtac gcggccagca gctcggcttg gtggcgcgcg tggcgcggat  46560
tccgcgcatc gaccttgctg ggcaccatgc caaggaattg cagcttggcg ttcttctggc  46620
gcacgttcgc aatggtcgtg accatcttct tgatgccctg gatgctgtac gcctcaagct  46680
cgatggggga cagcacatag tcggccgcga agagggcggc cgccaggccg acgccaaggg  46740
tcggggccgt gtcgatcagg cacacgtcga agccttggtt cgccagggcc ttgatgttcg  46800
ccccgaacag ctcgcgggcg tcgtccagcg acagccgttc ggcgttcgcc agtaccgggt  46860
tggactcgat gagggcgagg cgcgcggcct ggccgtcgcc ggctgcgggt gcggtttcgg  46920
tccagccgcc ggcagggaca gcgccgaaca gcttgcttgc atgcaggccg gtagcaaagt  46980
ccttgagcgt gtaggacgca ttgccctggg ggtccaggtc gatcacggca acccgcaagc  47040
cgcgctcgaa aaagtcgaag gcaagatgca caagggtcga agtcttgccg acgccgcctt  47100
tctggttggc cgtgaccaaa gttttcatcg tttggtttcc tgtttttttct tggcgtccgc  47160
ttcccacttc cggacgatgt acgcctgatg ttccggcaga accgccgtta cccgcgcgta  47220
cccctcgggc aagttcttgt cctcgaacgc ggcccacacg cgatgcaccg cttgcgacac  47280
tgcgcccctg gtcagtccca gcgacgttgc gaacgtcgcc tgtggcttcc catcgactaa  47340
gacgccccgc gctatctcga tggtctgctg ccccacttcc agcccctgga tcgcctcctg  47400
gaactggctt tcggtaagcc gtttcttcat ggataacacc cataatttgc tccgcgcctt  47460
ggttgaacat agcggtgaca gccgccagca catgagagaa gtttagctaa acatttctcg  47520
cacgtcaaca cctttagccg ctaaaactcg tccttggcgt aacaaaacaa aagcccggaa  47580
accgggcttt cgtctcttgc cgcttatggc tctgcacccg gctccatcac caacaggtcg  47640
cgcacgcgct tcactcggtt gcggatcgac actgccagcc caacaaagcc ggttgccgcc  47700
```

-continued gccgccagga tcgcgccgat gatgccggcc acaccggcca tcgcccacca ggtcgccgcc 47760
ttccggttcc attcctgctg gtactgcttc gcaatgctgg acctcggctc accataggct 47820
gaccgctcga tggcgtatgc cgcttctccc cttggcgtaa aacccagcgc cgcaggcggc 47880
attgccatgc tgcccgccgc tttcccgacc acgacgcgcg caccaggctt gcggtccaga 47940
ccttcggcca cggcgagctg cgcaaggaca taatcagccg ccgacttggc tccacgcgcc 48000
tcgatcagct cttgcactcg cgcgaaatcc ttggcctcca cggccgccat gaatcgcgca 48060
cgcggcgaag gctccgcagg gccggcgtcg tgatcgccgc cgagaatgcc cttcaccaag 48120
ttcgacgaca cgaaaatcat gctgacggct atcaccatca tgcagacgga tcgcacgaac 48180
ccgctgaatt gaacacgagc acggcacccg cgaccactat gccaagaatg cccaaggtaa 48240
aaattgccgg ccccgccatg aagtccgtga atgccccgac ggccgaagtg aagggcaggc 48300
cgccacccag gccgccgccc tcactgcccg gcacctggtc gctgaatgtc gatgccagca 48360
cctgcggcac gtcaatgctt ccgggcgtcg cgctcgggct gatcgcccat cccgttactg 48420
ccccgatccc ggcaatggca aggactgcca gcgctgccat ttttggggtg aggccgttcg 48480
cggccgaggg gcgcagcccc tggggggatg ggaggcccgc gttagcgggc cgggagggtt 48540
cgagaagggg gggcaccccc cttcggcgtg cgcggtcacg cgcacagggc gcagccctgg 48600
ttaaaaacaa ggtttataaa tattggttta aaagcaggtt aaaagacagg ttagcggtgg 48660
ccgaaaaacg ggcggaaacc cttgcaaatg ctggattttc tgcctgtgga cagcccctca 48720
aatgtcaata ggtgcgcccc tcatctgtca gcactctgcc cctcaagtgt caaggatcgc 48780
gcccctcatc tgtcagtagt cgcgcccctc aagtgtcaat accgcagggc acttatcccc 48840
aggcttgtcc acatcatctg tgggaaactc gcgtaaaatc aggcgttttc gccgatttgc 48900
gaggctggcc agctccacgt cgccggccga aatcgagcct gcccctcatc tgtcaacgcc 48960
gcgccgggtg agtcggcccc tcaagtgtca acgtccgccc ctcatctgtc agtgagggcc 49020
aagttttccg cgaggtatcc acaacgccgg cggccgcggt gtctcgcaca cggcttcgac 49080
ggcgtttctg gcgcgtttgc agggccatag acggccgcca gcccagcggc gagggcaacc 49140
agcccggtga gcgtcggaaa ggcgctggaa gccccgtagc gacgcggaga ggggcgagac 49200
aagccaaggg cgcaggctcg atgcgcagca cgacatagcc ggttctcgca aggacgagaa 49260
tttccctgcg gtgcccctca agtgtcaatg aaagtttcca acgcgagcca ttcgcgagag 49320
ccttgagtcc acgctagatg agagctttgt tgtaggtgga ccagttggtg attttgaact 49380
tttgctttgc cacggaacgg tctgcgttgt cgggaagatg cgtgatctga tccttcaact 49440
cagcaaaagt tcgatttatt caacaaagcc acgttgtgtc tcaaaatctc tgatgttaca 49500
ttgcacaaga taaaaatata tcatcatgaa caataaaact gtctgcttac ataaacagta 49560
atacaagggg tgttatgagc catattcaac gggaaac 49597

<210> SEQ ID NO 94
<211> LENGTH: 49579
<212> TYPE: DNA
<213> ORGANISM: vector

<400> SEQUENCE: 94
gtcttgctcg actctagagc tcgttcctcg aggcctcgag gcctcgagga acggtacctg 60
cggggaagct tacaataatg tgtgttgtta agtcttgttg cctgtcatcg tctgactgac 120
tttcgtcata aatcccggcc tccgtaaccc agctttgggc aagctcacgg atttgatccg 180
gcggaacggg aatatcgaga tgccgggctg aacgctgcag ttccagcttt ccctttcggg 240

-continued

```
acaggtactc cagctgattg attatctgct gaagggtctt ggttccacct cctggcacaa    300
tgcgaatgat tacttgagcg cgatcgggca tccaattttc tcccgtcagg tgcgtggtca    360
agtgctacaa ggcacctttc agtaacgagc gaccgtcgat ccgtcgccgg gatacggaca    420
aaatggagcg cagtagtcca tcgagggcgg cgaaagcctc gccaaaagca atacgttcat    480
ctcgcacagc ctccagatcc gatcgagggt cttcggcgta ggcagataga agcatggata    540
cattgcttga gagtattccg atggactgaa gtatggcttc catcttttct cgtgtgtctg    600
catctatttc gagaaagccc ccgatgcggc gcaccgcaac gcgaattgcc atactatccg    660
aaagtcccag caggcgcgct tgataggaaa aggtttcata ctcggccgat cgcagacggg    720
cactcacgac cttgaaccct tcaactttca gggatcgatg ctggttgatg gtagtctcac    780
tcgacgtggc tctggtgtgt tttgacatag cttcctccaa agaaagcgga aggtctggat    840
actccagcac gaaatgtgcc cgggtagacg gatggaagtc tagccctgct caatatgaaa    900
tcaacagtac atttacagtc aatactgaat atacttgcta catttgcaat tgtcttataa    960
cgaatgtgaa ataaaaatag tgtaacaacg cttttactca tcgataatca caaaaacatt   1020
tatacgaaca aaaatacaaa tgcactccgg tttcacagga taggcgggat cagaatatgc   1080
aacttttgac gttttgttct ttcaaagggg gtgctggcaa aaccaccgca ctcatgggcc   1140
tttgcgctgc tttggcaaat gacggtaaac gagtggccct ctttgatgcc gacgaaaacc   1200
ggcctctgac gcgatggaga gaaaacgcct tacaaagcag tactgggatc ctcgctgtga   1260
agtctattcc gccgacgaaa tgccccttct tgaagcagcc tatgaaaatg ccgagctcga   1320
aggatttgat tatgcgttgg ccgatacgcg tggcggctcg agcgagctca acaacacaat   1380
catcgctagc tcaaacctgc ttctgatccc caccatgcta acgccgctcg acatcgatga   1440
ggcactatct acctaccgct acgtcatcga gctgctgttg agtgaaaatt tggcaattcc   1500
tacagctgtt ttgcgccaac gcgtcccggt cggccgattg acaacatcgc aacgcaggat   1560
gtcagagacg ctagagagcc ttccagttgt accgtctccc atgcatgaaa gagatgcatt   1620
tgccgcgatg aaagaacgcg gcatgttgca tcttacatta ctaaacacgg gaactgatcc   1680
gacgatgcgc ctcatagaga ggaatcttcg gattgcgatg gaggaagtcg tggtcatttc   1740
gaaactgatc agcaaaatct tggaggcttg aagatggcaa ttcgcaagcc cgcattgtcg   1800
gtcggcgaag cacggcggct tgctggtgct cgacccgaga tccaccatcc caacccgaca   1860
cttgttcccc agaagctgga cctccagcac ttgcctgaaa aagccgacga gaaagaccag   1920
caacgtgagc ctctcgtcgc cgatcacatt tacagtcccg atcgacaact taagctaact   1980
gtggatgccc ttagtccacc tccgtccccg aaaaagctcc aggtttttct ttcagcgcga   2040
ccgcccgcgc ctcaagtgtc gaaaacatat gacaacctcg ttcggcaata cagtccctcg   2100
aagtcgctac aaatgatttt aaggcgcgcg ttggacgatt tcgaaagcat gctggcagat   2160
ggatcatttc gcgtggcccc gaaaagttat ccgatccctt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg taggtttgag gccgctggcc gcgtcctcag tcaccttttg   2460
agccagataa ttaagagcca aatgcaattg gctcaggctg ccatcgtccc cccgtgcgaa   2520
acctgcacgt ccgcgtcaaa gaaataaccg gcacctcttg ctgtttttat cagttgaggg   2580
cttgacggat ccgcctcaag tttgcggcgc agccgcaaaa tgagaacatc tatactcctg   2640
```

-continued tcgtaaacct cctcgtcgcg tactcgactg gcaatgagaa gttgctcgcg cgatagaacg 2700
tcgcggggtt tctctaaaaa cgcgaggaga agattgaact cacctgccgt aagtttcacc 2760
tcaccgccag cttcggacat caagcgacgt tgcctgagat taagtgtcca gtcagtaaaa 2820
caaaaagacc gtcggtcttt ggagcggaca acgttggggc gcacgcgcaa ggcaacccga 2880
atgcgtgcaa gaaactctct cgtactaaac ggcttagcga taaaatcact tgctcctagc 2940
tcgagtgcaa caactttatc cgtctcctca aggcggtcgc cactgataat tatgattgga 3000
atatcagact ttgccgccag atttcgaacg atctcaagcc catcttcacg acctaaattt 3060
agatcaacaa ccacgacatc gaccgtcgcg gaagagagta ctctagtgaa ctgggtgctg 3120
tcggctaccg cggtcacttt gaaggcgtgg atcgtaaggt attcgataat aagatgccgc 3180
atagcgacat cgtcatcgat aagaagaacg tgtttcaacg gctcaccttt caatctaaaa 3240
tctgaaccct tgttcacagc gcttgagaaa ttttcacgtg aaggatgtac aatcatctcc 3300
agctaaatgg gcagttcgtc agaattgcgg ctgaccgcgg atgacgaaaa tgcgaaccaa 3360
gtatttcaat tttatgacaa aagttctcaa tcgttgttac aagtgaaacg cttcgaggtt 3420
acagctacta ttgattaagg agatcgccta tggtctcgcc ccggcgtcgt gcgtccgccg 3480
cgagccagat ctcgcctact tcataaacgt cctcataggc acggaatgga atgatgacat 3540
cgatcgccgt agagagcatg tcaatcagtg tgcgatcttc caagctagca ccttgggcgc 3600
tacttttgac aagggaaaac agtttcttga atccttggat tggattcgcg ccgtgtattg 3660
ttgaaatcga tcccggatgt cccgagacga cttcactcag ataagcccat gctgcatcgt 3720
cgcgcatctc gccaagcaat atccggtccg gccgcatacg cagacttgct tggagcaagt 3780
gctcggcgct cacagcaccc agcccagcac cgttcttgga gtagagtagt ctaacatgat 3840
tatcgtgtgg aatgacgagt tcgagcgtat cttctatggt gattagcctt tcctgggggg 3900
ggatggcgct gatcaaggtc ttgctcattg ttgtcttgcc gcttccggta gggccacata 3960
gcaacatcgt cagtcggctg acgacgcatg cgtgcagaaa cgcttccaaa tccccgttgt 4020
caaaatgctg aaggatagct tcatcatcct gattttggcg tttccttcgt gtctgccact 4080
ggttccacct cgaagcatca taacgggagg agacttcttt aagaccagaa acacgcgagc 4140
ttggccgtcg aatggtcaag ctgacggtgc ccgagggaac ggtcggcggc agacagattt 4200
gtagtcgttc accaccagga agttcagtgg cgcagagggg gttacgtggt ccgacatcct 4260
gctttctcag cgcgcccgct aaaatagcga tatcttcaag atcatcataa gagacgggca 4320
aaggcatctt ggtaaaaatg ccggcttggc gcacaaatgc ctctccaggt cgattgatcg 4380
caatttcttc agtcttcggg tcatcgagcc attccaaaat cggcttcaga agaaagcgta 4440
gttgcggatc cacttccatt tacaatgtat cctatctcta agcggaaatt tgaattcatt 4500
aagagcggcg gttcctcccc cgcgtggcgc cgccagtcag gcggagctgg taaacaccaa 4560
agaaatcgag gtcccgtgct acgaaaatgg aaacggtgtc accctgattc ttcttcaggg 4620
ttggcggtat gttgatggtt gccttaaggg ctgtctcagt tgtctgctca ccgttatttt 4680
gaaagctgtt gaagctcatc ccgccacccg agctgccggc gtaggtgcta gctgcctgga 4740
aggcgccttg aacaacactc aagagcatag ctccgctaaa acgctgccag aagtggctgt 4800
cgaccgagcc cggcaatcct gagcgaccga gttcgtccgc gcttggcgat gttaacgaga 4860
tcatcgcatg gtcaggtgtc tcggcgcgat cccacaacac aaaaacgcgc ccatctccct 4920
gttgcaagcc acgctgtatt tcgccaacaa cggtggtgcc acgatcaaga agcacgatat 4980
tgttcgttgt tccacgaata tcctgaggca agacacactt tacatagcct gccaaatttg 5040

-continued

```
tgtcgattgc ggtttgcaag atgcacggaa ttattgtccc ttgcgttacc ataaaatcgg   5100
ggtgcggcaa gagcgtggcg ctgctgggct gcagctcggt gggtttcata cgtatcgaca   5160
aatcgttctc gccggacact tcgccattcg gcaaggagtt gtcgtcacgc ttgccttctt   5220
gtcttcggcc cgtgtcgccc tgaatggcgc gtttgctgac cccttgatcg ccgctgctat   5280
atgcaaaaat cggtgtttct tccggccgtg gctcatgccg ctccggttcg cccctcggcg   5340
gtagaggagc agcaggctga acagcctctt gaaccgctgg aggatccggc ggcacctcaa   5400
tcggagctgg atgaaatggc ttggtgtttg ttgcgatcaa agttgacggc gatgcgttct   5460
cattcacctt cttttggcgc ccacctagcc aaatgaggct taatgataac gcgagaacga   5520
cacctccgac gatcaatttc tgagaccccg aaagacgccg gcgatgtttg tcggagacca   5580
gggatccaga tgcatcaacc tcatgtgccg cttgctgact atcgttattc atcccttcgc   5640
ccccttcagg acgcgtttca catcgggcct caccgtgccc gtttgcggcc tttggccaac   5700
gggatcgtaa gcggtgttcc agatacatag tactgtgtgg ccatccctca gacgccaacc   5760
tcgggaaacc gaagaaatct cgacatcgct ccctttaact gaatagttgg caacagcttc   5820
cttgccatca ggattgatgg tgtagatgga gggtatgcgt acattgcccg gaaagtggaa   5880
taccgtcgta aatccattgt cgaagacttc gagtggcaac agcgaacgat cgccttgggc   5940
gacgtagtgc caattactgt ccgccgcacc aagggctgtg acaggctgat ccaataaatt   6000
ctcagctttc cgttgatatt gtgcttccgc gtgtagtctg tccacaacag ccttctgttg   6060
tgcctccctt cgccgagccg ccgcatcgtc ggcggggtag gcgaattgga cgctgtaata   6120
gagatcgggc tgctctttat cgaggtggga cagagtcttg gaacttatac tgaaaacata   6180
acggcgcatc ccggagtcgc ttgcggttag cacgattact ggctgaggcg tgaggacctg   6240
gcttgccttg aaaaatagat aatttccccg cggtagggct gctagatctt tgctatttga   6300
aacggcaacc gctgtcaccg tttcgttcgt ggcgaatgtt acgaccaaag tagctccaac   6360
cgccgtcgag aggcgcacca cttgatcggg attgtaagcc aaataacgca tgcgcggatc   6420
tagcttgccc gccattggag tgtcttcagc ctccgcacca gtcgcagcgg caaataaaca   6480
tgctaaaatg aaaagtgctt ttctgatcat ggttcgctgt ggcctacgtt tgaaacggta   6540
tcttccgatg tctgatagga ggtgacaacc agacctgccg ggttggttag tctcaatctg   6600
ccgggcaagc tggtcacctt ttcgtagcga actgtcgcgg tccacgtact caccacaggc   6660
attttgccgt caacgacgag ggtcctttta tagcgaattt gctgcgtgct tggagttaca   6720
tcatttgaag cgatgtgctc gacctccacc ctgccgcgtt tgccaagaat gacttgaggc   6780
gaactgggat tgggatagtt gaagaattgc tggtaatcct ggcgcactgt tggggcactg   6840
aagttcgata ccaggtcgta ggcgtactga gcggtgtcgg catcataact ctcgcgcagg   6900
cgaacgtact cccacaatga ggcgttaacg acggcctcct cttgagttgc aggcaatcgc   6960
gagacagaca cctcgctgtc aacggtgccg tccggccgta tccatagata tacgggcaca   7020
agcctgctca acggcaccat tgtggctata gcgaacgctt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgccccacat tcagcgggaa gatcgggcct ttgcagctcg ctaatgtgtc   7320
gtttgtctgg cagccgctca aagcgacaac taggcacagc aggcaatact tcatagaatt   7380
ctccattgag gcgaattttt gcgcgaccta gcctcgctca acctgagcga agcgacggta   7440
```

```
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact ttcgtgagaa ttccaacggc   7800
gtcgtaaact ccgaaggcag accagagcgt gccgtaaagg acccactgtg ccccttggaa   7860
agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccggcctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgatttttct ggttgagcga agtcagtagt ccagtaacgc cgtaggccga   8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
gagttgcctt cttgtgcctc gcgtagtcga gttgcaaagc gcaccgtgtt ggcacgcccc   9180
gaaagcacgg cgacatattc acgcatatcc cgcagatcaa attcgcagat gacgcttcca   9240
ctttctcgtt taagaagaaa cttacggctg ccgaccgtca tgtcttcacg gatcgcctga   9300
aattcctttt cggtacattt cagtccatcg acataagccg atcgatctgc ggttggtgat   9360
ggatagaaaa tcttcgtcat acattgcgca accaagctgg ctcctagcgg cgattccaga   9420
acatgctctg gttgctgcgt tgccagtatt agcatcccgt tgttttttcg aacggtcagg   9480
aggaatttgt cgacgacagt cgaaaattta gggtttaaca aataggcgcg aaactcatcg   9540
cagctcatca caaaacggcg gccgtcgatc atggctccaa tccgatgcag gagatatgct   9600
gcagcgggag cgcatacttc ctcgtattcg agaagatgcg tcatgtcgaa gccggtaatc   9660
gacggatcta actttacttc gtcaacttcg ccgtcaaatg cccagccaag cgcatggccc   9720
cggcaccagc gttggagccg cgctcctgcg ccttcggcgg gcccatgcaa caaaaattca   9780
cgtaaccccg cgattgaacg catttgtgga tcaaacgaga gctgacgatg gataccacgg   9840
```

-continued

```
accagacggc ggttctcttc cggagaaatc ccaccccgac catcactctc gatgagagcc   9900

acgatccatt cgcgcagaaa atcgtgtgag gctgctgtgt tttctaggcc acgcaacggc   9960

gccaacccgc tgggtgtgcc tctgtgaagt gccaaatatg ttcctcctgt ggcgcgaacc  10020

agcaattcgc caccccggtc cttgtcaaag aacacgaccg tacctgcacg gtcgaccatg  10080

ctctgttcga gcatggctag aacaaacatc atgagcgtcg tcttacccct cccgataggc  10140

ccgaatattg ccgtcatgcc aacatcgtgc tcatgcggga tatagtcgaa aggcgttccg  10200

ccattggtac gaaatcgggc aatcgcgttg ccccagtggc ctgagctggc gccctctgga  10260

aagttttcga aagagacaaa ccctgcgaaa ttgcgtgaag tgattgcgcc agggcgtgtg  10320

cgccacttaa aattccccgg caattgggac caataggccg cttccatacc aataccttct  10380

tggacaacca cggcacctgc atccgccatt cgtgtccgag cccgcgcgcc cctgtcccca  10440

agactattga gatcgtctgc atagacgcaa aggctcaaat gatgtgagcc cataacgaat  10500

tcgttgctcg caagtgcgtc ctcagcctcg gataatttgc cgatttgagt cacggcttta  10560

tcgccggaac tcagcatctg gctcgatttg aggctaagtt tcgcgtgcgc ttgcgggcga  10620

gtcaggaacg aaaaactctg cgtgagaaca agtggaaaat cgagggatag cagcgcgttg  10680

agcatgcccg gccgtgtttt tgcagggtat tcgcgaaacg aatagatgga tccaacgtaa  10740

ctgtcttttg gcgttctgat ctcgagtcct cgcttgccgc aaatgactct gtcggtataa  10800

atcgaagcgc cgagtgagcc gctgacgacc ggaaccggtg tgaaccgacc agtcatgatc  10860

aaccgtagcg cttcgccaat ttcggtgaag agcacaccct gcttctcgcg gatgccaaga  10920

cgatgcaggc catacgcttt aagagagcca gcgacaacat gccaaagatc ttccatgttc  10980

ctgatctggc ccgtgagatc gttttccctt tttccgctta gcttggtgaa cctcctcttt  11040

accttcccta aagccgcctg tgggtagaca atcaacgtaa ggaagtgttc attgcggagg  11100

agttggccgg agagcacgcg ctgttcaaaa gcttcgttca ggctagcggc gaaaacacta  11160

cggaagtgtc gcggcgccga tgatggcacg tcggcatgac gtacgaggtg agcatatatt  11220

gacacatgat catcagcgat attgcgcaac agcgtgttga acgcacgaca acgcgcattg  11280

cgcatttcag tttcctcaag ctcgaatgca acgccatcaa ttctcgcaat ggtcatgatc  11340

gatccgtctt caagaaggac gatatggtcg ctgaggtggc caatataagg gagatagatc  11400

tcaccggatc tttcggtcgt tccactcgcg ccgagcatca caccattcct ctccctcgtg  11460

ggggaaccct aattggattt gggctaacag tagcgccccc ccaaactgca ctatcaatgc  11520

ttcttcccgc ggtccgcaaa aatagcagga cgacgctcgc cgcattgtag tctcgctcca  11580

cgatgagccg ggctgcaaac cataacggca cgagaacgac ttcgtagagc gggttctgaa  11640

cgataacgat gacaaagccg gcgaacatca tgaataaccc tgccaatgtc agtggcaccc  11700

caagaaacaa tgcgggccgt gtggctgcga ggtaaagggt cgattcttcc aaacgatcag  11760

ccatcaacta ccgccagtga gcgtttggcc gaggaagctc gccccaaaca tgataacaat  11820

gccgccgacg acgccggcaa ccagcccaag cgaagcccgc ccgaacatcc aggagatccc  11880

gatagcgaca atgccgagaa cagcgagtga ctggccgaac ggaccaagga taaacgtgca  11940

tatattgtta accattgtgg cggggtcagt gccgccaccc gcagattgcg ctgcggcggg  12000

tccggatgag gaaatgctcc atgcaattgc accgcacaag cttggggcgc agctcgatat  12060

cacgcgcatc atcgcattcg agagcgagag gcgatttaga tgtaaacggt atctctcaaa  12120

gcatcgcatc aatgcgcacc tccttagtat aagtcgaata agacttgatt gtcgtctgcg  12180

gatttgccgt tgtcctggtg tggcggtggc ggagcgatta aaccgccagc gccatcctcc  12240
```

-continued

```
tgcgagcggc gctgatatga cccccaaaca tcccacgtct cttcggattt tagcgcctcg  12300
tgatcgtctt ttggaggctc gattaacgcg ggcaccagcg attgagcagc tgtttcaact  12360
tttcgcacgt agccgtttgc aaaaccgccg atgaaattac cggtgttgta agcggagatc  12420
gcccgacgaa gcgcaaattg cttctcgtca atcgtttcgc cgcctgcata acgacttttc  12480
agcatgtttg cagcggcaga taatgatgtg cacgcctgga gcgcaccgtc aggtgtcaga  12540
ccgagcatag aaaaatttcg agagtttatt tgcatgaggc caacatccag cgaatgccgt  12600
gcatcgagac ggtgcctgac gacttgggtt gcttggctgt gatcttgcca gtgaagcgtt  12660
tcgccggtcg tgttgtcatg aatcgctaaa ggatcaaagc gactctccac cttagctatc  12720
gccgcaagcg tagatgtcgc aactgatggg gcacacttgc gagcaacatg gtcaaactca  12780
gcagatgaga gtggcgtggc aaggctcgac gaacagaagg agaccatcaa ggcaagagaa  12840
agcgaccccg atctcttaag cataccttat ctccttagct cgcaactaac accgcctctc  12900
ccgttggaag aagtgcgttg ttttatgttg aagattatcg ggagggtcgg ttactcgaaa  12960
attttcaatt gcttctttat gatttcaatt gaagcgagaa acctcgcccg gcgtcttgga  13020
acgcaacatg gaccgagaac cgcgcatcca tgactaagca accggatcga cctattcagg  13080
ccgcagttgg tcaggtcagg ctcagaacga aaatgctcgg cgaggttacg ctgtctgtaa  13140
acccattcga tgaacgggaa gcttccttcc gattgctctt ggcaggaata ttggcccatg  13200
cctgcttgcg ctttgcaaat gctcttatcg cgttggtatc atatgccttg tccgccagca  13260
gaaacgcact ctaagcgatt atttgtaaaa atgtttcggt catgcggcgg tcatgggctt  13320
gacccgctgt cagcgcaaga cggatcggtc aaccgtcggc atcgacaaca gcgtgaatct  13380
tggtggtcaa accgccacgg gaacgtccca tacagccatc gtcttgatcc cgctgtttcc  13440
cgtcgccgca tgttggtgga cgcggacaca ggaactgtca atcatgacga cattctatcg  13500
aaagccttgg aaatcacact cagaatatga tcccagacgt ctgcctcacg ccatcgtaca  13560
aagcgattgt agcaggttgt acaggaaccg tatcgatcag gaacgtctgc ccagggcggg  13620
cccgtccgga agcgccacaa gatgacattg atcacccgcg tcaacgcgcg gcacgcgacg  13680
cggcttattt gggaacaaag gactgaacaa cagtccattc gaaatcggtg acatcaaagc  13740
ggggacgggt tatcagtggc ctccaagtca agcctcaatg aatcaaaatc agaccgattt  13800
gcaaacctga tttatgagtg tgcggcctaa atgatgaaat cgtccttcta gatcgcctcc  13860
gtggtgtagc aacacctcgc agtatcgccg tgctgacctt ggccagggaa ttgactggca  13920
agggtgcttt cacatgaccg ctcttttggc cgcgatagat gatttcgttg ctgctttggg  13980
cacgtagaag gagagaagtc atatcggaga aattcctcct ggcgcgagag cctgctctat  14040
cgcgacggca tcccactgtc gggaacagac cggatcattc acgaggcgaa agtcgtcaac  14100
acatgcgtta taggcatctt cccttgaagg atgatcttgt tgctgccaat ctggaggtgc  14160
ggcagccgca ggcagatgcg atctcagcgc aacttgcggc aaaacatctc actcacctga  14220
aaaccactag cgagtctcgc gatcagacga aggcctttta cttaacgaca caatatccga  14280
tgtctgcatc acaggcgtcg ctatcccagt caatactaaa gcggtgcagg aactaaagat  14340
tactgatgac ttaggcgtgc cacgaggcct gagacgacgc gcgtagacag tttttgaaa  14400
tcattatcaa agtgatggcc tccgctgaag cctatcacct ctgcgccggt ctgtcggaga  14460
gatgggcaag cattattacg gtcttcgcgc ccgtacatgc attggacgat tgcagggtca  14520
atggatctga gatcatccag aggattgccg cccttacctt ccgtttcgag ttggagccag  14580
cccctaaatg agacgacata gtcgacttga tgtgacaatg ccaagagaga gatttgctta  14640
```

-continued

```
acccgatttt tttgctcaag cgtaagccta ttgaagcttg ccggcatgac gtccgcgccg  14700
aaagaatatc ctacaagtaa aacattctgc acaccgaaat gcttggtgta gacatcgatt  14760
atgtgaccaa gatccttagc agtttcgctt ggggaccgct ccgaccagaa ataccgaagt  14820
gaactgacgc caatgacagg aatcccttcc gtctgcagat aggtaccatc gatagatctg  14880
ctgcctcgcg cgtttcggtg atgacggtga aaacctctga cacatgcagc tcccggagac  14940
ggtcacagct tgtctgtaag cggatgccgg gagcagacaa gcccgtcagg gcgcgtcagc  15000
gggtgttggc gggtgtcggg gcgcagccat gacccagtca cgtagcgata gcggagtgta  15060
tactggctta actatgcggc atcagagcag attgtactga gagtgcacca tatgcggtgt  15120
gaaataccgc acagatgcgt aaggagaaaa taccgcatca ggcgctcttc cgcttcctcg  15180
ctcactgact cgctgcgctc ggtcgttcgg ctgcggcgag cggtatcagc tcactcaaag  15240
gcggtaatac ggttatccac agaatcaggg gataacgcag gaaagaacat gtgagcaaaa  15300
ggccagcaaa aggccaggaa ccgtaaaaag gccgcgttgc tggcgttttt ccataggctc  15360
cgcccccctg acgagcatca caaaaatcga cgctcaagtc agaggtggcg aaacccgaca  15420
ggactataaa gataccaggc gtttccccct ggaagctccc tcgtgcgctc tcctgttccg  15480
accctgccgc ttaccggata cctgtccgcc tttctccctt cgggaagcgt ggcgctttct  15540
catagctcac gctgtaggta tctcagttcg gtgtaggtcg ttcgctccaa gctgggctgt  15600
gtgcacgaac cccccgttca gcccgaccgc tgcgccttat ccggtaacta tcgtcttgag  15660
tccaacccgg taagacacga cttatcgcca ctggcagcag ccactggtaa caggattagc  15720
agagcgaggt atgtaggcgg tgctacagag ttcttgaagt ggtggcctaa ctacggctac  15780
actagaagga cagtatttgg tatctgcgct ctgctgaagc cagttacctt cggaaaaaga  15840
gttggtagct cttgatccgg caaacaaacc accgctggta gcggtggttt ttttgtttgc  15900
aagcagcaga ttacgcgcag aaaaaaagga tctcaagaag atcctttgat cttttctacg  15960
gggtctgacg ctcagtggaa cgaaaactca cgttaaggga ttttggtcat gagattatca  16020
aaaaggatct tcacctagat ccttttaaat taaaaatgaa gttttaaatc aatctaaagt  16080
atatatgagt aaacttggtc tgacagttac caatgcttaa tcagtgaggc acctatctca  16140
gcgatctgtc tatttcgttc atccatagtt gcctgactcc ccgtcgtgta gataactacg  16200
atacgggagg gcttaccatc tggccccagt gctgcaatga taccgcgaga cccacgctca  16260
ccggctccag atttatcagc aataaaccag ccagccggaa gggccgagcg cagaagtggt  16320
cctgcaactt tatccgcctc catccagtct attaattgtt gccgggaagc tagagtaagt  16380
agttcgccag ttaatagttt gcgcaacgtt gttgccattg ctgcaggggg gggggggggg  16440
gggttccatt gttcattcca cggacaaaaa cagagaaagg aaacgacaga ggccaaaaag  16500
ctcgctttca gcacctgtcg tttcctttct tttcagaggg tattttaaat aaaaacatta  16560
agttatgacg aagaagaacg gaaacgcctt aaaccggaaa attttcataa atagcgaaaa  16620
cccgcgaggt ccctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc cccccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
```

-continued

```
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
aggccctttc gtcttcaaga attggtcgac gatcttgctg cgttcggata ttttcgtgga  17640
gttcccgcca cagacccgga ttgaaggcga gatccagcaa ctcgcgccag atcatcctgt  17700
gacggaactt tggcgcgtga tgactggcca ggacgtcggc cgaaagagcg acaagcagat  17760
cacgcttttc gacagcgtcg gatttgcgat cgaggatttt tcggcgctgc gctacgtccg  17820
cgaccgcgtt gagggatcaa gccacagcag cccactcgac cttctagccg acccagacga  17880
gccaagggat ctttttggaa tgctgctccg tcgtcaggct ttccgacgtt tgggtggttg  17940
aacagaagtc attatcgtac ggaatgccaa gcactcccga ggggaaccct gtggttggca  18000
tgcacataca aatggacgaa cggataaacc ttttcacgcc cttttaaata tccgttattc  18060
taataaacgc tcttttctct taggtttacc cgccaatata tcctgtcaaa cactgatagt  18120
ttaaactgaa ggcgggaaac gacaatctga tcatgagcgg agaattaagg gagtcacgtt  18180
atgacccccg ccgatgacgc gggacaagcc gttttacgtt tggaactgac agaaccgcaa  18240
cgttgaagga gccactcagc aagctggtac gattgtaata cgactcacta tagggcgaat  18300
tgagcgctgt ttaaacgctc ttcaactgga agagcggtta cccggaccga agcttgcatg  18360
cctgcagtgc agcgtgaccc ggtcgtgccc ctctctagag ataatgagca ttgcatgtct  18420
aagttataaa aaattaccac atattttttt tgtcacactt gtttgaagtg cagtttatct  18480
atctttatac atatatttaa actttactct acgaataata taatctatag tactacaata  18540
atatcagtgt tttagagaat catataaatg aacagttaga catggtctaa aggacaattg  18600
agtattttga caacaggact ctacagtttt atctttttag tgtgcatgtg ttctcctttt  18660
tttttgcaaa tagcttcacc tatataatac ttcatccatt ttattagtac atccatttag  18720
ggtttagggt taatggtttt tatagactaa ttttttagt acatctattt tattctattt  18780
tagcctctaa attaagaaaa ctaaaactct attttagttt ttttatttaa taatttagat  18840
ataaaataga ataaaataaa gtgactaaaa attaaacaaa taccctttaa gaaattaaaa  18900
aaactaagga aacatttttc ttgtttcgag tagataatgc cagcctgtta aacgccgtcg  18960
acgagtctaa cggacaccaa ccagcgaacc agcagcgtcg cgtcgggcca agcgaagcag  19020
acggcacggc atctctgtcg ctgcctctgg acccctctcg agagttccgc tccaccgttg  19080
gacttgctcc gctgtcggca tccagaaatt gcgtggcgga gcggcagacg tgagccggca  19140
cggcaggcgg cctcctcctc ctctcacggc acggcagcta cgggggattc ctttcccacc  19200
gctccttcgc tttcccttcc tcgcccgccg taataaatag acacccctc cacaccctct  19260
ttccccaacc tcgtgttgtt cggagcgcac acacacacaa ccagatctcc cccaaatcca  19320
cccgtcggca cctccgcttc aaggtacgcc gctcgtcctc cccccccccc cctctctacc  19380
ttctctagat cggcgttccg gtccatggtt agggcccggt agttctactt ctgttcatgt  19440
```

ttgtgttaga tccgtgtttg tgttagatcc gtgctgctag cgttcgtaca cggatgcgac 19500
ctgtacgtca gacacgttct gattgctaac ttgccagtgt ttctctttgg ggaatcctgg 19560
gatggctcta gccgttccgc agacgggatc gatttcatga tttttttgt ttcgttgcat 19620 agggtttggt ttgccctttt cctttatttc aatatatgcc gtgcacttgt ttgtcgggtc 19680
atcttttcat gcttttttt gtcttggttg tgatgatgtg gtctggttgg gcggtcgttc 19740
tagatcggag tagaattctg tttcaaacta cctggtggat ttattaattt tggatctgta 19800
tgtgtgtgcc atacatattc atagttacga attgaagatg atggatggaa atatcgatct 19860
aggataggta tacatgttga tgcgggtttt actgatgcat atacagagat gctttttgtt 19920
cgcttggttg tgatgatgtg gtgtggttgg gcggtcgttc attcgttcta gatcggagta 19980
gaatactgtt tcaaactacc tggtgtattt attaattttg gaactgtatg tgtgtgtcat 20040
acatcttcat agttacgagt ttaagatgga tggaaatatc gatctaggat aggtatacat 20100
gttgatgtgg gttttactga tgcatataca tgatggcata tgcagcatct attcatatgc 20160
tctaaccttg agtacctatc tattataata aacaagtatg ttttataatt attttgatct 20220
tgatatactt ggatgatggc atatgcagca gctatatgtg gattttttta gccctgcctt 20280
catacgctat ttatttgctt ggtactgttt cttttgtcga tgctcaccct gttgtttggt 20340
gttacttctg caggtcgact ctagaggatc tacaagtttg tacaaaaaag caggctccgc 20400
ggccgccccc ttcaccatga cgatggctcg tcctggggcg gctttgccgc tgctgctggt 20460
cgtggtcggc gcttgctgcg cgcgcctggc ggcggcagtg cacctctccg cgctcggcag 20520
gacactcatc gtcgaggcgt cgccgaaggc cggacaagtc ctgcacgccg gcgaggacac 20580
gataaccgtg acatggcacc tcaacgcgtc ggcgtccagc gtcgggtaca aggcgctgga 20640
ggtgaccctc tgctacgcgc cggcgagcca ggaggaccgc gggtggcgca aggccaacga 20700
cgacttgagc aaggacaagg cgtgccagtt caggatcgcc cggcatgcat acgccggcgg 20760
ccaggggacg ctccggtaca gggtcgcccg cgacgtcccc accgcgtcct accacgtgcg 20820
cgcctacgcg ctggacgcgt ccggggcgcc ggtgggctac ggccagaccg cgcccgccta 20880
ctacttccac gtcgcgggcg tctcgggcgt ccacgcgtcc ctccgggtcg ccgccgccgt 20940
gctctccgcg ttctccatcg ccgcgctcgc cttctttgtc gtcgtcgaga agaggaggaa 21000
ggacgagtag aagggtgggc gcgccgaccc agctttcttg tacaaagtgg tgttaaccta 21060
gacttgtcca tcttctggat tggccaactt aattaatgta tgaaataaaa ggatgcacac 21120
atagtgacat gctaatcact ataatgtggg catcaaagtt gtgtgttatg tgtaattact 21180
agttatctga ataaaagaga aagagatcat ccatatttct tatcctaaat gaatgtcacg 21240
tgtctttata attctttgat gaaccagatg catttcatta accaaatcca tatacatata 21300
aatattaatc atatataatt aatatcaatt gggttagcaa aacaaatcta gtctaggtgt 21360
gttttgcgaa ttgcggccgc caccgcggtg gagctcgaat tccggtccgg gtcacctttg 21420
tccaccaaga tggaactgcg gccgctcatt aattaagtca ggcgcgcctc tagttgaaga 21480
cacgttcatg tcttcatcgt aagaagacac tcagtagtct tcggccagaa tggccatctg 21540
gattcagcag gcctagaagg ccatttaaat cctgaggatc tggtcttcct aaggacccgg 21600
gcggtccgat taaactttaa ttcggaccga agcttgcatg cctgcagtgc agcgtgaccc 21660
ggtcgtgccc ctctctagag ataatgagca ttgcatgtct aagttataaa aaattaccac 21720
atattttttt tgtcacactt gtttgaagtg cagtttatct atctttatac atatatttaa 21780
actttactct acgaataata taatctatag tactacaata atatcagtgt tttagagaat 21840

-continued

```
catataaatg aacagttaga catggtctaa aggacaattg agtattttga caacaggact  21900
ctacagtttt atctttttag tgtgcatgtg ttctcctttt tttttgcaaa tagcttcacc  21960
tatataatac ttcatccatt ttattagtac atccatttag ggtttagggt taatggtttt  22020
tatagactaa ttttttagt acatctattt tattctattt tagcctctaa attaagaaaa  22080
ctaaaactct attttagttt ttttatttaa taatttagat ataaaataga ataaaataaa  22140
gtgactaaaa attaaacaaa taccctttaa gaaattaaaa aaactaagga aacatttttc  22200
ttgtttcgag tagataatgc cagcctgtta aacgccgtcg acgagtctaa cggacaccaa  22260
ccagcgaacc agcagcgtcg cgtcgggcca agcgaagcag acggcacggc atctctgtcg  22320
ctgcctctgg acccctctcg agagttccgc tccaccgttg gacttgctcc gctgtcggca  22380
tccagaaatt gcgtggcgga gcggcagacg tgagccggca cggcaggcgg cctcctcctc  22440
ctctcacggc accggcagct acgggggatt cctttcccac cgctccttcg ctttcccttc  22500
ctcgcccgcc gtaataaata gacaccccct ccacaccctc tttccccaac ctcgtgttgt  22560
tcggagcgca cacacacaca accagatctc ccccaaatcc acccgtcggc acctccgctt  22620
caaggtacgc cgctcgtcct cccccccccc cctctctacc ttctctagat cggcgttccg  22680
gtccatgcat ggttagggcc cggtagttct acttctgttc atgtttgtgt tagatccgtg  22740
tttgtgttag atccgtgctg ctagcgttcg tacacggatg cgacctgtac gtcagacacg  22800
ttctgattgc taacttgcca gtgtttctct ttggggaatc ctgggatggc tctagccgtt  22860
ccgcagacgg gatcgatttc atgatttttt ttgtttcgtt gcatagggtt tggtttgccc  22920
ttttccttta tttcaatata tgccgtgcac ttgtttgtcg ggtcatcttt tcatgctttt  22980
ttttgtcttg gttgtgatga tgtggtctgg ttgggcggtc gttctagatc ggagtagaat  23040
tctgtttcaa actacctggt ggatttatta attttggatc tgtatgtgtg tgccatacat  23100
attcatagtt acgaattgaa gatgatggat ggaaatatcg atctaggata ggtatacatg  23160
ttgatgcggg ttttactgat gcatatacag agatgctttt tgttcgcttg gttgtgatga  23220
tgtggtgtgg ttgggcggtc gttcattcgt tctagatcgg agtagaatac tgtttcaaac  23280
tacctggtgt atttattaat tttggaactg tatgtgtgtg tcatacatct tcatagttac  23340
gagtttaaga tggatggaaa tatcgatcta ggataggtat acatgttgat gtgggtttta  23400
ctgatgcata tacatgatgg catatgcagc atctattcat atgctctaac cttgagtacc  23460
tatctattat aataaacaag tatgttttat aattattttg atcttgatat acttggatga  23520
tggcatatgc agcagctata tgtggatttt tttagccctg ccttcatacg ctatttattt  23580
gcttggtact gtttcttttg tcgatgctca ccctgttgtt tggtgttact tctgcaggtc  23640
gactttaact tagcctagga tccacacgac accatgtccc ccgagcgccg ccccgtcgag  23700
atccgcccgg ccaccgccgc cgacatggcc gccgtgtgcg acatcgtgaa ccactacatc  23760
gagacctcca ccgtgaactt ccgcaccgag ccgcagaccc cgcaggagtg gatcgacgac  23820
ctggagcgcc tccaggaccg ctacccgtgg ctcgtggccg aggtggaggg cgtggtggcc  23880
ggcatcgcct acgccggccc gtggaaggcc cgcaacgcct acgactggac cgtggagtcc  23940
accgtgtacg tgtcccaccg ccaccagcgc ctcggcctcg gctccaccct ctacacccac  24000
ctcctcaaga gcatggaggc ccagggcttc aagtccgtgg tggccgtgat cggcctcccg  24060
aacgacccgt ccgtgcgcct ccacgaggcc ctcggctaca ccgcccgcgg caccctccgc  24120
gccgccggct acaagcacgg cggctggcac gacgtcggct tctggcagcg cgacttcgag  24180
ctgccggccc cgccgcgccc ggtgcgcccg gtgacgcaga tctgagtcga aacctagact  24240
```

-continued

```
tgtccatctt ctggattggc caacttaatt aatgtatgaa ataaaaggat gcacacatag  24300
tgacatgcta atcactataa tgtgggcatc aaagttgtgt gttatgtgta attactagtt  24360
atctgaataa aagagaaaga gatcatccat atttcttatc ctaaatgaat gtcacgtgtc  24420
tttataattc tttgatgaac cagatgcatt tcattaacca aatccatata catataaata  24480
ttaatcatat ataattaata tcaattgggt tagcaaaaca aatctagtct aggtgtgttt  24540
tgcgaattgc ggccgccacc gcggtggagc tcgaattcat tccgattaat cgtggcctct  24600
tgctcttcag gatgaagagc tatgtttaaa cgtgcaagcg ctactagaca attcagtaca  24660
ttaaaaacgt ccgcaatgtg ttattaagtt gtctaagcgt caatttgttt acaccacaat  24720
atatcctgcc accagccagc caacagctcc ccgaccggca gctcggcaca aaatcaccac  24780
tcgatacagg cagcccatca gtccgggacg gcgtcagcgg gagagccgtt gtaaggcggc  24840
agactttgct catgttaccg atgctattcg gaagaacggc aactaagctg ccgggtttga  24900
aacacggatg atctcgcgga gggtagcatg ttgattgtaa cgatgacaga gcgttgctgc  24960
ctgtgatcaa atatcatctc cctcgcagag atccgaatta tcagccttct tattcatttc  25020
tcgcttaacc gtgacaggct gtcgatcttg agaactatgc cgacataata ggaaatcgct  25080
ggataaagcc gctgaggaag ctgagtggcg ctatttcttt agaagtgaac gttgacgatc  25140
gtcgaccgta ccccgatgaa ttaattcgga cgtacgttct gaacacagct ggatacttac  25200
ttgggcgatt gtcatacatg acatcaacaa tgtacccgtt tgtgtaaccg tctcttggag  25260
gttcgtatga cactagtggt tcccctcagc ttgcgactag atgttgaggc ctaacatttt  25320
attagagagc aggctagttg cttagataca tgatcttcag gccgttatct gtcagggcaa  25380
gcgaaaattg gccatttatg acgaccaatg ccccgcagaa gctcccatct ttgccgccat  25440
agacgccgcg cccccctttt ggggtgtaga acatcctttt gccagatgtg gaaaagaagt  25500
tcgttgtccc attgttggca atgacgtagt agccggcgaa agtgcgagac ccatttgcgc  25560
tatatataag cctacgattt ccgttgcgac tattgtcgta attggatgaa ctattatcgt  25620
agttgctctc agagttgtcg taatttgatg gactattgtc gtaattgctt atggagttgt  25680
cgtagttgct tggagaaatg tcgtagttgg atggggagta gtcataggga agacgagctt  25740
catccactaa aacaattggc aggtcagcaa gtgcctgccc cgatgccatc gcaagtacga  25800
ggcttagaac caccttcaac agatcgcgca tagtcttccc cagctctcta acgcttgagt  25860
taagccgcgc cgcgaagcgg cgtcggcttg aacgaattgt tagacattat ttgccgacta  25920
ccttggtgat ctcgcctttc acgtagtgaa caaattcttc caactgatct gcgcgcgagg  25980
ccaagcgatc ttcttgtcca agataagcct gcctagcttc aagtatgacg ggctgatact  26040
gggccggcag gcgctccatt gcccagtcgg cagcgacatc cttcggcgcg attttgccgg  26100
ttactgcgct gtaccaaatg cgggacaacg taagcactac atttcgctca tcgccagccc  26160
agtcgggcgg cgagttccat agcgttaagg tttcatttag cgcctcaaat agatcctgtt  26220
caggaaccgg atcaaagagt tcctccgccg ctggacctac caaggcaacg ctatgttctc  26280
ttgcttttgt cagcaagata gccagatcaa tgtcgatcgt ggctggctcg aagatacctg  26340
caagaatgtc attgcgctgc cattctccaa attgcagttc gcgcttagct ggataacgcc  26400
acggaatgat gtcgtcgtgc acaacaatgg tgacttctac agcgcggaga atctcgctct  26460
ctccagggga agccgaagtt tccaaaaggt cgttgatcaa agctcgccgc gttgtttcat  26520
caagccttac agtcaccgta accagcaaat caatatcact gtgtggcttc aggccgccat  26580
ccactgcgga gccgtacaaa tgtacggcca gcaacgtcgg ttcgagatgg cgctcgatga  26640
```

-continued

```
cgccaactac ctctgatagt tgagtcgata cttcggcgat caccgcttcc ctcatgatgt  26700
ttaactcctg aattaagccg cgccgcgaag cggtgtcggc ttgaatgaat tgttaggcgt  26760
catcctgtgc tcccgagaac cagtaccagt acatcgctgt ttcgttcgag acttgaggtc  26820
tagttttata cgtgaacagg tcaatgccgc cgagagtaaa gccacatttt gcgtacaaat  26880
tgcaggcagg tacattgttc gtttgtgtct ctaatcgtat gccaaggagc tgtctgctta  26940
gtgcccactt tttcgcaaat tcgatgagac tgtgcgcgac tcctttgcct cggtgcgtgt  27000
gcgacacaac aatgtgttcg atagaggcta gatcgttcca tgttgagttg agttcaatct  27060
tcccgacaag ctcttggtcg atgaatgcgc catagcaagc agagtcttca tcagagtcat  27120
catccgagat gtaatccttc cggtaggggc tcacacttct ggtagatagt tcaaagcctt  27180
ggtcggatag gtgcacatcg aacacttcac gaacaatgaa atggttctca gcatccaatg  27240
tttccgccac ctgctcaggg atcaccgaaa tcttcatatg acgcctaacg cctggcacag  27300
cggatcgcaa acctggcgcg gcttttggca caaaaggcgt gacaggtttg cgaatccgtt  27360
gctgccactt gttaaccctt ttgccagatt tggtaactat aatttatgtt agaggcgaag  27420
tcttgggtaa aaactggcct aaaattgctg gggatttcag gaaagtaaac atcaccttcc  27480
ggctcgatgt ctattgtaga tatatgtagt gtatctactt gatcgggga tctgctgcct  27540
cgcgcgtttc ggtgatgacg gtgaaaacct ctgacacatg cagctcccgg agacggtcac  27600
agcttgtctg taagcggatg ccgggagcag acaagcccgt cagggcgcgt cagcgggtgt  27660
tggcgggtgt cggggcgcag ccatgaccca gtcacgtagc gatagcggag tgtatactgg  27720
cttaactatg cggcatcaga gcagattgta ctgagagtgc accatatgcg gtgtgaaata  27780
ccgcacagat gcgtaaggag aaaataccgc atcaggcgct cttccgcttc ctcgctcact  27840
gactcgctgc gctcggtcgt tcggctgcgg cgagcggtat cagctcactc aaaggcggta  27900
atacggttat ccacagaatc aggggataac gcaggaaaga acatgtgagc aaaaggccag  27960
caaaaggcca ggaaccgtaa aaaggccgcg ttgctggcgt ttttccatag gctccgcccc  28020
cctgacgagc atcacaaaaa tcgacgctca agtcagaggt ggcgaaaccc gacaggacta  28080
taaagatacc aggcgtttcc ccctggaagc tccctcgtgc gctctcctgt tccgaccctg  28140
ccgcttaccg gatacctgtc cgcctttctc ccttcgggaa gcgtggcgct ttctcatagc  28200
tcacgctgta ggtatctcag ttcggtgtag gtcgttcgct ccaagctggg ctgtgtgcac  28260
gaaccccccg ttcagcccga ccgctgcgcc ttatccggta actatcgtct tgagtccaac  28320
ccggtaagac acgacttatc gccactggca gcagccactg gtaacaggat tagcagagcg  28380
aggtatgtag gcggtgctac agagttcttg aagtggtggc ctaactacgg ctacactaga  28440
aggacagtat ttggtatctg cgctctgctg aagccagtta ccttcggaaa aagagttggt  28500
agctcttgat ccggcaaaca aaccaccgct ggtagcggtg gtttttttgt ttgcaagcag  28560
cagattacgc gcagaaaaaa aggatctcaa gaagatcctt tgatcttttc tacggggtct  28620
gacgctcagt ggaacgaaaa ctcacgttaa gggattttgg tcatgagatt atcaaaaagg  28680
atcttcacct agatcctttt aaattaaaaa tgaagtttta aatcaatcta aagtatatat  28740
gagtaaactt ggtctgacag ttaccaatgc ttaatcagtg aggcacctat ctcagcgatc  28800
tgtctatttc gttcatccat agttgcctga ctccccgtcg tgtagataac tacgatacgg  28860
gagggcttac catctggccc cagtgctgca atgataccgc gagacccacg ctcaccggct  28920
ccagatttat cagcaataaa ccagccagcc ggaagggccg agcgcagaag tggtcctgca  28980
actttatccg cctccatcca gtctattaat tgttgccggg aagctagagt aagtagttcg  29040
```

ccagttaata gtttgcgcaa cgttgttgcc attgctgcag gggggggggg ggggggggac 29100
ttccattgtt cattccacgg acaaaaacag agaaaggaaa cgacagaggc caaaaagcct 29160
cgctttcagc acctgtcgtt tcctttcttt tcagagggta ttttaaataa aaacattaag 29220
ttatgacgaa gaagaacgga aacgccttaa accggaaaat tttcataaat agcgaaaacc 29280
cgcgaggtcg ccgccccgta agccgccccg taacctgtcg gatcaccgga aaggacccgt 29340
aaagtgataa tgattatcat ctacatatca caacgtgcgt ggaggccatc aaaccacgtc 29400
aaataatcaa ttatgacgca ggtatcgtat taattgatct gcatcaactt aacgtaaaaa 29460
caacttcaga caatacaaat cagcgacact gaatacgggg caacctcatg tccccccccc 29520 cccccccccct gcaggcatcg tggtgtcacg ctcgtcgttt ggtatggctt cattcagctc 29580
cggttcccaa cgatcaaggc gagttacatg atcccccatg ttgtgcaaaa aagcggttag 29640
ctccttcggt cctccgatcg ttgtcagaag taagttggcc gcagtgttat cactcatggt 29700
tatggcagca ctgcataatt ctcttactgt catgccatcc gtaagatgct tttctgtgac 29760
tggtgagtac tcaaccaagt cattctgaga atagtgtatg cggcgaccga gttgctcttg 29820
cccggcgtca acacgggata ataccgcgcc acatagcaga actttaaaag tgctcatcat 29880
tggaaaacgt tcttcggggc gaaaactctc aaggatctta ccgctgttga gatccagttc 29940
gatgtaaccc actcgtgcac ccaactgatc ttcagcatct tttactttca ccagcgtttc 30000
tgggtgagca aaaacaggaa ggcaaaatgc cgcaaaaaag ggaataaggg cgacacggaa 30060
atgttgaata ctcatactct tcctttttca atattattga agcatttatc agggttattg 30120
tctcatgagc ggatacatat ttgaatgtat ttagaaaaat aaacaaatag gggttccgcg 30180
cacatttccc cgaaaagtgc cacctgacgt ctaagaaacc attattatca tgacattaac 30240
ctataaaaat aggcgtatca cgaggccctt tcgtcttcaa gaattcggag cttttgccat 30300
tctcaccgga ttcagtcgtc actcatggtg atttctcact tgataacctt atttttgacg 30360
aggggaaatt aataggttgt attgatgttg gacgagtcgg aatcgcagac cgataccagg 30420
atcttgccat cctatggaac tgcctcggtg agttttctcc ttcattacag aaacggcttt 30480
ttcaaaaata tggtattgat aatcctgata tgaataaatt gcagtttcat ttgatgctcg 30540
atgagttttt ctaatcagaa ttggttaatt ggttgtaaca ctggcagagc attacgctga 30600
cttgacggga cggcggcttt gttgaataaa tcgaactttt gctgagttga aggatcagat 30660
cacgcatctt cccgacaacg cagaccgttc cgtggcaaag caaaagttca aaatcaccaa 30720
ctggtccacc tacaacaaag ctctcatcaa ccgtggctcc ctcactttct ggctggatga 30780
tggggcgatt caggcctggt atgagtcagc aacaccttct tcacgaggca gacctcagcg 30840
ccagaaggcc gccagagagg ccgagcgcgg ccgtgaggct tggacgctag ggcagggcat 30900
gaaaaagccc gtagcgggct gctacgggcg tctgacgcgg tggaaagggg gaggggatgt 30960
tgtctacatg gctctgctgt agtgagtggg ttgcgctccg gcagcggtcc tgatcaatcg 31020
tcaccctttc tcggtccttc aacgttcctg acaacgagcc tccttttcgc caatccatcg 31080
acaatcaccg cgagtccctg ctcgaacgct gcgtccggac cggcttcgtc gaaggcgtct 31140
atcgcggccc gcaacagcgg cgagagcgga gcctgttcaa cggtgccgcc gcgctcgccg 31200
gcatcgctgt cgccggcctg ctcctcaagc acggccccaa cagtgaagta gctgattgtc 31260
atcagcgcat tgacggcgtc cccggccgaa aaacccgcct cgcagaggaa gcgaagctgc 31320
gcgtcggccg tttccatctg cggtgcgccc ggtcgcgtgc cggcatggat gcgcgcgcca 31380
tcgcggtagg cgagcagcgc ctgcctgaag ctgcgggcat tcccgatcag aaatgagcgc 31440

```
cagtcgtcgt cggctctcgg caccgaatgc gtatgattct ccgccagcat ggcttcggcc  31500
agtgcgtcga gcagcgcccg cttgttcctg aagtgccagt aaagcgccgg ctgctgaacc  31560
cccaaccgtt ccgccagttt gcgtgtcgtc agaccgtcta cgccgacctc gttcaacagg  31620
tccagggcgg cacggatcac tgtattcggc tgcaactttg tcatgcttga cactttatca  31680
ctgataaaca taatatgtcc accaacttat cagtgataaa gaatccgcgc gttcaatcgg  31740
accagcggag gctggtccgg aggccagacg tgaaacccaa catacccctg atcgtaattc  31800
tgagcactgt cgcgctcgac gctgtcggca tcggcctgat tatgccggtg ctgccgggcc  31860
tcctgcgcga tctggttcac tcgaacgacg tcaccgccca ctatggcatt ctgctggcgc  31920
tgtatgcgtt ggtgcaattt gcctgcgcac ctgtgctggg cgcgctgtcg gatcgtttcg  31980
ggcggcggcc aatcttgctc gtctcgctgg ccggcgccac tgtcgactac gccatcatgg  32040
cgacagcgcc tttcctttgg gttctctata tcgggcggat cgtggccggc atcaccgggg  32100
cgactggggc ggtagccggc gcttatattg ccgatatcac tgatggcgat gagcgcgcgc  32160
ggcacttcgg cttcatgagc gcctgtttcg ggttcgggat ggtcgcggga cctgtgctcg  32220
gtgggctgat gggcggtttc tccccccacg ctccgttctt cgccgcggca gccttgaacg  32280
gcctcaattt cctgacgggc tgtttccttt tgccggagtc gcacaaaggc gaacgccggc  32340
cgttacgccg ggaggctctc aacccgctcg cttcgttccg gtgggcccgg ggcatgaccg  32400
tcgtcgccgc cctgatggcg gtcttcttca tcatgcaact tgtcggacag gtgccggccg  32460
cgctttgggt cattttcggc gaggatcgct ttcactggga cgcgaccacg atcggcattt  32520
cgcttgccgc atttggcatt ctgcattcac tcgcccaggc aatgatcacc ggccctgtag  32580
ccgcccggct cggcgaaagg cgggcactca tgctcggaat gattgccgac ggcacaggct  32640
acatcctgct tgccttcgcg acacggggat ggatggcgtt cccgatcatg gtcctgcttg  32700
cttcgggtgg catcggaatg ccggcgctgc aagcaatgtt gtccaggcag gtggatgagg  32760
aacgtcaggg gcagctgcaa ggctcactgg cggcgctcac cagcctgacc tcgatcgtcg  32820
gacccctcct cttcacggcg atctatgcgg cttctataac aacgtggaac gggtgggcat  32880
ggattgcagg cgctgccctc tacttgctct gcctgccggc gctgcgtcgc gggctttgga  32940
gcggcgcagg gcaacgagcc gatcgctgat cgtggaaacg ataggcctat gccatgcggg  33000
tcaaggcgac ttccggcaag ctatacgcgc cctaggagtg cggttggaac gttggcccag  33060
ccagatactc ccgatcacga gcaggacgcc gatgatttga agcgcactca gcgtctgatc  33120
caagaacaac catcctagca acacggcggt ccccgggctg agaaagccca gtaaggaaac  33180
aactgtaggt tcgagtcgcg agatcccccg gaaccaaagg aagtaggtta aacccgctcc  33240
gatcaggccg agccacgcca ggccgagaac attggttcct gtaggcatcg ggattggcgg  33300
atcaaacact aaagctactg gaacgagcag aagtcctccg gccgccagtt gccaggcggt  33360
aaaggtgagc agaggcacgg gaggttgcca cttgcgggtc agcacggttc cgaacgccat  33420
ggaaaccgcc cccgccaggc ccgctgcgac gccgacagga tctagcgctg cgtttggtgt  33480
caacaccaac agcgccacgc ccgcagttcc gcaaatagcc cccaggaccg ccatcaatcg  33540
tatcgggcta cctagcagag cggcagagat gaacacgacc atcagcggct gcacagcgcc  33600
taccgtcgcc gcgaccccgc ccggcaggcg gtagaccgaa ataaacaaca agctccagaa  33660
tagcgaaata ttaagtgcgc cgaggatgaa gatgcgcatc caccagattc ccgttggaat  33720
ctgtcggacg atcatcacga gcaataaacc cgccggcaac gcccgcagca gcataccggc  33780
gacccctcgg cctcgctgtt cgggctccac gaaaacgccg gacagatgcg ccttgtgagc  33840
```

-continued

```
gtccttgggg ccgtcctcct gtttgaagac cgacagccca atgatctcgc cgtcgatgta  33900
ggcgccgaat gccacggcat ctcgcaaccg ttcagcgaac gcctccatgg gctttttctc  33960
ctcgtgctcg taaacggacc cgaacatctc tggagctttc ttcagggccg acaatcggat  34020
ctcgcggaaa tcctgcacgt cggccgctcc aagccgtcga atctgagcct taatcacaat  34080
tgtcaatttt aatcctctgt ttatcggcag ttcgtagagc gcgccgtgcg tcccgagcga  34140
tactgagcga agcaagtgcg tcgagcagtg cccgcttgtt cctgaaatgc cagtaaagcg  34200
ctggctgctg aacccccagc cggaactgac cccacaaggc cctagcgttt gcaatgcacc  34260
aggtcatcat tgacccaggc gtgttccacc aggccgctgc ctcgcaactc ttcgcaggct  34320
tcgccgacct gctcgcgcca cttcttcacg cgggtggaat ccgatccgca catgaggcgg  34380
aaggtttcca gcttgagcgg gtacggctcc cggtgcgagc tgaaatagtc gaacatccgt  34440
cgggccgtcg gcgacagctt gcggtacttc tcccatatga atttcgtgta gtggtcgcca  34500
gcaaacagca cgacgatttc ctcgtcgatc aggacctggc aacgggacgt tttcttgcca  34560
cggtccagga cgcggaagcg gtgcagcagc gacaccgatt ccaggtgccc aacgcggtcg  34620
gacgtgaagc ccatcgccgt cgcctgtagg cgcgacaggc attcctcggc cttcgtgtaa  34680
taccggccat tgatcgacca gcccaggtcc tggcaaagct cgtagaacgt gaaggtgatc  34740
ggctcgccga taggggtgcg cttcgcgtac tccaacacct gctgccacac cagttcgtca  34800
tcgtcggccc gcagctcgac gccggtgtag gtgatcttca cgtccttgtt gacgtggaaa  34860
atgaccttgt tttgcagcgc ctcgcgcggg attttcttgt tgcgcgtggt gaacagggca  34920
gagcgggccg tgtcgtttgg catcgctcgc atcgtgtccg gccacggcgc aatatcgaac  34980
aaggaaagct gcatttcctt gatctgctgc ttcgtgtgtt tcagcaacgc ggcctgcttg  35040
gcctcgctga cctgttttgc caggtcctcg ccggcggttt ttcgcttctt ggtcgtcata  35100
gttcctcgcg tgtcgatggt catcgacttc gccaaacctg ccgcctcctg ttcgagacga  35160
cgcgaacgct ccacggcggc cgatggcgcg ggcagggcag ggggagccag ttgcacgctg  35220
tcgcgctcga tcttggccgt agcttgctgg accatcgagc cgacggactg gaaggtttcg  35280
cggggcgcac gcatgacggt gcggcttgcg atggtttcgg catcctcggc ggaaaacccc  35340
gcgtcgatca gttcttgcct gtatgccttc cggtcaaacg tccgattcat tcaccctcct  35400
tgcgggattg ccccgactca cgccggggca atgtgccctt attcctgatt tgacccgcct  35460
ggtgccttgg tgtccagata atccacctta tcggcaatga agtcggtccc gtagaccgtc  35520
tggccgtcct tctcgtactt ggtattccga atcttgccct gcacgaatac cagcgacccc  35580
ttgcccaaat acttgccgtg ggcctcggcc tgagagccaa aacacttgat gcggaagaag  35640
tcggtgcgct cctgcttgtc gccggcatcg ttgcgccact cttcattaac cgctatatcg  35700
aaaattgctt gcggcttgtt agaattgcca tgacgtacct cggtgtcacg ggtaagatta  35760
ccgataaact ggaactgatt atggctcata tcgaaagtct ccttgagaaa ggagactcta  35820
gtttagctaa acattggttc cgctgtcaag aactttagcg gctaaaattt tgcgggccgc  35880
gaccaaaggt gcgaggggcg gcttccgctg tgtacaacca gatatttttc accaacatcc  35940
ttcgtctgct cgatgagcgg ggcatgacga aacatgagct gtcggagagg gcaggggttt  36000
caatttcgtt tttatcagac ttaaccaacg gtaaggccaa cccctcgttg aaggtgatgg  36060
aggccattgc cgacgccctg gaaactcccc tacctcttct cctggagtcc accgaccttg  36120
accgcgaggc actcgcggag attgcgggtc atcctttcaa gagcagcgtg ccgcccggat  36180
acgaacgcat cagtgtggtt ttgccgtcac ataaggcgtt tatcgtaaag aaatggggcg  36240
```

-continued

```
acgacacccg aaaaaagctg cgtggaaggc tctgacgcca agggttaggg cttgcacttc  36300
cttctttagc cgctaaaacg gccccttctc tgcgggccgt cggctcgcgc atcatatcga  36360
catcctcaac ggaagccgtg ccgcgaatgg catcgggcgg gtgcgctttg acagttgttt  36420
tctatcagaa cccctacgtc gtgcggttcg attagctgtt tgtcttgcag gctaaacact  36480
ttcggtatat cgtttgcctg tgcgataatg ttgctaatga tttgttgcgt aggggttact  36540
gaaaagtgag cgggaaagaa gagtttcaga ccatcaagga gcgggccaag cgcaagctgg  36600
aacgcgacat gggtgcggac ctgttggccg cgctcaacga cccgaaaacc gttgaagtca  36660
tgctcaacgc ggacggcaag gtgtggcacg aacgccttgg cgagccgatg cggtacatct  36720
gcgacatgcg gcccagccag tcgcaggcga ttatagaaac ggtggccgga ttccacggca  36780
aagaggtcac gcggcattcg cccatcctgg aaggcgagtt ccccttggat ggcagccgct  36840
ttgccggcca attgccgccg gtcgtggccg cgccaacctt tgcgatccgc aagcgcgcgg  36900
tcgccatctt cacgctggaa cagtacgtcg aggcgggcat catgacccgc gagcaatacg  36960
aggtcattaa aagcgccgtc gcggcgcatc gaaacatcct cgtcattggc ggtactggct  37020
cgggcaagac cacgctcgtc aacgcgatca tcaatgaaat ggtcgccttc aacccgtctg  37080
agcgcgtcgt catcatcgag gacaccggcg aaatccagtg cgccgcagag aacgccgtcc  37140
aataccacac cagcatcgac gtctcgatga cgctgctgct caagacaacg ctgcgtatgc  37200
gccccgaccg catcctggtc ggtgaggtac gtggccccga agcccttgat ctgttgatgg  37260
cctggaacac cgggcatgaa ggaggtgccg ccaccctgca cgcaaacaac cccaaagcgg  37320
gcctgagccg gctcgccatg cttatcagca tgcacccgga ttcaccgaaa cccattgagc  37380
cgctgattgg cgaggcggtt catgtggtcg tccatatcgc caggacccct agcggccgtc  37440
gagtgcaaga aattctcgaa gttcttggtt acgagaacgg ccagtacatc accaaaaccc  37500
tgtaaggagt atttccaatg acaacggctg ttccgttccg tctgaccatg aatcgcggca  37560
ttttgttcta ccttgccgtg ttcttcgttc tcgctctcgc gttatccgcg catccggcga  37620
tggcctcgga aggcaccggc ggcagcttgc catatgagag ctggctgacg aacctgcgca  37680
actccgtaac cggcccggtg gccttcgcgc tgtccatcat cggcatcgtc gtcgccggcg  37740
gcgtgctgat cttcggcggc gaactcaacg ccttcttccg aaccctgatc ttcctggttc  37800
tggtgatggc gctgctggtc ggcgcgcaga acgtgatgag caccttcttc ggtcgtggtg  37860
ccgaaatcgc ggccctcggc aacggggcgc tgcaccaggt gcaagtcgcg gcggcggatg  37920
ccgtgcgtgc ggtagcggct ggacggctcg cctaatcatg gctctgcgca cgatccccat  37980
ccgtcgcgca ggcaaccgag aaaacctgtt catgggtggt gatcgtgaac tggtgatgtt  38040
ctcgggcctg atggcgtttg cgctgatttt cagcgcccaa gagctgcggg ccaccgtggt  38100
cggtctgatc ctgtggttcg gggcgctcta tgcgttccga atcatggcga aggccgatcc  38160
gaagatgcgg ttcgtgtacc tgcgtcaccg ccggtacaag ccgtattacc cggcccgctc  38220
gaccccgttc cgcgagaaca ccaatagcca agggaagcaa taccgatgat ccaagcaatt  38280
gcgattgcaa tcgcgggcct cggcgcgctt ctgttgttca tcctctttgc ccgcatccgc  38340
gcggtcgatg ccgaactgaa actgaaaaag catcgttcca aggacgccgg cctggccgat  38400
ctgctcaact acgccgctgt cgtcgatgac ggcgtaatcg tgggcaagaa cggcagcttt  38460
atggctgcct ggctgtacaa gggcgatgac aacgcaagca gcaccgacca gcagcgcgaa  38520
gtagtgtccg cccgcatcaa ccaggccctc gcgggcctgg gaagtgggtg gatgatccat  38580
gtggacgccg tgcggcgtcc tgctccgaac tacgcggagc ggggcctgtc ggcgttccct  38640
```

-continued

```
gaccgtctga cggcagcgat tgaagaagag cgctcggtct tgccttgctc gtcggtgatg  38700
tacttcacca gctccgcgaa gtcgctcttc ttgatggagc gcatggggac gtgcttggca  38760
atcacgcgca ccccccggcc gttttagcgg ctaaaaaagt catggctctg ccctcgggcg  38820
gaccacgccc atcatgacct tgccaagctc gtcctgcttc tcttcgatct tcgccagcag  38880
ggcgaggatc gtggcatcac cgaaccgcgc cgtgcgcggg tcgtcggtga gccagagttt  38940
cagcaggccg cccaggcggc ccaggtcgcc attgatgcgg gccagctcgc ggacgtgctc  39000
atagtccacg acgcccgtga ttttgtagcc ctggccgacg gccagcaggt aggccgacag  39060
gctcatgccg gccgccgccg ccttttcctc aatcgctctt cgttcgtctg gaaggcagta  39120
caccttgata ggtgggctgc ccttcctggt tggcttggtt tcatcagcca tccgcttgcc  39180
ctcatctgtt acgccggcgg tagccggcca gcctcgcaga gcaggattcc cgttgagcac  39240
cgccaggtgc gaataaggga cagtgaagaa ggaacacccg ctcgcgggtg ggcctacttc  39300
acctatcctg cccggctgac gccgttggat acaccaagga aagtctacac gaaccctttg  39360
gcaaaatcct gtatatcgtg cgaaaaagga tggatatacc gaaaaaatcg ctataatgac  39420
cccgaagcag ggttatgcag cggaaaagcg ctgcttccct gctgttttgt ggaatatcta  39480
ccgactggaa acaggcaaat gcaggaaatt actgaactga ggggacaggc gagagacgat  39540
gccaaagagc tacaccgacg agctggccga gtgggttgaa tcccgcgcgg ccaagaagcg  39600
ccggcgtgat gaggctgcgg ttgcgttcct ggcggtgagg gcggatgtcg aggcggcgtt  39660
agcgtccggc tatgcgctcg tcaccatttg ggagcacatg cgggaaacgg ggaaggtcaa  39720
gttctcctac gagacgttcc gctcgcacgc caggcggcac atcaaggcca agcccgccga  39780
tgtgcccgca ccgcaggcca aggctgcgga acccgcgccg gcacccaaga cgccggagcc  39840
acggcggccg aagcaggggg gcaaggctga aaagccggcc cccgctgcgg ccccgaccgg  39900
cttcaccttc aacccaacac cggacaaaaa ggatctactg taatggcgaa aattcacatg  39960
gttttgcagg gcaagggcgg ggtcggcaag tcggccatcg ccgcgatcat tgcgcagtac  40020
aagatggaca aggggcagac acccttgtgc atcgacaccg acccggtgaa cgcgacgttc  40080
gagggctaca aggccctgaa cgtccgccgg ctgaacatca tggccggcga cgaaattaac  40140
tcgcgcaact tcgacaccct ggtcgagctg attgcgccga ccaaggatga cgtggtgatc  40200
gacaacggtg ccagctcgtt cgtgcctctg tcgcattacc tcatcagcaa ccaggtgccg  40260
gctctgctgc aagaaatggg gcatgagctg gtcatccata ccgtcgtcac cggcggccag  40320
gctctcctgg acacggtgag cggcttcgcc cagctcgcca gccagttccc ggccgaagcg  40380
cttttcgtgg tctggctgaa cccgtattgg gggcctatcg agcatgaggg caagagcttt  40440
gagcagatga aggcgtacac ggccaacaag gcccgcgtgt cgtccatcat ccagattccg  40500
gccctcaagg aagaaaccta cggccgcgat ttcagcgaca tgctgcaaga gcggctgacg  40560
ttcgaccagg cgctggccga tgaatcgctc acgatcatga cgcggcaacg cctcaagatc  40620
gtgcggcgcg gcctgtttga acagctcgac gcggcggccg tgctatgagc gaccagattg  40680
aagagctgat ccgggagatt gcggccaagc acggcatcgc cgtcggccgc gacgacccgg  40740
tgctgatcct gcataccatc aacgcccggc tcatggccga cagtgcggcc aagcaagagg  40800
aaatccttgc cgcgttcaag gaagagctgg aagggatcgc ccatcgttgg ggcgaggacg  40860
ccaaggccaa agcggagcgg atgctgaacg cggccctggc ggccagcaag gacgcaatgg  40920
cgaaggtaat gaaggacagc gccgcgcagg cggccgaagc gatccgcagg gaaatcgacg  40980
acggccttgg ccgccagctc gcggccaagg tcgcggacgc gcggcgcgtg gcgatgatga  41040
```

-continued

```
acatgatcgc cggcggcatg gtgttgttcg cggccgccct ggtggtgtgg gcctcgttat  41100
gaatcgcaga ggcgcagatg aaaaagcccg gcgttgccgg gctttgtttt tgcgttagct  41160
gggcttgttt gacaggccca agctctgact gcgcccgcgc tcgcgctcct gggcctgttt  41220
cttctcctgc tcctgcttgc gcatcagggc ctggtgccgt cgggctgctt cacgcatcga  41280
atcccagtcg ccggccagct cgggatgctc cgcgcgcatc ttgcgcgtcg ccagttcctc  41340
gatcttgggc gcgtgaatgc ccatgccttc cttgatttcg cgcaccatgt ccagccgcgt  41400
gtgcagggtc tgcaagcggg cttgctgttg ggcctgctgc tgctgccagg cggcctttgt  41460
acgcggcagg gacagcaagc cgggggcatt ggactgtagc tgctgcaaac gcgcctgctg  41520
acggtctacg agctgttcta ggcggtcctc gatgcgctcc acctggtcat gctttgcctg  41580
cacgtagagc gcaagggtct gctggtaggt ctgctcgatg ggcgcggatt ctaagagggc  41640
ctgctgttcc gtctcggcct cctgggccgc ctgtagcaaa tcctcgccgc tgttgccgct  41700
ggactgcttt actgccgggg actgctgttg ccctgctcgc gccgtcgtcg cagttcggct  41760
tgcccccact cgattgactg cttcatttcg agccgcagcg atgcgatctc ggattgcgtc  41820
aacggacggg gcagcgcgga ggtgtccggc ttctccttgg gtgagtcggt cgatgccata  41880
gccaaaggtt tccttccaaa atgcgtccat tgctggaccg tgtttctcat tgatgcccgc  41940
aagcatcttc ggcttgaccg ccaggtcaag cgcgccttca tgggcggtca tgacggacgc  42000
cgccatgacc ttgccgccgt tgttctcgat gtagccgcgt aatgaggcaa tggtgccgcc  42060
catcgtcagc gtgtcatcga caacgatgta cttctggccg gggatcacct cccccctcgaa  42120
agtcgggttg aacgccaggc gatgatctga accggctccg gttcgggcga ccttctcccg  42180
ctgcacaatg tccgtttcga cctcaaggcc aaggcggtcg gccagaacga ccgccatcat  42240
ggccggaatc ttgttgttcc ccgccgcctc gacggcgagg actggaacga tgcggggctt  42300
gtcgtcgccg atcagcgtct tgagctgggc aacagtgtcg tccgaaatca ggcgctcgac  42360
caaattaagc gccgcttccg cgtcgccctg cttcgcagcc tggtattcag gctcgttggt  42420
caaagaacca aggtcgccgt tgcgaaccac cttcgggaag tctccccacg gtgcgcgctc  42480
ggctctgctg tagctgctca agacgcctcc ctttttagcc gctaaaactc taacgagtgc  42540
gcccgcgact caacttgacg ctttcggcac ttacctgtgc cttgccactt gcgtcatagg  42600
tgatgctttt cgcactcccg atttcaggta ctttatcgaa atctgaccgg gcgtgcatta  42660
caaagttctt ccccacctgt tggtaaatgc tgccgctatc tgcgtggacg atgctgccgt  42720
cgtggcgctg cgacttatcg gccttttggg ccatatagat gttgtaaatg ccaggtttca  42780
gggccccggc tttatctacc ttctggttcg tccatgcgcc ttggttctcg gtctggacaa  42840
ttctttgccc attcatgacc aggaggcggt gtttcattgg gtgactcctg acggttgcct  42900
ctggtgttaa acgtgtcctg gtcgcttgcc ggctaaaaaa aagccgacct cggcagttcg  42960
aggccggctt tccctagagc cgggcgcgtc aaggttgttc catctatttt agtgaactgc  43020
gttcgattta tcagttactt tcctcccgct ttgtgtttcc tcccactcgt ttccgcgtct  43080
agccgacccc tcaacatagc ggcctcttct tgggctgcct ttgcctcttg ccgcgcttcg  43140
tcacgctcgg cttgcaccgt cgtaaagcgc tcggcctgcc tggccgcctc ttgcgccgcc  43200
aacttccttt gctcctggtg ggcctcggcg tcggcctgcg ccttcgcttt caccgctgcc  43260
aactccgtgc gcaaactctc cgcttcgcgc ctggtggcgt cgcgctcgcc gcgaagcgcc  43320
tgcatttcct ggttggccgc gtccagggtc ttgcggctct cttctttgaa tgcgcgggcg  43380
tcctggtgag cgtagtccag ctcggcgcgc agctcctgcg ctcgacgctc cacctcgtcg  43440
```

-continued gcccgctgcg tcgccagcgc ggcccgctgc tcggctcctg ccagggcggt gcgtgcttcg 43500
gccagggctt gccgctggcg tgcggccagc tcggccgcct cggcggcctg ctgctctagc 43560
aatgtaacgc gcgcctgggc ttcttccagc tcgcgggcct gcgcctcgaa ggcgtcggcc 43620
agctccccgc gcacggcttc caactcgttg cgctcacgat cccagccggc ttgcgctgcc 43680
tgcaacgatt cattggcaag ggcctgggcg gcttgccaga gggcggccac ggcctggttg 43740
ccggcctgct gcaccgcgtc cggcacctgg actgccagcg gggcggcctg cgccgtgcgc 43800
tggcgtcgcc attcgcgcat gccggcgctg gcgtcgttca tgttgacgcg ggcggcctta 43860
cgcactgcat ccacggtcgg gaagttctcc cggtcgcctt gctcgaacag ctcgtccgca 43920
gccgcaaaaa tgcggtcgcg cgtctctttg ttcagttcca tgttggctcc ggtaattggt 43980
aagaataata atactcttac ctaccttatc agcgcaagag tttagctgaa cagttctcga 44040
cttaacggca ggttttttag cggctgaagg gcaggcaaaa aaagccccgc acggtcggcg 44100
ggggcaaagg gtcagcggga aggggattag cgggcgtcgg gcttcttcat gcgtcggggc 44160
cgcgcttctt gggatggagc acgacgaagc gcgcacgcgc atcgtcctcg gccctatcgg 44220
cccgcgtcgc ggtcaggaac ttgtcgcgcg ctaggtcctc cctggtgggc accaggggca 44280
tgaactcggc ctgctcgatg taggtccact ccatgaccgc atcgcagtcg aggccgcgtt 44340
ccttcaccgt ctcttgcagg tcgcggtacg cccgctcgtt gagcggctgg taacgggcca 44400
attggtcgta aatggctgtc ggccatgagc ggcctttcct gttgagccag cagccgacga 44460
cgaagccggc aatgcaggcc cctggcacaa ccaggccgac gccgggggca ggggatggca 44520
gcagctcgcc aaccaggaac cccgccgcga tgatgccgat gccggtcaac cagcccttga 44580
aactatccgg ccccgaaaca cccctgcgca ttgcctggat gctgcgccgg atagcttgca 44640
acatcaggag ccgtttcttt tgttcgtcag tcatggtccg ccctcaccag ttgttcgtat 44700
cggtgtcgga cgaactgaaa tcgcaagagc tgccggtatc ggtccagccg ctgtccgtgt 44760
cgctgctgcc gaagcacggc gaggggtccg cgaacgccgc agacggcgta tccggccgca 44820
gcgcatcgcc cagcatggcc ccggtcagcg agccgccggc caggtagccc agcatggtgc 44880
tgttggtcgc ccccggccacc agggccgacg tgacgaaatc gccgtcattc cctctggatt 44940
gttcgctgct cggcggggca gtgcgccgcg ccggcggcgt cgtggatggc tcgggttggc 45000
tggcctgcga cggccggcga aaggtgcgca gcagctcgtt atcgaccggc tgcggcgtcg 45060
gggccgccgc cttgcgctgc ggtcggtgtt ccttcttcgg ctcgcgcagc ttgaacagca 45120
tgatcgcgga aaccagcagc aacgccgcgc ctacgcctcc cgcgatgtag aacagcatcg 45180
gattcattct tcggtcctcc ttgtagcgga accgttgtct gtgcggcgcg ggtggcccgc 45240
gccgctgtct ttggggatca gccctcgatg agcgcgacca gtttcacgtc ggcaaggttc 45300
gcctcgaact cctggccgtc gtcctcgtac ttcaaccagg catagccttc cgccggcggc 45360
cgacggttga ggataaggcg ggcagggcgc tcgtcgtgct cgacctggac gatggccttt 45420
ttcagcttgt ccgggtccgg ctccttcgcg cccttttcct tggcgtcctt accgtcctgg 45480
tcgccgtcct cgccgtcctg gccgtcgccg gcctccgcgt cacgctcggc atcagtctgg 45540
ccgttgaagg catcgacggt gttgggatcg cggccccttct cgtccaggaa ctcgcgcagc 45600
agcttgaccg tgccgcgcgt gatttcctgg gtgtcgtcgt caagccacgc ctcgacttcc 45660
tccgggcgct tcttgaaggc cgtcaccagc tcgttcacca cggtcacgtc gcgcacgcgg 45720
ccggtgttga acgcatcggc gatcttctcc ggcaggtcca gcagcgtgac gtgctgggtg 45780
atgaacgccg gcgacttgcc gatttccttg gcgatatcgc ctttcttctt gcccttcgcc 45840

-continued agctcgcggc caatgaagtc ggcaatttcg cgcggggtca gctcgttgcg ttgcaggttc 45900
tcgataacct ggtcggcttc gttgtagtcg ttgtcgatga acgccgggat ggacttcttg 45960
ccggcccact tcgagccacg gtagcggcgg gcgccgtgat tgatgatata gcggcccggc 46020
tgctcctggt tctcgcgcac cgaaatgggt gacttcaccc cgcgctcttt gatcgtggca 46080
ccgatttccg cgatgctctc cggggaaaag ccggggttgt cggccgtccg cggctgatgc 46140
ggatcttcgt cgatcaggtc caggtccagc tcgatagggc cggaaccgcc ctgagacgcc 46200
gcaggagcgt ccaggaggct cgacaggtcg ccgatgctat ccaaccccag gccggacggc 46260
tgcgccgcgc ctgcggcttc ctgagcggcc gcagcggtgt ttttcttggt ggtcttggct 46320
tgagccgcag tcattgggaa atctccatct tcgtgaacac gtaatcagcc agggcgcgaa 46380
cctctttcga tgccttgcgc gcggccgttt tcttgatctt ccagaccggc acaccggatg 46440
cgagggcatc ggcgatgctg ctgcgcaggc caacggtggc cggaatcatc atcttggggt 46500
acgcggccag cagctcggct tggtggcgcg cgtggcgcgg attccgcgca tcgaccttgc 46560
tgggcaccat gccaaggaat tgcagcttgg cgttcttctg gcgcacgttc gcaatggtcg 46620
tgaccatctt cttgatgccc tggatgctgt acgcctcaag ctcgatgggg gacagcacat 46680
agtcggccgc gaagagggcg gccgccaggc cgacgccaag ggtcggggcc gtgtcgatca 46740
ggcacacgtc gaagccttgg ttcgccaggg ccttgatgtt cgccccgaac agctcgcggg 46800
cgtcgtccag cgacagccgt tcggcgttcg ccagtaccgg gttggactcg atgagggcga 46860
ggcgcgcggc ctggccgtcg ccggctgcgg gtgcggtttc ggtccagccg ccggcaggga 46920
cagcgccgaa cagcttgctt gcatgcaggc cggtagcaaa gtccttgagc gtgtaggacg 46980
cattgccctg gggtccaggg tcgatcacgg caacccgcaa gccgcgctcg aaaaagtcga 47040
aggcaagatg cacaagggtc gaagtcttgc cgacgccgcc tttctggttg gccgtgacca 47100
aagttttcat cgtttggttt cctgtttttt cttggcgtcc gcttcccact tccggacgat 47160
gtacgcctga tgttccggca gaaccgccgt tacccgcgcg tacccctcgg gcaagttctt 47220
gtcctcgaac gcggcccaca cgcgatgcac cgcttgcgac actgcgcccc tggtcagtcc 47280
cagcgacgtt gcgaacgtcg cctgtggctt cccatcgact aagacgcccc gcgctatctc 47340
gatggtctgc tgccccactt ccagcccctg gatcgcctcc tggaactggc tttcggtaag 47400
ccgtttcttc atggataaca cccataattt gctccgcgcc ttggttgaac atagcggtga 47460
cagccgccag cacatgagag aagtttagct aaacatttct cgcacgtcaa cacctttagc 47520
cgctaaaact cgtccttggc gtaacaaaac aaaagcccgg aaaccgggct ttcgtctctt 47580
gccgcttatg gctctgcacc cggctccatc accaacaggt cgcgcacgcg cttcactcgg 47640
ttgcggatcg acactgccag cccaacaaag ccggttgccg ccgccgccag gatcgcgccg 47700
atgatgccgg ccacaccggc catcgcccac caggtcgccg ccttccggtt ccattcctgc 47760
tggtactgct tcgcaatgct ggacctcggc tcaccatagg ctgaccgctc gatggcgtat 47820
gccgcttctc cccttggcgt aaaacccagc gccgcaggcg gcattgccat gctgcccgcc 47880
gctttcccga ccacgacgcg cgcaccaggc ttgcggtcca gaccttcggc cacggcgagc 47940
tgcgcaagga cataatcagc cgccgacttg gctccacgcg cctcgatcag ctcttgcact 48000
cgcgcgaaat ccttggcctc cacggccgcc atgaatcgcg cacgcggcga aggctccgca 48060
gggccggcgt cgtgatcgcc gccgagaatg cccttcacca agttcgacga cacgaaaatc 48120
atgctgacgg ctatcaccat catgcagacg gatcgcacga acccgctgaa ttgaacacga 48180
gcacggcacc cgcgaccact atgccaagaa tgcccaaggt aaaaattgcc ggccccgcca 48240
tgaagtccgt gaatgccccg acggccgaag tgaagggcag gccgccaccc aggccgccgc 48300
cctcactgcc cggcacctgg tcgctgaatg tcgatgccag cacctgcggc acgtcaatgc 48360
ttccgggcgt cgcgctcggg ctgatcgccc atcccgttac tgccccgatc ccggcaatgg 48420
caaggactgc cagcgctgcc atttttgggg tgaggccgtt cgcggccgag ggcgcagcc 48480 cctgggggga tgggaggccc gcgttagcgg gccgggaggg ttcgagaagg gggggcaccc 48540
cccttcggcg tgcgcggtca cgcgcacagg gcgcagccct ggttaaaaac aaggtttata 48600
aatattggtt taaaagcagg ttaaaagaca ggttagcggt ggccgaaaaa cgggcggaaa 48660
cccttgcaaa tgctggattt tctgcctgtg gacagcccct caaatgtcaa taggtgcgcc 48720
cctcatctgt cagcactctg cccctcaagt gtcaaggatc gcgcccctca tctgtcagta 48780
gtcgcgcccc tcaagtgtca ataccgcagg gcacttatcc ccaggcttgt ccacatcatc 48840
tgtgggaaac tcgcgtaaaa tcaggcgttt tcgccgattt gcgaggctgg ccagctccac 48900
gtcgccggcc gaaatcgagc ctgcccctca tctgtcaacg ccgcgccggg tgagtcggcc 48960
cctcaagtgt caacgtccgc ccctcatctg tcagtgaggg ccaagttttc cgcgaggtat 49020
ccacaacgcc ggcggccgcg gtgtctcgca cacggcttcg acggcgtttc tggcgcgttt 49080
gcagggccat agacggccgc cagcccagcg gcgagggcaa ccagcccggt gagcgtcgga 49140
aaggcgctgg aagccccgta gcgacgcgga gaggggcgag acaagccaag ggcgcaggct 49200
cgatgcgcag cacgacatag ccggttctcg caaggacgag aatttccctg cggtgcccct 49260
caagtgtcaa tgaaagtttc caacgcgagc cattcgcgag agccttgagt ccacgctaga 49320
tgagagcttt gttgtaggtg gaccagttgg tgattttgaa cttttgcttt gccacggaac 49380
ggtctgcgtt gtcgggaaga tgcgtgatct gatccttcaa ctcagcaaaa gttcgattta 49440
ttcaacaaag ccacgttgtg tctcaaaatc tctgatgtta cattgcacaa gataaaaata 49500
tatcatcatg aacaataaaa ctgtctgctt acataaacag taatacaagg ggtgttatga 49560
gccatattca acgggaaac 49579

<210> SEQ ID NO 95
<211> LENGTH: 49015
<212> TYPE: DNA
<213> ORGANISM: vector

<400> SEQUENCE: 95
gtcttgctcg actctagagc tcgttcctcg aggcctcgag gcctcgagga acggtacctg 60
cggggaagct tacaataatg tgtgttgtta agtcttgttg cctgtcatcg tctgactgac 120
tttcgtcata aatcccggcc tccgtaaccc agctttgggc aagctcacgg atttgatccg 180
gcggaacggg aatatcgaga tgccgggctg aacgctgcag ttccagcttt ccctttcggg 240
acaggtactc cagctgattg attatctgct gaagggtctt ggttccacct cctggcacaa 300
tgcgaatgat tacttgagcg cgatcgggca tccaattttc tcccgtcagg tgcgtggtca 360
agtgctacaa ggcacctttc agtaacgagc gaccgtcgat ccgtcgccgg gatacggaca 420
aaatggagcg cagtagtcca tcgagggcgg cgaaagcctc gccaaaagca atacgttcat 480
ctcgcacagc ctccagatcc gatcgagggt cttcggcgta ggcagataga agcatggata 540
cattgcttga gagtattccg atggactgaa gtatggcttc catcttttct cgtgtgtctg 600
catctatttc gagaaagccc ccgatgcggc gcaccgcaac gcgaattgcc atactatccg 660
aaagtcccag caggcgcgct tgataggaaa aggtttcata ctcggccgat cgcagacggg 720
cactcacgac cttgaaccct tcaactttca gggatcgatg ctggttgatg gtagtctcac 780

-continued

```
tcgacgtggc tctggtgtgt tttgacatag cttcctccaa agaaagcgga aggtctggat    840
actccagcac gaaatgtgcc cgggtagacg gatggaagtc tagccctgct caatatgaaa    900
tcaacagtac atttacagtc aatactgaat atacttgcta catttgcaat tgtcttataa    960
cgaatgtgaa ataaaaatag tgtaacaacg cttttactca tcgataatca caaaaacatt   1020
tatacgaaca aaaatacaaa tgcactccgg tttcacagga taggcgggat cagaatatgc   1080
aacttttgac gttttgttct ttcaaagggg gtgctggcaa aaccaccgca ctcatgggcc   1140
tttgcgctgc tttggcaaat gacggtaaac gagtggccct ctttgatgcc gacgaaaacc   1200
ggcctctgac gcgatggaga gaaaacgcct tacaaagcag tactgggatc ctcgctgtga   1260
agtctattcc gccgacgaaa tgccccttct tgaagcagcc tatgaaaatg ccgagctcga   1320
aggatttgat tatgcgttgg ccgatacgcg tggcggctcg agcgagctca acaacacaat   1380
catcgctagc tcaaacctgc ttctgatccc caccatgcta acgccgctcg acatcgatga   1440
ggcactatct acctaccgct acgtcatcga gctgctgttg agtgaaaatt tggcaattcc   1500
tacagctgtt ttgcgccaac gcgtcccggt cggccgattg acaacatcgc aacgcaggat   1560
gtcagagacg ctagagagcc ttccagttgt accgtctccc atgcatgaaa gagatgcatt   1620
tgccgcgatg aaagaacgcg gcatgttgca tcttacatta ctaaacacgg gaactgatcc   1680
gacgatgcgc ctcatagaga ggaatcttcg gattgcgatg gaggaagtcg tggtcatttc   1740
gaaactgatc agcaaaatct tggaggcttg aagatggcaa ttcgcaagcc cgcattgtcg   1800
gtcggcgaag cacggcggct tgctggtgct cgacccgaga tccaccatcc caacccgaca   1860
cttgttcccc agaagctgga cctccagcac ttgcctgaaa aagccgacga gaaagaccag   1920
caacgtgagc ctctcgtcgc cgatcacatt tacagtcccg atcgacaact taagctaact   1980
gtggatgccc ttagtccacc tccgtccccg aaaaagctcc aggtttttct ttcagcgcga   2040
ccgcccgcgc ctcaagtgtc gaaaacatat gacaacctcg ttcggcaata cagtccctcg   2100
aagtcgctac aaatgatttt aaggcgcgcg ttggacgatt tcgaaagcat gctggcagat   2160
ggatcatttc gcgtggcccc gaaaagttat ccgatccctt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg taggtttgag gccgctggcc gcgtcctcag tcaccttttg   2460
agccagataa ttaagagcca aatgcaattg gctcaggctg ccatcgtccc cccgtgcgaa   2520
acctgcacgt ccgcgtcaaa gaaataaccg gcacctcttg ctgtttttat cagttgaggg   2580
cttgacggat ccgcctcaag tttgcggcgc agccgcaaaa tgagaacatc tatactcctg   2640
tcgtaaacct cctcgtcgcg tactcgactg gcaatgagaa gttgctcgcg cgatagaacg   2700
tcgcggggtt tctctaaaaa cgcgaggaga agattgaact cacctgccgt aagtttcacc   2760
tcaccgccag cttcggacat caagcgacgt tgcctgagat taagtgtcca gtcagtaaaa   2820
caaaaagacc gtcggtcttt ggagcggaca acgttggggc gcacgcgcaa ggcaacccga   2880
atgcgtgcaa gaaactctct cgtactaaac ggcttagcga taaaatcact tgctcctagc   2940
tcgagtgcaa caactttatc cgtctcctca aggcggtcgc cactgataat tatgattgga   3000
atatcagact ttgccgccag atttcgaacg atctcaagcc catcttcacg acctaaattt   3060
agatcaacaa ccacgacatc gaccgtcgcg gaagagagta ctctagtgaa ctgggtgctg   3120
tcggctaccg cggtcacttt gaaggcgtgg atcgtaaggt attcgataat aagatgccgc   3180
```

-continued

```
atagcgacat cgtcatcgat aagaagaacg tgtttcaacg gctcaccttt caatctaaaa   3240
tctgaaccct tgttcacagc gcttgagaaa ttttcacgtg aaggatgtac aatcatctcc   3300
agctaaatgg gcagttcgtc agaattgcgg ctgaccgcgg atgacgaaaa tgcgaaccaa   3360
gtatttcaat tttatgacaa aagttctcaa tcgttgttac aagtgaaacg cttcgaggtt   3420
acagctacta ttgattaagg agatcgccta tggtctcgcc ccggcgtcgt gcgtccgccg   3480
cgagccagat ctcgcctact tcataaacgt cctcataggc acggaatgga atgatgacat   3540
cgatcgccgt agagagcatg tcaatcagtg tgcgatcttc caagctagca ccttgggcgc   3600
tacttttgac aagggaaaac agtttcttga atccttggat tggattcgcg ccgtgtattg   3660
ttgaaatcga tcccggatgt cccgagacga cttcactcag ataagcccat gctgcatcgt   3720
cgcgcatctc gccaagcaat atccggtccg gccgcatacg cagacttgct tggagcaagt   3780
gctcggcgct cacagcaccc agcccagcac cgttcttgga gtagagtagt ctaacatgat   3840
tatcgtgtgg aatgacgagt tcgagcgtat cttctatggt gattagcctt tcctgggggg   3900
ggatggcgct gatcaaggtc ttgctcattg ttgtcttgcc gcttccggta gggccacata   3960
gcaacatcgt cagtcggctg acgacgcatg cgtgcagaaa cgcttccaaa tccccgttgt   4020
caaaatgctg aaggatagct tcatcatcct gattttggcg tttccttcgt gtctgccact   4080
ggttccacct cgaagcatca taacgggagg agacttcttt aagaccagaa acacgcgagc   4140
ttggccgtcg aatggtcaag ctgacggtgc ccgagggaac ggtcggcggc agacagattt   4200
gtagtcgttc accaccagga agttcagtgg cgcagagggg gttacgtggt ccgacatcct   4260
gctttctcag cgcgcccgct aaaatagcga tatcttcaag atcatcataa gagacgggca   4320
aaggcatctt ggtaaaaatg ccggcttggc gcacaaatgc ctctccaggt cgattgatcg   4380
caatttcttc agtcttcggg tcatcgagcc attccaaaat cggcttcaga agaaagcgta   4440
gttgcggatc cacttccatt tacaatgtat cctatctcta agcggaaatt tgaattcatt   4500
aagagcggcg gttcctcccc cgcgtggcgc cgccagtcag gcggagctgg taaacaccaa   4560
agaaatcgag gtcccgtgct acgaaaatgg aaacggtgtc accctgattc ttcttcaggg   4620
ttggcggtat gttgatggtt gccttaaggg ctgtctcagt tgtctgctca ccgttatttt   4680
gaaagctgtt gaagctcatc ccgccacccg agctgccggc gtaggtgcta gctgcctgga   4740
aggcgccttg aacaacactc aagagcatag ctccgctaaa acgctgccag aagtggctgt   4800
cgaccgagcc cggcaatcct gagcgaccga gttcgtccgc gcttggcgat gttaacgaga   4860
tcatcgcatg gtcaggtgtc tcggcgcgat cccacaacac aaaaacgcgc ccatctccct   4920
gttgcaagcc acgctgtatt tcgccaacaa cggtggtgcc acgatcaaga agcacgatat   4980
tgttcgttgt tccacgaata tcctgaggca agacacactt tacatagcct gccaaatttg   5040
tgtcgattgc ggtttgcaag atgcacggaa ttattgtccc ttgcgttacc ataaaatcgg   5100
ggtgcggcaa gagcgtggcg ctgctgggct gcagctcggt gggtttcata cgtatcgaca   5160
aatcgttctc gccggacact tcgccattcg gcaaggagtt gtcgtcacgc ttgccttctt   5220
gtcttcggcc cgtgtcgccc tgaatggcgc gtttgctgac cccttgatcg ccgctgctat   5280
atgcaaaaat cggtgtttct tccggccgtg gctcatgccg ctccggttcg cccctcggcg   5340
gtagaggagc agcaggctga acagcctctt gaaccgctgg aggatccggc ggcacctcaa   5400
tcggagctgg atgaaatggc ttggtgtttg ttgcgatcaa agttgacggc gatgcgttct   5460
cattcacctt cttttggcgc ccacctagcc aaatgaggct taatgataac gcgagaacga   5520
cacctccgac gatcaatttc tgagaccccg aaagacgccg gcgatgtttg tcggagacca   5580
```

-continued

```
gggatccaga tgcatcaacc tcatgtgccg cttgctgact atcgttattc atcccttcgc   5640
ccccttcagg acgcgtttca catcgggcct caccgtgccc gtttgcggcc tttggccaac   5700
gggatcgtaa gcggtgttcc agatacatag tactgtgtgg ccatccctca gacgccaacc   5760
tcgggaaacc gaagaaatct cgacatcgct ccctttaact gaatagttgg caacagcttc   5820
cttgccatca ggattgatgg tgtagatgga gggtatgcgt acattgcccg gaaagtggaa   5880
taccgtcgta aatccattgt cgaagacttc gagtggcaac agcgaacgat cgccttgggc   5940
gacgtagtgc caattactgt ccgccgcacc aagggctgtg acaggctgat ccaataaatt   6000
ctcagctttc cgttgatatt gtgcttccgc gtgtagtctg tccacaacag ccttctgttg   6060
tgcctccctt cgccgagccg ccgcatcgtc ggcggggtag gcgaattgga cgctgtaata   6120
gagatcgggc tgctctttat cgaggtggga cagagtcttg gaacttatac tgaaaacata   6180
acggcgcatc ccggagtcgc ttgcggttag cacgattact ggctgaggcg tgaggacctg   6240
gcttgccttg aaaaatagat aatttccccg cggtagggct gctagatctt tgctatttga   6300
aacggcaacc gctgtcaccg tttcgttcgt ggcgaatgtt acgaccaaag tagctccaac   6360
cgccgtcgag aggcgcacca cttgatcggg attgtaagcc aaataacgca tgcgcggatc   6420
tagcttgccc gccattggag tgtcttcagc ctccgcacca gtcgcagcgg caaataaaca   6480
tgctaaaatg aaaagtgctt ttctgatcat ggttcgctgt ggcctacgtt tgaaacggta   6540
tcttccgatg tctgatagga ggtgacaacc agacctgccg ggttggttag tctcaatctg   6600
ccgggcaagc tggtcacctt ttcgtagcga actgtcgcgg tccacgtact caccacaggc   6660
attttgccgt caacgacgag ggtcctttta tagcgaattt gctgcgtgct tggagttaca   6720
tcatttgaag cgatgtgctc gacctccacc ctgccgcgtt tgccaagaat gacttgaggc   6780
gaactgggat tgggatagtt gaagaattgc tggtaatcct ggcgcactgt tggggcactg   6840
aagttcgata ccaggtcgta ggcgtactga gcggtgtcgg catcataact ctcgcgcagg   6900
cgaacgtact cccacaatga ggcgttaacg acggcctcct cttgagttgc aggcaatcgc   6960
gagacagaca cctcgctgtc aacggtgccg tccggccgta tccatagata tacgggcaca   7020
agcctgctca acggcaccat tgtggctata gcgaacgctt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgccccacat tcagcgggaa gatcgggcct ttgcagctcg ctaatgtgtc   7320
gtttgtctgg cagccgctca aagcgacaac taggcacagc aggcaatact tcatagaatt   7380
ctccattgag gcgaattttt gcgcgaccta gcctcgctca acctgagcga agcgacggta   7440
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact ttcgtgagaa ttccaacggc   7800
gtcgtaaact ccgaaggcag accagagcgt gccgtaaagg acccactgtg ccccttggaa   7860
agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
```

-continued

```
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccggcctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgatttttct ggttgagcga agtcagtagt ccagtaacgc cgtaggccga   8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
gagttgcctt cttgtgcctc gcgtagtcga gttgcaaagc gcaccgtgtt ggcacgcccc   9180
gaaagcacgg cgacatattc acgcatatcc cgcagatcaa attcgcagat gacgcttcca   9240
ctttctcgtt taagaagaaa cttacggctg ccgaccgtca tgtcttcacg gatcgcctga   9300
aattcctttt cggtacattt cagtccatcg acataagccg atcgatctgc ggttggtgat   9360
ggatagaaaa tcttcgtcat acattgcgca accaagctgg ctcctagcgg cgattccaga   9420
acatgctctg gttgctgcgt tgccagtatt agcatcccgt tgtttttttcg aacggtcagg   9480
aggaatttgt cgacgacagt cgaaaattta gggtttaaca aataggcgcg aaactcatcg   9540
cagctcatca caaaacggcg gccgtcgatc atggctccaa tccgatgcag gagatatgct   9600
gcagcgggag cgcatacttc ctcgtattcg agaagatgcg tcatgtcgaa gccggtaatc   9660
gacggatcta actttacttc gtcaacttcg ccgtcaaatg cccagccaag cgcatggccc   9720
cggcaccagc gttggagccg cgctcctgcg ccttcggcgg gcccatgcaa caaaaattca   9780
cgtaaccccg cgattgaacg catttgtgga tcaaacgaga gctgacgatg gataccacgg   9840
accagacggc ggttctcttc cggagaaatc ccaccccgac catcactctc gatgagagcc   9900
acgatccatt cgcgcagaaa atcgtgtgag gctgctgtgt tttctaggcc acgcaacggc   9960
gccaacccgc tgggtgtgcc tctgtgaagt gccaaatatg ttcctcctgt ggcgcgaacc  10020
agcaattcgc caccccggtc cttgtcaaag aacacgaccg tacctgcacg gtcgaccatg  10080
ctctgttcga gcatggctag aacaaacatc atgagcgtcg tcttacccct cccgataggc  10140
ccgaatattg ccgtcatgcc aacatcgtgc tcatgcggga tatagtcgaa aggcgttccg  10200
ccattggtac gaaatcgggc aatcgcgttg ccccagtggc ctgagctggc gccctctgga  10260
aagttttcga aagagacaaa ccctgcgaaa ttgcgtgaag tgattgcgcc agggcgtgtg  10320
cgccacttaa aattccccgg caattgggac caataggccg cttccatacc aataccttct  10380
```

-continued

```
tggacaacca cggcacctgc atccgccatt cgtgtccgag cccgcgcgcc cctgtcccca  10440
agactattga gatcgtctgc atagacgcaa aggctcaaat gatgtgagcc cataacgaat  10500
tcgttgctcg caagtgcgtc ctcagcctcg gataatttgc cgatttgagt cacggcttta  10560
tcgccggaac tcagcatctg gctcgatttg aggctaagtt tcgcgtgcgc ttgcgggcga  10620
gtcaggaacg aaaaactctg cgtgagaaca agtggaaaat cgagggatag cagcgcgttg  10680
agcatgcccg gccgtgtttt tgcagggtat tcgcgaaacg aatagatgga tccaacgtaa  10740
ctgtcttttg gcgttctgat ctcgagtcct cgcttgccgc aaatgactct gtcggtataa  10800
atcgaagcgc cgagtgagcc gctgacgacc ggaaccggtg tgaaccgacc agtcatgatc  10860
aaccgtagcg cttcgccaat ttcggtgaag agcacaccct gcttctcgcg gatgccaaga  10920
cgatgcaggc catacgcttt aagagagcca gcgacaacat gccaaagatc ttccatgttc  10980
ctgatctggc ccgtgagatc gttttccctt tttccgctta gcttggtgaa cctcctcttt  11040
accttcccta aagccgcctg tgggtagaca atcaacgtaa ggaagtgttc attgcggagg  11100
agttggccgg agagcacgcg ctgttcaaaa gcttcgttca ggctagcggc gaaaacacta  11160
cggaagtgtc gcggcgccga tgatggcacg tcggcatgac gtacgaggtg agcatatatt  11220
gacacatgat catcagcgat attgcgcaac agcgtgttga acgcacgaca acgcgcattg  11280
cgcatttcag tttcctcaag ctcgaatgca acgccatcaa ttctcgcaat ggtcatgatc  11340
gatccgtctt caagaaggac gatatggtcg ctgaggtggc caatataagg gagatagatc  11400
tcaccggatc tttcggtcgt tccactcgcg ccgagcatca caccattcct ctccctcgtg  11460
ggggaaccct aattggattt gggctaacag tagcgccccc ccaaactgca ctatcaatgc  11520
ttcttcccgc ggtccgcaaa aatagcagga cgacgctcgc cgcattgtag tctcgctcca  11580
cgatgagccg ggctgcaaac cataacggca cgagaacgac ttcgtagagc gggttctgaa  11640
cgataacgat gacaaagccg gcgaacatca tgaataaccc tgccaatgtc agtggcaccc  11700
caagaaacaa tgcgggccgt gtggctgcga ggtaaagggt cgattcttcc aaacgatcag  11760
ccatcaacta ccgccagtga gcgtttggcc gaggaagctc gccccaaaca tgataacaat  11820
gccgccgacg acgccggcaa ccagcccaag cgaagcccgc ccgaacatcc aggagatccc  11880
gatagcgaca atgccgagaa cagcgagtga ctggccgaac ggaccaagga taaacgtgca  11940
tatattgtta accattgtgg cggggtcagt gccgccaccc gcagattgcg ctgcggcggg  12000
tccggatgag gaaatgctcc atgcaattgc accgcacaag cttggggcgc agctcgatat  12060
cacgcgcatc atcgcattcg agagcgagag gcgatttaga tgtaaacggt atctctcaaa  12120
gcatcgcatc aatgcgcacc tccttagtat aagtcgaata agacttgatt gtcgtctgcg  12180
gatttgccgt tgtcctggtg tggcggtggc ggagcgatta aaccgccagc gccatcctcc  12240
tgcgagcggc gctgatatga cccccaaaca tcccacgtct cttcggattt tagcgcctcg  12300
tgatcgtctt ttggaggctc gattaacgcg ggcaccagcg attgagcagc tgtttcaact  12360
tttcgcacgt agccgtttgc aaaaccgccg atgaaattac cggtgttgta agcggagatc  12420
gcccgacgaa gcgcaaattg cttctcgtca atcgtttcgc cgcctgcata acgacttttc  12480
agcatgtttg cagcggcaga taatgatgtg cacgcctgga gcgcaccgtc aggtgtcaga  12540
ccgagcatag aaaaatttcg agagtttatt tgcatgaggc caacatccag cgaatgccgt  12600
gcatcgagac ggtgcctgac gacttgggtt gcttggctgt gatcttgcca gtgaagcgtt  12660
tcgccggtcg tgttgtcatg aatcgctaaa ggatcaaagc gactctccac cttagctatc  12720
gccgcaagcg tagatgtcgc aactgatggg gcacacttgc gagcaacatg gtcaaactca  12780
```

```
gcagatgaga gtggcgtggc aaggctcgac gaacagaagg agaccatcaa ggcaagagaa  12840
agcgaccccg atctcttaag cataccttat ctccttagct cgcaactaac accgcctctc  12900
ccgttggaag aagtgcgttg ttttatgttg aagattatcg ggagggtcgg ttactcgaaa  12960
attttcaatt gcttctttat gatttcaatt gaagcgagaa acctcgcccg gcgtcttgga  13020
acgcaacatg gaccgagaac cgcgcatcca tgactaagca accggatcga cctattcagg  13080
ccgcagttgg tcaggtcagg ctcagaacga aaatgctcgg cgaggttacg ctgtctgtaa  13140
acccattcga tgaacgggaa gcttccttcc gattgctctt ggcaggaata ttggcccatg  13200
cctgcttgcg ctttgcaaat gctcttatcg cgttggtatc atatgccttg tccgccagca  13260
gaaacgcact ctaagcgatt atttgtaaaa atgtttcggt catgcggcgg tcatgggctt  13320
gacccgctgt cagcgcaaga cggatcggtc aaccgtcggc atcgacaaca gcgtgaatct  13380
tggtggtcaa accgccacgg gaacgtccca tacagccatc gtcttgatcc cgctgtttcc  13440
cgtcgccgca tgttggtgga cgcggacaca ggaactgtca atcatgacga cattctatcg  13500
aaagccttgg aaatcacact cagaatatga tcccagacgt ctgcctcacg ccatcgtaca  13560
aagcgattgt agcaggttgt acaggaaccg tatcgatcag gaacgtctgc ccagggcggg  13620
cccgtccgga agcgccacaa gatgacattg atcacccgcg tcaacgcgcg gcacgcgacg  13680
cggcttattt gggaacaaag gactgaacaa cagtccattc gaaatcggtg acatcaaagc  13740
ggggacgggt tatcagtggc ctccaagtca agcctcaatg aatcaaaatc agaccgattt  13800
gcaaacctga tttatgagtg tgcggcctaa atgatgaaat cgtccttcta gatcgcctcc  13860
gtggtgtagc aacacctcgc agtatcgccg tgctgacctt ggccagggaa ttgactggca  13920
agggtgcttt cacatgaccg ctcttttggc cgcgatagat gatttcgttg ctgctttggg  13980
cacgtagaag gagagaagtc atatcggaga aattcctcct ggcgcgagag cctgctctat  14040
cgcgacggca tcccactgtc gggaacagac cggatcattc acgaggcgaa agtcgtcaac  14100
acatgcgtta taggcatctt cccttgaagg atgatcttgt tgctgccaat ctggaggtgc  14160
ggcagccgca ggcagatgcg atctcagcgc aacttgcggc aaaacatctc actcacctga  14220
aaaccactag cgagtctcgc gatcagacga aggcctttta cttaacgaca caatatccga  14280
tgtctgcatc acaggcgtcg ctatcccagt caatactaaa gcggtgcagg aactaaagat  14340
tactgatgac ttaggcgtgc cacgaggcct gagacgacgc gcgtagacag tttttgaaa  14400
tcattatcaa agtgatggcc tccgctgaag cctatcacct ctgcgccggt ctgtcggaga  14460
gatgggcaag cattattacg gtcttcgcgc ccgtacatgc attggacgat tgcagggtca  14520
atggatctga gatcatccag aggattgccg cccttacctt ccgtttcgag ttggagccag  14580
cccctaaatg agacgacata gtcgacttga tgtgacaatg ccaagagaga gatttgctta  14640
acccgatttt tttgctcaag cgtaagccta ttgaagcttg ccggcatgac gtccgcgccg  14700
aaagaatatc ctacaagtaa aacattctgc acaccgaaat gcttggtgta gacatcgatt  14760
atgtgaccaa gatccttagc agtttcgctt ggggaccgct ccgaccagaa ataccgaagt  14820
gaactgacgc caatgacagg aatcccttcc gtctgcagat aggtaccatc gatagatctg  14880
ctgcctcgcg cgtttcggtg atgacggtga aaacctctga cacatgcagc tcccggagac  14940
ggtcacagct tgtctgtaag cggatgccgg gagcagacaa gcccgtcagg gcgcgtcagc  15000
gggtgttggc gggtgtcggg gcgcagccat gacccagtca cgtagcgata gcggagtgta  15060
tactggctta actatgcggc atcagagcag attgtactga gagtgcacca tatgcggtgt  15120
gaaataccgc acagatgcgt aaggagaaaa taccgcatca ggcgctcttc cgcttcctcg  15180
```

```
ctcactgact cgctgcgctc ggtcgttcgg ctgcggcgag cggtatcagc tcactcaaag  15240
gcggtaatac ggttatccac agaatcaggg gataacgcag gaaagaacat gtgagcaaaa  15300
ggccagcaaa aggccaggaa ccgtaaaaag gccgcgttgc tggcgttttt ccataggctc  15360
cgcccccctg acgagcatca caaaaatcga cgctcaagtc agaggtggcg aaacccgaca  15420
ggactataaa gataccaggc gtttccccct ggaagctccc tcgtgcgctc tcctgttccg  15480
accctgccgc ttaccggata cctgtccgcc tttctccctt cgggaagcgt ggcgctttct  15540
catagctcac gctgtaggta tctcagttcg gtgtaggtcg ttcgctccaa gctgggctgt  15600
gtgcacgaac cccccgttca gcccgaccgc tgcgccttat ccggtaacta tcgtcttgag  15660
tccaacccgg taagacacga cttatcgcca ctggcagcag ccactggtaa caggattagc  15720
agagcgaggt atgtaggcgg tgctacagag ttcttgaagt ggtggcctaa ctacggctac  15780
actagaagga cagtatttgg tatctgcgct ctgctgaagc cagttacctt cggaaaaaga  15840
gttggtagct cttgatccgg caaacaaacc accgctggta gcggtggttt ttttgtttgc  15900
aagcagcaga ttacgcgcag aaaaaaagga tctcaagaag atcctttgat cttttctacg  15960
gggtctgacg ctcagtggaa cgaaaactca cgttaaggga ttttggtcat gagattatca  16020
aaaaggatct tcacctagat ccttttaaat taaaaatgaa gttttaaatc aatctaaagt  16080
atatatgagt aaacttggtc tgacagttac caatgcttaa tcagtgaggc acctatctca  16140
gcgatctgtc tatttcgttc atccatagtt gcctgactcc ccgtcgtgta gataactacg  16200
atacgggagg gcttaccatc tggccccagt gctgcaatga taccgcgaga cccacgctca  16260
ccggctccag atttatcagc aataaaccag ccagccggaa gggccgagcg cagaagtggt  16320
cctgcaactt tatccgcctc catccagtct attaattgtt gccgggaagc tagagtaagt  16380
agttcgccag ttaatagttt gcgcaacgtt gttgccattg ctgcaggggg gggggggggg  16440
gggttccatt gttcattcca cggacaaaaa cagagaaagg aaacgacaga ggccaaaaag  16500
ctcgctttca gcacctgtcg tttcctttct tttcagaggg tattttaaat aaaaacatta  16560
agttatgacg aagaagaacg gaaacgcctt aaaccggaaa attttcataa atagcgaaaa  16620
cccgcgaggt ccctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc ccccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
```

-continued

```
aggccctttc gtcttcaaga attggtcgac gatcttgctg cgttcggata ttttcgtgga  17640
gttcccgcca cagacccgga ttgaaggcga gatccagcaa ctcgcgccag atcatcctgt  17700
gacggaactt tggcgcgtga tgactggcca ggacgtcggc cgaaagagcg acaagcagat  17760
cacgcttttc gacagcgtcg gatttgcgat cgaggatttt tcggcgctgc gctacgtccg  17820
cgaccgcgtt gagggatcaa gccacagcag cccactcgac cttctagccg acccagacga  17880
gccaagggat ctttttggaa tgctgctccg tcgtcaggct ttccgacgtt tgggtggttg  17940
aacagaagtc attatcgtac ggaatgccaa gcactcccga ggggaaccct gtggttggca  18000
tgcacataca aatggacgaa cggataaacc ttttcacgcc cttttaaata tccgttattc  18060
taataaacgc tcttttctct taggtttacc cgccaatata tcctgtcaaa cactgatagt  18120
ttaaactgaa ggcgggaaac gacaatctga tcatgagcgg agaattaagg gagtcacgtt  18180
atgacccccg ccgatgacgc gggacaagcc gttttacgtt tggaactgac agaaccgcaa  18240
cgttgaagga gccactcagc aagctggtac gattgtaata cgactcacta tagggcgaat  18300
tgagcgctgt ttaaacgctc ttcaactgga agagcggtta ccagagctgg tcacctttgt  18360
ccaccaagat ggaactgcgg ccgctcatta attaagtcag gcgcgcctct agttgaagac  18420
acgttcatgt cttcatcgta agaagacact cagtagtctt cggccagaat ggccatctgg  18480
attcagcagg cctagaaggc catttaaatc ctgaggatct ggtcttccta aggacccggg  18540
atatcgctat caactttgta tagaaaagtt gggccgaatt cgcccttgtt taaacttaat  18600
atttgtttaa actttttact aaattcatgt aataattaat gtatgcgtta tatatatatg  18660
tctaggttta taattattca tatgaatatg aacataaaaa tctagggcta aaacgactac  18720
tattttgaaa acggaaggag tagtaagtta tttaagcgga ggggaaccat gatgggctag  18780
tgatttaatt tacatatata tattggtgtt ctgggctctt acatgagaag atctagttaa  18840
ctgttgttac tgaacagcga agacaaatat ataatttaag ctccccaact gctagtgatt  18900
ctgttaagag gtaatgttta aagtaaattt acaagagccc gtctagctca gtcggtagag  18960
cgcaaggctc ttaaccttgt ggtcgtgggt tcgagcccca cggtgggcgc acaatttttt  19020
gtttttttgac atttttttgtt tgcttagttg cagacggttt ttcccctgct aggagatttc  19080
cgagagaaaa aaaaggcact acaggttaac caaaaccacc aacctttgga gcgtcgaggc  19140
gacggggcat ttgcgtagtt gaagcttaca aagttgcata tgagatgagt gccggacatg  19200
aagcggataa cgttttaaac tggcaacaat atctagctgt ttcaaattca ggcgtgggaa  19260
gctacgccta cgcgccctgg acggcgtgta aagagccagc atcggcatca ttgtcaaacg  19320
atcgacaagg ccaagaaatt ccaaatatat tattaataaa aaagaaggca ccaaattagt  19380
ttttgttttt tagtatgtgt ggcggaggaa attttgagaa cgaacgtatc caaagaaggc  19440
acaagacgat atagattgac gcggctagaa agttgcagca agacagtggg tacggtctta  19500
tatatcctaa taaataaaaa ataaaactat agtgtgtcaa atgtcaacaa gaggaggagg  19560
cagccaaatt agcagaggga gacaagtaga gcacgcctta ttagcttgct tatttatcgt  19620
ggtggtgtac ttgttaatta ctggcacgca ttatcaacaa cgcagttctg gatgtgaatc  19680
tagacaaaca tttgtctagg ttccgcacgt atagtttttt ttctttttttt ttgggggggg  19740
gggggaacgg aagctgtaat aaacggtact aggaacgaaa gcaaccgccg cgcgcatgtt  19800
tttgcaatag attacggtga ccttgatgca ccaccgcgtg ctataaaaac cagtgtcccc  19860
gagtctactc atcaaccaat ccataactcg aaaccttttc ttgtgctctg ttctgtctgt  19920
gtgtttccaa agcaagcgaa agaggtcgag gggatcagct tcaagtttgt acaaaaaagc  19980
```

```
aggctccgcg gccgcccct tcaccatggc tcggcagcaa agcgtgcagg ccttgtgtgt  20040
gctggcggcg cttctcttcg ccgcctccct gccgtcgccg gccgccgcgg gggtgcacct  20100
ctcctcgctg cccaaagcgc tcgacgtcac cacctccgcc aaacccggcc aagtcctgca  20160
cgccggcgtg gactcgctga cggtgacgtg gagcctgaac gccacggagc cggccggcgc  20220
cgacgccggg tacaagggcg tgaaggtgaa gctgtgctac gcgccggcga gccagaagga  20280
ccgcgggtgg cgcaagtccg aggacgacat cagcaaggac aaggcgtgcc agttcaaggt  20340
caccgagcag gcgtacgcgg cggcggcgcc cggcagcttc cagtacgccg tcgcccgcga  20400
cgtcccctcg ggctcctact acctgcgcgc cttcgccacg gacgcgtcgg gcgccgaggt  20460
ggcctacggc cagacggcgc ccaccgccgc cttcgacgtc gccggcatca ccggcatcca  20520
cgcctctctc aagatcgccg ccggcgtctt ctcggccttc tccgtcgtcg cgctcgcctt  20580
cttcttcgtc atcgagaccc gcaagaagaa caagtagaag ggtgggcgcg ccgacccagc  20640
tttcttgtac aaagtggccg ttaacggatc cagacttgtc catcttctgg attggccaac  20700
ttaattaatg tatgaaataa aaggatgcac acatagtgac atgctaatca ctataatgtg  20760
ggcatcaaag ttgtgtgtta tgtgtaatta ctagttatct gaataaaaga gaaagagatc  20820
atccatattt cttatcctaa atgaatgtca cgtgtcttta taattctttg atgaaccaga  20880
tgcatttcat taaccaaatc catatacata taaatattaa tcatatataa ttaatatcaa  20940
ttgggttagc aaaacaaatc tagtctaggt gtgttttgcg aattgcggca agcttgcggc  21000
cgccccgggc aactttatta tacaaagttg atagatatcg gaccgattaa actttaattc  21060
ggtccgaagc ttgcatgcct gcagtgcagc gtgacccggt cgtgcccctc tctagagata  21120
atgagcattg catgtctaag ttataaaaaa ttaccacata ttttttttgt cacacttgtt  21180
tgaagtgcag tttatctatc tttatacata tatttaaact ttactctacg aataatataa  21240
tctatagtac tacaataata tcagtgtttt agagaatcat ataaatgaac agttagacat  21300
ggtctaaagg acaattgagt attttgacaa caggactcta cagttttatc tttttagtgt  21360
gcatgtgttc tccttttttt ttgcaaatag cttcacctat ataatacttc atccatttta  21420
ttagtacatc catttagggt ttagggttaa tggtttttat agactaattt ttttagtaca  21480
tctattttat tctattttag cctctaaatt aagaaaacta aaactctatt ttagtttttt  21540
tatttaataa tttagatata aaatagaata aaataaagtg actaaaaatt aaacaaatac  21600
cctttaagaa attaaaaaaa ctaaggaaac atttttcttg tttcgagtag ataatgccag  21660
cctgttaaac gccgtcgacg agtctaacgg acaccaacca gcgaaccagc agcgtcgcgt  21720
cgggccaagc gaagcagacg gcacggcatc tctgtcgctg cctctggacc cctctcgaga  21780
gttccgctcc accgttggac ttgctccgct gtcggcatcc agaaattgcg tggcggagcg  21840
gcagacgtga gccggcacgg caggcggcct cctcctcctc tcacggcacc ggcagctacg  21900
ggggattcct ttcccaccgc tccttcgctt tcccttcctc gcccgccgta ataaatagac  21960
acccctcca caccctcttt ccccaacctc gtgttgttcg gagcgcacac acacacaacc  22020
agatctcccc caaatccacc cgtcggcacc tccgcttcaa ggtacgccgc tcgtcctccc  22080
cccccccct ctctaccttc tctagatcgg cgttccggtc catgcatggt tagggcccgg  22140
tagttctact tctgttcatg tttgtgttag atccgtgttt gtgttagatc cgtgctgcta  22200
gcgttcgtac acggatgcga cctgtacgtc agacacgttc tgattgctaa cttgccagtg  22260
tttctctttg gggaatcctg ggatggctct agccgttccg cagacgggat cgatttcatg  22320
attttttttg tttcgttgca tagggtttgg tttgcccttt tcctttattt caatatatgc  22380
```

```
cgtgcacttg tttgtcgggt catcttttca tgcttttttt tgtcttggtt gtgatgatgt  22440
ggtctggttg ggcggtcgtt ctagatcgga gtagaattct gtttcaaact acctggtgga  22500
tttattaatt ttggatctgt atgtgtgtgc catacatatt catagttacg aattgaagat  22560
gatggatgga aatatcgatc taggataggt atacatgttg atgcgggttt tactgatgca  22620
tatacagaga tgctttttgt tcgcttggtt gtgatgatgt ggtgtggttg ggcggtcgtt  22680
cattcgttct agatcggagt agaatactgt ttcaaactac ctggtgtatt tattaatttt  22740
ggaactgtat gtgtgtgtca tacatcttca tagttacgag tttaagatgg atggaaatat  22800
cgatctagga taggtataca tgttgatgtg ggttttactg atgcatatac atgatggcat  22860
atgcagcatc tattcatatg ctctaacctt gagtacctat ctattataat aaacaagtat  22920
gttttataat tattttgatc ttgatatact tggatgatgg catatgcagc agctatatgt  22980
ggattttttt agccctgcct tcatacgcta tttatttgct tggtactgtt tcttttgtcg  23040
atgctcaccc tgttgtttgg tgttacttct gcaggtcgac tttaacttag cctaggatcc  23100
acacgacacc atgtccccg agcgccgccc cgtcgagatc cgcccggcca ccgccgccga  23160
catggccgcc gtgtgcgaca tcgtgaacca ctacatcgag acctccaccg tgaacttccg  23220
caccgagccg cagaccccgc aggagtggat cgacgacctg gagcgcctcc aggaccgcta  23280
cccgtggctc gtggccgagg tggagggcgt ggtggccggc atcgcctacg ccggcccgtg  23340
gaaggcccgc aacgcctacg actggaccgt ggagtccacc gtgtacgtgt cccaccgcca  23400
ccagcgcctc ggcctcggct ccaccctcta cacccacctc ctcaagagca tggaggccca  23460
gggcttcaag tccgtggtgg ccgtgatcgg cctccccgaac gacccgtccg tgcgcctcca  23520
cgaggccctc ggctacaccg cccgcggcac cctccgcgcc gccggctaca agcacggcgg  23580
ctggcacgac gtcggcttct ggcagcgcga cttcgagctg ccggccccgc cgcgcccggt  23640
gcgcccggtg acgcagatct gagtcgaaac ctagacttgt ccatcttctg gattggccaa  23700
cttaattaat gtatgaaata aaaggatgca cacatagtga catgctaatc actataatgt  23760
gggcatcaaa gttgtgtgtt atgtgtaatt actagttatc tgaataaaag agaaagagat  23820
catccatatt tcttatccta aatgaatgtc acgtgtcttt ataattcttt gatgaaccag  23880
atgcatttca ttaaccaaat ccatatacat ataaatatta atcatatata attaatatca  23940
attgggttag caaaacaaat ctagtctagg tgtgttttgc gaatgcggcc gccaccgcgg  24000
tggagctcga attcattccg attaatcgtg gcctcttgct cttcaggatg aagagctatg  24060
tttaaacgtg caagcgctac tagacaattc agtacattaa aaacgtccgc aatgtgttat  24120
taagttgtct aagcgtcaat ttgtttacac cacaatatat cctgccacca gccagccaac  24180
agctccccga ccggcagctc ggcacaaaat caccactcga tacaggcagc ccatcagtcc  24240
gggacggcgt cagcgggaga gccgttgtaa ggcggcagac tttgctcatg ttaccgatgc  24300
tattcggaag aacggcaact aagctgccgg gtttgaaaca cggatgatct cgcggagggt  24360
agcatgttga ttgtaacgat gacagagcgt tgctgcctgt gatcaaatat catctccctc  24420
gcagagatcc gaattatcag ccttcttatt catttctcgc ttaaccgtga caggctgtcg  24480
atcttgagaa ctatgccgac ataataggaa atcgctggat aaagccgctg aggaagctga  24540
gtggcgctat ttctttagaa gtgaacgttg acgatcgtcg accgtacccc gatgaattaa  24600
ttcggacgta cgttctgaac acagctggat acttacttgg gcgattgtca tacatgacat  24660
caacaatgta cccgtttgtg taaccgtctc ttggaggttc gtatgacact agtggttccc  24720
ctcagcttgc gactagatgt tgaggcctaa cattttatta gagagcaggc tagttgctta  24780
```

-continued

```
gatacatgat cttcaggccg ttatctgtca gggcaagcga aaattggcca tttatgacga  24840
ccaatgcccc gcagaagctc ccatctttgc cgccatagac gccgcgcccc ccttttgggg  24900
tgtagaacat ccttttgcca gatgtggaaa agaagttcgt tgtcccattg ttggcaatga  24960
cgtagtagcc ggcgaaagtg cgagacccat ttgcgctata tataagccta cgatttccgt  25020
tgcgactatt gtcgtaattg gatgaactat tatcgtagtt gctctcagag ttgtcgtaat  25080
ttgatggact attgtcgtaa ttgcttatgg agttgtcgta gttgcttgga gaaatgtcgt  25140
agttggatgg ggagtagtca tagggaagac gagcttcatc cactaaaaca attggcaggt  25200
cagcaagtgc ctgccccgat gccatcgcaa gtacgaggct tagaaccacc ttcaacagat  25260
cgcgcatagt cttccccagc tctctaacgc ttgagttaag ccgcgccgcg aagcggcgtc  25320
ggcttgaacg aattgttaga cattatttgc cgactacctt ggtgatctcg cctttcacgt  25380
agtgaacaaa ttcttccaac tgatctgcgc gcgaggccaa gcgatcttct tgtccaagat  25440
aagcctgcct agcttcaagt atgacgggct gatactgggc cggcaggcgc tccattgccc  25500
agtcggcagc gacatccttc ggcgcgattt tgccggttac tgcgctgtac caaatgcggg  25560
acaacgtaag cactacattt cgctcatcgc cagcccagtc gggcggcgag ttccatagcg  25620
ttaaggtttc atttagcgcc tcaaatagat cctgttcagg aaccggatca aagagttcct  25680
ccgccgctgg acctaccaag gcaacgctat gttctcttgc ttttgtcagc aagatagcca  25740
gatcaatgtc gatcgtggct ggctcgaaga tacctgcaag aatgtcattg cgctgccatt  25800
ctccaaattg cagttcgcgc ttagctggat aacgccacgg aatgatgtcg tcgtgcacaa  25860
caatggtgac ttctacagcg cggagaatct cgctctctcc aggggaagcc gaagtttcca  25920
aaaggtcgtt gatcaaagct cgccgcgttg tttcatcaag ccttacagtc accgtaacca  25980
gcaaatcaat atcactgtgt ggcttcaggc cgccatccac tgcggagccg tacaaatgta  26040
cggccagcaa cgtcggttcg agatggcgct cgatgacgcc aactacctct gatagttgag  26100
tcgatacttc ggcgatcacc gcttccctca tgatgtttaa ctcctgaatt aagccgcgcc  26160
gcgaagcggt gtcggcttga atgaattgtt aggcgtcatc ctgtgctccc gagaaccagt  26220
accagtacat cgctgtttcg ttcgagactt gaggtctagt tttatacgtg aacaggtcaa  26280
tgccgccgag agtaaagcca cattttgcgt acaaattgca ggcaggtaca ttgttcgttt  26340
gtgtctctaa tcgtatgcca aggagctgtc tgcttagtgc ccactttttc gcaaattcga  26400
tgagactgtg cgcgactcct ttgcctcggt gcgtgtgcga cacaacaatg tgttcgatag  26460
aggctagatc gttccatgtt gagttgagtt caatcttccc gacaagctct tggtcgatga  26520
atgcgccata gcaagcagag tcttcatcag agtcatcatc cgagatgtaa tccttccggt  26580
aggggctcac acttctggta gatagttcaa agccttggtc ggataggtgc acatcgaaca  26640
cttcacgaac aatgaaatgg ttctcagcat ccaatgtttc cgccacctgc tcagggatca  26700
ccgaaatctt catatgacgc ctaacgcctg gcacagcgga tcgcaaacct ggcgcggctt  26760
ttggcacaaa aggcgtgaca ggtttgcgaa tccgttgctg ccacttgtta accccttttgc  26820
cagatttggt aactataatt tatgttagag gcgaagtctt gggtaaaaac tggcctaaaa  26880
ttgctgggga tttcaggaaa gtaaacatca ccttccggct cgatgtctat tgtagatata  26940
tgtagtgtat ctacttgatc gggggatctg ctgcctcgcg cgtttcggtg atgacggtga  27000
aaacctctga cacatgcagc tcccggagac ggtcacagct tgtctgtaag cggatgccgg  27060
gagcagacaa gcccgtcagg gcgcgtcagc gggtgttggc gggtgtcggg gcgcagccat  27120
gacccagtca cgtagcgata gcggagtgta tactggctta actatgcggc atcagagcag  27180
```

```
attgtactga gagtgcacca tatgcggtgt gaaataccgc acagatgcgt aaggagaaaa  27240
taccgcatca ggcgctcttc cgcttcctcg ctcactgact cgctgcgctc ggtcgttcgg  27300
ctgcggcgag cggtatcagc tcactcaaag gcggtaatac ggttatccac agaatcaggg  27360
gataacgcag gaaagaacat gtgagcaaaa ggccagcaaa aggccaggaa ccgtaaaaag  27420
gccgcgttgc tggcgttttt ccataggctc cgcccccctg acgagcatca caaaaatcga  27480
cgctcaagtc agaggtggcg aaacccgaca ggactataaa gataccaggc gtttccccct  27540
ggaagctccc tcgtgcgctc tcctgttccg accctgccgc ttaccggata cctgtccgcc  27600
tttctccctt cgggaagcgt ggcgctttct catagctcac gctgtaggta tctcagttcg  27660
gtgtaggtcg ttcgctccaa gctgggctgt gtgcacgaac cccccgttca gcccgaccgc  27720
tgcgccttat ccggtaacta tcgtcttgag tccaacccgg taagacacga cttatcgcca  27780
ctggcagcag ccactggtaa caggattagc agagcgaggt atgtaggcgg tgctacagag  27840
ttcttgaagt ggtggcctaa ctacggctac actagaagga cagtatttgg tatctgcgct  27900
ctgctgaagc cagttacctt cggaaaaaga gttggtagct cttgatccgg caaacaaacc  27960
accgctggta gcggtggttt ttttgtttgc aagcagcaga ttacgcgcag aaaaaaagga  28020
tctcaagaag atcctttgat cttttctacg gggtctgacg ctcagtggaa cgaaaactca  28080
cgttaaggga ttttggtcat gagattatca aaaaggatct tcacctagat ccttttaaat  28140
taaaaatgaa gttttaaatc aatctaaagt atatatgagt aaacttggtc tgacagttac  28200
caatgcttaa tcagtgaggc acctatctca gcgatctgtc tatttcgttc atccatagtt  28260
gcctgactcc ccgtcgtgta gataactacg atacgggagg gcttaccatc tggccccagt  28320
gctgcaatga taccgcgaga cccacgctca ccggctccag atttatcagc aataaaccag  28380
ccagccggaa gggccgagcg cagaagtggt cctgcaactt tatccgcctc catccagtct  28440
attaattgtt gccgggaagc tagagtaagt agttcgccag ttaatagttt gcgcaacgtt  28500
gttgccattg ctgcaggggg gggggggggg ggggacttcc attgttcatt ccacggacaa  28560
aaacagagaa aggaaacgac agaggccaaa aagcctcgct ttcagcacct gtcgtttcct  28620
ttcttttcag agggtatttt aaataaaaac attaagttat gacgaagaag aacggaaacg  28680
ccttaaaccg gaaaattttc ataaatagcg aaaacccgcg aggtcgccgc cccgtaagcc  28740
gccccgtaac ctgtcggatc accggaaagg acccgtaaag tgataatgat tatcatctac  28800
atatcacaac gtgcgtggag gccatcaaac cacgtcaaat aatcaattat gacgcaggta  28860
tcgtattaat tgatctgcat caacttaacg taaaaacaac ttcagacaat acaaatcagc  28920
gacactgaat acggggcaac ctcatgtccc cccccccccc cccccctgcag gcatcgtggt  28980
gtcacgctcg tcgtttggta tggcttcatt cagctccggt tcccaacgat caaggcgagt  29040
tacatgatcc cccatgttgt gcaaaaaagc ggttagctcc ttcggtcctc cgatcgttgt  29100
cagaagtaag ttggccgcag tgttatcact catggttatg gcagcactgc ataattctct  29160
tactgtcatg ccatccgtaa gatgcttttc tgtgactggt gagtactcaa ccaagtcatt  29220
ctgagaatag tgtatgcggc gaccgagttg ctcttgcccg gcgtcaacac gggataatac  29280
cgcgccacat agcagaactt taaaagtgct catcattgga aaacgttctt cggggcgaaa  29340
actctcaagg atcttaccgc tgttgagatc cagttcgatg taacccactc gtgcacccaa  29400
ctgatcttca gcatctttta ctttcaccag cgtttctggg tgagcaaaaa caggaaggca  29460
aaatgccgca aaaaagggaa taagggcgac acggaaatgt tgaatactca tactcttcct  29520
ttttcaatat tattgaagca tttatcaggg ttattgtctc atgagcggat acatatttga  29580
```

-continued

```
atgtatttag aaaaataaac aaataggggt tccgcgcaca tttccccgaa aagtgccacc  29640
tgacgtctaa gaaaccatta ttatcatgac attaacctat aaaaataggc gtatcacgag  29700
gccctttcgt cttcaagaat tcggagcttt tgccattctc accggattca gtcgtcactc  29760
atggtgattt ctcacttgat aaccttattt ttgacgaggg gaaattaata ggttgtattg  29820
atgttggacg agtcggaatc gcagaccgat accaggatct tgccatccta tggaactgcc  29880
tcggtgagtt ttctccttca ttacagaaac ggctttttca aaaatatggt attgataatc  29940
ctgatatgaa taaattgcag tttcatttga tgctcgatga gtttttctaa tcagaattgg  30000
ttaattggtt gtaacactgg cagagcatta cgctgacttg acgggacggc ggctttgttg  30060
aataaatcga acttttgctg agttgaagga tcagatcacg catcttcccg acaacgcaga  30120
ccgttccgtg gcaaagcaaa agttcaaaat caccaactgg tccacctaca acaaagctct  30180
catcaaccgt ggctccctca ctttctggct ggatgatggg gcgattcagg cctggtatga  30240
gtcagcaaca ccttcttcac gaggcagacc tcagcgccag aaggccgcca gagaggccga  30300
gcgcggccgt gaggcttgga cgctagggca gggcatgaaa aagcccgtag cgggctgcta  30360
cgggcgtctg acgcggtgga aagggggagg ggatgttgtc tacatggctc tgctgtagtg  30420
agtgggttgc gctccggcag cggtcctgat caatcgtcac cctttctcgg tccttcaacg  30480
ttcctgacaa cgagcctcct tttcgccaat ccatcgacaa tcaccgcgag tccctgctcg  30540
aacgctgcgt ccggaccggc ttcgtcgaag gcgtctatcg cggcccgcaa cagcggcgag  30600
agcggagcct gttcaacggt gccgccgcgc tcgccggcat cgctgtcgcc ggcctgctcc  30660
tcaagcacgg ccccaacagt gaagtagctg attgtcatca gcgcattgac ggcgtccccg  30720
gccgaaaaac ccgcctcgca gaggaagcga agctgcgcgt cggccgtttc catctgcggt  30780
gcgcccggtc gcgtgccggc atggatgcgc gcgccatcgc ggtaggcgag cagcgcctgc  30840
ctgaagctgc gggcattccc gatcagaaat gagcgccagt cgtcgtcggc tctcggcacc  30900
gaatgcgtat gattctccgc cagcatggct tcggccagtg cgtcgagcag cgcccgcttg  30960
ttcctgaagt gccagtaaag cgccggctgc tgaacccccca accgttccgc cagtttgcgt  31020
gtcgtcagac cgtctacgcc gacctcgttc aacaggtcca gggcggcacg gatcactgta  31080
ttcggctgca actttgtcat gcttgacact ttatcactga taaacataat atgtccacca  31140
acttatcagt gataaagaat ccgcgcgttc aatcggacca gcggaggctg gtccggaggc  31200
cagacgtgaa acccaacata cccctgatcg taattctgag cactgtcgcg ctcgacgctg  31260
tcggcatcgg cctgattatg ccggtgctgc cgggcctcct gcgcgatctg gttcactcga  31320
acgacgtcac cgcccactat ggcattctgc tggcgctgta tgcgttggtg caatttgcct  31380
gcgcacctgt gctgggcgcg ctgtcggatc gtttcgggcg gcggccaatc ttgctcgtct  31440
cgctggccgg cgccactgtc gactacgcca tcatggcgac agcgcctttc ctttgggttc  31500
tctatatcgg gcggatcgtg gccggcatca ccggggcgac tggggcggta gccggcgctt  31560
atattgccga tatcactgat ggcgatgagc gcgcgcggca cttcggcttc atgagcgcct  31620
gtttcgggtt cgggatggtc gcgggacctg tgctcggtgg gctgatgggc ggtttctccc  31680
cccacgctcc gttcttcgcc gcggcagcct tgaacggcct caatttcctg acgggctgtt  31740
tccttttgcc ggagtcgcac aaaggcgaac gccggccgtt acgccgggag gctctcaacc  31800
cgctcgcttc gttccggtgg gcccggggca tgaccgtcgt cgccgccctg atggcggtct  31860
tcttcatcat gcaacttgtc ggacaggtgc cggccgcgct ttgggtcatt ttcggcgagg  31920
atcgctttca ctgggacgcg accacgatcg gcatttcgct tgccgcattt ggcattctgc  31980
```

-continued

```
attcactcgc ccaggcaatg atcaccggcc ctgtagccgc ccggctcggc gaaaggcggg  32040
cactcatgct cggaatgatt gccgacggca caggctacat cctgcttgcc ttcgcgacac  32100
ggggatggat ggcgttcccg atcatggtcc tgcttgcttc gggtggcatc ggaatgccgg  32160
cgctgcaagc aatgttgtcc aggcaggtgg atgaggaacg tcaggggcag ctgcaaggct  32220
cactggcggc gctcaccagc ctgacctcga tcgtcggacc cctcctcttc acggcgatct  32280
atgcggcttc tataacaacg tggaacgggt gggcatggat tgcaggcgct gccctctact  32340
tgctctgcct gccggcgctg cgtcgcgggc tttggagcgg cgcagggcaa cgagccgatc  32400
gctgatcgtg gaaacgatag gcctatgcca tgcgggtcaa ggcgacttcc ggcaagctat  32460
acgcgcccta ggagtgcggt tggaacgttg gcccagccag atactcccga tcacgagcag  32520
gacgccgatg atttgaagcg cactcagcgt ctgatccaag aacaaccatc ctagcaacac  32580
ggcggtcccc gggctgagaa agcccagtaa ggaaacaact gtaggttcga gtcgcgagat  32640
cccccggaac caaaggaagt aggttaaacc cgctccgatc aggccgagcc acgccaggcc  32700
gagaacattg gttcctgtag gcatcgggat tggcggatca aacactaaag ctactggaac  32760
gagcagaagt cctccggccg ccagttgcca ggcggtaaag gtgagcagag gcacgggagg  32820
ttgccacttg cgggtcagca cggttccgaa cgccatggaa accgcccccg ccaggcccgc  32880
tgcgacgccg acaggatcta gcgctgcgtt tggtgtcaac accaacagcg ccacgcccgc  32940
agttccgcaa atagcccccca ggaccgccat caatcgtatc gggctaccta gcagagcggc  33000
agagatgaac acgaccatca gcggctgcac agcgcctacc gtcgccgcga ccccgcccgg  33060
caggcggtag accgaaataa acaacaagct ccagaatagc gaaatattaa gtgcgccgag  33120
gatgaagatg cgcatccacc agattcccgt tggaatctgt cggacgatca tcacgagcaa  33180
taaacccgcc ggcaacgccc gcagcagcat accggcgacc cctcggcctc gctgttcggg  33240
ctccacgaaa acgccggaca gatgcgcctt gtgagcgtcc ttggggccgt cctcctgttt  33300
gaagaccgac agcccaatga tctcgccgtc gatgtaggcg ccgaatgcca cggcatctcg  33360
caaccgttca gcgaacgcct ccatgggctt tttctcctcg tgctcgtaaa cggacccgaa  33420
catctctgga gctttcttca gggccgacaa tcggatctcg cggaaatcct gcacgtcggc  33480
cgctccaagc cgtcgaatct gagccttaat cacaattgtc aattttaatc ctctgtttat  33540
cggcagttcg tagagcgcgc cgtgcgtccc gagcgatact gagcgaagca agtgcgtcga  33600
gcagtgcccg cttgttcctg aaatgccagt aaagcgctgg ctgctgaacc cccagccgga  33660
actgacccca caaggcccta gcgtttgcaa tgcaccaggt catcattgac ccaggcgtgt  33720
tccaccaggc cgctgcctcg caactcttcg caggcttcgc cgacctgctc gcgccacttc  33780
ttcacgcggg tggaatccga tccgcacatg aggcggaagg tttccagctt gagcgggtac  33840
ggctcccggt gcgagctgaa atagtcgaac atccgtcggg ccgtcggcga cagcttgcgg  33900
tacttctccc atatgaattt cgtgtagtgg tcgccagcaa acagcacgac gatttcctcg  33960
tcgatcagga cctggcaacg ggacgttttc ttgccacggt ccaggacgcg gaagcggtgc  34020
agcagcgaca ccgattccag gtgcccaacg cggtcggacg tgaagcccat cgccgtcgcc  34080
tgtaggcgcg acaggcattc ctcggccttc gtgtaatacc ggccattgat cgaccagccc  34140
aggtcctggc aaagctcgta gaacgtgaag gtgatcggct cgccgatagg ggtgcgcttc  34200
gcgtactcca acacctgctg ccacaccagt tcgtcatcgt cggcccgcag ctcgacgccg  34260
gtgtaggtga tcttcacgtc cttgttgacg tggaaaatga ccttgttttg cagcgcctcg  34320
cgcgggattt tcttgttgcg cgtggtgaac agggcagagc gggccgtgtc gtttggcatc  34380
```

-continued

```
gctcgcatcg tgtccggcca cggcgcaata tcgaacaagg aaagctgcat ttccttgatc  34440
tgctgcttcg tgtgtttcag caacgcggcc tgcttggcct cgctgacctg ttttgccagg  34500
tcctcgccgg cggtttttcg cttcttggtc gtcatagttc ctcgcgtgtc gatggtcatc  34560
gacttcgcca aacctgccgc ctcctgttcg agacgacgcg aacgctccac ggcggccgat  34620
ggcgcgggca gggcaggggg agccagttgc acgctgtcgc gctcgatctt ggccgtagct  34680
tgctggacca tcgagccgac ggactggaag gtttcgcggg gcgcacgcat gacggtgcgg  34740
cttgcgatgg tttcggcatc ctcggcggaa aaccccgcgt cgatcagttc ttgcctgtat  34800
gccttccggt caaacgtccg attcattcac cctccttgcg ggattgcccc gactcacgcc  34860
ggggcaatgt gcccttattc ctgatttgac ccgcctggtg ccttggtgtc cagataatcc  34920
accttatcgg caatgaagtc ggtcccgtag accgtctggc cgtccttctc gtacttggta  34980
ttccgaatct tgccctgcac gaataccagc gaccccttgc ccaaatactt gccgtgggcc  35040
tcggcctgag agccaaaaca cttgatgcgg aagaagtcgg tgcgctcctg cttgtcgccg  35100
gcatcgttgc gccactcttc attaaccgct atatcgaaaa ttgcttgcgg cttgttagaa  35160
ttgccatgac gtacctcggt gtcacgggta agattaccga taaactggaa ctgattatgg  35220
ctcatatcga aagtctcctt gagaaaggag actctagttt agctaaacat tggttccgct  35280
gtcaagaact ttagcggcta aaattttgcg ggccgcgacc aaaggtgcga ggggcggctt  35340
ccgctgtgta caaccagata tttttcacca acatccttcg tctgctcgat gagcggggca  35400
tgacgaaaca tgagctgtcg gagagggcag gggtttcaat ttcgttttta tcagacttaa  35460
ccaacggtaa ggccaacccc tcgttgaagg tgatggaggc cattgccgac gccctggaaa  35520
ctcccctacc tcttctcctg gagtccaccg accttgaccg cgaggcactc gcggagattg  35580
cgggtcatcc tttcaagagc agcgtgccgc ccggatacga acgcatcagt gtggttttgc  35640
cgtcacataa ggcgtttatc gtaaagaaat ggggcgacga cacccgaaaa aagctgcgtg  35700
gaaggctctg acgccaaggg ttagggcttg cacttccttc tttagccgct aaaacggccc  35760
cttctctgcg ggccgtcggc tcgcgcatca tatcgacatc ctcaacggaa gccgtgccgc  35820
gaatggcatc gggcgggtgc gctttgacag ttgttttcta tcagaacccc tacgtcgtgc  35880
ggttcgatta gctgtttgtc ttgcaggcta aacactttcg gtatatcgtt tgcctgtgcg  35940
ataatgttgc taatgatttg ttgcgtaggg gttactgaaa agtgagcggg aaagaagagt  36000
ttcagaccat caaggagcgg gccaagcgca agctggaacg cgacatgggt gcggacctgt  36060
tggccgcgct caacgacccg aaaaccgttg aagtcatgct caacgcggac ggcaaggtgt  36120
ggcacgaacg ccttggcgag ccgatgcggt acatctgcga catgcggccc agccagtcgc  36180
aggcgattat agaaacggtg gccggattcc acggcaaaga ggtcacgcgg cattcgccca  36240
tcctggaagg cgagttcccc ttggatggca gccgctttgc cggccaattg ccgccggtcg  36300
tggccgcgcc aacctttgcg atccgcaagc gcgcggtcgc catcttcacg ctggaacagt  36360
acgtcgaggc gggcatcatg acccgcgagc aatacgaggt cattaaaagc gccgtcgcgg  36420
cgcatcgaaa catcctcgtc attggcggta ctggctcggg caagaccacg ctcgtcaacg  36480
cgatcatcaa tgaaatggtc gccttcaacc cgtctgagcg cgtcgtcatc atcgaggaca  36540
ccggcgaaat ccagtgcgcc gcagagaacg ccgtccaata ccacaccagc atcgacgtct  36600
cgatgacgct gctgctcaag acaacgctgc gtatgcgccc cgaccgcatc ctggtcggtg  36660
aggtacgtgg ccccgaagcc cttgatctgt tgatggcctg gaacaccggg catgaaggag  36720
gtgccgccac cctgcacgca aacaacccca aagcgggcct gagccggctc gccatgctta  36780
```

-continued

```
tcagcatgca cccggattca ccgaaaccca ttgagccgct gattggcgag gcggttcatg  36840
tggtcgtcca tatcgccagg acccctagcg gccgtcgagt gcaagaaatt ctcgaagttc  36900
ttggttacga gaacggccag tacatcacca aaaccctgta aggagtattt ccaatgacaa  36960
cggctgttcc gttccgtctg accatgaatc gcggcatttt gttctacctt gccgtgttct  37020
tcgttctcgc tctcgcgtta tccgcgcatc cggcgatggc ctcggaaggc accggcggca  37080
gcttgccata tgagagctgg ctgacgaacc tgcgcaactc cgtaaccggc ccggtggcct  37140
tcgcgctgtc catcatcggc atcgtcgtcg ccggcggcgt gctgatcttc ggcggcgaac  37200
tcaacgcctt cttccgaacc ctgatcttcc tggttctggt gatggcgctg ctggtcggcg  37260
cgcagaacgt gatgagcacc ttcttcggtc gtggtgccga aatcgcggcc ctcggcaacg  37320
gggcgctgca ccaggtgcaa gtcgcggcgg cggatgccgt gcgtgcggta gcggctggac  37380
ggctcgccta atcatggctc tgcgcacgat ccccatccgt cgcgcaggca accgagaaaa  37440
cctgttcatg ggtggtgatc gtgaactggt gatgttctcg ggcctgatgg cgtttgcgct  37500
gattttcagc gcccaagagc tgcgggccac cgtggtcggt ctgatcctgt ggttcggggc  37560
gctctatgcg ttccgaatca tggcgaaggc cgatccgaag atgcggttcg tgtacctgcg  37620
tcaccgccgg tacaagccgt attacccggc ccgctcgacc ccgttccgcg agaacaccaa  37680
tagccaaggg aagcaatacc gatgatccaa gcaattgcga ttgcaatcgc gggcctcggc  37740
gcgcttctgt tgttcatcct ctttgcccgc atccgcgcgg tcgatgccga actgaaactg  37800
aaaaagcatc gttccaagga cgccggcctg gccgatctgc tcaactacgc cgctgtcgtc  37860
gatgacggcg taatcgtggg caagaacggc agctttatgg ctgcctggct gtacaagggc  37920
gatgacaacg caagcagcac cgaccagcag cgcgaagtag tgtccgcccg catcaaccag  37980
gccctcgcgg gcctgggaag tgggtggatg atccatgtgg acgccgtgcg gcgtcctgct  38040
ccgaactacg cggagcgggg cctgtcggcg ttccctgacc gtctgacggc agcgattgaa  38100
gaagagcgct cggtcttgcc ttgctcgtcg gtgatgtact tcaccagctc cgcgaagtcg  38160
ctcttcttga tggagcgcat ggggacgtgc ttggcaatca cgcgcacccc ccggccgttt  38220
tagcggctaa aaaagtcatg gctctgccct cgggcggacc acgcccatca tgaccttgcc  38280
aagctcgtcc tgcttctctt cgatcttcgc cagcagggcg aggatcgtgg catcaccgaa  38340
ccgcgccgtg cgcgggtcgt cggtgagcca gagtttcagc aggccgccca ggcggcccag  38400
gtcgccattg atgcgggcca gctcgcggac gtgctcatag tccacgacgc ccgtgatttt  38460
gtagccctgg ccgacggcca gcaggtaggc cgacaggctc atgccggccg ccgccgcctt  38520
ttcctcaatc gctcttcgtt cgtctggaag gcagtacacc ttgataggtg ggctgccctt  38580
cctggttggc ttggtttcat cagccatccg cttgccctca tctgttacgc cggcggtagc  38640
cggccagcct cgcagagcag gattcccgtt gagcaccgcc aggtgcgaat aagggacagt  38700
gaagaaggaa cacccgctcg cgggtgggcc tacttcacct atcctgcccg gctgacgccg  38760
ttggatacac caaggaaagt ctacacgaac cctttggcaa aatcctgtat atcgtgcgaa  38820
aaaggatgga tataccgaaa aaatcgctat aatgaccccg aagcagggtt atgcagcgga  38880
aaagcgctgc ttccctgctg ttttgtggaa tatctaccga ctggaaacag gcaaatgcag  38940
gaaattactg aactgagggg acaggcgaga gacgatgcca aagagctaca ccgacgagct  39000
ggccgagtgg gttgaatccc gcgcggccaa gaagcgccgg cgtgatgagg ctgcggttgc  39060
gttcctggcg gtgagggcgg atgtcgaggc ggcgttagcg tccggctatg cgctcgtcac  39120
catttgggag cacatgcggg aaacggggaa ggtcaagttc tcctacgaga cgttccgctc  39180
```

gcacgccagg cggcacatca aggccaagcc cgccgatgtg cccgcaccgc aggccaaggc 39240
tgcggaaccc gcgccggcac ccaagacgcc ggagccacgg cggccgaagc aggggggcaa 39300
ggctgaaaag ccggcccccg ctgcggcccc gaccggcttc accttcaacc caacaccgga 39360
caaaaaggat ctactgtaat ggcgaaaatt cacatggttt tgcagggcaa gggcggggtc 39420
ggcaagtcgg ccatcgccgc gatcattgcg cagtacaaga tggacaaggg gcagacaccc 39480
ttgtgcatcg acaccgaccc ggtgaacgcg acgttcgagg gctacaaggc cctgaacgtc 39540
cgccggctga acatcatggc cggcgacgaa attaactcgc gcaacttcga caccctggtc 39600
gagctgattg cgccgaccaa ggatgacgtg gtgatcgaca acggtgccag ctcgttcgtg 39660
cctctgtcgc attacctcat cagcaaccag gtgccggctc tgctgcaaga aatggggcat 39720
gagctggtca tccataccgt cgtcaccggc ggccaggctc tcctggacac ggtgagcggc 39780
ttcgcccagc tcgccagcca gttcccggcc gaagcgcttt tcgtggtctg gctgaacccg 39840
tattggggggc ctatcgagca tgagggcaag agctttgagc agatgaaggc gtacacggcc 39900
aacaaggccc gcgtgtcgtc catcatccag attccggccc tcaaggaaga aacctacggc 39960
cgcgatttca gcgacatgct gcaagagcgg ctgacgttcg accaggcgct ggccgatgaa 40020
tcgctcacga tcatgacgcg gcaacgcctc aagatcgtgc ggcgcggcct gtttgaacag 40080
ctcgacgcgg cggccgtgct atgagcgacc agattgaaga gctgatccgg gagattgcgg 40140
ccaagcacgg catcgccgtc ggccgcgacg acccggtgct gatcctgcat accatcaacg 40200
cccggctcat ggccgacagt gcggccaagc aagaggaaat ccttgccgcg ttcaaggaag 40260
agctggaagg gatcgcccat cgttggggcg aggacgccaa ggccaaagcg gagcggatgc 40320
tgaacgcggc cctggcggcc agcaaggacg caatggcgaa ggtaatgaag gacagcgccg 40380
cgcaggcggc cgaagcgatc cgcagggaaa tcgacgacgg ccttggccgc cagctcgcgg 40440
ccaaggtcgc ggacgcgcgg cgcgtggcga tgatgaacat gatcgccggc ggcatggtgt 40500
tgttcgcggc cgccctggtg gtgtgggcct cgttatgaat cgcagaggcg cagatgaaaa 40560
agcccggcgt tgccgggctt tgtttttgcg ttagctgggc ttgtttgaca ggcccaagct 40620
ctgactgcgc ccgcgctcgc gctcctgggc ctgtttcttc tcctgctcct gcttgcgcat 40680
cagggcctgg tgccgtcggg ctgcttcacg catcgaatcc cagtcgccgg ccagctcggg 40740
atgctccgcg cgcatcttgc gcgtcgccag ttcctcgatc ttgggcgcgt gaatgcccat 40800
gccttccttg atttcgcgca ccatgtccag ccgcgtgtgc agggtctgca agcgggcttg 40860
ctgttgggcc tgctgctgct gccaggcggc ctttgtacgc ggcagggaca gcaagccggg 40920
ggcattggac tgtagctgct gcaaacgcgc ctgctgacgg tctacgagct gttctaggcg 40980
gtcctcgatg cgctccacct ggtcatgctt tgcctgcacg tagagcgcaa gggtctgctg 41040
gtaggtctgc tcgatgggcg cggattctaa gagggcctgc tgttccgtct cggcctcctg 41100
ggccgcctgt agcaaatcct cgccgctgtt gccgctggac tgctttactg ccggggactg 41160
ctgttgccct gctcgcgccg tcgtcgcagt tcggcttgcc cccactcgat tgactgcttc 41220
atttcgagcc gcagcgatgc gatctcggat tgcgtcaacg gacggggcag cgcggaggtg 41280
tccggcttct ccttgggtga gtcggtcgat gccatagcca aaggtttcct tccaaaatgc 41340
gtccattgct ggaccgtgtt tctcattgat gcccgcaagc atcttcggct tgaccgccag 41400
gtcaagcgcg ccttcatggg cggtcatgac ggacgccgcc atgaccttgc cgccgttgtt 41460
ctcgatgtag ccgcgtaatg aggcaatggt gccgcccatc gtcagcgtgt catcgacaac 41520
gatgtacttc tggccgggga tcacctcccc ctcgaaagtc gggttgaacg ccaggcgatg 41580

-continued

```
atctgaaccg gctccggttc gggcgacctt ctcccgctgc acaatgtccg tttcgacctc  41640
aaggccaagg cggtcggcca gaacgaccgc catcatggcc ggaatcttgt tgttccccgc  41700
cgcctcgacg gcgaggactg gaacgatgcg gggcttgtcg tcgccgatca gcgtcttgag  41760
ctgggcaaca gtgtcgtccg aaatcaggcg ctcgaccaaa ttaagcgccg cttccgcgtc  41820
gccctgcttc gcagcctggt attcaggctc gttggtcaaa gaaccaaggt cgccgttgcg  41880
aaccaccttc gggaagtctc cccacggtgc gcgctcggct ctgctgtagc tgctcaagac  41940
gcctcccttt ttagccgcta aaactctaac gagtgcgccc gcgactcaac ttgacgcttt  42000
cggcacttac ctgtgccttg ccacttgcgt cataggtgat gcttttcgca ctcccgattt  42060
caggtacttt atcgaaatct gaccgggcgt gcattacaaa gttcttcccc acctgttggt  42120
aaatgctgcc gctatctgcg tggacgatgc tgccgtcgtg gcgctgcgac ttatcggcct  42180
tttgggccat atagatgttg taaatgccag gtttcagggc cccggcttta tctaccttct  42240
ggttcgtcca tgcgccttgg ttctcggtct ggacaattct ttgcccattc atgaccagga  42300
ggcggtgttt cattgggtga ctcctgacgg ttgcctctgg tgttaaacgt gtcctggtcg  42360
cttgccggct aaaaaaaagc cgacctcggc agttcgaggc cggctttccc tagagccggg  42420
cgcgtcaagg ttgttccatc tattttagtg aactgcgttc gatttatcag ttactttcct  42480
cccgctttgt gtttcctccc actcgtttcc gcgtctagcc gacccctcaa catagcggcc  42540
tcttcttggg ctgcctttgc ctcttgccgc gcttcgtcac gctcggcttg caccgtcgta  42600
aagcgctcgg cctgcctggc cgcctcttgc gccgccaact tcctttgctc ctggtgggcc  42660
tcggcgtcgg cctgcgcctt cgctttcacc gctgccaact ccgtgcgcaa actctccgct  42720
tcgcgcctgg tggcgtcgcg ctcgccgcga agcgcctgca tttcctggtt ggccgcgtcc  42780
agggtcttgc ggctctcttc tttgaatgcg cgggcgtcct ggtgagcgta gtccagctcg  42840
gcgcgcagct cctgcgctcg acgctccacc tcgtcggccc gctgcgtcgc cagcgcggcc  42900
cgctgctcgg ctcctgccag ggcggtgcgt gcttcggcca gggcttgccg ctggcgtgcg  42960
gccagctcgg ccgcctcggc ggcctgctgc tctagcaatg taacgcgcgc ctgggcttct  43020
tccagctcgc gggcctgcgc ctcgaaggcg tcggccagct ccccgcgcac ggcttccaac  43080
tcgttgcgct cacgatccca gccggcttgc gctgcctgca acgattcatt ggcaagggcc  43140
tgggcggctt gccagagggc ggccacggcc tggttgccgg cctgctgcac cgcgtccggc  43200
acctggactg ccagcggggc ggcctgcgcc gtgcgctggc gtcgccattc gcgcatgccg  43260
gcgctggcgt cgttcatgtt gacgcgggcg gccttacgca ctgcatccac ggtcgggaag  43320
ttctcccggt cgccttgctc gaacagctcg tccgcagccg caaaaatgcg gtcgcgcgtc  43380
tctttgttca gttccatgtt ggctccggta attggtaaga ataataatac tcttacctac  43440
cttatcagcg caagagttta gctgaacagt tctcgactta acggcaggtt ttttagcggc  43500
tgaagggcag gcaaaaaaag ccccgcacgg tcggcggggg caaagggtca gcgggaaggg  43560
gattagcggg cgtcgggctt cttcatgcgt cggggccgcg cttcttggga tggagcacga  43620
cgaagcgcgc acgcgcatcg tcctcggccc tatcggcccg cgtcgcggtc aggaacttgt  43680
cgcgcgctag gtcctccctg gtgggcacca ggggcatgaa ctcggcctgc tcgatgtagg  43740
tccactccat gaccgcatcg cagtcgaggc cgcgttcctt caccgtctct tgcaggtcgc  43800
ggtacgcccg ctcgttgagc ggctggtaac gggccaattg gtcgtaaatg gctgtcggcc  43860
atgagcggcc tttcctgttg agccagcagc cgacgacgaa gccggcaatg caggcccctg  43920
gcacaaccag gccgacgccg gggcagggg atggcagcag ctcgccaacc aggaaccccg  43980
```

-continued

```
ccgcgatgat gccgatgccg gtcaaccagc ccttgaaact atccggcccc gaaacacccc  44040
tgcgcattgc ctggatgctg cgccggatag cttgcaacat caggagccgt ttcttttgtt  44100
cgtcagtcat ggtccgccct caccagttgt tcgtatcggt gtcggacgaa ctgaaatcgc  44160
aagagctgcc ggtatcggtc cagccgctgt ccgtgtcgct gctgccgaag cacggcgagg  44220
ggtccgcgaa cgccgcagac ggcgtatccg gccgcagcgc atcgcccagc atggccccgg  44280
tcagcgagcc gccggccagg tagcccagca tggtgctgtt ggtcgccccg gccaccaggg  44340
ccgacgtgac gaaatcgccg tcattccctc tggattgttc gctgctcggc ggggcagtgc  44400
gccgcgccgg cggcgtcgtg gatggctcgg gttggctggc ctgcgacggc cggcgaaagg  44460
tgcgcagcag ctcgttatcg accggctgcg gcgtcggggc cgccgccttg cgctgcggtc  44520
ggtgttcctt cttcggctcg cgcagcttga acagcatgat cgcggaaacc agcagcaacg  44580
ccgcgcctac gcctcccgcg atgtagaaca gcatcggatt cattcttcgg tcctccttgt  44640
agcggaaccg ttgtctgtgc ggcgcgggtg gcccgcgccg ctgtctttgg ggatcagccc  44700
tcgatgagcg cgaccagttt cacgtcggca aggttcgcct cgaactcctg gccgtcgtcc  44760
tcgtacttca accaggcata gccttccgcc ggcggccgac ggttgaggat aaggcgggca  44820
gggcgctcgt cgtgctcgac ctggacgatg gcctttttca gcttgtccgg gtccggctcc  44880
ttcgcgccct tttccttggc gtccttaccg tcctggtcgc cgtcctcgcc gtcctggccg  44940
tcgccggcct ccgcgtcacg ctcggcatca gtctggccgt tgaaggcatc gacggtgttg  45000
ggatcgcggc ccttctcgtc caggaactcg cgcagcagct tgaccgtgcc gcgcgtgatt  45060
tcctgggtgt cgtcgtcaag ccacgcctcg acttcctccg ggcgcttctt gaaggccgtc  45120
accagctcgt tcaccacggt cacgtcgcgc acgcggccgg tgttgaacgc atcggcgatc  45180
ttctccggca ggtccagcag cgtgacgtgc tgggtgatga acgccggcga cttgccgatt  45240
tccttggcga tatcgccttt cttcttgccc ttcgccagct cgcggccaat gaagtcggca  45300
atttcgcgcg gggtcagctc gttgcgttgc aggttctcga taacctggtc ggcttcgttg  45360
tagtcgttgt cgatgaacgc cgggatggac ttcttgccgg cccacttcga gccacggtag  45420
cggcgggcgc cgtgattgat gatatagcgg cccggctgct cctggttctc gcgcaccgaa  45480
atgggtgact tcaccccgcg ctctttgatc gtggcaccga tttccgcgat gctctccggg  45540
gaaaagccgg ggttgtcggc cgtccgcggc tgatgcggat cttcgtcgat caggtccagg  45600
tccagctcga tagggccgga accgccctga gacgccgcag gagcgtccag gaggctcgac  45660
aggtcgccga tgctatccaa ccccaggccg gacggctgcg ccgcgcctgc ggcttcctga  45720
gcggccgcag cggtgttttt cttggtggtc ttggcttgag ccgcagtcat tgggaaatct  45780
ccatcttcgt gaacacgtaa tcagccaggg cgcgaacctc tttcgatgcc ttgcgcgcgg  45840
ccgttttctt gatcttccag accggcacac cggatgcgag ggcatcggcg atgctgctgc  45900
gcaggccaac ggtggccgga atcatcatct tggggtacgc ggccagcagc tcggcttggt  45960
ggcgcgcgtg gcgcggattc cgcgcatcga ccttgctggg caccatgcca aggaattgca  46020
gcttggcgtt cttctggcgc acgttcgcaa tggtcgtgac catcttcttg atgccctgga  46080
tgctgtacgc ctcaagctcg atgggggaca gcacatagtc ggccgcgaag agggcggccg  46140
ccaggccgac gccaagggtc ggggccgtgt cgatcaggca cacgtcgaag ccttggttcg  46200
ccagggcctt gatgttcgcc ccgaacagct cgcgggcgtc gtccagcgac agccgttcgg  46260
cgttcgccag taccgggttg gactcgatga gggcgaggcg cgcggcctgg ccgtcgccgg  46320
ctgcgggtgc ggtttcggtc cagccgccgg cagggacagc gccgaacagc ttgcttgcat  46380
```

-continued

```
gcaggccggt agcaaagtcc ttgagcgtgt aggacgcatt gccctggggg tccaggtcga  46440
tcacggcaac ccgcaagccg cgctcgaaaa agtcgaaggc aagatgcaca agggtcgaag  46500
tcttgccgac gccgcctttc tggttggccg tgaccaaagt tttcatcgtt tggtttcctg  46560
ttttttcttg gcgtccgctt cccacttccg gacgatgtac gcctgatgtt ccggcagaac  46620
cgccgttacc cgcgcgtacc cctcgggcaa gttcttgtcc tcgaacgcgg cccacacgcg  46680
atgcaccgct tgcgacactg cgcccctggt cagtcccagc gacgttgcga acgtcgcctg  46740
tggcttccca tcgactaaga cgccccgcgc tatctcgatg gtctgctgcc ccacttccag  46800
cccctggatc gcctcctgga actggctttc ggtaagccgt ttcttcatgg ataacaccca  46860
taatttgctc cgcgccttgg ttgaacatag cggtgacagc cgccagcaca tgagagaagt  46920
ttagctaaac atttctcgca cgtcaacacc tttagccgct aaaactcgtc cttggcgtaa  46980
caaaacaaaa gcccggaaac cgggctttcg tctcttgccg cttatggctc tgcacccggc  47040
tccatcacca acaggtcgcg cacgcgcttc actcggttgc ggatcgacac tgccagccca  47100
acaaagccgg ttgccgccgc cgccaggatc gcgccgatga tgccggccac accggccatc  47160
gcccaccagg tcgccgcctt ccggttccat tcctgctggt actgcttcgc aatgctggac  47220
ctcggctcac cataggctga ccgctcgatg gcgtatgccg cttctcccct tggcgtaaaa  47280
cccagcgccg caggcggcat tgccatgctg cccgccgctt tcccgaccac gacgcgcgca  47340
ccaggcttgc ggtccagacc ttcggccacg gcgagctgcg caaggacata atcagccgcc  47400
gacttggctc cacgcgcctc gatcagctct tgcactcgcg cgaaatcctt ggcctccacg  47460
gccgccatga atcgcgcacg cggcgaaggc tccgcagggc cggcgtcgtg atcgccgccg  47520
agaatgccct tcaccaagtt cgacgacacg aaaatcatgc tgacggctat caccatcatg  47580
cagacggatc gcacgaaccc gctgaattga acacgagcac ggcacccgcg accactatgc  47640
caagaatgcc caaggtaaaa attgccggcc ccgccatgaa gtccgtgaat gccccgacgg  47700
ccgaagtgaa gggcaggccg ccacccaggc cgccgccctc actgcccggc acctggtcgc  47760
tgaatgtcga tgccagcacc tgcggcacgt caatgcttcc gggcgtcgcg ctcgggctga  47820
tcgcccatcc cgttactgcc ccgatcccgg caatggcaag gactgccagc gctgccattt  47880
ttggggtgag gccgttcgcg gccgaggggc gcagcccctg gggggatggg aggcccgcgt  47940
tagcgggccg ggagggttcg agaagggggg gcacccccct tcggcgtgcg cggtcacgcg  48000
cacagggcgc agccctggtt aaaaacaagg tttataaata ttggtttaaa agcaggttaa  48060
aagacaggtt agcggtggcc gaaaaacggg cggaaaccct tgcaaatgct ggattttctg  48120
cctgtggaca gcccctcaaa tgtcaatagg tgcgcccctc atctgtcagc actctgcccc  48180
tcaagtgtca aggatcgcgc ccctcatctg tcagtagtcg cgcccctcaa gtgtcaatac  48240
cgcagggcac ttatccccag gcttgtccac atcatctgtg ggaaactcgc gtaaaatcag  48300
gcgttttcgc cgatttgcga ggctggccag ctccacgtcg ccggccgaaa tcgagcctgc  48360
ccctcatctg tcaacgccgc gccgggtgag tcggcccctc aagtgtcaac gtccgcccct  48420
catctgtcag tgagggccaa gttttccgcg aggtatccac aacgccggcg gccgcggtgt  48480
ctcgcacacg gcttcgacgg cgtttctggc gcgtttgcag ggccatagac ggccgccagc  48540
ccagcggcga gggcaaccag cccggtgagc gtcggaaagg cgctggaagc cccgtagcga  48600
cgcggagagg ggcgagacaa gccaagggcg caggctcgat gcgcagcacg acatagccgg  48660
ttctcgcaag gacgagaatt tccctgcggt gcccctcaag tgtcaatgaa agtttccaac  48720
gcgagccatt cgcgagagcc ttgagtccac gctagatgag agctttgttg taggtggacc  48780
```

agttggtgat tttgaacttt tgctttgcca cggaacggtc tgcgttgtcg ggaagatgcg 48840
tgatctgatc cttcaactca gcaaaagttc gatttattca acaaagccac gttgtgtctc 48900
aaaatctctg atgttacatt gcacaagata aaaatatatc atcatgaaca ataaaactgt 48960
ctgcttacat aaacagtaat acaaggggtg ttatgagcca tattcaacgg gaaac 49015

<210> SEQ ID NO 96
<211> LENGTH: 48997
<212> TYPE: DNA
<213> ORGANISM: vector

<400> SEQUENCE: 96
gtcttgctcg actctagagc tcgttcctcg aggcctcgag gcctcgagga acggtacctg 60
cggggaagct tacaataatg tgtgttgtta agtcttgttg cctgtcatcg tctgactgac 120
tttcgtcata aatcccggcc tccgtaaccc agctttgggc aagctcacgg atttgatccg 180
gcggaacggg aatatcgaga tgccgggctg aacgctgcag ttccagcttt ccctttcggg 240
acaggtactc cagctgattg attatctgct gaagggtctt ggttccacct cctggcacaa 300
tgcgaatgat tacttgagcg cgatcgggca tccaattttc tcccgtcagg tgcgtggtca 360
agtgctacaa ggcacctttc agtaacgagc gaccgtcgat ccgtcgccgg gatacggaca 420
aaatggagcg cagtagtcca tcgagggcgg cgaaagcctc gccaaaagca atacgttcat 480
ctcgcacagc ctccagatcc gatcgagggt cttcggcgta ggcagataga agcatggata 540
cattgcttga gagtattccg atggactgaa gtatggcttc catcttttct cgtgtgtctg 600
catctatttc gagaaagccc ccgatgcggc gcaccgcaac gcgaattgcc atactatccg 660
aaagtcccag caggcgcgct tgataggaaa aggtttcata ctcggccgat cgcagacggg 720
cactcacgac cttgaaccct tcaactttca gggatcgatg ctggttgatg gtagtctcac 780
tcgacgtggc tctggtgtgt tttgacatag cttcctccaa agaaagcgga aggtctggat 840
actccagcac gaaatgtgcc cgggtagacg gatggaagtc tagccctgct caatatgaaa 900
tcaacagtac atttacagtc aatactgaat atacttgcta catttgcaat tgtcttataa 960
cgaatgtgaa ataaaaatag tgtaacaacg cttttactca tcgataatca caaaaacatt 1020
tatacgaaca aaaatacaaa tgcactccgg tttcacagga taggcgggat cagaatatgc 1080
aacttttgac gttttgttct ttcaaagggg gtgctggcaa aaccaccgca ctcatgggcc 1140
tttgcgctgc tttggcaaat gacggtaaac gagtggccct ctttgatgcc gacgaaaacc 1200
ggcctctgac gcgatggaga gaaaacgcct tacaaagcag tactgggatc ctcgctgtga 1260
agtctattcc gccgacgaaa tgccccttct tgaagcagcc tatgaaaatg ccgagctcga 1320
aggatttgat tatgcgttgg ccgatacgcg tggcggctcg agcgagctca acaacacaat 1380
catcgctagc tcaaacctgc ttctgatccc caccatgcta acgccgctcg acatcgatga 1440
ggcactatct acctaccgct acgtcatcga gctgctgttg agtgaaaatt tggcaattcc 1500
tacagctgtt ttgcgccaac gcgtcccggt cggccgattg acaacatcgc aacgcaggat 1560
gtcagagacg ctagagagcc ttccagttgt accgtctccc atgcatgaaa gagatgcatt 1620
tgccgcgatg aaagaacgcg gcatgttgca tcttacatta ctaaacacgg gaactgatcc 1680
gacgatgcgc ctcatagaga ggaatcttcg gattgcgatg gaggaagtcg tggtcatttc 1740
gaaactgatc agcaaaatct tggaggcttg aagatggcaa ttcgcaagcc cgcattgtcg 1800
gtcggcgaag cacggcggct tgctggtgct cgacccgaga tccaccatcc caacccgaca 1860
cttgttcccc agaagctgga cctccagcac ttgcctgaaa aagccgacga gaaagaccag 1920

-continued

```
caacgtgagc ctctcgtcgc cgatcacatt tacagtcccg atcgacaact taagctaact   1980
gtggatgccc ttagtccacc tccgtccccg aaaaagctcc aggtttttct ttcagcgcga   2040
ccgcccgcgc ctcaagtgtc gaaaacatat gacaacctcg ttcggcaata cagtccctcg   2100
aagtcgctac aaatgatttt aaggcgcgcg ttggacgatt tcgaaagcat gctggcagat   2160
ggatcatttc gcgtggcccc gaaaagttat ccgatccctt caactacaga aaaatccgtt   2220
ctcgttcaga cctcacgcat gttcccggtt gcgttgctcg aggtcgctcg aagtcatttt   2280
gatccgttgg ggttggagac cgctcgagct ttcggccaca agctggctac cgccgcgctc   2340
gcgtcattct ttgctggaga gaagccatcg agcaattggt gaagagggac ctatcggaac   2400
ccctcaccaa atattgagtg taggtttgag gccgctggcc gcgtcctcag tcaccttttg   2460
agccagataa ttaagagcca aatgcaattg gctcaggctg ccatcgtccc cccgtgcgaa   2520
acctgcacgt ccgcgtcaaa gaaataaccg gcacctcttg ctgtttttat cagttgaggg   2580
cttgacggat ccgcctcaag tttgcggcgc agccgcaaaa tgagaacatc tatactcctg   2640
tcgtaaacct cctcgtcgcg tactcgactg gcaatgagaa gttgctcgcg cgatagaacg   2700
tcgcggggtt tctctaaaaa cgcgaggaga agattgaact cacctgccgt aagtttcacc   2760
tcaccgccag cttcggacat caagcgacgt tgcctgagat taagtgtcca gtcagtaaaa   2820
caaaaagacc gtcggtcttt ggagcggaca acgttggggc gcacgcgcaa ggcaacccga   2880
atgcgtgcaa gaaactctct cgtactaaac ggcttagcga taaaatcact tgctcctagc   2940
tcgagtgcaa caactttatc cgtctcctca aggcggtcgc cactgataat tatgattgga   3000
atatcagact ttgccgccag atttcgaacg atctcaagcc catcttcacg acctaaattt   3060
agatcaacaa ccacgacatc gaccgtcgcg gaagagagta ctctagtgaa ctgggtgctg   3120
tcggctaccg cggtcacttt gaaggcgtgg atcgtaaggt attcgataat aagatgccgc   3180
atagcgacat cgtcatcgat aagaagaacg tgtttcaacg gctcaccttt caatctaaaa   3240
tctgaaccct tgttcacagc gcttgagaaa ttttcacgtg aaggatgtac aatcatctcc   3300
agctaaatgg gcagttcgtc agaattgcgg ctgaccgcgg atgacgaaaa tgcgaaccaa   3360
gtatttcaat tttatgacaa aagttctcaa tcgttgttac aagtgaaacg cttcgaggtt   3420
acagctacta ttgattaagg agatcgccta tggtctcgcc ccggcgtcgt gcgtccgccg   3480
cgagccagat ctcgcctact tcataaacgt cctcataggc acggaatgga atgatgacat   3540
cgatcgccgt agagagcatg tcaatcagtg tgcgatcttc caagctagca ccttgggcgc   3600
tacttttgac aagggaaaac agtttcttga atccttggat tggattcgcg ccgtgtattg   3660
ttgaaatcga tcccggatgt cccgagacga cttcactcag ataagcccat gctgcatcgt   3720
cgcgcatctc gccaagcaat atccggtccg gccgcatacg cagacttgct tggagcaagt   3780
gctcggcgct cacagcaccc agcccagcac cgttcttgga gtagagtagt ctaacatgat   3840
tatcgtgtgg aatgacgagt tcgagcgtat cttctatggt gattagcctt tcctgggggg   3900
ggatggcgct gatcaaggtc ttgctcattg ttgtcttgcc gcttccggta gggccacata   3960
gcaacatcgt cagtcggctg acgacgcatg cgtgcagaaa cgcttccaaa tccccgttgt   4020
caaaatgctg aaggatagct tcatcatcct gattttggcg tttccttcgt gtctgccact   4080
ggttccacct cgaagcatca taacgggagg agacttcttt aagaccagaa acacgcgagc   4140
ttggccgtcg aatggtcaag ctgacggtgc ccgagggaac ggtcggcggc agacagattt   4200
gtagtcgttc accaccagga agttcagtgg cgcagagggg gttacgtggt ccgacatcct   4260
gctttctcag cgcgcccgct aaaatagcga tatcttcaag atcatcataa gagacgggca   4320
```

-continued

```
aaggcatctt ggtaaaaatg ccggcttggc gcacaaatgc ctctccaggt cgattgatcg   4380
caatttcttc agtcttcggg tcatcgagcc attccaaaat cggcttcaga agaaagcgta   4440
gttgcggatc cacttccatt tacaatgtat cctatctcta agcggaaatt tgaattcatt   4500
aagagcggcg gttcctcccc cgcgtggcgc cgccagtcag gcggagctgg taaacaccaa   4560
agaaatcgag gtcccgtgct acgaaaatgg aaacggtgtc accctgattc ttcttcaggg   4620
ttggcggtat gttgatggtt gccttaaggg ctgtctcagt tgtctgctca ccgttatttt   4680
gaaagctgtt gaagctcatc ccgccacccg agctgccggc gtaggtgcta gctgcctgga   4740
aggcgccttg aacaacactc aagagcatag ctccgctaaa acgctgccag aagtggctgt   4800
cgaccgagcc cggcaatcct gagcgaccga gttcgtccgc gcttggcgat gttaacgaga   4860
tcatcgcatg gtcaggtgtc tcggcgcgat cccacaacac aaaaaacgcgc ccatctccct   4920
gttgcaagcc acgctgtatt tcgccaacaa cggtggtgcc acgatcaaga agcacgatat   4980
tgttcgttgt tccacgaata tcctgaggca agacacactt tacatagcct gccaaatttg   5040
tgtcgattgc ggtttgcaag atgcacggaa ttattgtccc ttgcgttacc ataaaatcgg   5100
ggtgcggcaa gagcgtggcg ctgctgggct gcagctcggt gggtttcata cgtatcgaca   5160
aatcgttctc gccggacact tcgccattcg gcaaggagtt gtcgtcacgc ttgccttctt   5220
gtcttcggcc cgtgtcgccc tgaatggcgc gtttgctgac cccttgatcg ccgctgctat   5280
atgcaaaaat cggtgtttct tccggccgtg gctcatgccg ctccggttcg cccctcggcg   5340
gtagaggagc agcaggctga acagcctctt gaaccgctgg aggatccggc ggcacctcaa   5400
tcggagctgg atgaaatggc ttggtgtttg ttgcgatcaa agttgacggc gatgcgttct   5460
cattcacctt cttttggcgc ccacctagcc aaatgaggct taatgataac gcgagaacga   5520
cacctccgac gatcaatttc tgagaccccg aaagacgccg gcgatgtttg tcggagacca   5580
gggatccaga tgcatcaacc tcatgtgccg cttgctgact atcgttattc atcccttcgc   5640
ccccttcagg acgcgtttca catcgggcct caccgtgccc gtttgcggcc tttggccaac   5700
gggatcgtaa gcggtgttcc agatacatag tactgtgtgg ccatccctca gacgccaacc   5760
tcgggaaacc gaagaaatct cgacatcgct ccctttaact gaatagttgg caacagcttc   5820
cttgccatca ggattgatgg tgtagatgga gggtatgcgt acattgcccg gaaagtggaa   5880
taccgtcgta aatccattgt cgaagacttc gagtggcaac agcgaacgat cgccttgggc   5940
gacgtagtgc caattactgt ccgccgcacc aagggctgtg acaggctgat ccaataaatt   6000
ctcagctttc cgttgatatt gtgcttccgc gtgtagtctg tccacaacag ccttctgttg   6060
tgcctccctt cgccgagccg ccgcatcgtc ggcggggtag gcgaattgga cgctgtaata   6120
gagatcgggc tgctctttat cgaggtggga cagagtcttg gaacttatac tgaaaacata   6180
acggcgcatc ccggagtcgc ttgcggttag cacgattact ggctgaggcg tgaggacctg   6240
gcttgccttg aaaaatagat aatttccccg cggtagggct gctagatctt tgctatttga   6300
aacggcaacc gctgtcaccg tttcgttcgt ggcgaatgtt acgaccaaag tagctccaac   6360
cgccgtcgag aggcgcacca cttgatcggg attgtaagcc aaataacgca tgcgcggatc   6420
tagcttgccc gccattggag tgtcttcagc ctccgcacca gtcgcagcgg caaataaaca   6480
tgctaaaatg aaaagtgctt ttctgatcat ggttcgctgt ggcctacgtt tgaaacggta   6540
tcttccgatg tctgatagga ggtgacaacc agacctgccg ggttggttag tctcaatctg   6600
ccgggcaagc tggtcacctt ttcgtagcga actgtcgcgg tccacgtact caccacaggc   6660
attttgccgt caacgacgag ggtcctttta tagcgaattt gctgcgtgct tggagttaca   6720
```

-continued

```
tcatttgaag cgatgtgctc gacctccacc ctgccgcgtt tgccaagaat gacttgaggc   6780
gaactgggat tgggatagtt gaagaattgc tggtaatcct ggcgcactgt tggggcactg   6840
aagttcgata ccaggtcgta ggcgtactga gcggtgtcgg catcataact ctcgcgcagg   6900
cgaacgtact cccacaatga ggcgttaacg acggcctcct cttgagttgc aggcaatcgc   6960
gagacagaca cctcgctgtc aacggtgccg tccggccgta tccatagata tacgggcaca   7020
agcctgctca acggcaccat tgtggctata gcgaacgctt gagcaacatt tcccaaaatc   7080
gcgatagctg cgacagctgc aatgagtttg gagagacgtc gcgccgattt cgctcgcgcg   7140
gtttgaaagg cttctacttc cttatagtgc tcggcaaggc tttcgcgcgc cactagcatg   7200
gcatattcag gccccgtcat agcgtccacc cgaattgccg agctgaagat ctgacggagt   7260
aggctgccat cgccccacat tcagcgggaa gatcgggcct ttgcagctcg ctaatgtgtc   7320
gtttgtctgg cagccgctca aagcgacaac taggcacagc aggcaatact tcatagaatt   7380
ctccattgag gcgaattttt gcgcgaccta gcctcgctca acctgagcga agcgacggta   7440
caagctgctg gcagattggg ttgcgccgct ccagtaactg cctccaatgt tgccggcgat   7500
cgccggcaaa gcgacaatga gcgcatcccc tgtcagaaaa aacatatcga gttcgtaaag   7560
accaatgatc ttggccgcgg tcgtaccggc gaaggtgatt acaccaagca taagggtgag   7620
cgcagtcgct tcggttagga tgacgatcgt tgccacgagg tttaagagga gaagcaagag   7680
accgtaggtg ataagttgcc cgatccactt agctgcgatg tcccgcgtgc gatcaaaaat   7740
atatccgacg aggatcagag gcccgatcgc gagaagcact ttcgtgagaa ttccaacggc   7800
gtcgtaaact ccgaaggcag accagagcgt gccgtaaagg acccactgtg ccccttggaa   7860
agcaaggatg tcctggtcgt tcatcggacc gatttcggat gcgattttct gaaaaacggc   7920
ctgggtcacg gcgaacattg tatccaactg tgccggaaca gtctgcagag gcaagccggt   7980
tacactaaac tgctgaacaa agtttgggac cgtcttttcg aagatggaaa ccacatagtc   8040
ttggtagtta gcctgcccaa caattagagc aacaacgatg gtgaccgtga tcacccgagt   8100
gataccgcta cgggtatcga cttcgccgcg tatgactaaa ataccctgaa caataatcca   8160
aagagtgaca caggcgatca atggcgcact caccgcctcc tggatagtct caagcatcga   8220
gtccaagcct gtcgtgaagg ctacatcgaa gatcgtatga atggccgtaa acggcgccgg   8280
aatcgtgaaa ttcatcgatt ggacctgaac ttgactggtt tgtcgcataa tgttggataa   8340
aatgagctcg cattcggcga ggatgcgggc ggatgaacaa atcgcccagc cttaggggag   8400
ggcaccaaag atgacagcgg tcttttgatg ctccttgcgt tgagcggccg cctcttccgc   8460
ctcgtgaagg ccggcctgcg cggtagtcat cgttaatagg cttgtcgcct gtacattttg   8520
aatcattgcg tcatggatct gcttgagaag caaaccattg gtcacggttg cctgcatgat   8580
attgcgagat cgggaaagct gagcagacgt atcagcattc gccgtcaagc gtttgtccat   8640
cgtttccaga ttgtcagccg caatgccagc gctgtttgcg gaaccggtga tctgcgatcg   8700
caacaggtcc gcttcagcat cactacccac gactgcacga tctgtatcgc tggtgatcgc   8760
acgtgccgtg gtcgacattg gcattcgcgg cgaaaacatt tcattgtcta ggtccttcgt   8820
cgaaggatac tgatttttct ggttgagcga agtcagtagt ccagtaacgc cgtaggccga   8880
cgtcaacatc gtaaccatcg ctatagtctg agtgagattc tccgcagtcg cgagcgcagt   8940
cgcgagcgtc tcagcctccg ttgccgggtc gctaacaaca aactgcgccc gcgcgggctg   9000
aatatataga aagctgcagg tcaaaactgt tgcaataagt tgcgtcgtct tcatcgtttc   9060
ctaccttatc aatcttctgc ctcgtggtga cgggccatga attcgctgag ccagccagat   9120
```

-continued

```
gagttgcctt cttgtgcctc gcgtagtcga gttgcaaagc gcaccgtgtt ggcacgcccc   9180
gaaagcacgg cgacatattc acgcatatcc cgcagatcaa attcgcagat gacgcttcca   9240
ctttctcgtt taagaagaaa cttacggctg ccgaccgtca tgtcttcacg gatcgcctga   9300
aattcctttt cggtacattt cagtccatcg acataagccg atcgatctgc ggttggtgat   9360
ggatagaaaa tcttcgtcat acattgcgca accaagctgg ctcctagcgg cgattccaga   9420
acatgctctg gttgctgcgt tgccagtatt agcatcccgt tgtttttttcg aacggtcagg   9480
aggaatttgt cgacgacagt cgaaaattta gggtttaaca aataggcgcg aaactcatcg   9540
cagctcatca caaaacggcg gccgtcgatc atggctccaa tccgatgcag gagatatgct   9600
gcagcgggag cgcatacttc ctcgtattcg agaagatgcg tcatgtcgaa gccggtaatc   9660
gacggatcta actttacttc gtcaacttcg ccgtcaaatg cccagccaag cgcatggccc   9720
cggcaccagc gttggagccg cgctcctgcg ccttcggcgg gcccatgcaa caaaaattca   9780
cgtaaccccg cgattgaacg catttgtgga tcaaacgaga gctgacgatg gataccacgg   9840
accagacggc ggttctcttc cggagaaatc ccaccccgac catcactctc gatgagagcc   9900
acgatccatt cgcgcagaaa atcgtgtgag gctgctgtgt tttctaggcc acgcaacggc   9960
gccaacccgc tgggtgtgcc tctgtgaagt gccaaatatg ttcctcctgt ggcgcgaacc  10020
agcaattcgc caccccggtc cttgtcaaag aacacgaccg tacctgcacg gtcgaccatg  10080
ctctgttcga gcatggctag aacaaacatc atgagcgtcg tcttacccct cccgataggc  10140
ccgaatattg ccgtcatgcc aacatcgtgc tcatgcggga tatagtcgaa aggcgttccg  10200
ccattggtac gaaatcgggc aatcgcgttg ccccagtggc ctgagctggc gccctctgga  10260
aagttttcga aagagacaaa ccctgcgaaa ttgcgtgaag tgattgcgcc agggcgtgtg  10320
cgccacttaa aattccccgg caattgggac caataggccg cttccatacc aataccttct  10380
tggacaacca cggcacctgc atccgccatt cgtgtccgag cccgcgcgcc cctgtcccca  10440
agactattga gatcgtctgc atagacgcaa aggctcaaat gatgtgagcc cataacgaat  10500
tcgttgctcg caagtgcgtc ctcagcctcg gataatttgc cgatttgagt cacggcttta  10560
tcgccggaac tcagcatctg gctcgatttg aggctaagtt tcgcgtgcgc ttgcgggcga  10620
gtcaggaacg aaaaactctg cgtgagaaca agtggaaaat cgagggatag cagcgcgttg  10680
agcatgcccg gccgtgtttt tgcagggtat tcgcgaaacg aatagatgga tccaacgtaa  10740
ctgtcttttg gcgttctgat ctcgagtcct cgcttgccgc aaatgactct gtcggtataa  10800
atcgaagcgc cgagtgagcc gctgacgacc ggaaccggtg tgaaccgacc agtcatgatc  10860
aaccgtagcg cttcgccaat ttcggtgaag agcacaccct gcttctcgcg gatgccaaga  10920
cgatgcaggc catacgcttt aagagagcca gcgacaacat gccaaagatc ttccatgttc  10980
ctgatctggc ccgtgagatc gttttccctt tttccgctta gcttggtgaa cctcctcttt  11040
accttcccta aagccgcctg tgggtagaca atcaacgtaa ggaagtgttc attgcggagg  11100
agttggccgg agagcacgcg ctgttcaaaa gcttcgttca ggctagcggc gaaaacacta  11160
cggaagtgtc gcggcgccga tgatggcacg tcggcatgac gtacgaggtg agcatatatt  11220
gacacatgat catcagcgat attgcgcaac agcgtgttga acgcacgaca acgcgcattg  11280
cgcatttcag tttcctcaag ctcgaatgca acgccatcaa ttctcgcaat ggtcatgatc  11340
gatccgtctt caagaaggac gatatggtcg ctgaggtggc caatataagg gagatagatc  11400
tcaccggatc tttcggtcgt tccactcgcg ccgagcatca caccattcct ctccctcgtg  11460
ggggaaccct aattggattt gggctaacag tagcgccccc ccaaactgca ctatcaatgc  11520
```

ttcttcccgc ggtccgcaaa aatagcagga cgacgctcgc cgcattgtag tctcgctcca 11580
cgatgagccg ggctgcaaac cataacggca cgagaacgac ttcgtagagc gggttctgaa 11640
cgataacgat gacaaagccg gcgaacatca tgaataaccc tgccaatgtc agtggcaccc 11700
caagaaacaa tgcgggccgt gtggctgcga ggtaaagggt cgattcttcc aaacgatcag 11760
ccatcaacta ccgccagtga gcgtttggcc gaggaagctc gccccaaaca tgataacaat 11820
gccgccgacg acgccggcaa ccagcccaag cgaagcccgc ccgaacatcc aggagatccc 11880
gatagcgaca atgccgagaa cagcgagtga ctggccgaac ggaccaagga taaacgtgca 11940
tatattgtta accattgtgg cggggtcagt gccgccaccc gcagattgcg ctgcggcggg 12000
tccggatgag gaaatgctcc atgcaattgc accgcacaag cttggggcgc agctcgatat 12060
cacgcgcatc atcgcattcg agagcgagag gcgatttaga tgtaaacggt atctctcaaa 12120
gcatcgcatc aatgcgcacc tccttagtat aagtcgaata agacttgatt gtcgtctgcg 12180
gatttgccgt tgtcctggtg tggcggtggc ggagcgatta aaccgccagc gccatcctcc 12240
tgcgagcggc gctgatatga cccccaaaca tcccacgtct cttcggattt tagcgcctcg 12300
tgatcgtctt ttggaggctc gattaacgcg ggcaccagcg attgagcagc tgtttcaact 12360
tttcgcacgt agccgtttgc aaaaccgccg atgaaattac cggtgttgta agcggagatc 12420
gcccgacgaa gcgcaaattg cttctcgtca atcgtttcgc cgcctgcata acgacttttc 12480
agcatgtttg cagcggcaga taatgatgtg cacgcctgga gcgcaccgtc aggtgtcaga 12540
ccgagcatag aaaaatttcg agagtttatt tgcatgaggc caacatccag cgaatgccgt 12600
gcatcgagac ggtgcctgac gacttgggtt gcttggctgt gatcttgcca gtgaagcgtt 12660
tcgccggtcg tgttgtcatg aatcgctaaa ggatcaaagc gactctccac cttagctatc 12720
gccgcaagcg tagatgtcgc aactgatggg gcacacttgc gagcaacatg gtcaaactca 12780
gcagatgaga gtggcgtggc aaggctcgac gaacagaagg agaccatcaa ggcaagagaa 12840
agcgaccccg atctcttaag catacettat ctccttagct cgcaactaac accgcctctc 12900
ccgttggaag aagtgcgttg ttttatgttg aagattatcg ggagggtcgg ttactcgaaa 12960
attttcaatt gcttctttat gatttcaatt gaagcgagaa acctcgcccg gcgtcttgga 13020
acgcaacatg gaccgagaac cgcgcatcca tgactaagca accggatcga cctattcagg 13080
ccgcagttgg tcaggtcagg ctcagaacga aaatgctcgg cgaggttacg ctgtctgtaa 13140
acccattcga tgaacgggaa gcttccttcc gattgctctt ggcaggaata ttggcccatg 13200
cctgcttgcg ctttgcaaat gctcttatcg cgttggtatc atatgccttg tccgccagca 13260
gaaacgcact ctaagcgatt atttgtaaaa atgtttcggt catgcggcgg tcatgggctt 13320
gacccgctgt cagcgcaaga cggatcggtc aaccgtcggc atcgacaaca gcgtgaatct 13380
tggtggtcaa accgccacgg gaacgtccca tacagccatc gtcttgatcc cgctgtttcc 13440
cgtcgccgca tgttggtgga cgcggacaca ggaactgtca atcatgacga cattctatcg 13500
aaagccttgg aaatcacact cagaatatga tcccagacgt ctgcctcacg ccatcgtaca 13560
aagcgattgt agcaggttgt acaggaaccg tatcgatcag gaacgtctgc ccagggcggg 13620
cccgtccgga agcgccacaa gatgacattg atcacccgcg tcaacgcgcg gcacgcgacg 13680
cggcttattt gggaacaaag gactgaacaa cagtccattc gaaatcggtg acatcaaagc 13740
ggggacgggt tatcagtggc ctccaagtca agcctcaatg aatcaaaatc agaccgattt 13800
gcaaacctga tttatgagtg tgcggcctaa atgatgaaat cgtccttcta gatcgcctcc 13860
gtggtgtagc aacacctcgc agtatcgccg tgctgacctt ggccagggaa ttgactggca 13920

-continued

```
agggtgcttt cacatgaccg ctcttttggc cgcgatagat gatttcgttg ctgctttggg  13980
cacgtagaag gagagaagtc atatcggaga aattcctcct ggcgcgagag cctgctctat  14040
cgcgacggca tcccactgtc gggaacagac cggatcattc acgaggcgaa agtcgtcaac  14100
acatgcgtta taggcatctt cccttgaagg atgatcttgt tgctgccaat ctggaggtgc  14160
ggcagccgca ggcagatgcg atctcagcgc aacttgcggc aaaacatctc actcacctga  14220
aaaccactag cgagtctcgc gatcagacga aggcctttta cttaacgaca caatatccga  14280
tgtctgcatc acaggcgtcg ctatcccagt caatactaaa gcggtgcagg aactaaagat  14340
tactgatgac ttaggcgtgc cacgaggcct gagacgacgc gcgtagacag tttttgaaa  14400
tcattatcaa agtgatggcc tccgctgaag cctatcacct ctgcgccggt ctgtcggaga  14460
gatgggcaag cattattacg gtcttcgcgc ccgtacatgc attggacgat tgcagggtca  14520
atggatctga gatcatccag aggattgccg ccccttacctt ccgtttcgag ttggagccag  14580
cccctaaatg agacgacata gtcgacttga tgtgacaatg ccaagagaga gatttgctta  14640
acccgatttt tttgctcaag cgtaagccta ttgaagcttg ccggcatgac gtccgcgccg  14700
aaagaatatc ctacaagtaa aacattctgc acaccgaaat gcttggtgta gacatcgatt  14760
atgtgaccaa gatccttagc agtttcgctt ggggaccgct ccgaccagaa ataccgaagt  14820
gaactgacgc caatgacagg aatcccttcc gtctgcagat aggtaccatc gatagatctg  14880
ctgcctcgcg cgtttcggtg atgacggtga aaacctctga cacatgcagc tcccggagac  14940
ggtcacagct tgtctgtaag cggatgccgg gagcagacaa gcccgtcagg gcgcgtcagc  15000
gggtgttggc gggtgtcggg gcgcagccat gacccagtca cgtagcgata gcggagtgta  15060
tactggctta actatgcggc atcagagcag attgtactga gagtgcacca tatgcggtgt  15120
gaaataccgc acagatgcgt aaggagaaaa taccgcatca ggcgctcttc cgcttcctcg  15180
ctcactgact cgctgcgctc ggtcgttcgg ctgcggcgag cggtatcagc tcactcaaag  15240
gcggtaatac ggttatccac agaatcaggg gataacgcag gaaagaacat gtgagcaaaa  15300
ggccagcaaa aggccaggaa ccgtaaaaag gccgcgttgc tggcgttttt ccataggctc  15360
cgcccccctg acgagcatca caaaaatcga cgctcaagtc agaggtggcg aaacccgaca  15420
ggactataaa gataccaggc gtttccccct ggaagctccc tcgtgcgctc tcctgttccg  15480
accctgccgc ttaccggata cctgtccgcc tttctccctt cgggaagcgt ggcgctttct  15540
catagctcac gctgtaggta tctcagttcg gtgtaggtcg ttcgctccaa gctgggctgt  15600
gtgcacgaac cccccgttca gcccgaccgc tgcgccttat ccggtaacta tcgtcttgag  15660
tccaacccgg taagacacga cttatcgcca ctggcagcag ccactggtaa caggattagc  15720
agagcgaggt atgtaggcgg tgctacagag ttcttgaagt ggtggcctaa ctacggctac  15780
actagaagga cagtatttgg tatctgcgct ctgctgaagc cagttacctt cggaaaaaga  15840
gttggtagct cttgatccgg caaacaaacc accgctggta gcggtggttt ttttgtttgc  15900
aagcagcaga ttacgcgcag aaaaaaagga tctcaagaag atcctttgat cttttctacg  15960
gggtctgacg ctcagtggaa cgaaaactca cgttaaggga ttttggtcat gagattatca  16020
aaaaggatct tcacctagat ccttttaaat taaaaatgaa gttttaaatc aatctaaagt  16080
atatatgagt aaacttggtc tgacagttac caatgcttaa tcagtgaggc acctatctca  16140
gcgatctgtc tatttcgttc atccatagtt gcctgactcc ccgtcgtgta gataactacg  16200
atacgggagg gcttaccatc tggccccagt gctgcaatga taccgcgaga cccacgctca  16260
ccggctccag atttatcagc aataaaccag ccagccggaa gggccgagcg cagaagtggt  16320
```

```
cctgcaactt tatccgcctc catccagtct attaattgtt gccgggaagc tagagtaagt  16380
agttcgccag ttaatagttt gcgcaacgtt gttgccattg ctgcaggggg gggggggggg  16440
gggttccatt gttcattcca cggacaaaaa cagagaaagg aaacgacaga ggccaaaaag  16500
ctcgctttca gcacctgtcg tttcctttct tttcagaggg tattttaaat aaaaacatta  16560
agttatgacg aagaagaacg gaaacgcctt aaaccggaaa attttcataa atagcgaaaa  16620
cccgcgaggt ccctgtcgga tcaccggaaa ggacccgtaa agtgataatg attatcatct  16680
acatatcaca acgtgcgtgg aggccatcaa accacgtcaa ataatcaatt atgacgcagg  16740
tatcgtatta attgatctgc atcaacttaa cgtaaaaaca acttcagaca atacaaatca  16800
gcgacactga atacggggca acctcatgtc cccccccccc ccccccctgc aggcatcgtg  16860
gtgtcacgct cgtcgtttgg tatggcttca ttcagctccg gttcccaacg atcaaggcga  16920
gttacatgat cccccatgtt gtgcaaaaaa gcggttagct ccttcggtcc tccgatcgtt  16980
gtcagaagta agttggccgc agtgttatca ctcatggtta tggcagcact gcataattct  17040
cttactgtca tgccatccgt aagatgcttt tctgtgactg gtgagtactc aaccaagtca  17100
ttctgagaat agtgtatgcg gcgaccgagt tgctcttgcc cggcgtcaac acgggataat  17160
accgcgccac atagcagaac tttaaaagtg ctcatcattg gaaaacgttc ttcggggcga  17220
aaactctcaa ggatcttacc gctgttgaga tccagttcga tgtaacccac tcgtgcaccc  17280
aactgatctt cagcatcttt tactttcacc agcgtttctg ggtgagcaaa aacaggaagg  17340
caaaatgccg caaaaaaggg aataagggcg acacggaaat gttgaatact catactcttc  17400
ctttttcaat attattgaag catttatcag ggttattgtc tcatgagcgg atacatattt  17460
gaatgtattt agaaaaataa acaaataggg gttccgcgca catttccccg aaaagtgcca  17520
cctgacgtct aagaaaccat tattatcatg acattaacct ataaaaatag gcgtatcacg  17580
aggccctttc gtcttcaaga attggtcgac gatcttgctg cgttcggata ttttcgtgga  17640
gttcccgcca cagacccgga ttgaaggcga gatccagcaa ctcgcgccag atcatcctgt  17700
gacggaactt tggcgcgtga tgactggcca ggacgtcggc cgaaagagcg acaagcagat  17760
cacgcttttc gacagcgtcg gatttgcgat cgaggatttt tcggcgctgc gctacgtccg  17820
cgaccgcgtt gagggatcaa gccacagcag cccactcgac cttctagccg acccagacga  17880
gccaagggat ctttttggaa tgctgctccg tcgtcaggct ttccgacgtt tgggtggttg  17940
aacagaagtc attatcgtac ggaatgccaa gcactcccga ggggaaccct gtggttggca  18000
tgcacataca aatggacgaa cggataaacc ttttcacgcc cttttaaata tccgttattc  18060
taataaacgc tcttttctct taggtttacc cgccaatata tcctgtcaaa cactgatagt  18120
ttaaactgaa ggcgggaaac gacaatctga tcatgagcgg agaattaagg gagtcacgtt  18180
atgacccccg ccgatgacgc gggacaagcc gttttacgtt tggaactgac agaaccgcaa  18240
cgttgaagga gccactcagc aagctggtac gattgtaata cgactcacta tagggcgaat  18300
tgagcgctgt ttaaacgctc ttcaactgga agagcggtta ccagagctgg tcacctttgt  18360
ccaccaagat ggaactgcgg ccgctcatta attaagtcag gcgcgcctct agttgaagac  18420
acgttcatgt cttcatcgta agaagacact cagtagtctt cggccagaat ggccatctgg  18480
attcagcagg cctagaaggc catttaaatc ctgaggatct ggtcttccta aggacccggg  18540
atatcgctat caactttgta tagaaaagtt gggccgaatt cgcccttgtt taaacttaat  18600
atttgtttaa actttttact aaattcatgt aataattaat gtatgcgtta tatatatatg  18660
tctaggttta taattattca tatgaatatg aacataaaaa tctagggcta aaacgactac  18720
```

-continued

```
tattttgaaa acggaaggag tagtaagtta tttaagcgga ggggaaccat gatgggctag  18780
tgatttaatt tacatatata tattggtgtt ctgggctctt acatgagaag atctagttaa  18840
ctgttgttac tgaacagcga agacaaatat ataatttaag ctccccaact gctagtgatt  18900
ctgttaagag gtaatgttta aagtaaattt acaagagccc gtctagctca gtcggtagag  18960
cgcaaggctc ttaaccttgt ggtcgtgggt tcgagcccca cggtgggcgc acaatttttt  19020
gtttttgac atttttgtt tgcttagttg cagacggttt ttcccctgct aggagatttc  19080
cgagagaaaa aaaaggcact acaggttaac caaaaccacc aacctttgga gcgtcgaggc  19140
gacggggcat ttgcgtagtt gaagcttaca aagttgcata tgagatgagt gccggacatg  19200
aagcggataa cgttttaaac tggcaacaat atctagctgt ttcaaattca ggcgtgggaa  19260
gctacgccta cgcgccctgg acggcgtgta aagagccagc atcggcatca ttgtcaaacg  19320
atcgacaagg ccaagaaatt ccaaatatat tattaataaa aaagaaggca ccaaattagt  19380
ttttgttttt tagtatgtgt ggcggaggaa attttgagaa cgaacgtatc caaagaaggc  19440
acaagacgat atagattgac gcggctagaa agttgcagca agacagtggg tacggtctta  19500
tatatcctaa taaataaaaa ataaaactat agtgtgtcaa atgtcaacaa gaggaggagg  19560
cagccaaatt agcagaggga gacaagtaga gcacgcctta ttagcttgct tatttatcgt  19620
ggtggtgtac ttgttaatta ctggcacgca ttatcaacaa cgcagttctg gatgtgaatc  19680
tagacaaaca tttgtctagg ttccgcacgt atagtttttt ttcttttttt ttgggggggg  19740
gggggaacgg aagctgtaat aaacggtact aggaacgaaa gcaaccgccg cgcgcatgtt  19800
tttgcaatag attacggtga ccttgatgca ccaccgcgtg ctataaaaac cagtgtcccc  19860
gagtctactc atcaaccaat ccataactcg aaaccttttc ttgtgctctg ttctgtctgt  19920
gtgtttccaa agcaagcgaa agaggtcgag gggatcagct tcaagtttgt acaaaaaagc  19980
aggctccgcg gccgccccct tcaccatgac gatggctcgt cctggggcgg ctttgccgct  20040
gctgctggtc gtggtcggcg cttgctgcgc gcgcctggcg gcggcagtgc acctctccgc  20100
gctcggcagg acactcatcg tcgaggcgtc gccgaaggcc ggacaagtcc tgcacgccgg  20160
cgaggacacg ataaccgtga catggcacct caacgcgtcg gcgtccagcg tcgggtacaa  20220
ggcgctggag gtgaccctct gctacgcgcc ggcgagccag gaggaccgcg ggtggcgcaa  20280
ggccaacgac gacttgagca aggacaaggc gtgccagttc aggatcgccc ggcatgcata  20340
cgccggcggc caggggacgc tccggtacag ggtcgcccgc gacgtcccca ccgcgtccta  20400
ccacgtgcgc gcctacgcgc tggacgcgtc cggggcgccg gtgggctacg gccagaccgc  20460
gcccgcctac tacttccacg tcgcgggcgt ctcgggcgtc cacgcgtccc tccgggtcgc  20520
cgccgccgtg ctctccgcgt tctccatcgc cgcgctcgcc ttctttgtcg tcgtcgagaa  20580
gaggaggaag gacgagtaga agggtgggcg cgccgaccca gctttcttgt acaaagtggc  20640
cgttaacgga tccagacttg tccatcttct ggattggcca acttaattaa tgtatgaaat  20700
aaaaggatgc acacatagtg acatgctaat cactataatg tgggcatcaa agttgtgtgt  20760
tatgtgtaat tactagttat ctgaataaaa gagaaagaga tcatccatat ttcttatcct  20820
aaatgaatgt cacgtgtctt tataattctt tgatgaacca gatgcatttc attaaccaaa  20880
tccatataca tataaatatt aatcatatat aattaatatc aattgggtta gcaaaacaaa  20940
tctagtctag gtgtgttttg cgaattgcgg caagcttgcg gccgccccgg gcaactttat  21000
tatacaaagt tgatagatat cggaccgatt aaactttaat tcggtccgaa gcttgcatgc  21060
ctgcagtgca gcgtgacccg gtcgtgcccc tctctagaga taatgagcat tgcatgtcta  21120
```

agttataaaa aattaccaca tatttttttt gtcacacttg tttgaagtgc agtttatcta 21180
tctttataca tatatttaaa ctttactcta cgaataatat aatctatagt actacaataa 21240
tatcagtgtt ttagagaatc atataaatga acagttagac atggtctaaa ggacaattga 21300
gtattttgac aacaggactc tacagtttta tctttttagt gtgcatgtgt tctccttttt 21360
ttttgcaaat agcttcacct atataatact tcatccattt tattagtaca tccatttagg 21420
gtttagggtt aatggttttt atagactaat ttttttagta catctatttt attctatttt 21480
agcctctaaa ttaagaaaac taaaactcta ttttagtttt tttatttaat aatttagata 21540
taaaatagaa taaaataaag tgactaaaaa ttaaacaaat accctttaag aaattaaaaa 21600
aactaaggaa acattttttct tgtttcgagt agataatgcc agcctgttaa acgccgtcga 21660
cgagtctaac ggacaccaac cagcgaacca gcagcgtcgc gtcgggccaa gcgaagcaga 21720
cggcacggca tctctgtcgc tgcctctgga cccctctcga gagttccgct ccaccgttgg 21780
acttgctccg ctgtcggcat ccagaaattg cgtggcggag cggcagacgt gagccggcac 21840
ggcaggcggc ctcctcctcc tctcacggca ccggcagcta cgggggattc ctttcccacc 21900
gctccttcgc tttcccttcc tcgcccgccg taataaatag acaccccctc cacaccctct 21960
ttccccaacc tcgtgttgtt cggagcgcac acacacacaa ccagatctcc cccaaatcca 22020
cccgtcggca cctccgcttc aaggtacgcc gctcgtcctc cccccccccc ctctctacct 22080
tctctagatc ggcgttccgg tccatgcatg gttagggccc ggtagttcta cttctgttca 22140
tgtttgtgtt agatccgtgt ttgtgttaga tccgtgctgc tagcgttcgt acacggatgc 22200
gacctgtacg tcagacacgt tctgattgct aacttgccag tgtttctctt tggggaatcc 22260
tgggatggct ctagccgttc cgcagacggg atcgatttca tgattttttt tgtttcgttg 22320
catagggttt ggtttgccct tttcctttat ttcaatatat gccgtgcact tgtttgtcgg 22380
gtcatctttt catgcttttt tttgtcttgg ttgtgatgat gtggtctggt tgggcggtcg 22440
ttctagatcg gagtagaatt ctgtttcaaa ctacctggtg gatttattaa ttttggatct 22500
gtatgtgtgt gccatacata ttcatagtta cgaattgaag atgatggatg gaaatatcga 22560
tctaggatag gtatacatgt tgatgcgggt tttactgatg catatacaga gatgcttttt 22620
gttcgcttgg ttgtgatgat gtggtgtggt tgggcggtcg ttcattcgtt ctagatcgga 22680
gtagaatact gtttcaaact acctggtgta tttattaatt ttggaactgt atgtgtgtgt 22740
catacatctt catagttacg agtttaagat ggatggaaat atcgatctag gataggtata 22800
catgttgatg tgggttttac tgatgcatat acatgatggc atatgcagca tctattcata 22860
tgctctaacc ttgagtacct atctattata ataaacaagt atgttttata attattttga 22920
tcttgatata cttggatgat ggcatatgca gcagctatat gtggattttt ttagccctgc 22980
cttcatacgc tatttatttg cttggtactg tttcttttgt cgatgctcac cctgttgttt 23040
ggtgttactt ctgcaggtcg actttaactt agcctaggat ccacacgaca ccatgtcccc 23100
cgagcgccgc cccgtcgaga tccgcccggc caccgccgcc gacatggccg ccgtgtgcga 23160
catcgtgaac cactacatcg agacctccac cgtgaacttc cgcaccgagc cgcagacccc 23220
gcaggagtgg atcgacgacc tggagcgcct ccaggaccgc tacccgtggc tcgtggccga 23280
ggtggagggc gtggtggccg gcatcgccta cgccggcccg tggaaggccc gcaacgccta 23340
cgactggacc gtggagtcca ccgtgtacgt gtcccaccgc caccagcgcc tcggcctcgg 23400
ctccaccctc tacacccacc tcctcaagag catggaggcc cagggcttca agtccgtggt 23460
ggccgtgatc ggcctcccga acgacccgtc cgtgcgcctc cacgaggccc tcggctacac 23520

```
cgcccgcggc accctccgcg ccgccggcta caagcacggc ggctggcacg acgtcggctt  23580
ctggcagcgc gacttcgagc tgccggcccc gccgcgcccg gtgcgcccgg tgacgcagat  23640
ctgagtcgaa acctagactt gtccatcttc tggattggcc aacttaatta atgtatgaaa  23700
taaaaggatg cacacatagt gacatgctaa tcactataat gtgggcatca aagttgtgtg  23760
ttatgtgtaa ttactagtta tctgaataaa agagaaagag atcatccata tttcttatcc  23820
taaatgaatg tcacgtgtct ttataattct ttgatgaacc agatgcattt cattaaccaa  23880
atccatatac atataaatat taatcatata taattaatat caattgggtt agcaaaacaa  23940
atctagtcta ggtgtgtttt gcgaatgcgg ccgccaccgc ggtggagctc gaattcattc  24000
cgattaatcg tggcctcttg ctcttcagga tgaagagcta tgtttaaacg tgcaagcgct  24060
actagacaat tcagtacatt aaaaacgtcc gcaatgtgtt attaagttgt ctaagcgtca  24120
atttgtttac accacaatat atcctgccac cagccagcca acagctcccc gaccggcagc  24180
tcggcacaaa atcaccactc gatacaggca gcccatcagt ccgggacggc gtcagcggga  24240
gagccgttgt aaggcggcag actttgctca tgttaccgat gctattcgga agaacggcaa  24300
ctaagctgcc gggtttgaaa cacggatgat ctcgcggagg gtagcatgtt gattgtaacg  24360
atgacagagc gttgctgcct gtgatcaaat atcatctccc tcgcagagat ccgaattatc  24420
agccttctta ttcatttctc gcttaaccgt gacaggctgt cgatcttgag aactatgccg  24480
acataatagg aaatcgctgg ataaagccgc tgaggaagct gagtggcgct atttctttag  24540
aagtgaacgt tgacgatcgt cgaccgtacc ccgatgaatt aattcggacg tacgttctga  24600
acacagctgg atacttactt gggcgattgt catacatgac atcaacaatg tacccgtttg  24660
tgtaaccgtc tcttggaggt tcgtatgaca ctagtggttc ccctcagctt gcgactagat  24720
gttgaggcct aacattttat tagagagcag gctagttgct tagatacatg atcttcaggc  24780
cgttatctgt cagggcaagc gaaaattggc catttatgac gaccaatgcc ccgcagaagc  24840
tcccatcttt gccgccatag acgccgcgcc ccccttttgg ggtgtagaac atccttttgc  24900
cagatgtgga aaagaagttc gttgtcccat tgttggcaat gacgtagtag ccggcgaaag  24960
tgcgagaccc atttgcgcta tatataagcc tacgatttcc gttgcgacta ttgtcgtaat  25020
tggatgaact attatcgtag ttgctctcag agttgtcgta atttgatgga ctattgtcgt  25080
aattgcttat ggagttgtcg tagttgcttg gagaaatgtc gtagttggat ggggagtagt  25140
catagggaag acgagcttca tccactaaaa caattggcag gtcagcaagt gcctgccccg  25200
atgccatcgc aagtacgagg cttagaacca ccttcaacag atcgcgcata gtcttcccca  25260
gctctctaac gcttgagtta agccgcgccg cgaagcggcg tcggcttgaa cgaattgtta  25320
gacattattt gccgactacc ttggtgatct cgcctttcac gtagtgaaca aattcttcca  25380
actgatctgc gcgcgaggcc aagcgatctt cttgtccaag ataagcctgc ctagcttcaa  25440
gtatgacggg ctgatactgg gccggcaggc gctccattgc ccagtcggca gcgacatcct  25500
tcggcgcgat tttgccggtt actgcgctgt accaaatgcg ggacaacgta agcactacat  25560
ttcgctcatc gccagcccag tcgggcggcg agttccatag cgttaaggtt tcatttagcg  25620
cctcaaatag atcctgttca ggaaccggat caaagagttc ctccgccgct ggacctacca  25680
aggcaacgct atgttctctt gcttttgtca gcaagatagc cagatcaatg tcgatcgtgg  25740
ctggctcgaa gatacctgca agaatgtcat tgcgctgcca ttctccaaat tgcagttcgc  25800
gcttagctgg ataacgccac ggaatgatgt cgtcgtgcac aacaatggtg acttctacag  25860
cgcggagaat ctcgctctct ccaggggaag ccgaagtttc caaaaggtcg ttgatcaaag  25920
```

-continued

```
ctcgccgcgt tgtttcatca agccttacag tcaccgtaac cagcaaatca atatcactgt  25980
gtggcttcag gccgccatcc actgcggagc cgtacaaatg tacggccagc aacgtcggtt  26040
cgagatggcg ctcgatgacg ccaactacct ctgatagttg agtcgatact tcggcgatca  26100
ccgcttccct catgatgttt aactcctgaa ttaagccgcg ccgcgaagcg gtgtcggctt  26160
gaatgaattg ttaggcgtca tcctgtgctc ccgagaacca gtaccagtac atcgctgttt  26220
cgttcgagac ttgaggtcta gttttatacg tgaacaggtc aatgccgccg agagtaaagc  26280
cacattttgc gtacaaattg caggcaggta cattgttcgt ttgtgtctct aatcgtatgc  26340
caaggagctg tctgcttagt gcccactttt tcgcaaattc gatgagactg tgcgcgactc  26400
ctttgcctcg gtgcgtgtgc gacacaacaa tgtgttcgat agaggctaga tcgttccatg  26460
ttgagttgag ttcaatcttc ccgacaagct cttggtcgat gaatgcgcca tagcaagcag  26520
agtcttcatc agagtcatca tccgagatgt aatccttccg gtaggggctc acacttctgg  26580
tagatagttc aaagccttgg tcggataggt gcacatcgaa cacttcacga acaatgaaat  26640
ggttctcagc atccaatgtt tccgccacct gctcagggat caccgaaatc ttcatatgac  26700
gcctaacgcc tggcacagcg gatcgcaaac ctggcgcggc ttttggcaca aaaggcgtga  26760
caggtttgcg aatccgttgc tgccacttgt taacccttt gccagatttg gtaactataa  26820
tttatgttag aggcgaagtc ttgggtaaaa actggcctaa aattgctggg gatttcagga  26880
aagtaaacat caccttccgg ctcgatgtct attgtagata tatgtagtgt atctacttga  26940
tcgggggatc tgctgcctcg cgcgtttcgg tgatgacggt gaaaacctct gacacatgca  27000
gctcccggag acggtcacag cttgtctgta agcggatgcc gggagcagac aagcccgtca  27060
gggcgcgtca gcgggtgttg gcgggtgtcg gggcgcagcc atgacccagt cacgtagcga  27120
tagcggagtg tatactggct taactatgcg gcatcagagc agattgtact gagagtgcac  27180
catatgcggt gtgaaatacc gcacagatgc gtaaggagaa aataccgcat caggcgctct  27240
tccgcttcct cgctcactga ctcgctgcgc tcggtcgttc ggctgcggcg agcggtatca  27300
gctcactcaa aggcggtaat acggttatcc acagaatcag gggataacgc aggaaagaac  27360
atgtgagcaa aaggccagca aaaggccagg aaccgtaaaa aggccgcgtt gctggcgttt  27420
ttccataggc tccgcccccc tgacgagcat cacaaaaatc gacgctcaag tcagaggtgg  27480
cgaaacccga caggactata aagataccag gcgtttcccc ctggaagctc cctcgtgcgc  27540
tctcctgttc cgaccctgcc gcttaccgga tacctgtccg cctttctccc ttcgggaagc  27600
gtggcgcttt ctcatagctc acgctgtagg tatctcagtt cggtgtaggt cgttcgctcc  27660
aagctgggct gtgtgcacga accccccgtt cagcccgacc gctgcgcctt atccggtaac  27720
tatcgtcttg agtccaaccc ggtaagacac gacttatcgc cactggcagc agccactggt  27780
aacaggatta gcagagcgag gtatgtaggc ggtgctacag agttcttgaa gtggtggcct  27840
aactacggct acactagaag gacagtattt ggtatctgcg ctctgctgaa gccagttacc  27900
ttcggaaaaa gagttggtag ctcttgatcc ggcaaacaaa ccaccgctgg tagcggtggt  27960
tttttgttt gcaagcagca gattacgcgc agaaaaaaag gatctcaaga agatcctttg  28020
atcttttcta cggggtctga cgctcagtgg aacgaaaact cacgttaagg gattttggtc  28080
atgagattat caaaaaggat cttcacctag atccttttaa attaaaaatg aagttttaaa  28140
tcaatctaaa gtatatatga gtaaacttgg tctgacagtt accaatgctt aatcagtgag  28200
gcacctatct cagcgatctg tctatttcgt tcatccatag ttgcctgact ccccgtcgtg  28260
tagataacta cgatacggga gggcttacca tctggcccca gtgctgcaat gataccgcga  28320
```

-continued

```
gacccacgct caccggctcc agatttatca gcaataaacc agccagccgg aagggccgag  28380
cgcagaagtg gtcctgcaac tttatccgcc tccatccagt ctattaattg ttgccgggaa  28440
gctagagtaa gtagttcgcc agttaatagt ttgcgcaacg ttgttgccat tgctgcaggg  28500
gggggggggg ggggggactt ccattgttca ttccacggac aaaaacagag aaaggaaacg  28560
acagaggcca aaaagcctcg ctttcagcac ctgtcgtttc ctttcttttc agagggtatt  28620
ttaaataaaa acattaagtt atgacgaaga agaacggaaa cgccttaaac cggaaaattt  28680
tcataaatag cgaaaacccg cgaggtcgcc gccccgtaag ccgccccgta acctgtcgga  28740
tcaccggaaa ggacccgtaa agtgataatg attatcatct acatatcaca acgtgcgtgg  28800
aggccatcaa accacgtcaa ataatcaatt atgacgcagg tatcgtatta attgatctgc  28860
atcaacttaa cgtaaaaaca acttcagaca atacaaatca gcgacactga atacggggca  28920
acctcatgtc cccccccccc cccccccctgc aggcatcgtg gtgtcacgct cgtcgtttgg  28980
tatggcttca ttcagctccg gttcccaacg atcaaggcga gttacatgat cccccatgtt  29040
gtgcaaaaaa gcggttagct ccttcggtcc tccgatcgtt gtcagaagta agttggccgc  29100
agtgttatca ctcatggtta tggcagcact gcataattct cttactgtca tgccatccgt  29160
aagatgcttt tctgtgactg gtgagtactc aaccaagtca ttctgagaat agtgtatgcg  29220
gcgaccgagt tgctcttgcc cggcgtcaac acgggataat accgcgccac atagcagaac  29280
tttaaaagtg ctcatcattg gaaaacgttc ttcggggcga aaactctcaa ggatcttacc  29340
gctgttgaga tccagttcga tgtaacccac tcgtgcaccc aactgatctt cagcatcttt  29400
tactttcacc agcgtttctg ggtgagcaaa aacaggaagg caaaatgccg caaaaaaggg  29460
aataagggcg acacggaaat gttgaatact catactcttc ctttttcaat attattgaag  29520
catttatcag ggttattgtc tcatgagcgg atacatattt gaatgtattt agaaaaataa  29580
acaaataggg gttccgcgca catttccccg aaaagtgcca cctgacgtct aagaaaccat  29640
tattatcatg acattaacct ataaaaatag gcgtatcacg aggccctttc gtcttcaaga  29700
attcggagct tttgccattc tcaccggatt cagtcgtcac tcatggtgat ttctcacttg  29760
ataaccttat ttttgacgag gggaaattaa taggttgtat tgatgttgga cgagtcggaa  29820
tcgcagaccg ataccaggat cttgccatcc tatggaactg cctcggtgag ttttctcctt  29880
cattacagaa acggcttttt caaaaatatg gtattgataa tcctgatatg aataaattgc  29940
agtttcattt gatgctcgat gagtttttct aatcagaatt ggttaattgg ttgtaacact  30000
ggcagagcat tacgctgact tgacgggacg gcggctttgt tgaataaatc gaacttttgc  30060
tgagttgaag gatcagatca cgcatcttcc cgacaacgca gaccgttccg tggcaaagca  30120
aaagttcaaa atcaccaact ggtccaccta caacaaagct ctcatcaacc gtggctccct  30180
cactttctgg ctggatgatg gggcgattca ggcctggtat gagtcagcaa caccttcttc  30240
acgaggcaga cctcagcgcc agaaggccgc cagagaggcc gagcgcggcc gtgaggcttg  30300
gacgctaggg cagggcatga aaaagcccgt agcgggctgc tacgggcgtc tgacgcggtg  30360
gaaaggggga ggggatgttg tctacatggc tctgctgtag tgagtgggtt gcgctccggc  30420
agcggtcctg atcaatcgtc accctttctc ggtccttcaa cgttcctgac aacgagcctc  30480
cttttcgcca atccatcgac aatcaccgcg agtccctgct cgaacgctgc gtccggaccg  30540
gcttcgtcga aggcgtctat cgcggcccgc aacagcggcg agagcggagc ctgttcaacg  30600
gtgccgccgc gctcgccggc atcgctgtcg ccggcctgct cctcaagcac ggccccaaca  30660
gtgaagtagc tgattgtcat cagcgcattg acggcgtccc cggccgaaaa acccgcctcg  30720
```

```
cagaggaagc gaagctgcgc gtcggccgtt tccatctgcg gtgcgcccgg tcgcgtgccg  30780
gcatggatgc gcgcgccatc gcggtaggcg agcagcgcct gcctgaagct gcgggcattc  30840
ccgatcagaa atgagcgcca gtcgtcgtcg gctctcggca ccgaatgcgt atgattctcc  30900
gccagcatgg cttcggccag tgcgtcgagc agcgcccgct tgttcctgaa gtgccagtaa  30960
agcgccggct gctgaacccc caaccgttcc gccagtttgc gtgtcgtcag accgtctacg  31020
ccgacctcgt tcaacaggtc cagggcggca cggatcactg tattcggctg caactttgtc  31080
atgcttgaca ctttatcact gataaacata atatgtccac caacttatca gtgataaaga  31140
atccgcgcgt tcaatcggac cagcggaggc tggtccggag gccagacgtg aaacccaaca  31200
taccccctgat cgtaattctg agcactgtcg cgctcgacgc tgtcggcatc ggcctgatta  31260
tgccggtgct gccgggcctc ctgcgcgatc tggttcactc gaacgacgtc accgcccact  31320
atggcattct gctggcgctg tatgcgttgg tgcaatttgc ctgcgcacct gtgctgggcg  31380
cgctgtcgga tcgtttcggg cggcggccaa tcttgctcgt ctcgctggcc ggcgccactg  31440
tcgactacgc catcatggcg acagcgcctt tcctttgggt tctctatatc gggcggatcg  31500
tggccggcat caccggggcg actggggcgg tagccggcgc ttatattgcc gatatcactg  31560
atggcgatga gcgcgcgcgg cacttcggct tcatgagcgc ctgtttcggg ttcgggatgg  31620
tcgcgggacc tgtgctcggt gggctgatgg gcggtttctc cccccacgct ccgttcttcg  31680
ccgcggcagc cttgaacggc ctcaatttcc tgacgggctg tttccttttg ccggagtcgc  31740
acaaaggcga acgccggccg ttacgccggg aggctctcaa cccgctcgct tcgttccggt  31800
gggcccgggg catgaccgtc gtcgccgccc tgatggcggt cttcttcatc atgcaacttg  31860
tcggacaggt gccggccgcg ctttgggtca ttttcggcga ggatcgcttt cactgggacg  31920
cgaccacgat cggcatttcg cttgccgcat ttggcattct gcattcactc gcccaggcaa  31980
tgatcaccgg ccctgtagcc gcccggctcg gcgaaaggcg ggcactcatg ctcggaatga  32040
ttgccgacgg cacaggctac atcctgcttg ccttcgcgac acggggatgg atggcgttcc  32100
cgatcatggt cctgcttgct tcgggtggca tcggaatgcc ggcgctgcaa gcaatgttgt  32160
ccaggcaggt ggatgaggaa cgtcaggggc agctgcaagg ctcactggcg gcgctcacca  32220
gcctgacctc gatcgtcgga cccctcctct tcacggcgat ctatgcggct tctataacaa  32280
cgtggaacgg gtgggcatgg attgcaggcg ctgccctcta cttgctctgc ctgccggcgc  32340
tgcgtcgcgg gctttggagc ggcgcagggc aacgagccga tcgctgatcg tggaaacgat  32400
aggcctatgc catgcgggtc aaggcgactt ccggcaagct atacgcgccc taggagtgcg  32460
gttggaacgt tggcccagcc agatactccc gatcacgagc aggacgccga tgatttgaag  32520
cgcactcagc gtctgatcca agaacaacca tcctagcaac acggcggtcc ccgggctgag  32580
aaagcccagt aaggaaacaa ctgtaggttc gagtcgcgag atcccccgga accaaaggaa  32640
gtaggttaaa cccgctccga tcaggccgag ccacgccagg ccgagaacat tggttcctgt  32700
aggcatcggg attggcggat caaacactaa agctactgga acgagcagaa gtcctccggc  32760
cgccagttgc caggcggtaa aggtgagcag aggcacggga ggttgccact tgcgggtcag  32820
cacggttccg aacgccatgg aaaccgcccc cgccaggccc gctgcgacgc cgacaggatc  32880
tagcgctgcg tttggtgtca acaccaacag cgccacgccc gcagttccgc aaatagcccc  32940
caggaccgcc atcaatcgta tcgggctacc tagcagagcg gcagagatga acacgaccat  33000
cagcggctgc acagcgccta ccgtcgccgc gaccccgccc ggcaggcggt agaccgaaat  33060
aaacaacaag ctccagaata gcgaaatatt aagtgcgccg aggatgaaga tgcgcatcca  33120
```

```
ccagattccc gttggaatct gtcggacgat catcacgagc aataaacccg ccggcaacgc  33180
ccgcagcagc ataccggcga cccctcggcc tcgctgttcg ggctccacga aaacgccgga  33240
cagatgcgcc ttgtgagcgt ccttggggcc gtcctcctgt ttgaagaccg acagcccaat  33300
gatctcgccg tcgatgtagg cgccgaatgc cacggcatct cgcaaccgtt cagcgaacgc  33360
ctccatgggc tttttctcct cgtgctcgta aacggacccg aacatctctg gagctttctt  33420
cagggccgac aatcggatct cgcggaaatc ctgcacgtcg gccgctccaa gccgtcgaat  33480
ctgagcctta atcacaattg tcaattttaa tcctctgttt atcggcagtt cgtagagcgc  33540
gccgtgcgtc ccgagcgata ctgagcgaag caagtgcgtc gagcagtgcc cgcttgttcc  33600
tgaaatgcca gtaaagcgct ggctgctgaa cccccagccg gaactgaccc cacaaggccc  33660
tagcgtttgc aatgcaccag gtcatcattg acccaggcgt gttccaccag gccgctgcct  33720
cgcaactctt cgcaggcttc gccgacctgc tcgcgccact tcttcacgcg ggtggaatcc  33780
gatccgcaca tgaggcggaa ggtttccagc ttgagcgggt acggctcccg gtgcgagctg  33840
aaatagtcga acatccgtcg ggccgtcggc gacagcttgc ggtacttctc ccatatgaat  33900
ttcgtgtagt ggtcgccagc aaacagcacg acgatttcct cgtcgatcag gacctggcaa  33960
cgggacgttt tcttgccacg gtccaggacg cggaagcggt gcagcagcga caccgattcc  34020
aggtgcccaa cgcggtcgga cgtgaagccc atcgccgtcg cctgtaggcg cgacaggcat  34080
tcctcggcct tcgtgtaata ccggccattg atcgaccagc ccaggtcctg gcaaagctcg  34140
tagaacgtga aggtgatcgg ctcgccgata ggggtgcgct tcgcgtactc caacacctgc  34200
tgccacacca gttcgtcatc gtcggcccgc agctcgacgc cggtgtaggt gatcttcacg  34260
tccttgttga cgtggaaaat gaccttgttt tgcagcgcct cgcgcgggat tttcttgttg  34320
cgcgtggtga acagggcaga gcgggccgtg tcgtttggca tcgctcgcat cgtgtccggc  34380
cacggcgcaa tatcgaacaa ggaaagctgc atttccttga tctgctgctt cgtgtgtttc  34440
agcaacgcgg cctgcttggc ctcgctgacc tgttttgcca ggtcctcgcc ggcggttttt  34500
cgcttcttgg tcgtcatagt tcctcgcgtg tcgatggtca tcgacttcgc caaacctgcc  34560
gcctcctgtt cgagacgacg cgaacgctcc acggcggccg atggcgcggg cagggcaggg  34620
ggagccagtt gcacgctgtc gcgctcgatc ttggccgtag cttgctggac catcgagccg  34680
acggactgga aggtttcgcg gggcgcacgc atgacggtgc ggcttgcgat ggtttcggca  34740
tcctcggcgg aaaaccccgc gtcgatcagt tcttgcctgt atgccttccg gtcaaacgtc  34800
cgattcattc accctccttg cgggattgcc ccgactcacg ccggggcaat gtgcccttat  34860
tcctgatttg acccgcctgg tgccttggtg tccagataat ccaccttatc ggcaatgaag  34920
tcggtcccgt agaccgtctg gccgtccttc tcgtacttgg tattccgaat cttgccctgc  34980
acgaatacca gcgacccctt gcccaaatac ttgccgtggg cctcggcctg agagccaaaa  35040
cacttgatgc ggaagaagtc ggtgcgctcc tgcttgtcgc cggcatcgtt gcgccactct  35100
tcattaaccg ctatatcgaa aattgcttgc ggcttgttag aattgccatg acgtacctcg  35160
gtgtcacggg taagattacc gataaactgg aactgattat ggctcatatc gaaagtctcc  35220
ttgagaaagg agactctagt ttagctaaac attggttccg ctgtcaagaa ctttagcggc  35280
taaaattttg cgggccgcga ccaaaggtgc gaggggcggc ttccgctgtg tacaaccaga  35340
tatttttcac caacatcctt cgtctgctcg atgagcgggg catgacgaaa catgagctgt  35400
cggagagggc aggggtttca atttcgtttt tatcagactt aaccaacggt aaggccaacc  35460
cctcgttgaa ggtgatggag gccattgccg acgccctgga aactccccta cctcttctcc  35520
```

-continued

```
tggagtccac cgaccttgac cgcgaggcac tcgcggagat tgcgggtcat cctttcaaga  35580
gcagcgtgcc gcccggatac gaacgcatca gtgtggtttt gccgtcacat aaggcgttta  35640
tcgtaaagaa atggggcgac gacacccgaa aaaagctgcg tggaaggctc tgacgccaag  35700
ggttagggct tgcacttcct tctttagccg ctaaaacggc cccttctctg cgggccgtcg  35760
gctcgcgcat catatcgaca tcctcaacgg aagccgtgcc gcgaatggca tcgggcgggt  35820
gcgctttgac agttgttttc tatcagaacc cctacgtcgt gcggttcgat tagctgtttg  35880
tcttgcaggc taaacacttt cggtatatcg tttgcctgtg cgataatgtt gctaatgatt  35940
tgttgcgtag gggttactga aaagtgagcg ggaaagaaga gtttcagacc atcaaggagc  36000
gggccaagcg caagctggaa cgcgacatgg gtgcggacct gttggccgcg ctcaacgacc  36060
cgaaaaccgt tgaagtcatg ctcaacgcgg acggcaaggt gtggcacgaa cgccttggcg  36120
agccgatgcg gtacatctgc gacatgcggc ccagccagtc gcaggcgatt atagaaacgg  36180
tggccggatt ccacggcaaa gaggtcacgc ggcattcgcc catcctggaa ggcgagttcc  36240
ccttggatgg cagccgcttt gccggccaat tgccgccggt cgtggccgcg ccaacctttg  36300
cgatccgcaa gcgcgcggtc gccatcttca cgctggaaca gtacgtcgag gcgggcatca  36360
tgacccgcga gcaatacgag gtcattaaaa gcgccgtcgc ggcgcatcga aacatcctcg  36420
tcattggcgg tactggctcg ggcaagacca cgctcgtcaa cgcgatcatc aatgaaatgg  36480
tcgccttcaa cccgtctgag cgcgtcgtca tcatcgagga caccggcgaa atccagtgcg  36540
ccgcagagaa cgccgtccaa taccacacca gcatcgacgt ctcgatgacg ctgctgctca  36600
agacaacgct gcgtatgcgc cccgaccgca tcctggtcgg tgaggtacgt ggccccgaag  36660
cccttgatct gttgatggcc tggaacaccg ggcatgaagg aggtgccgcc accctgcacg  36720
caaacaaccc caaagcgggc ctgagccggc tcgccatgct tatcagcatg cacccggatt  36780
caccgaaacc cattgagccg ctgattggcg aggcggttca tgtggtcgtc catatcgcca  36840
ggacccctag cggccgtcga gtgcaagaaa ttctcgaagt tcttggttac gagaacggcc  36900
agtacatcac caaaaccctg taaggagtat ttccaatgac aacggctgtt ccgttccgtc  36960
tgaccatgaa tcgcggcatt ttgttctacc ttgccgtgtt cttcgttctc gctctcgcgt  37020
tatccgcgca tccggcgatg gcctcggaag gcaccggcgg cagcttgcca tatgagagct  37080
ggctgacgaa cctgcgcaac tccgtaaccg gcccggtggc cttcgcgctg tccatcatcg  37140
gcatcgtcgt cgccggcggc gtgctgatct tcggcggcga actcaacgcc ttcttccgaa  37200
ccctgatctt cctggttctg gtgatggcgc tgctggtcgg cgcgcagaac gtgatgagca  37260
ccttcttcgg tcgtggtgcc gaaatcgcgg ccctcggcaa cggggcgctg caccaggtgc  37320
aagtcgcggc ggcggatgcc gtgcgtgcgg tagcggctgg acggctcgcc taatcatggc  37380
tctgcgcacg atccccatcc gtcgcgcagg caaccgagaa aacctgttca tgggtggtga  37440
tcgtgaactg gtgatgttct cgggcctgat ggcgtttgcg ctgattttca gcgcccaaga  37500
gctgcgggcc accgtggtcg gtctgatcct gtggttcggg gcgctctatg cgttccgaat  37560
catggcgaag gccgatccga agatgcggtt cgtgtacctg cgtcaccgcc ggtacaagcc  37620
gtattacccg gcccgctcga ccccgttccg cgagaacacc aatagccaag ggaagcaata  37680
ccgatgatcc aagcaattgc gattgcaatc gcgggcctcg gcgcgcttct gttgttcatc  37740
ctctttgccc gcatccgcgc ggtcgatgcc gaactgaaac tgaaaaagca tcgttccaag  37800
gacgccggcc tggccgatct gctcaactac gccgctgtcg tcgatgacgg cgtaatcgtg  37860
ggcaagaacg gcagctttat ggctgcctgg ctgtacaagg gcgatgacaa cgcaagcagc  37920
```

accgaccagc agcgcgaagt agtgtccgcc cgcatcaacc aggccctcgc gggcctggga 37980
agtgggtgga tgatccatgt ggacgccgtg cggcgtcctg ctccgaacta cgcggagcgg 38040
ggcctgtcgg cgttccctga ccgtctgacg gcagcgattg aagaagagcg ctcggtcttg 38100
ccttgctcgt cggtgatgta cttcaccagc tccgcgaagt cgctcttctt gatggagcgc 38160
atggggacgt gcttggcaat cacgcgcacc ccccggccgt tttagcggct aaaaaagtca 38220
tggctctgcc ctcgggcgga ccacgcccat catgaccttg ccaagctcgt cctgcttctc 38280
ttcgatcttc gccagcaggg cgaggatcgt ggcatcaccg aaccgcgccg tgcgcgggtc 38340
gtcggtgagc cagagtttca gcaggccgcc caggcggccc aggtcgccat tgatgcgggc 38400
cagctcgcgg acgtgctcat agtccacgac gcccgtgatt ttgtagccct ggccgacggc 38460
cagcaggtag gccgacaggc tcatgccggc cgccgccgcc ttttcctcaa tcgctcttcg 38520
ttcgtctgga aggcagtaca ccttgatagg tgggctgccc ttcctggttg gcttggtttc 38580
atcagccatc cgcttgccct catctgttac gccggcggta gccggccagc ctcgcagagc 38640
aggattcccg ttgagcaccg ccaggtgcga ataagggaca gtgaagaagg aacacccgct 38700
cgcgggtggg cctacttcac ctatcctgcc cggctgacgc cgttggatac accaaggaaa 38760
gtctacacga accctttggc aaaatcctgt atatcgtgcg aaaaaggatg gatataccga 38820
aaaaatcgct ataatgaccc cgaagcaggg ttatgcagcg gaaaagcgct gcttccctgc 38880
tgttttgtgg aatatctacc gactggaaac aggcaaatgc aggaaattac tgaactgagg 38940
ggacaggcga gagacgatgc caaagagcta caccgacgag ctggccgagt gggttgaatc 39000
ccgcgcggcc aagaagcgcc ggcgtgatga ggctgcggtt gcgttcctgg cggtgagggc 39060
ggatgtcgag gcggcgttag cgtccggcta tgcgctcgtc accatttggg agcacatgcg 39120
ggaaacgggg aaggtcaagt tctcctacga gacgttccgc tcgcacgcca ggcggcacat 39180
caaggccaag cccgccgatg tgcccgcacc gcaggccaag gctgcggaac ccgcgccggc 39240
acccaagacg ccggagccac ggcggccgaa gcaggggggc aaggctgaaa agccggcccc 39300
cgctgcggcc ccgaccggct tcaccttcaa cccaacaccg gacaaaaagg atctactgta 39360
atggcgaaaa ttcacatggt tttgcagggc aagggcgggg tcggcaagtc ggccatcgcc 39420
gcgatcattg cgcagtacaa gatggacaag gggcagacac ccttgtgcat cgacaccgac 39480
ccggtgaacg cgacgttcga gggctacaag gccctgaacg tccgccggct gaacatcatg 39540
gccggcgacg aaattaactc gcgcaacttc gacaccctgg tcgagctgat tgcgccgacc 39600
aaggatgacg tggtgatcga caacggtgcc agctcgttcg tgcctctgtc gcattacctc 39660
atcagcaacc aggtgccggc tctgctgcaa gaaatggggc atgagctggt catccatacc 39720
gtcgtcaccg gcggccaggc tctcctggac acggtgagcg gcttcgccca gctcgccagc 39780
cagttcccgg ccgaagcgct tttcgtggtc tggctgaacc cgtattgggg gcctatcgag 39840
catgagggca agagctttga gcagatgaag gcgtacacgg ccaacaaggc ccgcgtgtcg 39900
tccatcatcc agattccggc cctcaaggaa gaaacctacg gccgcgattt cagcgacatg 39960
ctgcaagagc ggctgacgtt cgaccaggcg ctggccgatg aatcgctcac gatcatgacg 40020
cggcaacgcc tcaagatcgt gcggcgcggc ctgtttgaac agctcgacgc ggcggccgtg 40080
ctatgagcga ccagattgaa gagctgatcc gggagattgc ggccaagcac ggcatcgccg 40140
tcggccgcga cgacccggtg ctgatcctgc ataccatcaa cgcccggctc atggccgaca 40200
gtgcggccaa gcaagaggaa atccttgccg cgttcaagga agagctggaa gggatcgccc 40260
atcgttgggg cgaggacgcc aaggccaaag cggagcggat gctgaacgcg gccctggcgg 40320

-continued

```
ccagcaagga cgcaatggcg aaggtaatga aggacagcgc cgcgcaggcg gccgaagcga  40380
tccgcaggga aatcgacgac ggccttggcc gccagctcgc ggccaaggtc gcggacgcgc  40440
ggcgcgtggc gatgatgaac atgatcgccg gcggcatggt gttgttcgcg gccgccctgg  40500
tggtgtgggc ctcgttatga atcgcagagg cgcagatgaa aaagcccggc gttgccgggc  40560
tttgtttttg cgttagctgg gcttgtttga caggcccaag ctctgactgc gcccgcgctc  40620
gcgctcctgg gcctgtttct tctcctgctc ctgcttgcgc atcagggcct ggtgccgtcg  40680
ggctgcttca cgcatcgaat cccagtcgcc ggccagctcg ggatgctccg cgcgcatctt  40740
gcgcgtcgcc agttcctcga tcttgggcgc gtgaatgccc atgccttcct tgatttcgcg  40800
caccatgtcc agccgcgtgt gcagggtctg caagcgggct tgctgttggg cctgctgctg  40860
ctgccaggcg gcctttgtac gcggcaggga cagcaagccg gggccattgg actgtagctg  40920
ctgcaaacgc gcctgctgac ggtctacgag ctgttctagg cggtcctcga tgcgctccac  40980
ctggtcatgc tttgcctgca cgtagagcgc aagggtctgc tggtaggtct gctcgatggg  41040
cgcggattct aagagggcct gctgttccgt ctcggcctcc tgggccgcct gtagcaaatc  41100
ctcgccgctg ttgccgctgg actgctttac tgccggggac tgctgttgcc ctgctcgcgc  41160
cgtcgtcgca gttcggcttg cccccactcg attgactgct tcatttcgag ccgcagcgat  41220
gcgatctcgg attgcgtcaa cggacggggc agcgcggagg tgtccggctt ctccttgggt  41280
gagtcggtcg atgccatagc caaaggtttc cttccaaaat gcgtccattg ctggaccgtg  41340
tttctcattg atgcccgcaa gcatcttcgg cttgaccgcc aggtcaagcg cgccttcatg  41400
ggcggtcatg acggacgccg ccatgacctt gccgccgttg ttctcgatgt agccgcgtaa  41460
tgaggcaatg gtgccgccca tcgtcagcgt gtcatcgaca acgatgtact tctggccggg  41520
gatcacctcc ccctcgaaag tcgggttgaa cgccaggcga tgatctgaac cggctccggt  41580
tcgggcgacc ttctcccgct gcacaatgtc cgtttcgacc tcaaggccaa ggcggtcggc  41640
cagaacgacc gccatcatgg ccggaatctt gttgttcccc gccgcctcga cggcgaggac  41700
tggaacgatg cggggcttgt cgtcgccgat cagcgtcttg agctgggcaa cagtgtcgtc  41760
cgaaatcagg cgctcgacca aattaagcgc cgcttccgcg tcgccctgct tcgcagcctg  41820
gtattcaggc tcgttggtca aagaaccaag gtcgccgttg cgaaccacct tcgggaagtc  41880
tccccacggt gcgcgctcgg ctctgctgta gctgctcaag acgcctccct ttttagccgc  41940
taaaactcta acgagtgcgc ccgcgactca acttgacgct ttcggcactt acctgtgcct  42000
tgccacttgc gtcataggtg atgcttttcg cactcccgat ttcaggtact ttatcgaaat  42060
ctgaccgggc gtgcattaca aagttcttcc ccacctgttg gtaaatgctg ccgctatctg  42120
cgtggacgat gctgccgtcg tggcgctgcg acttatcggc cttttgggcc atatagatgt  42180
tgtaaatgcc aggtttcagg gccccggctt tatctacctt ctggttcgtc catgcgcctt  42240
ggttctcggt ctggacaatt ctttgcccat tcatgaccag gaggcggtgt ttcattgggt  42300
gactcctgac ggttgcctct ggtgttaaac gtgtcctggt cgcttgccgg ctaaaaaaaa  42360
gccgacctcg gcagttcgag gccggctttc cctagagccg ggcgcgtcaa ggttgttcca  42420
tctattttag tgaactgcgt tcgatttatc agttactttc ctcccgcttt gtgtttcctc  42480
ccactcgttt ccgcgtctag ccgacccctc aacatagcgg cctcttcttg ggctgccttt  42540
gcctcttgcc gcgcttcgtc acgctcggct tgcaccgtcg taaagcgctc ggcctgcctg  42600
gccgcctctt gcgccgccaa cttcctttgc tcctggtggg cctcggcgtc ggcctgcgcc  42660
ttcgctttca ccgctgccaa ctccgtgcgc aaactctccg cttcgcgcct ggtggcgtcg  42720
```

-continued

```
cgctcgccgc gaagcgcctg catttcctgg ttggccgcgt ccagggtctt gcggctctct  42780
tctttgaatg cgcgggcgtc ctggtgagcg tagtccagct cggcgcgcag ctcctgcgct  42840
cgacgctcca cctcgtcggc ccgctgcgtc gccagcgcgg cccgctgctc ggctcctgcc  42900
agggcggtgc gtgcttcggc cagggcttgc cgctggcgtg cggccagctc ggccgcctcg  42960
gcggcctgct gctctagcaa tgtaacgcgc gcctgggctt cttccagctc gcgggcctgc  43020
gcctcgaagg cgtcggccag ctccccgcgc acggcttcca actcgttgcg ctcacgatcc  43080
cagccggctt gcgctgcctg caacgattca ttggcaaggg cctgggcggc ttgccagagg  43140
gcggccacgg cctggttgcc ggcctgctgc accgcgtccg gcacctggac tgccagcggg  43200
gcggcctgcg ccgtgcgctg gcgtcgccat tcgcgcatgc cggcgctggc gtcgttcatg  43260
ttgacgcggg cggccttacg cactgcatcc acggtcggga agttctcccg gtcgccttgc  43320
tcgaacagct cgtccgcagc cgcaaaaatg cggtcgcgcg tctctttgtt cagttccatg  43380
ttggctccgg taattggtaa gaataataat actcttacct accttatcag cgcaagagtt  43440
tagctgaaca gttctcgact taacggcagg ttttttagcg gctgaagggc aggcaaaaaa  43500
agccccgcac ggtcggcggg ggcaaagggt cagcgggaag gggattagcg ggcgtcgggc  43560
ttcttcatgc gtcggggccg cgcttcttgg gatggagcac gacgaagcgc gcacgcgcat  43620
cgtcctcggc cctatcggcc cgcgtcgcgg tcaggaactt gtcgcgcgct aggtcctccc  43680
tggtgggcac caggggcatg aactcggcct gctcgatgta ggtccactcc atgaccgcat  43740
cgcagtcgag gccgcgttcc ttcaccgtct cttgcaggtc gcggtacgcc cgctcgttga  43800
gcggctggta acgggccaat tggtcgtaaa tggctgtcgg ccatgagcgg cctttcctgt  43860
tgagccagca gccgacgacg aagccggcaa tgcaggcccc tggcacaacc aggccgacgc  43920
cgggggcagg ggatggcagc agctcgccaa ccaggaaccc cgccgcgatg atgccgatgc  43980
cggtcaacca gcccttgaaa ctatccggcc ccgaaacacc cctgcgcatt gcctggatgc  44040
tgcgccggat agcttgcaac atcaggagcc gtttcttttg ttcgtcagtc atggtccgcc  44100
ctcaccagtt gttcgtatcg gtgtcggacg aactgaaatc gcaagagctg ccggtatcgg  44160
tccagccgct gtccgtgtcg ctgctgccga agcacggcga ggggtccgcg aacgccgcag  44220
acggcgtatc cggccgcagc gcatcgccca gcatggcccc ggtcagcgag ccgccggcca  44280
ggtagcccag catggtgctg ttggtcgccc cggccaccag ggccgacgtg acgaaatcgc  44340
cgtcattccc tctggattgt tcgctgctcg gcggggcagt gcgccgcgcc ggcggcgtcg  44400
tggatggctc gggttggctg gcctgcgacg gccggcgaaa ggtgcgcagc agctcgttat  44460
cgaccggctg cggcgtcggg gccgccgcct tgcgctgcgg tcggtgttcc ttcttcggct  44520
cgcgcagctt gaacagcatg atcgcggaaa ccagcagcaa cgccgcgcct acgcctcccg  44580
cgatgtagaa cagcatcgga ttcattcttc ggtcctcctt gtagcggaac cgttgtctgt  44640
gcggcgcggg tggcccgcgc cgctgtcttt ggggatcagc cctcgatgag cgcgaccagt  44700
ttcacgtcgg caaggttcgc ctcgaactcc tggccgtcgt cctcgtactt caaccaggca  44760
tagccttccg ccggcggccg acggttgagg ataaggcggg cagggcgctc gtcgtgctcg  44820
acctggacga tggccttttt cagcttgtcc gggtccggct ccttcgcgcc cttttccttg  44880
gcgtccttac cgtcctggtc gccgtcctcg ccgtcctggc cgtcgccggc ctccgcgtca  44940
cgctcggcat cagtctggcc gttgaaggca tcgacggtgt tgggatcgcg gcccttctcg  45000
tccaggaact cgcgcagcag cttgaccgtg ccgcgcgtga tttcctgggt gtcgtcgtca  45060
agccacgcct cgacttcctc cgggcgcttc ttgaaggccg tcaccagctc gttcaccacg  45120
```

-continued gtcacgtcgc gcacgcggcc ggtgttgaac gcatcggcga tcttctccgg caggtccagc 45180
agcgtgacgt gctgggtgat gaacgccggc gacttgccga tttccttggc gatatcgcct 45240
ttcttcttgc ccttcgccag ctcgcggcca atgaagtcgg caatttcgcg cggggtcagc 45300
tcgttgcgtt gcaggttctc gataacctgg tcggcttcgt tgtagtcgtt gtcgatgaac 45360
gccgggatgg acttcttgcc ggcccacttc gagccacggt agcggcgggc gccgtgattg 45420
atgatatagc ggcccggctg ctcctggttc tcgcgcaccg aaatgggtga cttcaccccg 45480
cgctctttga tcgtggcacc gatttccgcg atgctctccg gggaaaagcc ggggttgtcg 45540
gccgtccgcg gctgatgcgg atcttcgtcg atcaggtcca ggtccagctc gatagggccg 45600
gaaccgccct gagacgccgc aggagcgtcc aggaggctcg acaggtcgcc gatgctatcc 45660
aaccccaggc cggacggctg cgccgcgcct gcggcttcct gagcggccgc agcggtgttt 45720
ttcttggtgg tcttggcttg agccgcagtc attgggaaat ctccatcttc gtgaacacgt 45780
aatcagccag ggcgcgaacc tctttcgatg ccttgcgcgc ggccgttttc ttgatcttcc 45840
agaccggcac accggatgcg agggcatcgg cgatgctgct gcgcaggcca acggtggccg 45900
gaatcatcat cttggggtac gcggccagca gctcggcttg gtggcgcgcg tggcgcggat 45960
tccgcgcatc gaccttgctg ggcaccatgc caaggaattg cagcttggcg ttcttctggc 46020
gcacgttcgc aatggtcgtg accatcttct tgatgccctg gatgctgtac gcctcaagct 46080
cgatggggga cagcacatag tcggccgcga agagggcggc cgccaggccg acgccaaggg 46140
tcggggccgt gtcgatcagg cacacgtcga agccttggtt cgccagggcc ttgatgttcg 46200
ccccgaacag ctcgcgggcg tcgtccagcg acagccgttc ggcgttcgcc agtaccgggt 46260
tggactcgat gagggcgagg cgcgcggcct ggccgtcgcc ggctgcgggt gcggtttcgg 46320
tccagccgcc ggcagggaca gcgccgaaca gcttgcttgc atgcaggccg gtagcaaagt 46380
ccttgagcgt gtaggacgca ttgccctggg ggtccaggtc gatcacggca acccgcaagc 46440
cgcgctcgaa aaagtcgaag gcaagatgca caagggtcga agtcttgccg acgccgcctt 46500
tctggttggc cgtgaccaaa gttttcatcg tttggtttcc tgtttttttct tggcgtccgc 46560
ttcccacttc cggacgatgt acgcctgatg ttccggcaga accgccgtta cccgcgcgta 46620
cccctcgggc aagttcttgt cctcgaacgc ggcccacacg cgatgcaccg cttgcgacac 46680
tgcgcccctg gtcagtccca gcgacgttgc gaacgtcgcc tgtggcttcc catcgactaa 46740
gacgccccgc gctatctcga tggtctgctg ccccacttcc agcccctgga tcgcctcctg 46800
gaactggctt tcggtaagcc gtttcttcat ggataacacc cataatttgc tccgcgcctt 46860
ggttgaacat agcggtgaca gccgccagca catgagagaa gtttagctaa acatttctcg 46920
cacgtcaaca cctttagccg ctaaaactcg tccttggcgt aacaaaacaa aagcccggaa 46980
accgggcttt cgtctcttgc cgcttatggc tctgcacccg gctccatcac caacaggtcg 47040
cgcacgcgct tcactcggtt gcggatcgac actgccagcc caacaaagcc ggttgccgcc 47100
gccgccagga tcgcgccgat gatgccggcc acaccggcca tcgcccacca ggtcgccgcc 47160
ttccggttcc attcctgctg gtactgcttc gcaatgctgg acctcggctc accataggct 47220
gaccgctcga tggcgtatgc cgcttctccc cttggcgtaa aacccagcgc cgcaggcggc 47280
attgccatgc tgcccgccgc tttcccgacc acgacgcgcg caccaggctt gcggtccaga 47340
ccttcggcca cggcgagctg cgcaaggaca taatcagccg ccgacttggc tccacgcgcc 47400
tcgatcagct cttgcactcg cgcgaaatcc ttggcctcca cggccgccat gaatcgcgca 47460
cgcggcgaag gctccgcagg gccggcgtcg tgatcgccgc cgagaatgcc cttcaccaag 47520

-continued

```
ttcgacgaca cgaaaatcat gctgacggct atcaccatca tgcagacgga tcgcacgaac  47580
ccgctgaatt gaacacgagc acggcacccg cgaccactat gccaagaatg cccaaggtaa  47640
aaattgccgg ccccgccatg aagtccgtga atgccccgac ggccgaagtg aagggcaggc  47700
cgccacccag gccgccgccc tcactgcccg gcacctggtc gctgaatgtc gatgccagca  47760
cctgcggcac gtcaatgctt ccgggcgtcg cgctcgggct gatcgcccat cccgttactg  47820
ccccgatccc ggcaatggca aggactgcca gcgctgccat ttttggggtg aggccgttcg  47880
cggccgaggg gcgcagcccc tggggggatg ggaggcccgc gttagcgggc cgggagggtt  47940
cgagaagggg gggcaccccc cttcggcgtg cgcggtcacg cgcacagggc gcagccctgg  48000
ttaaaaacaa ggtttataaa tattggttta aaagcaggtt aaaagacagg ttagcggtgg  48060
ccgaaaaacg ggcggaaacc cttgcaaatg ctggattttc tgcctgtgga cagcccctca  48120
aatgtcaata ggtgcgcccc tcatctgtca gcactctgcc cctcaagtgt caaggatcgc  48180
gcccctcatc tgtcagtagt cgcgcccctc aagtgtcaat accgcagggc acttatcccc  48240
aggcttgtcc acatcatctg tgggaaactc gcgtaaaatc aggcgttttc gccgatttgc  48300
gaggctggcc agctccacgt cgccggccga aatcgagcct gcccctcatc tgtcaacgcc  48360
gcgccgggtg agtcggcccc tcaagtgtca acgtccgccc ctcatctgtc agtgagggcc  48420
aagttttccg cgaggtatcc acaacgccgg cggccgcggt gtctcgcaca cggcttcgac  48480
ggcgtttctg gcgcgtttgc agggccatag acggccgcca gcccagcggc gagggcaacc  48540
agcccggtga gcgtcggaaa ggcgctggaa gccccgtagc gacgcggaga ggggcgagac  48600
aagccaaggg cgcaggctcg atgcgcagca cgacatagcc ggttctcgca aggacgagaa  48660
tttccctgcg gtgcccctca agtgtcaatg aaagtttcca acgcgagcca ttcgcgagag  48720
ccttgagtcc acgctagatg agagctttgt tgtaggtgga ccagttggtg attttgaact  48780
tttgctttgc cacggaacgg tctgcgttgt cgggaagatg cgtgatctga tccttcaact  48840
cagcaaaagt tcgatttatt caacaaagcc acgttgtgtc tcaaaatctc tgatgttaca  48900
ttgcacaaga taaaaatata tcatcatgaa caataaaact gtctgcttac ataaacagta  48960
atacaagggg tgttatgagc catattcaac gggaaac                           48997
```